(12) United States Patent
Natunen et al.

(10) Patent No.: US 9,399,764 B2
(45) Date of Patent: Jul. 26, 2016

(54) FUSION ENZYMES

(75) Inventors: Jari Natunen, Vantaa (FI); Anne Kanerva, Helsinki (FI); Jukka Hiltunen, Helsinki (FI); Markku Saloheimo, Helsinki (FI); Heli Viskari, Nummela (FI); Anne Huuskonen, Helsinki (FI)

(73) Assignees: Novartis International Pharmaceutical, Ltd., Hamilton (BM); Glykos Finland Oy, Helsinki (FI)

( * ) Notice: Subject to any disclaimer, the term of this patent is extended or adjusted under 35 U.S.C. 154(b) by 199 days.

(21) Appl. No.: 13/989,084

(22) PCT Filed: Nov. 24, 2011

(86) PCT No.: PCT/EP2011/070956
§ 371 (c)(1),
(2), (4) Date: Aug. 13, 2013

(87) PCT Pub. No.: WO2012/069593
PCT Pub. Date: May 31, 2012

(65) Prior Publication Data
US 2013/0330780 A1  Dec. 12, 2013

Related U.S. Application Data

(60) Provisional application No. 61/417,144, filed on Nov. 24, 2010.

(51) Int. Cl.
| | |
|---|---|
| *C12N 9/10* | (2006.01) |
| *C12P 21/00* | (2006.01) |
| *C12P 19/18* | (2006.01) |
| *C07K 19/00* | (2006.01) |
| *C12N 15/80* | (2006.01) |

(52) U.S. Cl.
CPC .............. *C12N 9/1051* (2013.01); *C12N 15/80* (2013.01); *C12P 19/18* (2013.01); *C12P 21/005* (2013.01); *C12Y 204/01101* (2013.01); *C12Y 204/01143* (2013.01); *C07K 2319/03* (2013.01); *Y02P 20/52* (2015.11)

(58) Field of Classification Search
None
See application file for complete search history.

(56) References Cited

U.S. PATENT DOCUMENTS

| | | | | |
|---|---|---|---|---|
| 7,381,544 | B2 * | 6/2008 | Gilbert | C12P 19/26 435/193 |
| 2005/0170452 | A1 | 8/2005 | Wildt et al. | |
| 2006/0040353 | A1 | 2/2006 | Davidson et al. | |
| 2006/0073542 | A1 * | 4/2006 | Bayer et al. | 435/68.1 |
| 2008/0026376 | A1 | 1/2008 | Wang et al. | |
| 2011/0207214 | A1 | 8/2011 | Helenius et al. | |

FOREIGN PATENT DOCUMENTS

| | | |
|---|---|---|
| WO | 2006026992 A1 | 3/2006 |
| WO | WO 2010049177 A1 * | 5/2010 ........... C12N 9/1048 |
| WO | 2012069593 A3 | 5/2012 |

OTHER PUBLICATIONS

Hassinen et al., Golgi N-Glycosyltransferases Form Both Homo- and Heterodimeric Enzyme Complexes in Live Cells, J. Biol. Chem., Apr. 2010, 285, 17771-77.*
Kuriyan et al., The origin of protein interactions and allostery in colocalization, Nature, 2007, 450, 983-90.*
Choi et al., Use of combinatorial genetic libraries to humanize N-linked glycosylation in the yeast *Pichia pastoris*, Proc. Natl. Acad. Sci. USA, 2003, 100, 5022-27.*
Baldwin, et al. Develop Systems for Manufacturing 1000,000,000 Doses of an Emergency Pharmaceutical (e.g. Vaccine or Monoclonal Antibody) Within 2 Months of Product Identification. Contract No. W911NF-05-C-0072 by the Defense Advanced Research Projects Agency (DARPA). Jun. 6, 2006.
Hintz, J. Improved Gene Expression in *Aspergillus nidulans*. Can. J. Botany, 73: 876-884 (1995).
Bobrowicz Piotr et al: "Engineering of an artificial glycosylation pathway blocked in core oligosaccharide assembly in the yeast *Pichia pastoris*: production of complex humanized glycoproteins with terminal galactose", Glycobiology, Oxford University Press, US, vol. 14, n°9, Sep. 1, 2004, pp. 757-766.
De Pourcq et al: "Engineering of glycosylation in yeast and other fungi: current state and perspectives", Applied Microbiology and Biotechnology, Springer, Berlin, DE, vol. 87, n°5, Jun. 29, 2010, pp. 1617-1631.
Hamilton et al: "Glycosylation engineering in yeast: the advent of fully humanized yeast", Current Opinion in Biotechnology, London,GB, vol. 18, n°5, Oct. 24, 2007, pp. 387-392.
Kainz et al: "N-Glycan Modification in Aspergillus Species", Applied and Environmental Microbiology, vol. 74, n°4, Feb. 15, 2008, pp. 1076-1086.
Ohashi T et al: "Production of heterologous glycoproteins by a glycosylation-defective alg3och1 mutant of *Schizosaccharomyces pombe*", Journal of Biotechnology, Elsevier Science Publishers, Amsterdam, NL, vol. 150, n°3, Nov. 1, 2010, pp. 348-356.

* cited by examiner

*Primary Examiner* — Robert Mondesi
*Assistant Examiner* — Todd M Epstein
(74) *Attorney, Agent, or Firm* — Patrick J. Halloran

(57) ABSTRACT

The present disclosure relates to recombinant proteins having N-acetylglucosaminyltransferase activity. The present disclosure further relates to methods for producing complex N-glycans including the steps of providing host cells containing such recombinant proteins and culturing the host cells such that the recombinant proteins are expressed.

21 Claims, 49 Drawing Sheets

Figure 1, cont.
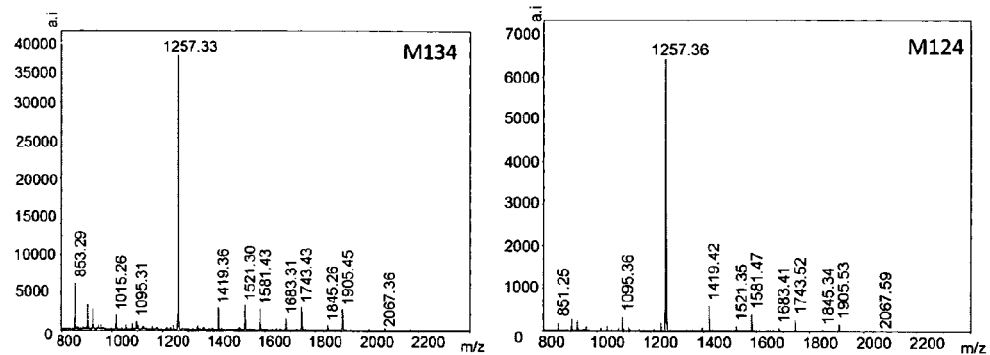
Figure 2
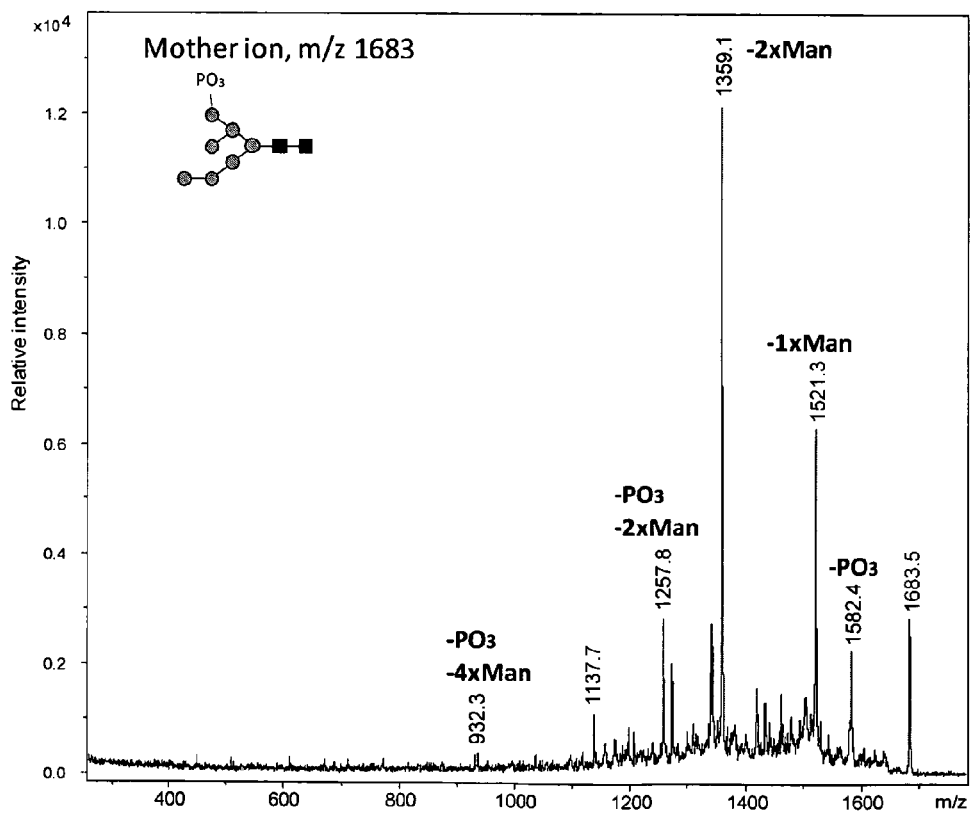

Figure 3, cont.
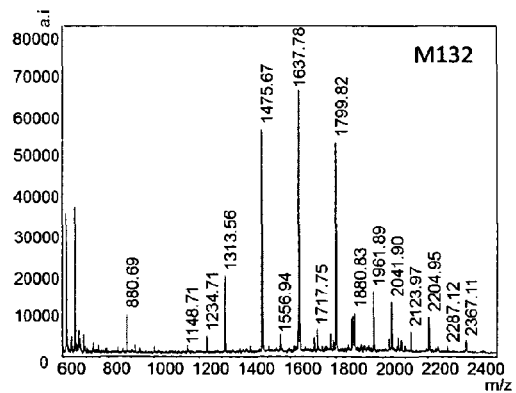
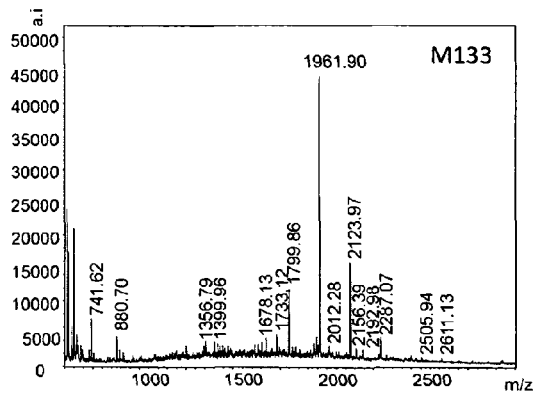
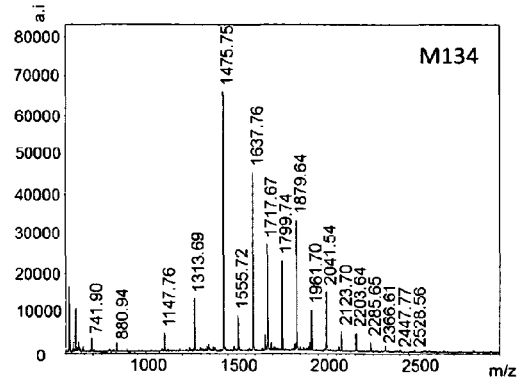
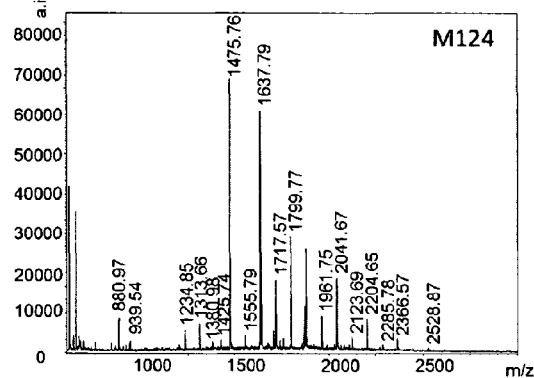

```
Aoryzae_gi|169779159|ref|XP_00       ----------------------MELKHFIHELCLN-PRHTKWIAPLLVI 26
Aniger_gi|317037568|ref|XP_001       ----------------------MDWMRLIRDLCFN-PRHTKWMAPLLVL 26
Nfischeri_ci|119478936|ref|XP_       ----------------------MDLKHTLRDLCMN-PRHTRWVAPLLIL 26
Treesei_jgi|Trire2|104121|fgen       --------MA--------------SLIKTAVDIANGRHALSRYVIFGLWL 28
Tvirens_jgi|TriviGv29_8_2|1944       --------MA--------------SLIKFASDVANGRHALSKFIPMGLWL 28
Tatroviride_jgi|Triat2|270085|       --------MA--------------SLIKFASDVATGRHALSKLIPVGLFL 28
Foxysporum_gi|342880904|gb|EGU       MPESASGTLS--------------QGVRFLRNVLNGRHALSKLIPIALWL 36
Gzea_gi|46136275|ref|XP_389829       MADPAPGALA--------------RGTRFVRNVLTGQHALSKLIPVALWL 36
Mthermophila_gi|347013322|gb|A       MTRMRSSPKTPTATMADQNRPTHTRATRLVFDILNGRHVLSKLIPPLVFL 50
Ncrassa_gi|85106839|ref|XP_962       MAAPSSRPES---------NPPLYKQALDFALDVANGRHALSKLIPPALFL 42
Moryzae_gi|145611997|ref|XP_36       MAAERPSTLG--------------KPVQFVFDVANGRHPLSRAIPPMLLA 36
Spombe_gi|19114765|ref|NP_5938       MSSVET------------------RNSFNPFRVLFDLGSYGWLHPSRLLL 32
                                                             :   .            :

Aoryzae_gi|169779159|ref|XP_00       GDAFLCALIIWKIPYTEIDWTTYMQQIALYISGERDYTLIKGSTGPLVYP 76
Aniger_gi|317037568|ref|XP_001       GDAFLCALIIWKVPYTEIDWATYMQQISLYLSGERDYTLIRGSTGPLVYP 76
Nfischeri_ci|119478936|ref|XP_       GDAVLCALIIWKVPYTEIDWTTYMQQISLYISGERDYTLIKGSTGPLVYP 76
Treesei_jgi|Trire2|104121|fgen       ADAVLCGLIIWKVPYTEIDWVAYMEQVTQFVHGERDYPKMEGGTGPLVYP 78
Tvirens_jgi|TriviGv29_8_2|1944       ADAVLCGLIIWKVPYTEIDWVAYMEQITQFVHGERDYPKMEGGTGPLVYP 78
Tatroviride_jgi|Triat2|270085|       ADAILCGLVIWKVPYTEIDWTAYMEQVFVNGERDYPKMEGGTGPLVYP 78
Foxysporum_gi|342880904|gb|EGU       VDALGCGLIIWKIPYTEIDWVAYMQQISQFVSGERDYTKMEGDTGPLVYP 86
Gzea_gi|46136275|ref|XP_389829       ADAVGTSLIIWKVPYTEIDWEAYMQQVSQFISGERDYTKIEGGTGPLVYP 86
Mthermophila_gi|347013322|gb|A       ADALLCALIIWKVPYTEIDWNAYMEQVAQILSGERDYTKIRGNTGPLVYP 100
Ncrassa_gi|85106839|ref|XP_962       VDALGCGLIIWKVPYTEIDWAAYMEQVSQILSGERDYTKVRGGTGPLVYP 92
Moryzae_gi|145611997|ref|XP_36       FDGLLCGLIIKKVP------------------------------------ 50
Spombe_gi|19114765|ref|NP_5938       LEIPFVFAIISKVPYTEIDWIAYMEQVNSFLLGERDYKSLVGCTGPLVYP 82
                                        :     :*  *:*

Aoryzae_gi|169779159|ref|XP_00       AAHVYSYMALYHLTDEGRDILFGQILFAVLYLVTLAVVMVCYRQSGAPPY 126
Aniger_gi|317037568|ref|XP_001       AAHVYSYTALYHLTDEGRDIFFGQILFAVLYLITLVVVLCCYRQSGAPPY 126
Nfischeri_ci|119478936|ref|XP_       AAHVIFNILYHLTDEGRDIFLGQILFAILYLATLTVAMTCYRQAGAPPY 126
Treesei_jgi|Trire2|104121|fgen       AAHVYIYTGLYYLTNKGTDILLAQQLFAVLYMATLAVVMTCYSKAKVPPY 128
Tvirens_jgi|TriviGv29_8_2|1944       AAHVYIYTGLYYLTNKGTDILLAQQLFAVLYMATLGVVMLCYWKAKVPPY 128
Tatroviride_jgi|Triat2|270085|       AAHVYIYTGLYHLTDEGQDILLAQQLFAVLYMATLGVVMLSYWKARVPPY 128
Foxysporum_gi|342880904|gb|EGU       AAHVYTYTGLYYITDKGTNILLAQQIFAVLYMALAVVMLCYWKAKVPPY 136
Gzea_gi|46136275|ref|XP_389829       AAHVYTFTGLYHITNEGENIFLAQQIFGVLYMATLAVVMLCYWKAKVPPY 136
Mthermophila_gi|347013322|gb|A       AAHVYIYTGLYHLTDEGRNILTAQKLFGFLYMVTLAVVMACYWQAKVPPY 150
Ncrassa_gi|85106839|ref|XP_962       AAHVYIYTGLYHLTDEGRNILLAQQLFAGLYMVTLAVVMGCYWQAKAPPY 142
Moryzae_gi|145611997|ref|XP_36       ----------------------------------------SCYRKAKVPPY 61
Spombe_gi|19114765|ref|NP_5938       GGHVFLYTLLYYLTDGGTNIVRAQYIFAFVYWITTAIVGYLFKIVRAPFY 132
                                                                              .* *

Aoryzae_gi|169779159|ref|XP_00       LFPLLVLSKRLHSVFVLRLFNDGLAVCAMWIAILLFQNKKWTAGVTAWTV 176
Aniger_gi|317037568|ref|XP_001       LLPLLVLSKRLHSVYVLRLFNDGLAAIAMWVATLLFMNRKWTAAVAVWST 176
Nfischeri_ci|119478936|ref|XP_       LLVPLVLSKRLHSVFMLRLFNDGFAAYAMWVSILLFMNKKWTAGAIVWST 176
Treesei_jgi|Trire2|104121|fgen       IFPLLILSKRLHSVFVLRCFNDCFAAFFLWLCIFFFQRREWTIGALAYSI 178
Tvirens_jgi|TriviGv29_8_2|1944       IFPLLILSKRLHSVFVLRCFNDCFAAFFLWLSIFFFQRRVWTLGAIAYTI 178
Tatroviride_jgi|Triat2|270085|       IFPLLILSKRLHSVFVLRCFNDCFAAFFLWLCIYSFQNRAWTFGALAYTL 178
Foxysporum_gi|342880904|gb|EGU       MFIFLIASKRLHSLFVLRCFNDCFAVFFLWLTIFLFQRRQWTVGSLVYSW 186
Gzea_gi|46136275|ref|XP_389829       MFVFLIASKRLHSLFVLRCFNDCFAVFFLWLSIYFFQRRNWTFGSLAYTW 186
Mthermophila_gi|347013322|gb|A       VFPLLLLSKRLHSIFVLRCFNDCFATLFLWLAIFALQRRAWRTGALMYTL 200
Ncrassa_gi|85106839|ref|XP_962       LFPLLTLSKRLHSIFVLRCFNDCFAVLFLWLAIFFFQRRNWQAGALLYTL 192
Moryzae_gi|145611997|ref|XP_36       VLPLLVLSKRLHSIFVLRCFNDCFAVLFFWLAIYCFQRRAWSLGGVFYSF 111
Spombe_gi|19114765|ref|NP_5938       IYVLLILSKRLHSIFILRLFNDGFNSLFSSLFILSSCKKKWVRASILLSV 182
                                       *  ******:::** ***  :        :*     .:*  .  :
```

Figure 42 (cont.)

```
Aoryzae_gi|169779159|ref|XP_00      GVGIKMTLLLLAPAIAVVTVLSLS-LVPSIRLGILALLIQVLLAIPFLQG 225
Aniger_gi|317037568|ref|XP_001      GVAIKMTLLLLAPAIAVVTVLSLS-LGPSVGLGVLAVLVQVLLAIPFLQN 225
Nfischeri_gi|119478936|ref|XP_      GVGIKMTLLLLAPAIAVVTVLSLS-LGPSMQLGFLAVLIQVLFGIPFLQN 225
Treesei_jgi|Trire2|104121|fgen     GLGVKMSLLLVLPAVVIVLYLGRG-FKGALRLLWLMVQVQLLLAIPFITT 227
Tvirens_jgi|TriviGv29_8_2|1944     GLGVKMSLLLVLPAVVIVLFLGRG-FKGALRLLWLMVQVQLLLAIPFITT 227
Tatroviride_jgi|Triat2|270085|     GLGVKMSLLLVLPAVVIILFLGRG-FKGALRLVWLMAQVQLVLAIPFITT 227
Foxysporum_gi|342880904|gb|EGU     GLGIKMSLLLVLPAIGVILFLGRG-LWPSLRLAWLMAQIQFAIGLPFITK 235
Gzea_gi|46136275|ref|XP_389829     GLGIKMSLLLVLPAIGVILLLGRG-FWPGLRLAWLMAQVQFAIGIPFIMK 235
Mthermophila_gi|347013322|gb|A     GLGVKMSLLLVLPAVGVVLLLGAC-FATSLRLAAVIGLVQVLIAVPFLSN 249
Ncrassa_gi|85106839|ref|XP_962     GLGVKMTLLLSLPAVGIVLFLGSGSFVTTLQLVATMGLVQILIGVFFLAH 242
Moryzae_gi|145611997|ref|XP_36     GLGIKMTVLLSLPAVGILLLGRG-FGGALNVASIMGQLQVAIGLFFLSK 160
Spombe_gi|19114765|ref|NP_5938     ACSVKMSSLLYVPAYLVLLLQILG-PKKTWMHIFVIIIVQILFSIPFLAY 231
                                     . :**: **  **   ::            :*. :.:**:

Aoryzae_gi|169779159|ref|XP_00      NPIGYVARAFELTRQFMFKWTVNWRFVGEDLFLSKQFSLALLGLHIFLLG 275
Aniger_gi|317037568|ref|XP_001      NPAGYLSRAFELTRQFMFKWTVNWRFVGEEVFLSKSFSLALLAVHIVLLG 275
Nfischeri_gi|119478936|ref|XP_      NPAGYVSRAFELTRQFMFKWTVNWRFVGEELFLSRKFSLALLALHILLLG 275
Treesei_jgi|Trire2|104121|fgen     NWRGYLGRAFELSRQFKFEWTVNWRMLGEDLFLSRGFSITLLAFHAIFLL 277
Tvirens_jgi|TriviGv29_8_2|1944     NWKGYLGRAFELSRQFKFEWTVNWRMLGEELFLSRGFSITLLAFHALFLL 277
Tatroviride_jgi|Triat2|270085|     NWAGYLGRAFELSRQFKFEWTVNWRMMGEETFLSRGFSITLLTFHVVTLL 277
Foxysporum_gi|342880904|gb|EGU     NPRGYAARAFELSRQFQFKWTVNWRFVGEEVFLSKYFALSLLACHILVLL 285
Gzea_gi|46136275|ref|XP_389829     NSRGYAARAFELSREFKFEWTVNWRMLGEEVFLSKSFAIFLLACHVTALL 285
Mthermophila_gi|347013322|gb|A     NPWGYLGRAFELSRQFFFKWTVNWRFVGEEVFLSKEFSLALLGLHVAVLA 299
Ncrassa_gi|85106839|ref|XP_962     YPTEYLSRAFELSRQFFFKWTVNWRFVGEEIFLSKGFALTLLALHVLVLG 292
Moryzae_gi|145611997|ref|XP_36     NAWGYLSRAFELSRQFMFKWTVNWRFVGEETFLSKPFAITLLALHASVLL 210
Spombe_gi|19114765|ref|NP_5938     FWS-YWTQAFDFGRAFDYKWTVNWRFIPRSIFESTSFSTSILFLHVALLV 280
                                         *  :**::  *  *  ::******::  ..  *  *  *:    :*   *      *

Aoryzae_gi|169779159|ref|XP_00      LFVTTGWLRPSGSNVPDFLRSLLQG         RQRTVVLSKSFIMTV 315
Aniger_gi|317037568|ref|XP_001      AFAVTGWLRYSRSSLPAFIRNLLAG---------RHRTVSLPKPYIMSV 315
Nfischeri_gi|119478936|ref|XP_      LFVATVWLKPSGSDLPSFLQRLIQR---------RYRTASLSKSFIMTA 315
Treesei_jgi|Trire2|104121|fgen     AFILGRWLKIRERTVLGMIPYVIRFRSPFTEQEERAISNRVVTPGYVMST 327
Tvirens_jgi|TriviGv29_8_2|1944     IFILGRWLRIKERSFLGMIPYVLRFTSPFTEHEEASISHRVVTPEYIMSA 327
Tatroviride_jgi|Triat2|270085|     VFIAARWLKLQERSLLGIITYAVRFQSPFTEQEEAKVSKKVVTPRYVLAT 327
Foxysporum_gi|342880904|gb|EGU     IFISKRWIQPTGRSLYDLIPSFLR LKSPFTMQEQLRISH-YVTPEYAMTT 334
Gzea_gi|46136275|ref|XP_389829     VFISQRWLQPTGRPLSAMIPSFLQLKSPFTLQEQLRISH-YVTPEYVMTT 334
Mthermophila_gi|347013322|gb|A     IFVTTRWLKPARKPVSQLIVPILLG-KSPFTEEEQRAVSRDVTPRFILTS 348
Ncrassa_gi|85106839|ref|XP_962     IFITTRWIKPARKSLVQLISPVLLAGKPPLTVPEHRAAARDVTPRYIMTT 342
Moryzae_gi|145611997|ref|XP_36     AFVTKRWLKPASKSIGGLIAPLLSG-RPIFTAEEAQTAARAVTPEYVMTT 259
Spombe_gi|19114765|ref|NP_5938     AFTCKHWNKLSRATPFAMVNSMLTLKP--------LPKLQLATPNFIFTA 322
                                        *    *  :         ::       :                  .  : ::

Aoryzae_gi|169779159|ref|XP_00      MLTSLAIGLLCARSLHYQFFAYLSWATPCLLWRARLHPILIYAIWALQEW 365
Aniger_gi|317037568|ref|XP_001      MLSSLTVGLLCARSLHYQFFAYLSWATPFLLWRAGFHPILLYLIWAMQEW 365
Nfischeri_gi|119478936|ref|XP_      MLSSLAIGLLCARSLHYQFFAYLACATPFLLWQAGFHPILVYVVWVAQEW 365
Treesei_jgi|Trire2|104121|fgen     ILSANVVGLLFARSLHYQFYAYLAWATPYLLWTACPNLLVVAPLWAAQEW 377
Tvirens_jgi|TriviGv29_8_2|1944     MLSANVVGLLFARSLHYQFYAYLAWATPFLLWTASPNLLVVVPLWAAQEW 377
Tatroviride_jgi|Triat2|270085|     ILSANVIGLLFARSLHYQFYAYLAWATPFLLWTAYPNLLVVVPLWLAQEW 377
Foxysporum_gi|342880904|gb|EGU     MLTANLIGLLFARSLHYQFYAYLAWATPYLLWRATEDPVIVAIIWAAQEW 384
Gzea_gi|46136275|ref|XP_389829     MLSANVIGLLFARSLHYQFYAYLAWASPYLIWRATEDPFIVLLIWAAQEW 384
Mthermophila_gi|347013322|gb|A     ILSANVVGLLFARSLHYQFYSYLAWMTPYLLWRSGVHPILQYAIWTAQEW 398
Ncrassa_gi|85106839|ref|XP_962     ILSANAVGLLFARSLHYQFYAYVAWSTPFLLWRAGLHPVLVYLLWAVHEW 392
Moryzae_gi|145611997|ref|XP_36     MLTANIVGMLFARSLHYQFYAYLAWSTPYLLWRSGIHPLLQWGLWALQEW 309
Spombe_gi|19114765|ref|NP_5938     LATSNLIGILCARSLHYQFYAWFAWYSPYLCYQASFPAPIVIGLWMLQEY 372
                                    : ::    :*:* *******:::.: :* * :: :       :* :*:
```

Figure 42 (cont.)

```
Aoryzae_gi|169779159|ref|XP_00      AWNVYPSTNASSSVVVFSLAVQVFG------------------------V 391
Aniger_gi|317037568|ref|XP_001      AWNTFPSTNLSSIIVVLSLATQSFG------------------------V 391
Nfischeri_gi|119478936|ref|XP_      AWNTYPSTNASSLVVILSLAAQVFG------------------------V 391
Treesei_jgi|Trire2|104121|fgen      AWNVFPSTPLSSSVVVSVLAVTVA-------------------------MA 403
Tvirens_jgi|TriviGv29_8_2|1944      AWNVFPSTPLSSNVVVSVLAVTVA-------------------------MA 403
Tatroviride_jgi|Triat2|270085|      AWNVFPSTPLSSSVVISLVPVCLLSPQLLVSEDIYNFANCSAILRPRGIA 427
Foxysporum_gi|342880904|gb|EGU      AWNVYPSTDLSSTIAVNTMLATVV-------------------------LV 410
Gzea_gi|46136275|ref|XP_389829      AWNVFPSTDLSSRVTVGAMLATVV-------------------------LA 410
Mthermophila_ci|347013322|gb|A      AWNVYPSTPISSGVVVGVLALTAA-------------------------LV 424
Ncrassa_gi|85106839|ref|XP_962      AWNVFPSTPASSAVVVGVLGVTVA-------------------------GV 418
Moryzae_gi|145611997|ref|XP_36      AWNVYPSTPVSSGVVVGVMAITVG-------------------------AV 335
Spombe_gi|19114765|ref|NP_5938      AWNVFPSTKLSSLIAVCVPLITILK------------------------L 398
                                    ***.:***  ** :.:
```

```
Aoryzae_gi|169779159        LLNSRNALSDAPPRRKGKEHIQ                         413  (SEQ ID NO: 133)
Aniger_gi|317037568|        LANSASAFYTMRSNPSGKEHNQ-----------------------  413  (SEQ ID NO: 135)
Nfischeri_gi|1194789        LGNSFSRKHLDQS  SQKEHLQ                         411  (SEQ ID NO: 134)
Treesei_jgi|Trire2|1        F---AGSNPQPRETSKPKQH-------------------------  420  (SEQ ID NO: 126)
Tvirens_jgi|TriviGv2        F---VGSNPQ-RGAPKPKQL-------------------------  419  (SEQ ID NO: 128)
Tatroviride_jgi|Tria        FGQDISATLNPDGVAKPLGELENDGLRVWHLASVQVVSFGLEHAHNELGG 477  (SEQ ID NO: 127)
Foxysporum_gi|342880        YLGTARRAVPAPAAQVGNVDDKNK---------------------  434  (SEQ ID NO: 129)
Gzea_gi|46136275|ref        YRGTARLAVPP--SQARKIEAKNK---------------------  432  (SEQ ID NO: 130)
Mthermophila_ci|3470        WLGAREDWEP--RRVLLKGEAAKR---------------------  446  (SEQ ID NO: 131)
Ncrassa_gi|85106839|        WFGAREEWEPGMKSSSKKEEAAMR---------------------  442  (SEQ ID NO: 132)
Moryzae_gi|145611997        MVGAKAEFRP--QVPVAKKVEAKR---------------------  357  (SEQ ID NO: 136)
Spombe_gi|19114765|r        YTSDYRKP-------------------------------------  406  (SEQ ID NO: 137)
```

FUSION ENZYMES

CROSS-REFERENCE TO RELATED APPLICATION

This application was filed under 35 U.S.C. §371 and claims priority to International Application No. PCT/EP2011/070956 filed Nov. 24, 2011, and claims the benefit of U.S. Provisional Application No. 61/417,144, filed Nov. 24, 2010, which are hereby incorporated by reference in their entirety.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 619672001040SEQLIST.txt, date recorded: Nov. 22, 2011, size: 305 KB).

FIELD OF THE INVENTION

The present disclosure relates to compositions and methods useful for the production of N-glycans.

BACKGROUND

Posttranslational modification of proteins is often necessary for proper protein folding and function. A common protein modification is the addition of oligosaccharides (glycans) to nascent polypeptides in the endoplasmic reticulum to form glycoproteins, a process known as glycosylation. N-glycosylation is of particular importance in the production of recombinant proteins used for therapeutic purposes. Because standard prokaryotic expression systems lack the proper machinery necessary for such modifications, alternative expression systems have to be used in production of these therapeutic proteins. Yeast and fungi are attractive options for expressing proteins as they can be easily grown at a large scale in simple media, which allows low production costs. Moreover, tools are available to manipulate the relatively simple genetic makeup of yeast and fungal cells as well as more complex eukaryotic cells such as mammalian or insect cells (De Pourcq et al., Appl Microbiol Biotechnol, 87(5): 1617-31).

Fungal cells and mammalian cells share common steps in the early stages of glycosylation that result in the formation of mannose(8)N-acetylglucosamine(2) (Man8GlcNAc2). However, significant differences exist in the later stages of the process. For example, in yeast, additional mannose subunits are added to Man8GlcNAc2 by mannosyltransferases and mannan polymerases to yield high-mannose type N-glycans. In contrast, mannose sugars are removed from the human Man8GlcNAc2 to yield Man5GlcNAc2, followed by three sequential reactions involving the enzymes N-acetylglucosaminyltransferase I (GnTI), mannosidase II (Mns II), and N-acetylglucosaminyltransferase II (GnTII), to convert Man5GlcNAc2 into GlcNAc2Man3GlcNAc2.

The differences between the glycosylation process in mammalian and fungal cells pose a challenge to the expression of glycosylated mammalian proteins in fungal cells since glycoproteins with high-mannose type N-glycans are not suitable for therapeutic use in humans (De Pourcq et al., 2010; Wildt and Gerngross, Nature Reviews Microbiology, 3: 119-128). Consequently, studies have been conducted to re-engineer the glycosylation pathways in yeast and fungal species to enable them to express recombinant human proteins. The general approach in glycoengineering of yeast or fungal cells has been to disrupt endogenous genes that are involved in formation of high-mannose type N-glycans. These gene disruptions can be combined with over-expression of endogenous mannosidases and/or glycosyltransferases and glycosidases from different species (Chiba et al., 1998, J Biol Chem 273: 26298-304; Kainz et al., 2008, Appl Environ Microbiol 74: 1076-86; Maras et al., 1997, Euro J Biochem 249: 701-07; Maras et al., 1999, Febs Letters 452: 365-70; Hamilton et al., 2003, Science 301: 1244-6; De Pourcq et al., 2010). However, the production of glycosylated mammalian proteins in non-mammalian cells still requires complicated and time-consuming genetic engineering and can be inefficient at producing a desired glycoprotein.

Thus, a need remains in the art for a simpler and more efficient system to express complex N-glycans in non-mammalian cells.

SUMMARY

Described herein are compositions including recombinant proteins having N-acetylglucosaminyltransferase activity. Further described herein are methods of producing complex N-glycans and methods of producing Man3GlcNAc2 glycans.

Thus one aspect includes recombinant proteins having N-acetylglucosaminyltransferase activity, where the recombinant proteins catalyze the transfer of N-acetylglucosamine to a terminal Manα3 residue and catalyze the transfer of N-acetylglucosamine to a terminal Manα6 residue of an acceptor glycan, and where the recombinant protein contains catalytic domains from at least two different enzymes. In certain embodiments, the acceptor glycan is attached to a molecule selected from an amino acid, a peptide, or a polypeptide. In certain embodiments, the molecule is a heterologous polypeptide. In certain embodiments that may be combined with the preceding embodiments, the acceptor glycan is Man3. In certain embodiments that may be combined with the preceding embodiments, the recombinant protein is a fusion protein containing an N-acetylglucosaminyltransferase I catalytic domain and an N-acetylglucosaminyltransferase II catalytic domain. In certain embodiments, the N-acetylglucosaminyltransferase I catalytic domain and the N-acetylglucosaminyltransferase II catalytic domain are from human enzymes. In certain embodiments, the N-acetylglucosaminyltransferase I catalytic domain includes a sequence that is at least 70%, at least 75%, at least 80%, at least 85%, at least 90%, at least 95%, at least 96%, at least 97%, at least 98%, at least 99%, or 100% identical to amino acid residues 105-445 of SEQ ID NO: 1. In certain embodiments that may be combined with the previous embodiments, the N-acetylglucosaminyltransferase II catalytic domain includes a sequence that is at least 70%, at least 75%, at least 80%, at least 85%, at least 90%, at least 95%, at least 96%, at least 97%, at least 98%, at least 99%, or 100% identical amino acid residues 30-447 of SEQ ID NO: 21. In certain embodiments that may be combined with the preceding embodiments, the N-acetylglucosaminyltransferase I catalytic domain is N-terminal to the N-acetylglucosaminyltransferase II catalytic domain. In certain embodiments that may be combined with the preceding embodiments, the N-acetylglucosaminyltransferase II catalytic domain is N-terminal to the N-acetylglucosaminyltransferase I catalytic domain.

In certain embodiments that may be combined with the preceding embodiments, the recombinant proteins further contain a spacer in between the N-acetylglucosaminyltransferase I catalytic domain and the N-acetylglucosaminyltransferase II catalytic domain. In certain embodiments, the spacer contains sequence from a stem domain. In certain embodiments that may be combined with the preceding embodiments, the spacer is at least 5, at least 10, at least 15, at least 20, at least 30, at least 40, or at least 50 amino acids in length. In certain embodiments that may be combined with the preceding embodiments, the spacer contains a sequence that is selected from SEQ ID NO: 118, SEQ ID NO: 120, SEQ ID NO: 122, and SEQ ID NO: 124. In certain embodiments, the spacer contains a sequence that is selected from SEQ ID NO: 118, SEQ ID NO: 120, and SEQ ID NO: 124. In certain embodiments, the spacer contains the sequence of SEQ ID NO: 120 or SEQ ID NO: 124. In certain embodiments, the spacer contains the sequence of SEQ ID NO: 124.

In certain embodiments that may be combined with the preceding embodiments, the recombinant proteins further contain a targeting peptide linked to the N-terminal end of the catalytic domains. In certain embodiments, the targeting peptide contains a stem domain. In certain embodiments, the stem domain is from an N-acetylglucosaminyltransferase I enzyme or an N-acetylglucosaminyltransferase II enzyme. In certain embodiments, the N-acetylglucosaminyltransferase I enzyme and the N-acetylglucosaminyltransferase II enzyme are human enzymes. In certain embodiments that may be combined with the preceding embodiments, the stem domain is from a protein selected from a mannosidase, a mannosyltransferase, a glycosyltransferase, a Type 2 Golgi protein, MNN2, MNN4, MNN6, MNN9, MNN10, MNS1, KRE2, VAN1, or OCH1. In certain embodiments, the protein is from an organism selected from *Acremonium, Aspergillus, Aureobasidium, Cryptococcus, Chrysosporium, Chrysosporium lucknowense, Filibasidium, Fusarium, Gibberella, Humicola, Magnaporthe, Mucor, Myceliophthora, Myrothecium, Neocallimastix, Neurospora, Paecilomyces, Penicillium, Piromyces, Schizophyllum, Talaromyces, Thermoascus, Thielavia, Tolypocladium*, or *Trichoderma*. In certain embodiments that may be combined with the preceding embodiments, the targeting peptide is a Kre2 targeting peptide. In certain embodiments, the targeting peptide contains a transmembrane domain. In certain embodiments that may be combined with the preceding embodiments, the targeting peptide further contains a transmembrane domain linked to the N-terminal end of the stem domain. In certain embodiments that may be combined with the preceding embodiments, the transmembrane domain is from an N-acetylglucosaminyltransferase I enzyme or an N-acetylglucosaminyltransferase II enzyme. In certain embodiments, the N-acetylglucosaminyltransferase I enzyme and the N-acetylglucosaminyltransferase II enzyme are human enzymes. In certain embodiments that may be combined with the preceding embodiments, the transmembrane domain is from a protein selected from a mannosidase, a mannosyltransferase, a glycosyltransferase, a Type 2 Golgi protein, MNN2, MNN4, MNN6, MNN9, MNN10, MNS1, KRE2, VAN1, or OCH1. In certain embodiments, the protein is from an organism selected from *Acremonium, Aspergillus, Aureobasidium, Cryptococcus, Chrysosporium, Chrysosporium lucknowense, Filibasidium, Fusarium, Gibberella, Humicola, Magnaporthe, Mucor, Myceliophthora, Myrothecium, Neocallimastix, Neurospora, Paecilomyces, Penicillium, Piromyces, Schizophyllum, Talaromyces, Thermoascus, Thielavia, Tolypocladium*, or *Trichoderma*. In certain embodiments, the targeting peptide contains a cytoplasmic domain. In certain embodiments that may be combined with the preceding embodiments, the targeting peptide further contains a cytoplasmic domain linked to the N-terminal end of the stem domain. In certain embodiments that may be combined with the preceding embodiments, the targeting peptide further contains a cytoplasmic domain linked to the N-terminal end of the transmembrane domain. In certain embodiments that may be combined with the preceding embodiments, the cytoplasmic domain is from an N-acetylglucosaminyltransferase I enzyme or an N-acetylglucosaminyltransferase II enzyme. In certain embodiments, the N-acetylglucosaminyltransferase I enzyme and the N-acetylglucosaminyltransferase II enzyme are human enzymes. In certain embodiments that may be combined with the preceding embodiments, the cytoplasmic domain is from a protein selected from a mannosidase, a mannosyltransferase, a glycosyltransferase, a Type 2 Golgi protein, MNN2, MNN4, MNN6, MNN9, MNN10, MNS1, KRE2, VAN1, or OCH1. In certain embodiments, the protein is from an organism selected from *Acremonium, Aspergillus, Aureobasidium, Cryptococcus, Chrysosporium, Chrysosporium lucknowense, Filibasidium, Fusarium, Gibberella, Humicola, Magnaporthe, Mucor, Myceliophthora, Myrothecium, Neocallimastix, Neurospora, Paecilomyces, Penicillium, Piromyces, Schizophyllum, Talaromyces, Thermoascus, Thielavia, Tolypocladium*, or *Trichoderma*.

Another aspect includes recombinant proteins containing a human N-acetylglucosaminyltransferase II catalytic domain and a human N-acetylglucosaminyltransferase I catalytic domain where the N-acetylglucosaminyltransferase II catalytic domain is located N-terminal to the N-acetylglucosaminyltransferase I catalytic domain, a spacer sequence containing sequence from a human N-acetylglucosaminyltransferase I stem domain located in between the catalytic domains, and a targeting peptide located N-terminal to the N-acetylglucosaminyltransferase II catalytic domain where the targeting peptide contains a cytoplasmic domain, a transmembrane domain, and a stem domain from human N-acetylglucosaminyltransferase II. Another aspect includes a recombinant protein containing a sequence that is at least 70%, at least 75%, at least 80%, at least 85%, at least 90%, at least 95%, at least 96%, at least 97%, at least 98%, at least 99%, or 100% identical to SEQ ID NO: 95.

Another aspect includes recombinant proteins containing N-acetylglucosaminyltransferase II catalytic domain and a N-acetylglucosaminyltransferase I catalytic domain, where the N-acetylglucosaminyltransferase II catalytic domain is located N-terminal to the N-acetylglucosaminyltransferase I catalytic domain; a spacer located in between the catalytic domains, where the spacer contains a sequence selected from SEQ ID NO: 118, SEQ ID NO: 120, SEQ ID NO: 122, and SEQ ID NO: 124; and a targeting peptide located N-terminal to the N-acetylglucosaminyltransferase II catalytic domain where the targeting peptide contains a cytoplasmic domain, a transmembrane domain, and a stem domain from human N-acetylglucosaminyltransferase II. In certain embodiments, the spacer contains a sequence that is selected from SEQ ID NO: 118, SEQ ID NO: 120, and SEQ ID NO: 124. In certain embodiments, the spacer contains the sequence of SEQ ID NO: 120 or SEQ ID NO: 124. In certain embodiments, the spacer contains the sequence of SEQ ID NO: 124.

Another aspect includes isolated polynucleotides encoding the recombinant protein of any of the preceding embodiments. Another aspect includes expression vectors containing the isolated polynucleotide of the preceding embodiment operably linked to a promoter. In certain embodiments, the promoter is a constitutive promoter. In certain embodiments, the promoter is an inducible promoter. In certain embodiments, the promoter is from a gene selected from gpdA, cbh1, *Aspergillus oryzae* TAKA amylase, *Rhizomucor miehei* aspartic proteinase, *Aspergillus niger* neutral alpha-amylase,

*Aspergillus niger* acid stable alpha-amylase, *Aspergillus niger* glucoamylase (glaA), *Aspergillus awamori* glaA, *Rhizomucor miehei* lipase, *Aspergillus oryzae* alkaline protease, *Aspergillus oryzae* triose phosphate isomerase, *Aspergillus nidulans* acetamidase, *Aspergillus oryzae* acetamidase, *Fusarium oxysporum* trypsin-like protease, fungal endo α-L-arabinase (abnA), fungal α-L-arabinofuranosidase A (abfA), fungal α-L-arabinofuranosidase B (abfB), fungal xylanase (xlnA), fungal phytase, fungal ATP-synthetase, fungal subunit 9 (oliC), fungal triose phosphate isomerase (tpi), fungal alcohol dehydrogenase (adhA), fungal α-amylase (amy), fungal amyloglucosidase (glaA), fungal acetamidase (amdS), fungal glyceraldehyde-3-phosphate dehydrogenase (gpd), yeast alcohol dehydrogenase, yeast alcohol oxidase, yeast lactase, yeast 3-phosphoglycerate kinase, yeast triosephosphate isomerase, bacterial α-amylase, bacterial Spo2, or SSO. Another aspect includes host cells containing the expression vector of any of the preceding embodiments.

Another aspect includes methods of producing the recombinant protein of any the preceding embodiments, including the steps of introducing an isolated polynucleotide that encodes the recombinant protein into a host cell, and culturing the host cell such that the recombinant protein is expressed. In certain embodiments, the methods further include a step of purifying the recombinant protein from the host cell. In certain embodiments that may be combined with the preceding embodiments, the host cell is a fungal cell. In certain embodiments, the fungal cell is selected from yeast or filamentous fungus.

Another aspect includes methods of producing a complex N-glycan including the steps of providing a host cell, where the host cell contains a polynucleotide encoding a fusion protein containing an N-acetylglucosaminyltransferase I catalytic domain and an N-acetylglucosaminyltransferase II catalytic domain, and culturing the host cell such that the fusion protein is expressed, where the fusion protein catalyzes the transfer of N-acetylglucosamine to a terminal Manα3 residue and N-acetylglucosamine to a terminal Manα6 residue of an acceptor glycan to produce a complex N-glycan. In certain embodiments, the complex N-glycan is attached to a molecule selected from an amino acid, a peptide, or a polypeptide. In certain embodiments, the molecule is a heterologous polypeptide. In certain embodiments that may be combined with the preceding embodiments, the acceptor glycan is Man3. In certain embodiments that may be combined with the preceding embodiments, the complex N-glycan is GlcNAcβ2Manα3(GlcNAcβ2Manα6)Manβ4GlcNAcβ4GlcNAc. In certain embodiments that may be combined with the preceding embodiments, the host cell is a eukaryotic cell. In certain embodiments that may be combined with the preceding embodiments, the host cell is a fungal cell. In certain embodiments, the fungal cell is a yeast cell selected from *S. cerevisiae*, *K lactis*, *P. pastoris*, *H. polymorpha*, *C. albicans*, *Schizosaccharomyces*, or *Yarrowia*. In certain embodiments that may be combined with the preceding embodiments, the fungal cell is a filamentous fungal cell selected from *Trichoderma* sp., *Acremonium*, *Aspergillus*, *Aureobasidium*, *Cryptococcus*, *Chrysosporium*, *Chrysosporium lucknowense*, *Filibasidium*, *Fusarium*, *Gibberella*, *Magnaporthe*, *Mucor*, *Myceliophthora*, *Myrothecium*, *Neocallimastix*, *Neurospora*, *Paecilomyces*, *Penicillium*, *Piromyces*, *Schizophyllum*, *Talaromyces*, *Thermoascus*, *Thielavia*, or *Tolypocladium*. In certain embodiments that may be combined with the preceding embodiments, the host cell further contains a polynucleotide encoding a UDP-GlcNAc transporter. In certain embodiments that may be combined with the preceding embodiments, the host cell has a reduced level of activity of a dolichyl-P-Man:Man(5)GlcNAc(2)-PP-dolichyl mannosyltransferase compared to the level of activity in a wild-type host cell. In certain embodiments, the host cell has a reduced level of expression of an alg3 gene compared to the level of expression in a wild-type host cell. In certain embodiments, the alg3 gene is deleted from the host cell. In certain embodiments that may be combined with the preceding embodiments, the host cell has a reduced level of activity of an α-1,6-mannosyltransferase compared to the level of activity in a wild-type host cell. In certain embodiments, the host cell has a reduced level of expression of an och1 gene compared to the level of expression in a wild-type host cell. In certain embodiments, the och1 gene is deleted from the host cell. In certain embodiments that may be combined with the preceding embodiments, the host cell further contains a polynucleotide encoding an α-1,2-mannosidase. In certain embodiments that may be combined with the preceding embodiments, the host cell further contains a polynucleotide encoding a β-1,4-galactosyltransferase. In certain embodiments that may be combined with the preceding embodiments, the host cell further contains a polynucleotide encoding a sialyltransferase. In certain embodiments that may be combined with the preceding embodiments, the host cell is a *Trichoderma* cell that has a reduced level of activity of a dolichyl-P-Man:Man(5)GlcNAc(2)-PP-dolichyl mannosyltransferase compared to the level of activity in a wild-type *Trichoderma* cell. In certain embodiments that may be combined with the preceding embodiments, the host cell is a yeast or fungal cell that has a reduced level of activity of a dolichyl-P-Man:Man(5)GlcNAc(2)-PP-dolichyl mannosyltransferase and a reduced level of activity of an alpha-1,6-mannosyltransferase compared to the levels of activity in a wild-type yeast cell and further contains a polynucleotide encoding an α-1,2-mannosidase.

Another aspect includes methods of producing a complex N-glycan including the steps of providing a *Trichoderma* host cell, where the host cell has a reduced level of expression of an alg3 gene compared to the level of expression in a wild-type host cell and contains a first polynucleotide encoding an N-acetylglucosaminyltransferase I catalytic domain and a second polynucleotide encoding an N-acetylglucosaminyltransferase II catalytic domain, and culturing the host cell to produce a complex N-glycan.

Another aspect includes methods of producing a complex N-glycan including the steps of incubating a fusion protein containing an N-acetylglucosaminyltransferase I catalytic domain and an N-acetylglucosaminyltransferase II catalytic domain, an acceptor glycan, and an N-acetylglucosamine donor together in a buffer, where the fusion protein catalyzes the transfer of N-acetylglucosamine to a terminal Manα3 residue and N-acetylglucosamine to a terminal Manα6 residue of an acceptor glycan to produce a complex N-glycan. In certain embodiments, the acceptor glycan is attached to a molecule selected from an amino acid, a peptide, or a polypeptide. In certain embodiments, the molecule is a heterologous polypeptide. In certain embodiments, the acceptor glycan is Man3. In certain embodiments that may be combined with the preceding embodiments, the N-acetylglucosamine donor is a UDP-GlcNAc transporter.

Another aspect includes filamentous fungal cells containing a mutation of alg3 and Man3GlcNAc2, where the Man3GlcNAc2 includes at least 50%, at least 60%, at least 70%, at least 80%, at least 90%, or 100% (mol %) of neutral N-glycans secreted by the cells. The neutral N-glycans may be attached to a molecule selected from the group consisting of an amino acid, a peptide, and a polypeptide. In certain embodiments, the mutation of alg3 is a deletion of alga. In certain embodiments that may be combined with the preceding embodiments, the cell is a *Trichoderma reesei* cell. In certain embodiments that may be combined with the preceding embodiments, the filamentous fungal cell further contains a first polynucleotide encoding an N-acetylglucosaminyl-transferase I catalytic domain and a second polynucleotide encoding an N-acetylglucosaminyltransferase II catalytic domain. In certain embodiments that may be combined with the preceding embodiments, the filamentous fungal cell further contains a polynucleotide encoding a fusion protein containing an N-acetylglucosaminyltransferase I catalytic domain and an N-acetylglucosaminyltransferase II catalytic domain.

Another aspect includes methods of producing a Man3GlcNAc2 glycan in a host cell including the steps of providing a host cell with a reduced level of activity of a mannosyltransferase compared to the level of activity in a wild-type host cell and culturing the host cell to produce a Man3GlcNAc2 glycan, where the Man3GlcNAc2 glycan includes at least 50%, at least 60%, at least 70%, at least 80%, at least 90%, or 100% (mol %) of the neutral N-glycans secreted by the host cell. The neutral N-glycans may be attached to a molecule selected from an amino acid, a peptide, and a polypeptide. In certain embodiments, the Man3GlcNAc2 glycan is attached to a heterologous polypeptide. In certain embodiments that may be combined with the preceding embodiments, the mannosyltransferase is a dolichyl-P-Man:Man(5)GlcNAc(2)-PP-dolichyl mannosyltransferase. In certain embodiments that may be combined with the preceding embodiments, the host cell has a reduced level of expression of an alg3 gene compared to the level of expression in a wild-type host cell. In certain embodiments, the alg3 gene is deleted from the host cell. In certain embodiments that may be combined with the preceding embodiments, the host cell is a *Trichoderma* cell. In certain embodiments that may be combined with the preceding embodiments, the level of activity of alpha-1,6-mannosyltransferase in the host cell is reduced compared to the level of activity in a wild-type host cell. In certain embodiments that may be combined with the preceding embodiments, the host cell contains an endogenous polynucleotide encoding an α-1,2-mannosidase.

Another aspect includes a filamentous fungal cell having a reduced level of expression of an alg3 gene compared to the level of expression in a wild-type filamentous fungal cell, where the filamentous fungal cell contains a recombinant protein of any of the preceding embodiments. In certain embodiments, the alg3 gene contains a mutation. Preferably, the recombinant protein has N-acetylglucosaminyltransferase activity, where the recombinant protein catalyzes the transfer of N-acetylglucosamine to a terminal Manα3 residue and catalyzes the transfer of N-acetylglucosamine to a terminal Manα6 residue of an acceptor glycan, and where the recombinant protein is a fusion protein containing an N-acetylglucosaminyltransferase I catalytic domain and an N-acetylglucosaminyltransferase II catalytic domain. In certain embodiments, the mutation of the alg3 gene is a deletion of the alg3 gene. In certain embodiments that may be combined with the preceding embodiments, the fusion protein is encoded by a polynucleotide operably linked to a promoter. In certain embodiments, the promoter is an inducible promoter. In certain embodiments, the inducible promoter is the cbh1 promoter. In certain embodiments that may be combined with the preceding embodiments, the filamentous fungal cell further contains a polynucleotide encoding a UDP-GlcNAc transporter. In certain embodiments that may be combined with the preceding embodiments, the filamentous fungal has a reduced level of activity of an α-1,6-mannosyltransferase compared to the level of activity in a wild-type filamentous fungal cell. In certain embodiments, the filamentous fungal has a reduced level of expression of an och1 gene compared to the level of expression in a wild-type filamentous fungal cell. In certain embodiments that may be combined with the preceding embodiments, the filamentous fungal cell further contains a polynucleotide encoding an α-1,2-mannosidase. In certain embodiments that may be combined with the preceding embodiments, the filamentous fungal cell further contains a polynucleotide encoding a β-1,4-galactosyltransferase. In certain embodiments that may be combined with the preceding embodiments, the filamentous fungal cell further contains a polynucleotide encoding a sialyltransferase. In certain embodiments that may be combined with the preceding embodiments, the filamentous fungal cell is selected from *Trichoderma* sp., *Acremonium*, *Aspergillus*, *Aureobasidium*, *Cryptococcus*, *Chrysosporium*, *Chrysosporium lucknowense*, *Filibasidium*, *Fusarium*, *Gibberella*, *Magnaporthe*, *Mucor*, *Myceliophthora*, *Myrothecium*, *Neocallimastix*, *Neurospora*, *Paecilomyces*, *Penicillium*, *Piromyces*, *Schizophyllum*, *Talaromyces*, *Thermoascus*, *Thielavia*, and *Tolypocladium*.

DESCRIPTION OF THE FIGURES

FIG. 2 shows fragmentation analysis of monophosphorylated Man7Gn2. Only one example structure of monophosphorylated Man7Gn2 is shown.

FIG. 42 shows a multiple amino acid sequence alignment of *T. reesei* ALG3 and ALG3 homologs.

DETAILED DESCRIPTION

Figure 1:
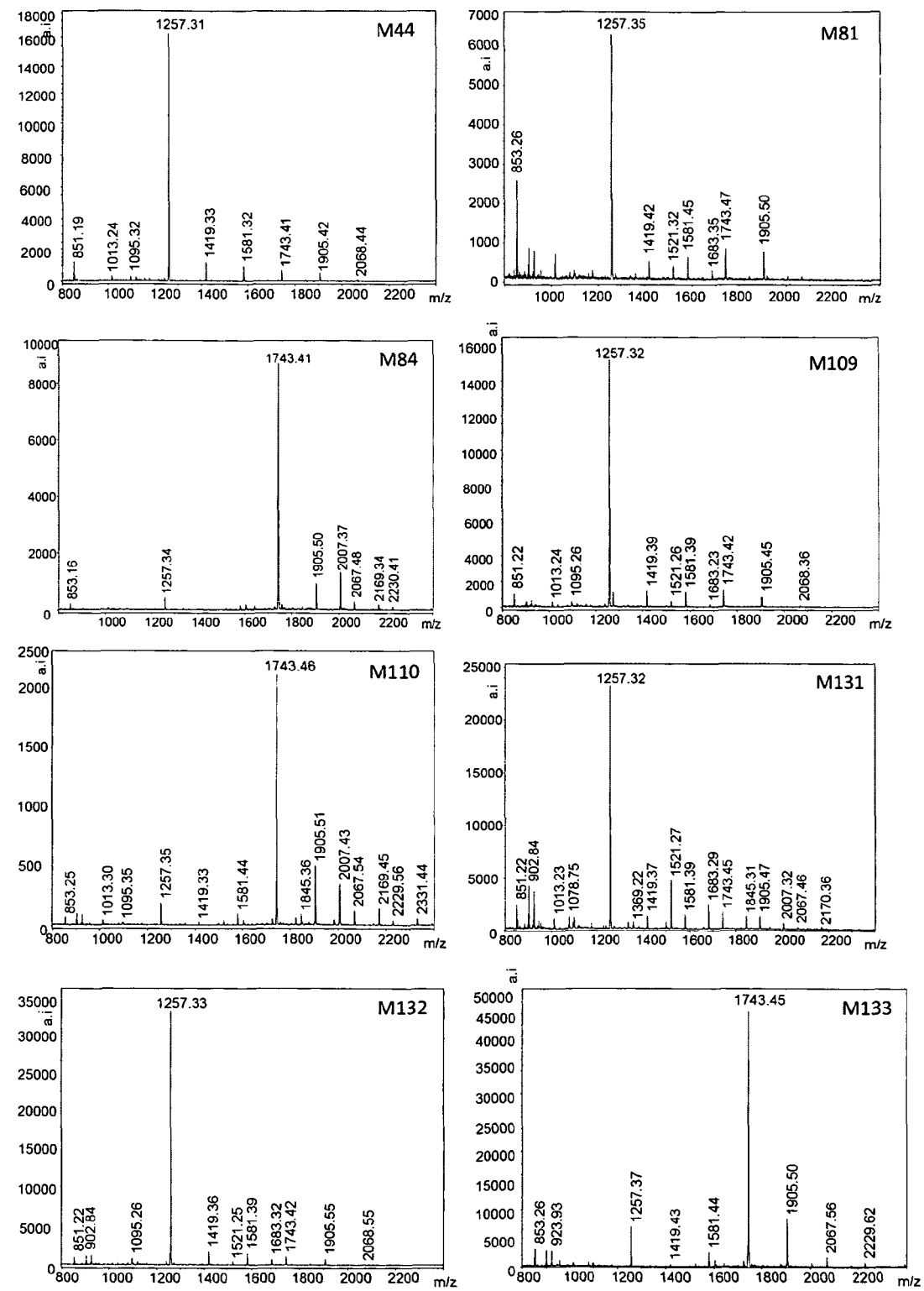
FIG. 1 shows mass spectrometric neutral N-glycan profiles of average glycosylation on *T. reesei* strains M44, M81, M84, M109, M110, M131, M132, M133, M134, and M124.

The present invention relates to recombinant proteins having N-acetylglucosaminyltransferase activity where the recombinant protein catalyzes the transfer of N-acetylglucosamine (GlcNAc) to a terminal Manα3 residue and catalyzes the transfer of N-acetylglucosamine to a terminal Manα6 residue of an acceptor glycan, and where the recombinant protein contains catalytic domains from at least two different enzymes.

In some embodiments, the recombinant proteins of the invention include two catalytic domains, where one catalytic domain has N-acetylglucosaminyltransferase I (GnTI) activity (e.g., reacts with a terminal Manα3 residue), and the other catalytic domain has N-acetylglucosaminyltransferase II (GnTII) activity (e.g., reacts with a terminal Manα6 residue).

In some embodiments, the recombinant proteins of the present invention catalyze reactions that occur essentially sequentially. For example, the recombinant proteins of the present invention may catalyze the transfer of GlcNAc to a terminal Manα3-residue, first, and then catalyze the transfer of GlcNAc to a terminal Manα6-residue of an acceptor glycan. In one embodiment, the essentially sequential reactions are at least 10 fold, at least 20 fold, at least 30 fold, at least 40 fold, at least 50 fold, at least 60 fold, at least 70 fold, at least 80 fold, at least 90 fold, or at least 100 fold, more effective than the two reactions in the reversed order. In certain embodiments, a sequential reaction means that essentially or absolutely no GlcNAc can be transferred to the terminal Manα6-residue if GlcNAc has not yet been transferred to the terminal Manα3-residue. In a specific embodiment, the acceptor glycan contains a GlcNAcβ2Manα3-branch.

In some embodiments, the recombinant proteins react specifically with both Manα3 and Manα6 residues, optionally in branched acceptor glycans but not substantially or absolutely with other Manα-structures, e.g. Manα-monosaccharide conjugates, with Manαbenzyl and/or ManαSer/Thr-peptide. The non-substantial reactivity is preferably below 10%, below 8%, below 6%, below 4%, below 2%, below 1%, or below 0.1% of the Vmax with 0.1 mM acceptor glycan concentrations of reactions with terminal Manα3 and Manα6 residues. In a specific embodiment, the recombinant proteins have substantially similar reactivities with the terminal Manα3 (preferably as GnTI reaction) and the terminal Manα6 residue (preferably as GnTII reaction) of the acceptor glycan. Preferably neither catalytic activity has more than a 10-fold, 5-fold, 3-fold or 2-fold difference in reaction effectiveness compared to the other catalytic activity under the same conditions.

In a specific embodiment, the transfer of GlcNAc to the terminal Manα3 and Manα6 cause a conversion of at least 10%, at least 25%, at least 50%, at least 70%, at least 90%, or at least 95% of Man3 glycan to a glycan with two terminal GlcNAcs. The effectiveness of the reaction can be measured by in vitro or in vivo assays as described in the examples disclosed herein. The effectiveness of the GlcNAc transfer reactions can be measured essentially as described in the Examples or as maximal reaction rate Vmax with 0.1 mM acceptor concentrations and saturating donor concentrations. In a specific embodiment, the effectiveness of the reaction is measured with a Man3 acceptor glycan attached to an amino acid, a peptide, or a polypeptide.

The present disclosure further relates to methods of producing a complex N-glycan, including the steps of providing a host cell, where the host cell contains a nucleic acid encoding a fusion protein containing an N-acetylglucosaminyl-transferase I catalytic domain and an N-acetylglucosaminyl-transferase II catalytic domain, and culturing the host cell such that the fusion protein is expressed, where the fusion protein catalyzes the transfer of N-acetylglucosamine to a terminal Manα3 residue and N-acetylglucosamine to a terminal Manα6 residue of an acceptor glycan to produce a complex N-glycan.

The present invention also relates to a filamentous fungal cell having a reduced level of expression of an alg3 gene compared to the level of expression in a wild-type filamentous fungal cell, where the filamentous fungal cell contains a recombinant protein of the invention.

Definitions

As used herein, "recombinant protein" refers to any protein that has been produced from a recombinant nucleic acid. "Recombinant nucleic acid" as used herein refers to a polymer of nucleic acids where at least one of the following is true: (a) the sequence of nucleic acids is foreign to (i.e., not naturally found in) a given host cell; (b) the sequence may be naturally found in a given host cell, but is present in an unnatural (e.g., greater than expected) amount or expressed at a level that is more or less than the natural level of expression; or (c) the sequence of nucleic acids includes two or more sub-sequences that are not found in the same relationship to each other in nature. For example, regarding instance (c), a recombinant nucleic acid sequence will have two or more sequences from unrelated genes arranged to make a new functional nucleic acid. In another example, a recombinant nucleic acid sequence will contain a promoter sequence and a gene-encoding sequence that are not naturally found adjacent to one another.

As used herein, "N-acetylglucosaminyltransferase activity" refers to the activity of an enzyme that transfers an N-acetylglucosaminyl residue (GlcNAc) to an acceptor glycan. Typically, enzymes having this activity are N-acetylglucosaminyltransferases (GlcNAc transferases). In certain embodiments, GlcNAc transferases are eukaryotic. In certain embodiments, the GlcNAc transferases are mammalian enzymes forming a β3-linkage from the 1-position of a GlcNAc-residue to the terminal mannose residues. In certain embodiments, the GlcNAc transferases are β2-N-acetylglucosaminyltransferases transferring β2-linked GlcNAc-residue(s) to the 2-position terminal mannose residues of glycans, in particular to an N-linked glycan. In certain embodiments, the β2-GlcNAc transferases are enzymes having GnTI activity and GnTII activity. GnTI activity transfers a GlcNAc residue to a Manα3 branch. The Manα3 branch may be a Manα3(R-Manα6)Manβ-branch of on N-linked glycan core structure, such as Man3GlcNAc2 or Man3 or Man5GlcNAc2 or Man5. GnTI enzymes may be mammalian enzymes, plant enzymes, or lower eukaryotic enzymes. GnTII activity transfers a GlcNAc residue to a Manα6-branch such as a Manα6(GlcNAcβ2GlcNAcβ2Manα3)Manβ-branch of an N-linked glycan core structure. An example of such a Manα6-branch is GlcNAc1Man3GlcNAc2.

As used herein, "N-acetylglucosamine" refers to an N-acetylglucosamine residue (GlcNAc). GlcNAc may be part of a glycan structure. The amine group is on position 2, has a D-configuration, and has a pyranose structure as a residue. It may be alternatively named 2-acetamido-2-deoxy-D-glucopyranose (D-GlcpNAc). GlcNAc may also be a free reducing monosaccharide (i.e., not part of glycan).

As used herein, "Man" refers to a mannose residue. A "terminal Manα3" or a "terminal Manα6" refers to a mannose that is not substituted to the non-reducing end terminal residue by another monosaccharide residue or residues.

As used herein, "glycan" refers to an oligosaccharide chain that can be linked to a carrier such as an amino acid, peptide, polypeptide, lipid or a reducing end conjugate. In certain embodiments, the invention relates to N-linked glycans conjugated to a polypeptide N-glycosylation site such as -Asn-Xxx-Ser/Thr- by N-linkage to side-chain amide nitrogen of asparagine residue (Asn), where Xxx is any amino acid residue except Pro. The invention may further relate to glycans as part of dolichol-phospho-oligosaccharide (Dol-P-P-OS) precursor lipid structures, which are precursors of N-linked glycans in the endoplasmic reticulum of eukaryotic cells. The precursor oligosaccharides are linked from their reducing end to two phosphate residues on the dolichol lipid. For example, α3-mannosyltransferase Alg3 modifies the Dol-P-P-oligosaccharide precursor of N-glycans. Generally, the glycan structures described herein are terminal glycan structures, where the non-reducing residues are not modified by other monosaccharide residue or residues.

As used herein, "glycoprotein" refers to a peptide or polypeptide attached to a glycan. The glycan may be attached to the peptide or polypeptide in a cotranslational or posttranslational modification.

As used herein, "glycolipid" refers to a lipid attached to a glycan and includes glyceroglycolipids, glycosphingolipids, and glycosylphosphatidylinositols.

As used throughout the present disclosure, glycolipid and carbohydrate nomenclature is essentially according to recommendations by the IUPAC-IUB Commission on Biochemical Nomenclature (e.g. Carbohydrate Res. 1998, 312, 167; Carbohydrate Res. 1997, 297, 1; Eur. J. Biochem. 1998, 257, 29). It is assumed that Gal (galactose), Glc (glucose), GlcNAc (N-acetylglucosamine), GalNAc (N-acetylgalactosamine), Man (mannose), and Neu5Ac are of the D-configuration, Fuc of the L-configuration, and all the monosaccharide units in the pyranose form (D-Galp, D-Glcp, D-GlcpNAc, D-Galp-NAc, D-Manp, L-Fucp, D-Neup5Ac). The amine group is as defined for natural galactose and glucosamines on the 2-position of GalNAc or GlcNAc. Glycosidic linkages are shown partly in shorter and partly in longer nomenclature, the linkages of the sialic acid SA/Neu5X-residues α3 and α6 mean the same as α2-3 and α2-6, respectively, and for hexose monosaccharide residues α1-3, α1-6, β1-2, β1-3, β1-4, and β1-6 can be shortened as α3, α6, β2, β3, β4, and β6, respectively. Lactosamine refers to type II N-acetyllactosamine, Galβ4GlcNAc, and/or type I N-acetyllactosamine. Galβ3GlcNAc and sialic acid (SA) refer to N-acetylneuraminic acid (Neu5Ac), N-glycolylneuraminic acid (Neu5Gc), or any other natural sialic acid including derivatives of Neu5X. Sialic acid is referred to as NeuNX or Neu5X, where preferably X is Ac or Gc. Occasionally Neu5Ac/Gc/X may be referred to as NeuNAc/NeuNGc/NeuNX.

Recombinant Proteins of the Invention

The invention herein relates to recombinant proteins having N-acetylglucosaminyltransferase activity, where the recombinant proteins catalyze the transfer of N-acetylglucosamine to a terminal Manα3 residue and catalyze the transfer of N-acetylglucosamine to a terminal Manα6 residue of an acceptor glycan. Recombinant proteins of the invention may include, without limitation, full length proteins having N-acetylglucosaminyltransferase activity, fragments of proteins having N-acetylglucosaminyltransferase activity, catalytic domains having N-acetylglucosaminyltransferase activity, and fusion proteins having N-acetylglucosaminyltransferase activity. A single recombinant protein of the invention has the capability to catalyze both transfers of N-acetylglucosamines. The transfer of N-acetylglucosamine to a terminal Manα3 residue may occur before or after the transfer of N-acetylglucosamine to a terminal Manα6 residue. Alternatively, the transfers may occur simultaneously.

The acceptor glycan may be attached to a molecule such as an amino acid, a peptide, or a polypeptide. In certain embodiments, the amino acid is an asparagine residue. The asparagine residue may be in aminoglycosidic linkage from the side-chain amide (a biologic mammalian polypeptide N-glycan linkage structure) and may be part of a peptide chain such as a dipeptide, an oligopeptide, or a polypeptide. The glycan may be a reducing end derivative such as an N-, O-, or C-linked, preferably glycosidic, derivative of the reducing GlcNAc or Man, such as a spacer or terminal organic residue with a certain glycan linked structure selected from the group of an amino acid, alkyl, heteroalkyl, acyl, alkyloxy, aryl, arylalkyl, or heteroarylalkyl. The spacer may be further linked to a polyvalent carrier or a solid phase. In certain embodiments, alkyl-containing structures include methyl, ethyl, propyl, and C4-C26 alkyls, lipids such as glycerolipids, phospholipids, dolichol-phospholipids and ceramides and derivatives. The reducing end may also be derivatized by reductive amination to a secondary amine linkage or a derivative structure. Certain carriers include biopoly- or oligomers such as (poly)peptides, poly(saccharides) such as dextran, cellulose, amylose, or glycosaminoglycans, and other organic polymers or oligomers such as plastics including polyethylene, polypropylene, polyamides (e.g., nylon or polystyrene), polyacrylamide, and polylactic acids, dendrimers such as PAMAM, Starburst or Starfish dendrimers, or polylysine, and polyalkylglycols such as polyethylene glycol (PEG). Solid phases may include microtiter wells, silica particles, glass, metal (including steel, gold, and silver), polymer beads such as polystyrene or resin beads, polylactic acid beads, polysaccharide beads or organic spacers containing magnetic beads.

In certain embodiments, the acceptor glycan is attached to a heterologous polypeptide. As used herein, a "peptide" and a "polypeptide" are amino acid sequences including a plurality of consecutive polymerized amino acid residues. For purpose of this invention, typically, peptides are those molecules including up to 50 amino acid residues, and polypeptides include more than 50 amino acid residues. The peptide or polypeptide may include modified amino acid residues, naturally occurring amino acid residues not encoded by a codon, and non-naturally occurring amino acid residues. As used herein, "protein" may refer to a peptide or a polypeptide of any size. The term "heterologous polypeptide" refers to a polypeptide that is not naturally found in a given host cell or is not endogenous to a given host cell. In certain embodiments, the heterologous polypeptide is a therapeutic protein. Therapeutic proteins, for example, may include monoclonal antibodies, erythropoietins, interferons, growth hormones, enzymes, or blood-clotting factors. For example, the acceptor glycan may be attached to a therapeutic protein such as rituximab.

Acceptor Glycans

In certain embodiments, the structure of the acceptor glycan has the following formula, $[R_1]_y Man\alpha3([R_2]_z Man\alpha6)Man\{\beta4GlcNAc(Fuc\alpha x)_n[\beta4GlcNAc]_m\}_q$, where q, y, z, n and m are 0 or 1; x is linkage position 3 or 6, of optional fucose residue; R1 is GlcNAc, preferably GlcNAcβ2; and R2 is a branched structure Manα3(Manα6), with the provision that when z is 1, then y is 0, and when z is 0, then y is 0 or 1. ( ) defines a branch in the regular N-glycan core structure, either present or absent. [ ] and { } define a part of the glycan structure either present or absent in a linear sequence. When z is 0 and y is 0 then the structure is a Man3 glycan, and when z is 0 and y is 1, the structure is a GlcNAcMan3 glycan. When y is 0 and z is 1, the glycan is a Man5 glycan. The acceptor glycan may be beta-glycosidically linked to an Asn residue, preferably from the reducing end GlcNAc. In one embodiment, the acceptor glycan is a polypeptide linked N-glycan, where m and q are 1, and the acceptor structure contains a derivative of $[R_1]_y Man\alpha3([R_2]_z Man\alpha6)Man\beta4GlcNAc(Fuc\alpha x)_n\beta4GlcNAc$. Optional derivatives include substitutions by monosaccharide residues such as GlcNAc or xylose.

The acceptor glycan may be Man3, GlcNAcMan3, or Man5. In certain embodiments, the acceptor glycan is Man3 or GlcNAcMan3. Man3 is a trimannosyl glycan comprising at least one of Manα3 or Manα6 residues and is preferably a branched oligosaccharide, such as Manα3(Manα6)Man. Other certain Man3 oligosaccharides are Manα3(Manα6)Manβ, Manα3(Manα6)Manβ4GlcNAc, and polypeptide-linked Manα3(Manα6)Manβ4GlcNAcβ4GlcNAc. In addition, depending on the host cell, the glycan can contain Fuc, Xyl or GlcNAc in Manβ and/or GlcNAc residues, such as Manα3(Manα6)Manβ4GlcNAcβ4(Fucαx)$_n$GlcNAc, where x is 3 or 6 and n is 0 or 1, also described by a monosaccharide composition formula indicating the terminal mannose structure and reducing end composition as Man3GlcNAc2 (n is 0) and Man3GlcNAc2Fuc (n is 1). In certain embodiments, especially those with a polypeptide-linked structure, the Man3 structure is a Manα3(Manα6)Manβ4GlcNAcβ4(Fucα6)$_n$GlcNAc. In certain embodiments, the polypeptide-linked GlcNAcMan3 structure is GlcNAcβ2Manα3(Manα6)Manβ4GlcNAcβ4(Fucα6)$_n$GlcNAc, also described by a monosaccharide composition formula GlcNAcMan3GlcNAc2 (n is 0) and GlcNAcMan3GlcNAc2Fuc (n is 1). In certain embodiments, the polypeptide-linked Man5 structure is Manα3{Manα3(Manα6)Manα6}Manβ4GlcNAcβ4(Fucα6)$_n$GlcNAc, where { } and ( ) indicate a branch and n is 0 or 1, also described by a monosaccharide composition formula Man5GlcNAc2 (n is 0) and Man5GlcNAc2Fuc (n is 1).

Accordingly, the certain Man3 glycans have structures according to the following formula, Manα3(Manα6)Manβ4GlcNAc(Fucαx)$_n$β4GlcNAc, where n is 0 or 1, indicating presence or absence of part of the molecule, where x is 3 or 6, and where ( ) defines a branch in the structure. In embodiments of the invention where the acceptor glycan is Man3, the recombinant protein catalyzes the transfer of N-acetylglucosamine to the terminal Manα3 and Manα6 of Man3, thus resulting in GlcNAc2Man3, GlcNAcβ2Manα3(GlcNAcβ2Manα6)Man134GlcNAcβ4(Fucαx)$_n$GlcNAc, where n is 0 or 1, also described by a monosaccharide composition formula GlcNAc2Man3GlcNAc2 (n is 0) and GlcNAc2Man3GlcNAc2Fuc (n is 1).

In embodiments of the invention where the acceptor glycan is Man5, the recombinant protein catalyzes the transfer of N-acetylglucosamine to the terminal Manα3 of Man5. After 2 mannoses have been removed from GlcNAcMan5 (for example, by mannosidase II) to form GlcNAcMan3, the recombinant protein catalyzes the transfer of N-acetylglucosamine to the terminal Manα6, thus resulting in GlcNAc2Man3 (which has the structure GlcNAcβ2Manα3(GlcNAcβ2GlcNAcβ2Manα6)Manβ4GlcNAcβ4(Fucαx)$_n$GlcNAc, where n is 0 or 1, also referred to as G0 if attached to an antibody).

Fusion Proteins Containing N-acetylglucosaminyltransferase Catalytic Domains

In certain embodiments, the recombinant proteins of the invention are fusion proteins containing an N-acetylglucosaminyltransferase I catalytic domain and an N-acetylglucosaminyltransferase II catalytic domain. The term "fusion protein" refers to any protein or polypeptide containing a protein or polypeptide linked to heterologous amino acids.

N-acetylglucosaminyltransferase I (GlcNAc-TI; GnTI; EC 2.4.1.101) catalyzes the reaction UDP-N-acetyl-D-glucosamine+3-(alpha-D-mannosyl)-beta-D-mannosyl-R <=>UDP+3-(2-(N-acetyl-beta-D-glucosaminyl)-alpha-D-mannosyl)-beta-D-mannosyl-R, where R represents the remainder of the N-linked oligosaccharide in the glycan acceptor. An N-acetylglucosaminyltransferase I catalytic domain is any portion of an N-acetylglucosaminyltransferase I enzyme that is capable of catalyzing this reaction. Amino acid sequences for N-acetylglucosaminyltransferase I enzymes from various organisms are listed in SEQ ID NOs: 1-19. Additional GnTI enzymes are listed in the CAZy database in the glycosyltransferase family 13 (cazy.org/GT13_all). Enzymatically characterized species includes A. thaliana AAR78757.1 (U.S. Pat. No. 6,653,459), C. elegans AAD03023.1 (Chen S. et al J. Biol. Chem. 1999; 274(1):288-97), D. melanogaster AAF57454.1 (Sarkar & Schachter Biol. Chem. 2001 February; 382(2):209-17); C. griseus AAC52872.1 (Puthalakath H. et al J. Biol. Chem. 1996 271 (44):27818-22); H. sapiens AAA52563.1 (Kumar R. et al Proc Natl Acad Sci USA. 1990 December; 87(24):9948-52); M. auratus AAD04130.1 (Opat As et al Biochem J. 1998 Dec. 15; 336 (Pt 3):593-8), (including an example of deactivating mutant), Rabbit, O. cuniculus AAA31493.1 (Sarkar M et al. Proc Natl Acad Sci USA. 1991 Jan. 1; 88(1):234-8). Additional examples of characterized active enzymes can be found at cazy.org/GT13_characterized. The 3D structure of the catalytic domain of rabbit GnTI was defined by X-ray crystallography in Unligil U M et al. EMBO J. 2000 Oct. 16; 19(20):5269-80. The Protein Data Bank (PDB) structures for GnTI are 1FO8, 1FO9, 1FOA, 2AM3, 2AM4, 2AM5, and 2APC. In certain embodiments, the N-acetylglucosaminyltransferase I catalytic domain is from the human N-acetylglucosaminyltransferase I enzyme (SEQ ID NO: 1), or variants thereof. In certain embodiments, the N-acetylglucosaminyltransferase I catalytic domain contains a sequence that is at least 70%, at least 75%, at least 80%, at least 85%, at least 90%, at least 95%, at least 96%, at least 97%, at least 98%, at least 99%, or 100% identical to amino acid residues 84-445 of SEQ ID NO: 1. In some embodiments, a shorter sequence can be used as a catalytic domain (e.g. amino acid residues 105-445 of the human enzyme or amino acid residues 107-447 of the rabbit enzyme; Sarkar et al. (1998) Glycoconjugate J 15:193-197). Additional sequences that can be used as the GnTI catalytic domain include amino acid residues from about amino acid 30 to 445 of the human enzyme or any C-terminal stem domain starting between amino acid residue 30 to 105 and continuing to about amino acid 445 of the human enzyme, or corresponding homologous sequence of another GnTI or a catalytically active variant or mutant thereof. The catalytic domain may include N-terminal parts of the enzyme such as all or part of the stem domain, the transmembrane domain, or the cytoplasmic domain.

As used herein, "cytoplasmic" is used to refer to a part of a protein that interacts with the cytoplasm of a cell.

N-acetylglucosaminyltransferase II (GlcNAc-TII; GnTII; EC 2.4.1.143) catalyzes the reaction UDP-N-acetyl-D-glucosamine+6-(alpha-D-mannosyl)-beta-D-mannosyl-R <=>UDP+6-(2-(N-acetyl-beta-D-glucosaminyl)-alpha-D-mannosyl)-beta-D-mannosyl-R, where R represents the remainder of the N-linked oligosaccharide in the glycan acceptor. An N-acetylglucosaminyltransferase II catalytic domain is any portion of an N-acetylglucosaminyltransferase II enzyme that is capable of catalyzing this reaction. Amino acid sequences for N-acetylglucosaminyltransferase II enzymes from various organisms are listed in SEQ ID NOs: 20-33. In certain embodiments, the N-acetylglucosaminyltransferase II catalytic domain is from the human N-acetylglucosaminyltransferase II enzyme (SEQ ID NO: 20). Additional GnTII species are listed in the CAZy database in the glycosyltransferase family 16 (cazy.org/GT16_all). Enzymatically characterized species include GnTII of C. elegans, D. melanogaster, Homo sapiens, Rattus norvegigus, Sus scrofa (cazy.org/GT16_characterized). In certain embodiments, the N-acetylglucosaminyltransferase II catalytic domain contains a sequence that is at least 70%, at least 75%, at least 80%, at least 85%, at least 90%, at least 95%, at least 96%, at least 97%, at least 98%, at least 99%, or 100% identical to amino acid residues from about 30 to about 447 of SEQ ID NO: 21. The catalytic domain may include N-terminal parts of the enzyme such as all or part of the stem domain, the transmembrane domain, or the cytoplasmic domain.

In certain embodiments, the N-acetylglucosaminyltransferase I catalytic domain is N-terminal to the N-acetylglucosaminyltransferase II catalytic domain. In other embodiments, the N-acetylglucosaminyltransferase II catalytic domain is N-terminal to the N-acetylglucosaminyltransferase I catalytic domain. The term "N-terminal" refers to the positioning of a set of amino acid residues closer to the end of a polypeptide that is terminated by an amino acid with a free amine group (—NH$_2$) compared to a reference set of amino acid residues.

Spacers

In certain embodiments of the invention, the recombinant protein contains a spacer in between the N-acetylglucosaminyltransferase I catalytic domain and the N-acetylglucosaminyltransferase II catalytic domain. The term "spacer" refers to any number of consecutive amino acids of any sequence separating the N-acetylglucosaminyltransferase I catalytic domain and the N-acetylglucosaminyltransferase II catalytic domain such that the spacer has no effect on the enzymatic function of the catalytic domains. Typically, the spacer is at least 5, at least 10, at least 15, at least 20, at least 30, at least 40, or at least 50 amino acids in length. In certain embodiments, the spacer contains sequence from a stem domain. "Stem domain" refers to a protein domain, or a fragment thereof, which is located adjacent to the transmembrane domain of a native enzyme, such as a glycosyltransferase or a glycosyl hydrolase, and optionally targets the enzyme to or assists in retention of the enzyme in the ER/Golgi. Stem domains generally start with the first amino acid following the hydrophobic transmembrane domain and end at the catalytic domain. Exemplary stem domains include, but are not limited to, the stem domain of human GnTI, amino acid residues from about 30 to about 83 or from about 30 to about 105 for the human GnTII, or amino acid residues from about 26 to about 106 or from about 26 to about 83 for the *T. reesei* KRE2. In certain embodiments where the spacer contains sequence from a stem domain, the spacer includes amino acids 30-83 of the human GnTI sequence (SEQ ID NO: 34). In other embodiments, the spacer may include any of the sequences listed in SEQ ID NOs: 35-38.

Further examples of suitable spacers include, without limitation, the flexible spacer 3×G4S (SEQ ID NO: 118), the flexible spacer 2×G4S (SEQ ID NO: 120), the spacer for the *T. reesei* CBHI (SEQ ID NO: 122); and the spacer for the *T. reesei* EGIV cellulase (SEQ ID NO: 124).

In certain embodiments, the length of the spacer is about the same as the length of a stem domain of GnTI. In certain embodiments, the length is about 74 amino acid residues, plus or minus about 37 amino acids. For example, the spacer length is about 30 amino acids to about 110 amino acids, or from about 35 amino acids to about 100 amino acids, or as exemplified in the examples described herein, plus or minus 2, 3, 4, or 5 amino acids. In one embodiment, the spacer length corresponds to a truncated stem domain of GnT1, for example, start from amino acid 25 to amino acid 104, or between amino acid 30 to amino acid 101, to the end of the GnT1 stem domain. In certain embodiments, the spacer may include a part of the stem domain of human GnT1, which may start from an amino acid positioned between amino acid 70 to amino acid 87 (according to numbering in SEQ ID NO: 34), or between amino acid 76 and amino acid 104, or beginning from amino acid 30, 35, 40, 45, 50, 60, 70, 73, 74, 75, 76, 80, 83, 84, 85, 86, 87, 100, 101, 102, 103, or 104, to the end of the human GnT1 stem domain. In other embodiments, the spacer may include a heterologous spacer peptide, which may include a fungal spacer peptide and/or a repetitive oligomer spacer peptide.

Typically, the spacer is an elongated peptide without specific conformation and contains amino acid residues allowing high flexibility (e.g., Gly and Ala), hydroplicity (e.g., Ser and Thr), and optionally Pro to prevent conformation. The spacer may be glycosylated. In certain embodiments the spacer is O-glycosylated including fungal O-mannosylation. In certain embodiments the spacer is an endogenous fungal, filamentous fungal, or *Trichoderma* spacer peptide, such as a spacer that naturally separates protein domains. The spacer may be derived from a secreted or cellulolytic enzyme of a fungus such as a filamentous fungus (e.g., *T. reesei*), a fragment thereof, or a multimer of the spacer and/or its fragment or mutated analog or equivalent thereof. The natural fungal spacer may contain dimeric or oligomeric proline and/or glycine and/or serine and/or threonine, and/or multiple amino acid residues selected from Ser, Thr, Gly, Pro or Ala or any combinations thereof. In certain embodiments, the spacer is a repeating oligomer containing a monomer with 1-10 or 1-5 amino acid residues selected from Ser, Thr, Gly, Pro or Ala and optionally a charged amino acid residue selected from negatively charged residues Glu or Asp or positively charged residues Lys or Arg. In certain embodiments the charged residue is negatively charged. In certain embodiments the monomer contains dimeric or oligomeric amino acid residues, and/or multiple single amino acid residues selected from Ser, Thr, Gly, Pro and Ala. In certain embodiments the oligomer contains a monomer of a dimer or oligomer of glycine and a single residue selected from the Ser, Thr, Gly, Pro and Ala. In certain embodiments the single residue is Ser or Thr. In certain embodiments the residue is Ser. In certain embodiments, the sequence of the repeating spacer is $\{(Yyy)_n Xxx\}_m$ where n is 2 to 10, m is 2 to 10, and Xxx and Yyy are selected from Ser, Thr, Gly, Pro and Ala, with the proviso that Xxx and Yyy are not the same amino acid residue. In certain embodiments the repeating spacer is $\{(Gly)_n Xxx\}_m$ where n is 2 to 10, m is 2 to 10, and Xxx is selected from Ser, Thr, Gly, Pro and Ala. In certain embodiments Xxx is Ser or Thr. In certain embodiments Xxx is Ser.

Targeting Peptides

In certain embodiments, recombinant proteins of the invention include a targeting peptide linked to the catalytic domains. The term "linked" as used herein means that two polymers of amino acid residues in the case of a polypeptide or two polymers of nucleotides in the case of a polynucleotide are either coupled directly adjacent to each other or are within the same polypeptide or polynucleotide but are separated by intervening amino acid residues or nucleotides. A "targeting peptide", as used herein, refers to any number of consecutive amino acid residues of the recombinant protein that are capable of localizing the recombinant protein to the endoplasmic reticulum (ER) or Golgi apparatus (Golgi) within the host cell. The targeting peptide may be N-terminal or C-terminal to the catalytic domains. In certain embodiments, the targeting peptide is N-terminal to the catalytic domains. In certain embodiments, the targeting peptide provides binding to an ER or Golgi component, such as to a mannosidase II enzyme. In other embodiments, the targeting peptide provides direct binding to the ER or Golgi membrane.

Components of the targeting peptide may come from any enzyme that normally resides in the ER or Golgi apparatus. Such enzymes include mannosidases, mannosyltransferases, glycosyltransferases, Type 2 Golgi proteins, and MNN2, MNN4, MNN6, MNN9, MNN10, MNS1, KRE2, VAN1, and OCH1 enzymes. Such enzymes may come from a yeast or fungal species such as those of *Acremonium, Aspergillus, Aureobasidium, Cryptococcus, Chrysosporium, Chrysosporium lucknowense, Filobasidium, Fusarium, Gibberella,*

*Humicola, Magnaporthe, Mucor, Myceliophthora, Myrothecium, Neocallimastix, Neurospora, Paecilomyces, Penicillium, Piromyces, Schizophyllum, Talaromyces, Thermoascus, Thielavia, Tolypocladium*, and *Trichoderma*. Sequences for such enzymes can be found in the GenBank sequence database.

In certain embodiments the targeting peptide comes from the same enzyme and organism as one of the catalytic domains of the recombinant protein. For example, if the recombinant protein includes a human GnTII catalytic domain, the targeting peptide of the recombinant protein is from the human GnTII enzyme. In other embodiments, the targeting peptide may come from a different enzyme and/or organism as the catalytic domains of the recombinant protein.

Examples of various targeting peptides for use in targeting proteins to the ER or Golgi that may be used for targeting recombinant proteins of the invention include: Kre2/Mnt1 N-terminal peptide fused to galactosyltransferase (Schwientek, JBC 1996, 3398), HDEL for localization of mannosidase to ER of yeast cells to produce Man5 (Chiba, JBC 1998, 26298-304; Callewaert, FEBS Lett 2001, 173-178), OCH₁ targeting peptide fused to GnTI catalytic domain (Yoshida et al, Glycobiology 1999, 53-8), yeast N-terminal peptide of Mns1 fused to α2-mannosidase (Martinet et al, Biotech Lett 1998, 1171), N-terminal portion of Kre2 linked to catalytic domain of GnTI or β4GalT (Vervecken, Appl. Environ Microb 2004, 2639-46), various approaches reviewed in Wildt and Gerngross (Nature Rev Biotech 2005, 119), full-length GnTI in *Aspergillus nidulans* (Kalsner et al, Glycocon. J 1995, 360-370), full-length GnTI in *Aspergillus oryzae* (Kasajima et al, Biosci Biotech Biochem 2006, 2662-8), portion of yeast Sec12 localization structure fused to *C. elegans* GnTI in *Aspergillus* (Kainz et al 2008), N-terminal portion of yeast Mnn9 fused to human GnTI in *Aspergillus* (Kainz et al 2008), N-terminal portion of *Aspergillus* Mnn10 fused to human GnTI (Kainz et al, Appl. Environ Microb 2008, 1076-86), and full-length human GnTI in *T. reesei* (Maras et al, FEBS Lett 1999, 365-70).

In certain embodiments the targeting peptide is the Kre2/Mnt1 (i.e., Kre2) targeting peptide having the amino acid sequence of SEQ ID NO: 115 or SEQ ID NO: 116.

Further examples of sequences that may be used for targeting peptides include the sequences listed in Table 1 below.

TABLE 1

Targeting peptides. Putative transmembrane domains are underlined. In KRE2, the stem domain enabling Golgi localization is underlined and double-underlined. Other1 and Other02 are putative mannosylation-related proteins.

| Homologous to | Cytoplasmic | Transmembrane | Luminal |
|---|---|---|---|
| KRE2 estExt_fgenesh1_ pm.C_30039 | MASTNARYVR SEQ ID NO: 39 | YLLIAFFTILVFYF VSN SEQ ID NO: 40 | SKYEGVDLNKGTFTAPDSTKTTPKPPATGDAKDFPLALTPNDP GFNDLVGIAPGPRMNATFVTLARNSDVWIARSIRQVEDRFNRRYNY DWVFLNDKPFDNTFKKVTTSLVSGKTHYGEIAPEHWSFPDWIDQDKA KKVREDMAERKIIYGDSVSYRHMCRFESGFFFRQPLMMNYEYYWRV EPSIELYCDIHYDPFRLMVEQGKKYSFVISLYEYPATIATLWESTKKFM KNHPEHIAPDNSMRFLSDDGGETYNNCHFWSNFEIGSLEWLRSKQYI DFFESLDKDGGFFYERWGDAPVHSIAAGLMLNRSEIHFFNDIAYWHV PFTHCPTGEKTRLDLKCHCDPKENFDWKGYSCTSRFFEMNGMDKPE GWENQQD SEQ ID NO: 41 |
| KRE2 alternative1 e_gw1.28.231.1 | MAIARPVR SEQ ID NO: 42 | ALGGLAAILWCFF LY SEQ ID NO: 43 | QLLRPSSSYNSPGDRYINFERDPNLDPTGEPEGILVRTSDRYAPDAK DTDRASATLLALVRNEEVDDMVASMVDLERTWNSKFNYPWTFFNDK PFSEEFKKKTSAVTNATCNYELIPKEHWDAPSWIDPAIFEESAAVLKK NGVQYANMMSYHQMCRWNSGMFYKHPALKDVRYYWRVEPKVHFF CDVDYDVFRYMQDNNKTYGFTINLYDDPHTLPTLWPQTAKFLADHPN YLHEHSAIKWVIDDARRPQHNREAQGFSTCHFWSNFEVADMEFWRS KVYEDYFEHLDRAGGFFYERWGDAPVHSIALGLFEDSSKIHWFRDIG YQHIPFFNCPNSPKCKGCVTGRLTDGEPFLHREDCRPNWFKYAGMG SEQ ID NO: 44 |
| OCH1 e_gw1.16.371.1 | MLNPRR SEQ ID NO: 45 | ALIAAAFILTVFFLI SEQ ID NO: 46 | SRSHNSESASTSEPKDAEAEALSAANAQQRAAPPPPPQKPMIDMSG MSTYDKLAYAYEYDIESKFPAYIWQTWRKTPSEGDFEFREQEASWSI EHPGFIHEVITDSVADTLLQLLYGSIPEVLEAYHALPLPVLKADLFRYLIL YARGGIYSDIDTYAIRSALEWIPPQIPKETVGLVIGIEADPDRPDWADW YSRRIQFCQWTIQSKPGHPVLRDIISRITNQTLEMKKSGKLSAFQGNR VVDLTGPAVWTDTIMDYFNDERYFDMENSKGRIDYRNFTGMETSKRV GDVVVLPITSFSPGVGQMGAKDYDDPMAFVKHDFEGTWKPESERHI GEIVQELGEGQGEAPKEQ SEQ ID NO: 47 |
| OCH1 alternative1 fgenesh1_pm.C_s caffold_13000080 | MGMGQCQWSPF RNKVPTQMRRC SEQ ID NO: 48 | LPLYITVVCVFLVI V SEQ ID NO: 49 | NFDWILAIPNPASVLRREPKAPPLPGSTFPQKIWQTWKVDPLNFDERD LVTARTWTTINPGMRYEVVTDANEMAYIEDRYGPNGFDRPDIVEFYK MINLPIIKADLLRYMIMYAEGGIYADIDVETMKPFHRFIPDRYDEKDIDIII GVEIDQPDFKDHPILGKKSMSFCQWTFVARPQQPVMMRLIENIMKWF KTVARDQGVPLGEVQLDFDQVISGTGPSAFTKAMLEEMNRKTKGPKV TWDAFHNLDESKLVGGVLVLTVEAFCAGQGHSDSGNHNARNALVKH HFHASNWPSRHPRYKHPAYGQVEDCNWVPECVRKWDEDTSNWDK YSENEQKKILQDIENARLERERQQQALAALP SEQ ID NO: 50 |
| MNN9 e_gw1.5.262.1 | MARPMGSVRLKK ANPST SEQ ID NO: 51 | LILGAVLCIFIIIFLV SEQ ID NO: 52 | SPSSPASASRLSIVSAQHHLSPPTSPYQSPRSGAVQGPPPVTRYNLN KVTVTSDPVRNQEHILILTPMARFYQEYWDNLLRLNYPHELITLGFILP KTKEGNQATSMLQKQIQKTQNYGPEKDRFKSIIILRQDFDPAVVSQDE SERHKLANQKARREVMAKARNSLLFTTLGPSTSWVLWLDADITETAP TLIQDLASHDKPIIVANCFQKYYDPESKKMAERPYDFNSWQDSETALK |

TABLE 1-continued

Targeting peptides. Putative transmembrane domains are underlined. In KRE2, the stem domain enabling Golgi localization is underlined and double-underlined. Other1 and Other02 are putative mannosylation-related proteins.

| Homologous to | Cytoplasmic | Transmembrane | Luminal |
|---|---|---|---|
| | | | MAEQMGPDDILLEGYAEMATYRTLLAYMSTPGGSKDLVVPLDGVGG TALLVKADVHRDGAMFPPFAFYHLIESEGFAKMAKRLGWQPYGLPNY KVYHYNE SEQ ID NO: 53 |
| MNN9 alternative1 estExt_GeneWise Plus.C_230146 | MLLPKGGLDWRS ARAQIPPTRAL WNAVTRTR SEQ ID NO: 54 | FILLVGITGLILLLW SEQ ID NO: 55 | RGVSTSASEMQSFYCWGPAKPPMEMSPNEHNRWNGHLQTPVIFNH HAPVEVNSSTIEHVDLNPINSTKQAVTKEERILILTPLKDAAPYLSKYFE LLAELTYPHRLIDLAFLVSDSTDDTLAVLASELDRIQKRPDQIPFHSATV IEKDFGFKLSQNVEERHSFEAQGPRRKAMGRARNYLLYTALKPEHSW VYWRDVDIVDSPTGILEDFIAHDRDILVPNIWFHRYRDGVDIEGRFDYN SWVESDKGRKLANSLDKDVVLAEGYKQYDTGRTYMAKMGDWRENK DVELELDGIGGVNILVKADVHRSGINFPCYAFENQAETEGFAKMAKRA GYEVYGLPNYVVWHIDTEEKGGNA SEQ ID NO: 56 |
| MNN9 alternative2 estExt_GeneWise Plus.C_400029 | MMPRHHSSGFSN GYPRADTFEI SPHRFQPRATLPP HRKRKRTAIR SEQ ID NO: 57 | VGIAVVVILVLVL WFG SEQ ID NO: 58 | QPRSVASLISLGILSGYDDLKLETVRYYDLSNVQGTARGWEREERILL CVPLRDAEQHLPMFFSHLKNFTYPHNLIDLAFLVSDSKDHTLESLTEH LEAIQADPDPKQPYGEISIIEKDFGQKVNQDVESRHGFAAQASRRKLM AQARNWLLSAALRPYHSWVYWRDVDVETAPFTILEDLMRHNKDVIVP NVWRPLPDWLGGEQPYDLNSWQESETALALADTLDEDAVIVEGYAE YATWRPHLAYLRDPYGDPDMEMEIDGVGGVSILAKAKVFRAGVHFPA FSFEKHAETEGFGKMAKRMHFSVVGLPHYTIWHLYEPSVDDIKHMEE MERERIAREKEEEERKKKEAQIKEEFGDANSQWEQDKQQMQDLKLQ DRGGDKEAAAAGVNQGAAAKAAGAMEGQKN SEQ ID NO: 59 |
| MNN10 fgenesh5_pg.C_s caffold_5000342 | MSLSRSPSPVPG GGWSSPGLNINS GRSSPSNAAGSS VSWESAKMRKQG ANGYPSFSTQNQ GFFTRHMRRI SSSLPRFAAGPG NTYAEREKYERG GHSPHAGGGRLR AFLARIGRRLKWR SEQ ID NO: 60 | ILLPLIIICTIVAYY SEQ ID NO: 61 | GTHEAPGFVHWWRRISMGGGGEKFVIILGANVGGGVMEWKGAREW AIERDSVRNKRKYATRWGYDLEIVDMKTKKRYAHEWRESWEKVDFIR AAMRKYPKAEWFWWLDLNTYVMEPSYSLQRHLFNHLDRHVYRDINV FNPLNITHPPTEEYLDAEARSPVGDGNINSVNLMLTQDCSGFNLGSFF IRRSAWTEQLLDIWWDPVLYEQKHMEWEHKEQDALEQLYRTQPWIR QHTGFLPQRLINSFPPAACADESGLNNTRIHYNEKDRDFVVNMAGCE WGRDCWGEMYHYREFSYWLNRNPWELFKEEIVAVIWYKLTGQRVKL SEQ ID NO: 62 |
| MNN10 alternative1 estExt_GeneWise Plus.C_150339 | MHFAYPSRKSSN PPPPFRPRSTRLPG LRRSRIKT SEQ ID NO: 63 | IGIVLFLVLATLWF F SEQ ID NO: 64 | SNPRVPRPDPERVPSGRPPVVLVTVIDPTQYPNAYLKTIKENREQYAA KHGYEAFIVKAYDYDTQGAPQSWSKLMAMRHALTKFPECRFVWYLD QDAYIMDMSKSLEEQLLNRQKLESLMIKNYPVVPPPDSIIKTFSHLRPDE VDLIVSQDSSGLVAGSVVVRNSQWSKFLLETWMDPLYRSYNFQKAE RHALEHIVQWHPTILSKLALVPQRTLGPYTRTDQGDAYQDGDFVVMF TGCTKSGEQSCETVSASYYQKWSSSL SEQ ID NO: 65 |
| MNS1 fgenesh1_pm.C_s caffold_3000175 | MIRDPFGIHSKNA FKATALRAARDIK EAATQAGANALE MSFSLPKHVPDF GDPSRALEDRAW AALLPMYKDKPYA YAPSMRLRPWWR RRK SEQ ID NO: 66 | VLGMIAAAVMFVL YVTGFF SEQ ID NO: 67 | SSGQTEEAKKKASGSAFSWLGLSQERGGVDWDERRKSVVEAFEVW DAYERYAWGKDEFHPISKNGRNMAPKGLGWIIIDSLDTMMLMNQTTR LQHAREWISTSLTWDQDQDVNTFETTIRMLGGLLSAHYLSTEFPELAP LTEDDEGAPGEDLYLEKAKDLADRLLSAFESESGIPYASVNIGEYKGP SHSDNGASSTAEATTLQLEFKYLAKLTGEKNFWDKVEKVMEVVDDN QPEDGLVPIYIYATTGEFRGQNIRLGSRGDSYYEYLIKQYLQTNKQEPI YEEMWDEALAGVRKHLVTYTEPSEFTIIAERPDGLEHPMSPKMDHLV CFMPGTIALAATGGLTEAEARKLSTWNKKKDDDMQLARELMHTCWG MYKYMKTGLAPEIMYFNIPNPPPESSAPHQAPAAFDEDPHAEWRKDF VVHSNDVHNLQRPETVESLFYMWRITGDVKYREWGWDMFKSFVNYT AVEDQGGFTSLLDANSIPPTPKDNMESFWLAETLKYMYLLFSPNDVLP LHKIVLNTEAHPFPRFDMGPLFSTGWKRKPRDGSAKKKATTAATTDA E SEQ ID NO: 68 |
| MNS1 alternative1 estExt_fgenesh1_ pm.C_80182 | MARRRYR SEQ ID NO: 69 | LFMICAAVILFLLY R SEQ ID NO: 70 | VSQNTWDDSAHYATLRHPPASNPPAAGGESPLKPAAKPEHEHEHEN GYAPESKPKPQSEPKPESKPAPEHAAGGQKSQGKPSYEDDEETGKN PPKSAVIPSDTRLPPDNKVHWRPVKEHFPVPSESVISLPTGKPLKVPR VQHEFGVESPEAKSRRVARQERVGKEIERAWSGYKKFAWMHDELSP VSAKHRDPFCGWAATLVDSLDTLWIAGLKEQFDEAARAVEQIDFTTTP RNNIPVFETTIRYLGGLLGAFDVSGGHDGGYPMLLTKAVELAEILMGIF DTPNRMPILYYQWQPEYASQPHRAGSVGIAELGTLSMEFTRLAQLTS QYKYYDAVDRITDALIELQKQGTSIPGLFPENLDASGCNHTATALRSSL SEAAQKQMDEDLSNKPENYRPGKNSKADPQTVEKQPAKKQNEPVEK AKQVPTQQTAKRGKPPFGANGFTANWDCVPQGLVVGGYGFQQY HMGGGQDSAYEYFPKEYLLLGGLESKYQKLYVDAVEAINEWLLYRPM TDGDWDILFPAKVSTAGNPSQDLVATFEVTHLTCFIGGMYGLGGKIFG REKDLETAKRLTDGCVWAYQSTVSGIMPEGSQVLACPTLEKCDFN |

TABLE 1-continued

Targeting peptides. Putative transmembrane domains are underlined. In KRE2, the stem domain enabling Golgi localization is underlined and double-underlined. Other1 and Other02 are putative mannosylation-related proteins.

| Homologous to | Cytoplasmic | Transmembrane | Luminal |
|---|---|---|---|
| | | | ETLWWEKLDPAKDWRDKQVADDKDKATVGEALKETANSHDAAGGS KAVHKRAAVPLPKPGADDDVGSELPQSLKDKIGFKNGEQKKPTGSSV GIQRDPDAPVDSVLEAHRLPPQEPEEQQVILPDKPQTHEEFVKQRIAE MGFAPGVVHIQSRQYILRPEAIESVWYMYRITGDPIWMEKGWKMFEA TIRATRTEIANSAIDDVNSEEPGLKDEMESFWLAETLKYYYLLFSEPSVI SLDEWVLNTEAHPFKRPGGSVIGHSI SEQ ID NO: 71 |
| MNS1 alternative2 estExt_GeneWise Plus.C_120298 | MLNQLQGRVPRR Y SEQ ID NO: 72 | IALVAFAFFVAFLL W SEQ ID NO: 73 | SGYDFVPRTATVGRFKYVPSSYDWSKAKVYYPVKDMKTLPQGTPVT FPRLQLRNQSEAQDDTTKARKQAVKDAFVKSWEAYKTYAWTKDQLQ PLSLSGKETFSGWSAQLVDALDTLWIMDLKDDFFLAVKEVAVIDWSKT KDNKVINLFEVTIRYLGGLIAAYDLSQEPVLRAKAIELGDTLYATFDTPN RLPSHWLDYSKAKKGTQRADDSMSGAAGGTLCMEFTRLSQITGDPK YYDATERIKQFFYRFQNETTLPGMWPVMMNYREETMVESRYSMGGS ADSLYEYLVKMPALLGGLDPQYPEMAIRALDTARDNLLFRPMTEKGD NILALGNALVDHGNVQRITEMQHLTCFAGGMYAMAGKLFKRDDYVDL GSRISSGCVWAYDSFPSGIMPESADMAACAKLDGPCPYDEVKAPVD PDGRRPHGFIHVKSRHYLLRPEAIESVFYMWRITGDQVWRDTAWRM WENIVREAETEHAFAIVEDVTRTASKLTNNYLLQTFWLAETLKYFYLIF DDESAIDLDKWVFNTEAHPFKRPAV SEQ ID NO: 74 |
| MNS1 alternative3 estExt_GeneWise Plus.C_160228 | MLVVGRPRLVRN S SEQ ID NO: 75 | IILTLAILSIWHLGL L SEQ ID NO: 76 | SRTPTSASALVSASVSASSEWSRLERLMNRGAPLTPYPDSNSSFDW SAIPFRYPPHNTTHLPPRHKQPPLPRIQHRFGPESPAAAKERIKRLKA VKQVFLRAWQAYKGYAWKQDALLPISGGGREQFSGWAATLVDALDT LWIMGLREEFDEAVAAVAEIDFGSSTSSRVNIFETNIRYLGGLLAAYDL SGREVLLKKAVELGDLIYAGFNTENGMPVDFLNFYSAKSGEGLVVES SVVSASPGTLSLELAHLSQVTGDDKYYSAVSQVMDVFYQGQNKTRLP GVWPIDVNMRAKDVVSGSRFTLGGCADSLYEYLPKMHQLLGGGEPK YETMSRTFLQAADRHFVFRPMLPGAEEDVLMPGNVNVDEDSGEAVL DPETEHLACFVGGMFGLAGRLFSRPDDVETGVRLTNGCVYAYRAFP TGMMPERLDLAPCRDRSSRCPWDEEHWLEERAKRPEWEPHLPRGF TSAKDPRYLLRPEAIESVFYSYRITGRQEFQTAAWDMFTAVEKGTRT QFANAAVLDVTRAADELPQEDYMESFWLAETLKYFYLMFTTPDIISLD DYVLNTEAHPFKLVG SEQ ID NO: 77 |
| MNS1 alternative4 e_gw1.13.279.1 | — | MVMLVAIALAWL GCSLL SEQ ID NO: 78 | RPVDAMRADYLAQLRQETVDMFYHGYSNYMEHAFPEDELRPISCTPL TRDRDNPGRISLNDALGNYSLTLIDSLSTLAILAGGPQNGPYTGPQAL SDFQDGVAEFVRHYGDGRSGPSGAGIRARGFDLDSKVQVFETVIRG VGGLLSAHLFAIGELPITGYVPRPEGVAGDDPLELAPIPWPNGFRYDG QLLRLALDLSERLLPAFYTPTGIPYPRVNLRSGIPFYVNSPLHQNLGEA VEEQSGRPEITETCSAGAGSLVLEFTVLSRLTGDARFEQAAKRAFWE VWHRRSEIGLIGNGIDAERGLWIGPHAGIGAGMDSFFEYALKSHILLS GLGMPNASTSRRQSTTSWLDPNSLHPPLPPEMHTSDAFLQAWHQAH ASVKRYLYTDRSHFPYYSNNHRATGQPYAMWIDSLGAFYPGLLALAG EVEEAIEEANLVYTALWTRYSALPERWSVREGNVEAGIGWWPGRPEFI ESTYHIYRATRDPWYLHVGEMVLRDIRRRCYAECGWAGLQDVQTGE KQDRMESFFLGETAKYMYLLFDPDHPLNKLDAAYVFTTEGHPLIIPKS KRGSGSHNRQDRARKAKKSRDVAVYTYYDESFTNSCPAPRPPSEHH LIGASATAARPDLFSVSRFTDLYRTPNVHGPLEKVEMRDKKKGRVVRY RATSNHTIFPWTLPPAMLPENGTCAAPPERIISLIEFPANDITSGITSRF GNHLSWQTHLGPTVNILEGLRLQLEQVSDPATGEDKWRITHIG NTQLGRHETVFFHAEHVRHLKDEVFSCRRRRDAVEIELLVDKPSDTN NNNTLASSDDDVVVDAKAEEQDGMLADDDGDTLNAETLSSNSLFQSL LRAVSSVFEPVYTAIPESDPSAGTAKVYSFDAYTSTGPGAYPMPSI SDTPIPGNPFYNFRNPASNFPWSTVFLAGQACEGPLPASAPREHQVI VMLRGGCSFSRKLDNIPSFSPHDRALQLVVVLDEPPPPPPPPPANDR RDVTRPLLDTEQTTPKGMKRLHGIPMVLVRAARGDYELFGHAIGVG MRRKYRVESQGLVVENAVVL SEQ ID NO: 79 |
| VAN1 estExt_GeneWise Plus.C_400029 | MMPRHHSSGFSN GYPRADTFEISPH RFQPRATLPPHRK RKRTAIR SEQ ID NO: 80 | VGIAVVVILVLVL WFG SEQ ID NO: 81 | QPRSVASLISLGILSGYDDLKLETVRYYDLSNVQGTARGWEREERILL CVPLRDAEQHLPMFFSHLKNFTYPHNLIDLAFLVSDSKDHTLESLTEH LEAIQADPDPKQPYGEISIIEKDFGQKVNQDVESRHGFAAQASRRKLM AQARNWLLSAALRPYHSWVYWRDVDVETAPFTILEDLMRHNKDVIVP NVWRPLPDWLGGEQPYDLNSWQEESETALALADTLDEDAVIVEGYAE YATWRPHLAYLRDPYGDPDMEMEIDGVGGVSILAKAKVFRAGVHFPA FSFEKHAETEGFGKMAKRMHFSVVGLPHYTIWHLYEPSVDDIKHMEE MERERIAREKEEEERKKKEAQIKEEFGDANSQWEQDKQQMQDLKLQ DRGGDKEAAAAGVNQGAAAKAAGAMEGQKN SEQ ID NO: 82 |

TABLE 1-continued

Targeting peptides. Putative transmembrane domains are underlined. In
KRE2, the stem domain enabling Golgi localization is underlined and double-
underlined. Other1 and Other02 are putative mannosylation-related proteins.

| Homologous to | Cytoplasmic | Transmembrane | Luminal |
|---|---|---|---|
| VAN1 alternative1 estExt_GeneWise Plus.C_230146 | MLLPKGGLDWRS ARAQIPPTR ALWNAVTRTR SEQ ID NO: 83 | FILLVGITGLILLLW SEQ ID NO: 84 | RGVSTSASEMQSFYCWGPAKPPMEMSPNEHNRWNGHLQTPVIFNH HAPVEVNSSTIEHVDLNPINSTKQAVTKEERILILTPLKDAAPYLSKYF ELLAELTYPHRLIDLAFLVSDSTDDTLAVLASELDRIQKRPDQIPFHSAT VIEKDFGFKLSQNVEERHSFEAQGPRRKAMGRARNYLLYTALKPEHS WVYWRDVDIVDSPTGILEDFIAHDRDILVPNIWFHRYRDGVDIEGRFD YNSWVESDKGRKLANSLDKDVVLAEGYKQYDTGRTYMAKMGDWRE NKDVELELDGIGGVNILVKADVHRSGINFPCYAFENQAETEGFAKMAK RAGYEVYGLPNYVVWHIDTEEKGGNA SEQ ID NO: 85 |
| VAN1 alternative2 e_gw1.5.262.1 | MARPMGSVRLKK ANPST SEQ ID NO: 86 | LILGAVLCIFIIIFLV SEQ ID NO: 87 | SPSSPASASRLSIVSAQHHLSPPTSPYQSPRSGAVQGPPPVTRYNLN KVTVTSDPVRNQEHILILTPMARFYQEYVVDNLLRLNYPHELITLGFILP KTKEGNQATSMLQKQIQKTQNYGPEKDRFKSIIILRQDFDPAVVSQDE SERHKLANQKARREVMAKARNSLLFTTLGPSTSWVLWLDADITETAP TLIQDLASHDKPIIVANCFQKYYDPESKKMAERPYDFNSWQDSETALK MAEQMGPDDILLEGYAEMATYRTLLAYMSTPGGSKDLVVPLDGVGG TALLVKADVHRDGAMFPPFAFYHLIESEGFAKMAKRLGWQPYGLPNY KVYHYNE SEQ ID NO: 88 |
| Other01 estExt_GeneWise Plus.C_150339 | MHFAYPSRKSSN PPPFRPRSTRLPG LRRSRIKT SEQ ID NO: 89 | IGIVLFLVLATLWF F SEQ ID NO: 90 | SNPRVPRPDPERVPSGRPPVVLVTVIDPTQYPNAYLKTIKENREQYAA KHGYEAFIVKAYDYDTQGAPQSWSKLMAMRHALTKFPECRFVWYLD QDAYIMDMSKSLEEQLLNRQKLESLMIKNYPVVPPDSIIKTFSHLRPDE VDLIVSQDSSGLVAGSVVVRNSQWSKFLLETWMDPLYRSYNFQKAE RHALEHIVQWHPTILSKLALVPQRTLGPYTRTDQGDAYQDGDFVVMF TGCTKSGEQSCETVSASYYQKWSSSL SEQ ID NO: 91 |
| Other02 fgenesh5_pg.C_s caffold_5000342 | MSLSRSPSPVPG GGWSSPGLNINS GRSSPSNAAGSS VSWESAKMRKQG ANGYPSFSTQNQ GFFTRHMRRISSS LPRFAAGPGNTYA EREKYERGGHSP HAGGGRLRAFLA RIGRRLKWR SEQ ID NO: 92 | ILLPLIIICTIVAYYG SEQ ID NO: 93 | THEAPGFVHWWRRISMGGGGEKFVIILGANVGGGVMEWKGAREWAI ERDSVRNKRKYATRWGYDLEIVDMKTKKRYAHEWRESWEKVDFIRA AMRKYPKAEWFWWLDLNTYVMEPSYSLQRHLFNHLDRHVYRDINVF NPLNITHPPTEEYLDAEARSPVGDGNINSVNLMLTQDCSGFNLGSFFI RRSAWTEQLLDIWWDPVLYEQKHMEWEHKEQDALEQLYRTQPWIR QHTGFLPQRLINSFPPAACADESGLNNTRIHYNEKDRDFVVNMAGCE WGRDCWGEMYHYREFSYWLNRNPWELFKEEIVAVIWYKLTGQRVKL SEQ ID NO: 94 |

Uncharacterized sequences may be tested for use as targeting peptides by expressing proteins in the glycosylation pathway in a host cell, where one of the proteins contains the uncharacterized sequence as the sole targeting peptide, and measuring the glycans produced in view of the cytoplasmic localization of glycan biosynthesis (e.g. as in Schwientek JBC 1996 3398), or by expressing a fluorescent reporter protein fused with the targeting peptide, and analyzing the localization of the protein in the Golgi by immunofluorescence or by fractionating the cytoplasmic membranes of the Golgi and measuring the location of the protein.

The targeting peptide may include a stem domain. In certain embodiments, the stem domain is from an N-acetylglucosaminyltransferase I enzyme or an N-acetylglucosaminyltransferase II enzyme. In especially certain embodiments, the stem domain is from a human N-acetylglucosaminyltransferase I enzyme or a human N-acetylglucosaminyltransferase II enzyme. The sequence corresponding to the stem domain from human N-acetylglucosaminyltransferase I enzyme is SEQ ID NO: 34. The sequence corresponding to the stem domain from human N-acetylglucosaminyltransferase II enzyme is residues 30-85 of SEQ ID NO: 20.

The targeting peptide may include a transmembrane domain. A "transmembrane domain" refers to any sequence of amino acid residues that is thermodynamically stable in a membrane as a three-dimensional structure. In embodiments where the targeting peptide also includes a stem domain, the transmembrane domain is N-terminal to the stem domain. In certain embodiments, the transmembrane domain is from an N-acetylglucosaminyltransferase I enzyme or an N-acetylglucosaminyltransferase II enzyme. In especially certain embodiments, the transmembrane domain is from a human N-acetylglucosaminyltransferase I enzyme or a human N-acetylglucosaminyltransferase II enzyme. The sequence corresponding to the transmembrane domain from human N-acetylglucosaminyltransferase I enzyme is residues 7-29 of SEQ ID NO: 1. The sequence corresponding to the transmembrane domain from human N-acetylglucosaminyltransferase II enzyme is residues 10-29 of SEQ ID NO: 20.

The targeting peptide may include a cytoplasmic domain. The term "cytoplasmic domain" refers to an amino acid sequence that is thermodynamically stable in a cytoplasmic environment as a three-dimensional structure. In embodiments where the targeting peptide also includes a stem domain, the cytoplasmic domain is N-terminal to the stem domain. In embodiments where the targeting peptide also includes a transmembrane domain, the cytoplasmic domain is N-terminal to the transmembrane domain. In certain embodiments, the cytoplasmic domain is from an N-acetylglucosaminyltransferase I enzyme or an N-acetylglucosaminyltransferase II enzyme. In especially certain embodiments, the cytoplasmic domain is from a human N-acetylglucosaminyltransferase I enzyme or a human N-acetylglucosaminyltransferase II enzyme. The sequence corresponding to the cytoplasmic domain from human N-acetylglucosaminyltransferase I enzyme is residues 1-6 of SEQ ID NO: 1. The sequence corresponding to the cytoplasmic domain from human N-acetylglucosaminyltransferase II enzyme is residues 1-9 of SEQ ID NO: 20.

In certain embodiments, the recombinant protein contains a human GnTII catalytic domain N-terminal to a human GnTI catalytic domain with a spacer sequence containing human GnTI stem domain sequence in between the catalytic domains. In this embodiment, the recombinant protein also includes a targeting peptide N-terminal to the GnTII catalytic domain with cytoplasmic, transmembrane, and stem domains from human GnTII. The sequence of the recombinant protein in this embodiment is at least 70%, at least 75%, at least 80%, at least 85%, at least 90%, at least 95%, at least 96%, at least 97%, at least 98%, at least 99%, or 100% identical to SEQ ID NO: 95, and the sequence of a possible cDNA encoding the recombinant protein of this embodiment is SEQ ID NO: 96.

In other embodiments, the recombinant protein contains a human GnTII catalytic domain N-terminal to a human GnTI catalytic domain with a spacer sequence. The spacer sequence may include, without limitation, a sequence that is at least 70%, at least 75%, at least 80%, at least 85%, at least 90%, at least 95%, at least 96%, at least 97%, at least 98%, at least 99%, or 100% identical to SEQ ID NOs: 118, 120, 122, or 124. In this embodiment, the recombinant protein also includes a targeting peptide N-terminal to the GnTII catalytic domain with cytoplasmic, transmembrane, and stem domains from human GnTII. Accordingly, in certain embodiments, the sequence of the recombinant protein is at least 70%, at least 75%, at least 80%, at least 85%, at least 90%, at least 95%, at least 96%, at least 97%, at least 98%, at least 99%, or 100% identical to a sequence selected from SEQ ID NOs: 119, 121, 123, and 125. In certain embodiments, the sequence of a possible cDNA encoding the recombinant protein of SEQ ID NO: 119 is SEQ ID NO: 141. In other embodiments, the sequence of a possible cDNA encoding the recombinant protein of SEQ ID NO: 121 is SEQ ID NO: 139. In still other embodiments, the sequence of a possible cDNA encoding the recombinant protein of SEQ ID NO: 123 is SEQ ID NO: 143. In further embodiments, the sequence of a possible cDNA encoding the recombinant protein of SEQ ID NO: 125 is SEQ ID NO: 145.

Production of Recombinant Proteins of the Invention

Another aspect of the invention includes isolated polynucleotides encoding the recombinant proteins of the invention. As used herein, the terms "polynucleotide," "nucleic acid sequence," "sequence of nucleic acids," and variations thereof shall be generic to polydeoxyribonucleotides (containing 2-deoxy-D-ribose), to polyribonucleotides (containing D-ribose), to any other type of polynucleotide that is an N-glycoside of a purine or pyrimidine base, and to other polymers containing non-nucleotidic backbones, provided that the polymers contain nucleobases in a configuration that allows for base pairing and base stacking, as found in DNA and RNA. Thus, these terms include known types of nucleic acid sequence modifications, for example, substitution of one or more of the naturally-occurring nucleotides with an analog; inter-nucleotide modifications, such as, for example, those with uncharged linkages (e.g., methyl phosphonates, phosphotriesters, phosphoramidates, carbamates, etc.), with negatively charged linkages (e.g., phosphorothioates, phosphorodithioates, etc.), and with positively charged linkages (e.g., aminoalkylphosphoramidates, aminoalkylphosphotriesters); those containing pendant moieties, such as, for example, proteins (including nucleases, toxins, antibodies, signal peptides, poly-L-lysine, etc.); those with intercalators (e.g., acridine, psoralen, etc.); and those containing chelators (e.g., metals, radioactive metals, boron, oxidative metals, etc.). As used herein, the symbols for nucleotides and polynucleotides are those recommended by the IUPAC-IUB Commission of Biochemical Nomenclature (Biochem. 9:4022, 1970).

Sequences of the isolated polynucleotides are prepared by any suitable method known to those of ordinary skill in the art, including, for example, direct chemical synthesis or cloning. For direct chemical synthesis, formation of a polymer of nucleic acids typically involves sequential addition of 3'-blocked and 5'-blocked nucleotide monomers to the terminal 5'-hydroxyl group of a growing nucleotide chain, where each addition is effected by nucleophilic attack of the terminal 5'-hydroxyl group of the growing chain on the 3'-position of the added monomer, which is typically a phosphorus derivative, such as a phosphotriester, phosphoramidite, or the like. Such methodology is known to those of ordinary skill in the art and is described in the pertinent texts and literature [e.g., in Matteucci et al., (1980) Tetrahedron Lett 21:719-722; U.S. Pat. Nos. 4,500,707; 5,436,327; and 5,700,637]. In addition, the desired sequences may be isolated from natural sources by splitting DNA using appropriate restriction enzymes, separating the fragments using gel electrophoresis, and thereafter, recovering the desired nucleic acid sequence from the gel via techniques known to those of ordinary skill in the art, such as utilization of polymerase chain reactions (PCR; e.g., U.S. Pat. No. 4,683,195).

Each polynucleotide of the invention can be incorporated into an expression vector. "Expression vector" or "vector" refers to a compound and/or composition that transduces, transforms, or infects a host cell, thereby causing the cell to express nucleic acids and/or proteins other than those native to the cell, or in a manner not native to the cell. An "expression vector" contains a sequence of nucleic acids (ordinarily RNA or DNA) to be expressed by the host cell. Optionally, the expression vector also comprises materials to aid in achieving entry of the nucleic acid into the host cell, such as a virus, liposome, protein coating, or the like. The expression vectors contemplated for use in the present invention include those into which a nucleic acid sequence can be inserted, along with any certain or required operational elements. Further, the expression vector must be one that can be transferred into a host cell and replicated therein. Certain expression vectors are plasmids, particularly those with restriction sites that have been well documented and that contain the operational elements certain or required for transcription of the nucleic acid sequence. Such plasmids, as well as other expression vectors, are well known to those of ordinary skill in the art.

Incorporation of the individual polynucleotides may be accomplished through known methods that include, for example, the use of restriction enzymes (such as BamHI, EcoRI, HhaI, XhoI, XmaI, and so forth) to cleave specific sites in the expression vector, e.g., plasmid. The restriction enzyme produces single-stranded ends that may be annealed to a polynucleotide having, or synthesized to have, a terminus with a sequence complementary to the ends of the cleaved expression vector. Annealing is performed using an appropriate enzyme, e.g., DNA ligase. As will be appreciated by those of ordinary skill in the art, both the expression vector and the desired polynucleotide are often cleaved with the same restriction enzyme, thereby assuring that the ends of the expression vector and the ends of the polynucleotide are complementary to each other. In addition, DNA linkers may be used to facilitate linking of nucleic acids sequences into an expression vector.

A series of individual polynucleotides can also be combined by utilizing methods that are known to those having ordinary skill in the art (e.g., U.S. Pat. No. 4,683,195).

For example, each of the desired polynucleotides can be initially generated in a separate PCR. Thereafter, specific primers are designed such that the ends of the PCR products contain complementary sequences. When the PCR products are mixed, denatured, and reannealed, the strands having the matching sequences at their 3' ends overlap and can act as primers for each other. Extension of this overlap by DNA polymerase produces a molecule in which the original sequences are "spliced" together. In this way, a series of individual polynucleotides may be "spliced" together and subsequently transduced into a host cell simultaneously. Thus, expression of each of the plurality of polynucleotides is affected.

Individual polynucleotides, or "spliced" polynucleotides, are then incorporated into an expression vector. The invention is not limited with respect to the process by which the polynucleotide is incorporated into the expression vector. Those of ordinary skill in the art are familiar with the necessary steps for incorporating a polynucleotide into an expression vector. A typical expression vector contains the desired polynucleotide preceded by one or more regulatory regions, along with a ribosome binding site, e.g., a nucleotide sequence that is 3-9 nucleotides in length and located 3-11 nucleotides upstream of the initiation codon in *E. coli*. See Shine and Dalgarno (1975) Nature 254(5495):34-38 and Steitz (1979) Biological Regulation and Development (ed. Goldberger, R. F.), 1:349-399 (Plenum, New York).

The term "operably linked" as used herein refers to a configuration in which a control sequence is placed at an appropriate position relative to the coding sequence of a DNA sequence or polynucleotide such that the control sequence directs the expression of a polypeptide.

Regulatory regions include, for example, those regions that contain a promoter and an operator. A promoter is operably linked to the desired polynucleotide or portion of a polynucleotide encoding a polypeptide, thereby initiating transcription of the polynucleotide, or portion of the polynucleotide encoding a polypeptide, via an RNA polymerase enzyme. An operator is a sequence of nucleic acids adjacent to the promoter, which contains a protein-binding domain where a repressor protein can bind. In the absence of a repressor protein, transcription initiates through the promoter. When present, the repressor protein specific to the protein-binding domain of the operator binds to the operator, thereby inhibiting transcription. In this way, control of transcription is accomplished, based upon the particular regulatory regions used and the presence or absence of the corresponding repressor protein. Examples include lactose promoters (LacI repressor protein changes conformation when contacted with lactose, thereby preventing the LacI repressor protein from binding to the operator) and tryptophan promoters (when complexed with tryptophan, TrpR repressor protein has a conformation that binds the operator; in the absence of tryptophan, the TrpR repressor protein has a conformation that does not bind to the operator). Another example is the tac promoter (see de Boer et al., (1983) Proc Natl Acad Sci USA 80(1):21-25). As will be appreciated by those of ordinary skill in the art, these and other regulatory regions may be used in the present invention, and the invention is not limited in this respect.

Examples of certain promoters for linkage to the isolated polynucleotides encoding the recombinant proteins of the invention include promoters from the following genes: gpdA, cbh1, *Aspergillus oryzae* TAKA amylase, *Rhizomucor miehei* aspartic proteinase, *Aspergillus niger* neutral alpha-amylase, *Aspergillus niger* acid stable alpha-amylase, *Aspergillus niger* glucoamylase (glaA), *Aspergillus awamori* glaA, *Rhizomucor miehei* lipase, *Aspergillus oryzae* alkaline protease, *Aspergillus oryzae* triose phosphate isomerase, *Aspergillus nidulans* acetamidase, *Aspergillus oryzae* acetamidase, *Fusarium oxysporum* trypsin-like protease, fungal endo α-L-arabinase (abnA), fungal α-L-arabinofuranosidase A (abfA), fungal α-L-arabinofuranosidase B (abfB), fungal xylanase (xlnA), fungal phytase, fungal ATP-synthetase, fungal subunit 9 (oliC), fungal triose phosphate isomerase (tpi), fungal alcohol dehydrogenase (adhA), fungal α-amylase (amy), fungal amyloglucosidase (glaA), fungal acetamidase (amdS), fungal glyceraldehyde-3-phosphate dehydrogenase (gpd), yeast alcohol dehydrogenase, yeast lactase, yeast 3-phosphoglycerate kinase, yeast triosephosphate isomerase, bacterial α-amylase, bacterial Spo2, and SSO. In certain embodiments, isolated polynucleotides encoding the recombinant proteins of the invention are operably linked to a constitutive promoter. In other embodiments, isolated polynucleotides encoding the recombinant proteins of the invention are operably linked to an inducible promoter. In certain preferred embodiments, the inducible promoter is from a cbh1 gene.

Although any suitable expression vector may be used to incorporate the desired sequences, readily available expression vectors include, without limitation: plasmids, such as pSClO1, pBR322, pBBR1MCS-3, pUR, pEX, pMR1OO, pCR4, pBAD24, pUC19; bacteriophages, such as M13 phage and λ. phage. Of course, such expression vectors may only be suitable for particular host cells. One of ordinary skill in the art, however, can readily determine through routine experimentation whether any particular expression vector is suited for any given host cell. For example, the expression vector can be introduced into the host cell, which is then monitored for viability and expression of the sequences contained in the vector. In addition, reference may be made to the relevant texts and literature, which describe expression vectors and their suitability to any particular host cell.

Another aspect of the invention includes host cells containing expression vectors containing isolated polynucleotides that encode the recombinant proteins of the invention. "Host cell" as used herein refers to a living biological cell that can be transformed via insertion of recombinant DNA or RNA. Such recombinant DNA or RNA can be in an expression vector. Thus, a host cell as described herein may be a prokaryotic organism (e.g., an organism of the kingdom eubacteria) or a eukaryotic cell. As will be appreciated by one of ordinary skill in the art, a prokaryotic cell lacks a membrane-bound nucleus, while a eukaryotic cell has a membrane-bound nucleus. In certain embodiments, host cells used for production of the recombinant proteins of the invention are fungal cells such as yeast or filamentous fungi. In other embodiments, the host cells are mammalian cells. Such cells may be human or non-human.

Another aspect of the invention includes methods of producing the recombinant proteins of the invention. The method includes the steps of introducing an isolated polynucleotide that encodes the recombinant protein into a host cell, and culturing the host cell such that the recombinant protein is expressed. The method may also include a step of purifying the recombinant protein from the host cell.

Methods of producing the recombinant proteins of the invention may include the introduction or transfer of expression vectors containing the recombinant polynucleotides of the invention into the host cell. Such methods for transferring expression vectors into host cells are well known to those of ordinary skill in the art. For example, one method for transforming *E. coli* with an expression vector involves a calcium chloride treatment where the expression vector is introduced via a calcium precipitate. Other salts, e.g., calcium phosphate, may also be used following a similar procedure. In addition, electroporation (i.e., the application of current to increase the permeability of cells to nucleic acid sequences) may be used to transfect the host cell. Also, microinjection of the nucleic acid sequences provides the ability to transfect host cells. Other means, such as lipid complexes, liposomes, and dendrimers, may also be employed. Those of ordinary skill in the art can transfect a host cell with a desired sequence using these or other methods.

The vector may be an autonomously replicating vector, i.e., a vector which exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one which, when introduced into the host, is integrated into the genome and replicated together with the chromosome(s) into which it has been integrated. Furthermore, a single vector or plasmid or two or more vectors or plasmids which together contain the total DNA to be introduced into the genome of the host, or a transposon may be used.

The vectors may contain one or more selectable markers which permit easy selection of transformed hosts. A selectable marker is a gene, the product of which provides, for example, biocide or viral resistance, resistance to heavy metals, prototrophy to auxotrophs, and the like. Selection of bacterial cells may be based upon antimicrobial resistance that has been conferred by genes such as the amp, gpt, neo, and hyg genes.

Suitable markers for yeast hosts are, for example, ADE2, HIS3, LEU2, LYS2, MET3, TRP1, and URA3. Selectable markers for use in a filamentous fungal host include, but are not limited to, amdS (acetamidase), argB (ornithine carbamoyltransferase), bar (phosphinothricin acetyltransferase), hph (hygromycin phosphotransferase), niaD (nitrate reductase), pyrG (orotidine 5'-phosphate decarboxylase), sC (sulfate adenyltransferase), and trpC (anthranilate synthase), as well as equivalents thereof. Certain for use in *Aspergillus* are the amdS and pyrG genes of *Aspergillus nidulans* or *Aspergillus oryzae* and the bar gene of *Streptomyces hygroscopicus*. Certain for use in *Trichoderma* are bar, pyr4, and amdS.

The vectors may contain an element(s) that permits integration of the vector into the host's genome or autonomous replication of the vector in the cell independent of the genome.

For integration into the host genome, the vector may rely on the gene's sequence or any other element of the vector for integration of the vector into the genome by homologous or nonhomologous recombination. Alternatively, the vector may contain additional nucleotide sequences for directing integration by homologous recombination into the genome of the host. The additional nucleotide sequences enable the vector to be integrated into the host genome at a precise location(s) in the chromosome(s). To increase the likelihood of integration at a precise location, the integrational elements may contain a sufficient number of nucleic acids, such as 100 to 10,000 base pairs, preferably 400 to 10,000 base pairs, and most preferably 800 to 10,000 base pairs, which are highly homologous with the corresponding target sequence to enhance the probability of homologous recombination. The integrational elements may be any sequence that is homologous with the target sequence in the genome of the host. Furthermore, the integrational elements may be non-encoding or encoding nucleotide sequences. On the other hand, the vector may be integrated into the genome of the host by non-homologous recombination.

For autonomous replication, the vector may further comprise an origin of replication enabling the vector to replicate autonomously in the host in question. The origin of replication may be any plasmid replicator mediating autonomous replication which functions in a cell. The term "origin of replication" or "plasmid replicator" is defined herein as a sequence that enables a plasmid or vector to replicate in vivo. Examples of origins of replication for use in a yeast host are the 2 micron origin of replication, ARS1, ARS4, the combination of ARS1 and CEN3, and the combination of ARS4 and CEN6. Examples of origins of replication useful in a filamentous fungal cell are AMA1 and ANSI (Gems et al., 1991; Cullen et al., 1987; WO 00/24883). Isolation of the AMA1 gene and construction of plasmids or vectors comprising the gene can be accomplished according to the methods disclosed in WO 00/24883.

For other hosts, transformation procedures may be found, for example, in Jeremiah D. Read, et al., Applied and Environmental Microbiology, August 2007, p. 5088-5096, for *Kluyveromyces*, in Osvaldo Delgado, et al., FEMS Microbiology Letters 132, 1995, 23-26, for *Zymomonas*, in U.S. Pat. No. 7,501,275 for *Pichia stipitis*, and in WO 2008/040387 for *Clostridium*.

More than one copy of a gene may be inserted into the host to increase production of the gene product. An increase in the copy number of the gene can be obtained by integrating at least one additional copy of the gene into the host genome or by including an amplifiable selectable marker gene with the nucleotide sequence where cells containing amplified copies of the selectable marker gene, and thereby additional copies of the gene, can be selected for by cultivating the cells in the presence of the appropriate selectable agent.

The procedures used to ligate the elements described above to construct the recombinant expression vectors of the present invention are well-known to one skilled in the art (see, e.g., Sambrook et al., 1989, supra).

The host cell is transformed with at least one expression vector. When only a single expression vector is used (without the addition of an intermediate), the vector will contain all of the nucleic acid sequences necessary.

Once the host cell has been transformed with the expression vector, the host cell is allowed to grow. Methods of the invention may include culturing the host cell such that recombinant nucleic acids in the cell are expressed. For microbial hosts, this process entails culturing the cells in a suitable medium. Typically, cells are grown at 35° C. in appropriate media. Certain growth media in the present invention include, for example, common commercially-prepared media such as Luria-Bertani (LB) broth, Sabouraud Dextrose (SD) broth or Yeast medium (YM) broth. Other defined or synthetic growth media may also be used and the appropriate medium for growth of the particular host cell will be known by someone skilled in the art of microbiology or fermentation science. Temperature ranges and other conditions suitable for growth are known in the art (see, e.g., Bailey and Ollis 1986).

Methods for purifying recombinant proteins of the invention from the host cell are well known in the art (see E. L. V. Harris and S. Angel, Eds. (1989) Protein Purification Methods: A Practical Approach, IRL Press, Oxford, England). Such methods include, without limitation, preparative disc-gel electrophoresis, isoelectric focusing, high-performance liquid chromatography (HPLC), reversed-phase HPLC, gel filtration, ion exchange and partition chromatography, and countercurrent distribution, and combinations thereof. In certain embodiments, the recombinant proteins carry additional sequence tags to facilitate purification. Such markers include epitope tags and protein tags. Non-limiting examples of epitope tags include c-myc, hemagglutinin (HA), polyhistidine (6x-HIS), GLU-GLU, and DYKDDDDK (FLAG) (SEQ ID NO: 117) epitope tags. Epitope tags can be added to peptides by a number of established methods. DNA sequences of epitope tags can be inserted into recombinant protein coding sequences as oligonucleotides or through primers used in PCR amplification. As an alternative, peptide-coding sequences can be cloned into specific vectors that create fusions with epitope tags; for example, pRSET vectors (Invitrogen Corp., San Diego, Calif.). Non-limiting examples of protein tags include glutathione-S-transferase (GST), green fluorescent protein (GFP), and maltose binding protein (MBP). Protein tags are attached to peptides or polypeptides by several well-known methods. In one approach, the coding sequence of a polypeptide or peptide can be cloned into a vector that creates a fusion between the polypeptide or peptide and a protein tag of interest. Suitable vectors include, without limitation, the exemplary plasmids, pGEX (Amersham Pharmacia Biotech, Inc., Piscataway, N.J.), pEGFP (CLONTECH Laboratories, Inc., Palo Alto, Calif.), and pMAL™ (New England BioLabs, Inc., Beverly, Mass.). Following expression, the epitope or protein-tagged polypeptide or peptide can be purified from a crude lysate of the host cell by chromatography on an appropriate solid-phase matrix. In some cases, it may be preferable to remove the epitope or protein tag (i.e., via protease cleavage) following purification.

Methods of Producing Complex Glycans

Another aspect of the invention includes methods of producing a complex N-glycan, including the steps of providing a host cell, where the host cell contains a polynucleotide encoding a fusion protein comprising an N-acetylglucosaminyltransferase I catalytic domain and an N-acetylglucosaminyltransferase II catalytic domain and culturing the host cell such that the fusion protein is expressed, where the fusion protein catalyzes the transfer of N-acetylglucosamine to a terminal Manα3 residue and N-acetylglucosamine to a terminal Manα6 residue of an acceptor glycan to produce a complex N-glycan. In certain embodiments, this aspect includes methods of producing human-like N-glycans in a *Trichoderma* cell.

As used herein, the term "complex N-glycan" refers to an N-glycan comprising a terminal GlcNAc$_2$Man$_3$ structure.

The complex N-glycan includes any glycan having the formula [GlcNAcβ2]$_z$Manα3([GlcNAcβ2]$_w$Manα6)Man{β4GlcNAcβ3(Fucαx)$_n$[β4GlcNAc]$_m$}$_p$, where n, m, and p are 0 or 1, indicating presence or absence of part of the molecule, with the provision that when m is 0, then n is 0 (fucose is a branch linked to the GlcNAc), where x is 3 or 6, where ( ) defines a branch in the structure, where [ ] defines a part of the glycan structure either present or absent in a linear sequence, and where z and w are 0 or 1. Preferably w and z are 1. In certain embodiments, the complex N-glycan includes GlcNAcβ2Manα3(GlcNAcβ2GlcNAcβ2Manα6)Manβ4GlcNAcβ4GlcNAc, GlcNAcβ2Manα3(Manα6)Manβ4GlcNAcβ4GlcNAc, GlcNAcβ2Manα3(GlcNAcβ2GlcNAcβ2Manα6)Manβ4GlcNAcβ4(Fucα6)GlcNAc, GlcNAcβ2Manα3(Manα6)Manβ4GlcNAcβ4(Fucα6)GlcNAc, and Manα3(Manα6)Manβ4GlcNAcβ4GlcNAc. In certain embodiments, the complex N-glycans are fungal non-fucosylated GlcNAc-Man3, GlcNAc2Man3, and or Man3

In certain embodiments, the method of producing a complex N-glycan will generate a mixture of different glycans. The complex N-glycan may constitute at least 1%, at least 3%, at least 5%, at least 10%, at least 15%, at least 20%, at least 25%, at least 50%, or at least 75% or more of such a glycan mixture.

The acceptor glycan, and thus the complex N-glycan, may be attached to a molecule such as an amino acid, a peptide, or a polypeptide. In certain embodiments, the amino acid derivative is an asparagine residue. The asparagine residue may be in aminoglycosidic linkage from the side-chain amide (a biologic mammalian polypeptide N-glycan linkage structure) and may be part of a peptide chain such as a dipeptide, an oligopeptide, or a polypeptide. The glycan may be a reducing end derivative such as an N-, O-, or C-linked, preferably glycosidic, derivative of the reducing GlcNAc or Man, such as a spacer or terminal organic residue with a certain glycan linked structure selected from the group of an amino acid, alkyl, heteroalkyl, acyl, alkyloxy, aryl, arylalkyl, and heteroarylalkyl. The spacer may be further linked to a polyvalent carrier or a solid phase. In certain embodiments, alkyl-containing structures include methyl, ethyl, propyl, and C4-C26 alkyls, lipids such as glycerolipids, phospholipids, dolichol-phospholipids and ceramides and derivatives. The reducing end may also be derivatized by reductive amination to a secondary amine linkage or a derivative structure. Certain carriers include biopoly- or oligomers such as (poly)peptides, poly(saccharides) such as dextran, cellulose, amylose, or glycosaminoglycans, and other organic polymers or oligomers such as plastics including polyethylene, polypropylene, polyamides (e.g., nylon or polystyrene), polyacrylamide, and polylactic acids, dendrimers such as PAMAM, Starburst or Starfish dendrimers, or polylysine, and polyalkylglycols such as polyethylene glycol (PEG). Solid phases may include microtiter wells, silica particles, glass, metal (including steel, gold and silver), polymer beads such as polystyrene or resin beads, polylactic acid beads, polysaccharide beads or organic spacers containing magnetic beads.

In certain embodiments, the acceptor glycan is attached to a heterologous polypeptide. In certain embodiments, the heterologous polypeptide is a therapeutic protein. Therapeutic proteins may include monoclonal antibodies, erythropoietins, interferons, growth hormones, enzymes, or blood-clotting factors and may be useful in the treatment of humans or animals. For example, the acceptor glycan may be attached to a therapeutic protein such as rituximab.

The acceptor glycan may be any of the acceptor glycans described in the section entitled, "Recombinant Proteins of the Invention."

In certain embodiments, the acceptor glycan may be Man5. In such embodiments, a Man5 expressing *T. reesei* strain is transformed with a GnTII/GnTI fusion enzyme using random integration or by targeted integration to a known site known not to affect Man5 glycosylation. Strains that produce GlcNAcMan5 are selected. The selected strains are further transformed with a catalytic domain of a mannosidase II-type mannosidase capable of cleaving Man5 structures to generate GlcNAcMan3. In certain embodiments mannosidase II-type enzymes belong to glycoside hydrolase family 38 (cazy.org/GH38_all.html). Characterized enzymes include enzymes listed in cazy.org/GH38_characterized.html. Especially useful enzymes are Golgi-type enzymes that cleaving glycoproteins, such as those of subfamily α-mannosidase II (Man2A1; Manα2). Examples of such enzymes include human enzyme AAC50302, *D. melanogaster* enzyme (Van den Elsen J. M. et al (2001) EMBO J. 20: 3008-3017), those with the 3D structure according to PDB-reference 1HTY, and others referenced with the catalytic domain in PDB. For cytoplasmic expression, the catalytic domain of the mannosidase is typically fused with an N-terminal targeting peptide or expressed with endogenous animal or plant Golgi targeting structures of animal or plant mannosidase II enzymes. After transformation with the catalytic domain of a mannosidase II-type mannosidase, a strain effectively producing GlcNAc2Man3 is selected.

Host Cells

The methods of producing a complex N-glycan include a first step of providing a host cell. Any prokaryotic or eukaryotic host cell may be used in the present invention so long as it remains viable after being transformed with a sequence of nucleic acids. Preferably, the host cell is not adversely affected by the transduction of the necessary nucleic acid sequences, the subsequent expression of recombinant proteins, or the resulting intermediates. Suitable eukaryotic cells include, but are not limited to, fungal, plant, insect or mammalian cells.

In certain embodiments, the host is a fungal strain. "Fungi" as used herein includes the phyla Ascomycota, Basidiomycota, Chytridiomycota, and Zygomycota (as defined by Hawksworth et al., In, Ainsworth and Bisby's Dictionary of The Fungi, 8th edition, 1995, CAB International, University Press, Cambridge, UK) as well as the Oomycota (as cited in Hawksworth et al., 1995, supra, page 171) and all mitosporic fungi (Hawksworth et al., 1995, supra).

In particular embodiments, the fungal host is a yeast strain. "Yeast" as used herein includes ascosporogenous yeast (Endomycetales), basidiosporogenous yeast, and yeast belonging to the Fungi Imperfecti (Blastomycetes). Since the classification of yeast may change in the future, for the purposes of this invention, yeast shall be defined as described in Biology and Activities of Yeast (Skinner, F. A., Passmore, S. M., and Davenport, R. R., eds, Soc. App. Bacteriol. Symposium Series No. 9, 1980).

In certain embodiments, the yeast host is a *Candida, Hansenula, Kluyveromyces, Pichia, Saccharomyces, Schizosaccharomyces*, or *Yarrowia* strain.

In certain embodiments, the yeast host is *Saccharomyces cerevisiae, Kluyveromyces lactis, Pichia pastoris, Candida albicans, Hansenula polymorpha, Schizosaccharomyces*, or *Yarrowia*.

In another particular embodiment, the fungal host cell is a filamentous fungal strain. "Filamentous fungi" include all filamentous forms of the subdivision Eumycota and Oomycota (as defined by Hawksworth et al., 1995, supra). The filamentous fungi are generally characterized by a mycelial wall composed of chitin, cellulose, glucan, chitosan, mannan, and other complex polysaccharides. Vegetative growth is by hyphal elongation and carbon catabolism is obligately aerobic. In contrast, vegetative growth by yeasts such as *Saccharomyces cerevisiae* is by budding of a unicellular thallus and carbon catabolism may be fermentative.

The filamentous fungal host cell may be, for example, an *Acremonium, Aspergillus, Fusarium, Humicola, Mucor, Myceliophthora, Neurospora, Penicillium, Scytalidium, Thielavia, Tolypocladium*, or *Trichoderma* strain.

In certain embodiments, the filamentous fungal host cell is a *Trichoderma* sp., *Acremonium, Aspergillus, Aureobasidium, Cryptococcus, Chrysosporium, Chrysosporium lucknowense, Filibasidium, Fusarium, Gibberella, Magnaporthe, Mucor, Myceliophthora, Myrothecium, Neocallimastix, Neurospora, Paecilomyces, Penicillium, Piromyces, Schizophyllum, Talaromyces, Thermoascus, Thielavia*, or *Tolypocladium* strain.

In certain embodiments, the host cell is a mammalian cell. Such cells may be human or non-human.

In other certain embodiments, the host cell is prokaryotic, and in certain embodiments, the prokaryotes are *E. coli, Bacillus subtilis, Zymomonas mobilis, Clostridium* sp., *Clostridium phytofermentans, Clostridium thermocellum, Clostridium beijerinckii, Clostridium acetobutylicum* (*Moorella thermoacetica*), *Thermoanaerobacterium saccharolyticum*, or *Klebsiella oxytoca*. In other embodiments, the prokaryotic host cells are *Carboxydocella* sp., *Corynebacterium glutamicum*, Enterobacteriaceae, *Erwinia chrysanthemi, Lactobacillus* sp., *Pediococcus acidilactici, Rhodopseudomonas capsulata, Streptococcus lactis, Vibrio furnissii, Vibrio furnissii* M1, *Caldicellulosiruptor saccharolyticus*, or *Xanthomonas campestris*. In other embodiments, the host cells are cyanobacteria. Additional examples of bacterial host cells include, without limitation, those species assigned to the *Escherichia, Enterobacter, Azotobacter, Erwinia, Bacillus, Pseudomonas, Klebsiella, Proteus, Salmonella, Serratia, Shigella, Rhizobia, Vitreoscilla, Synechococcus, Synechocystis*, and *Paracoccus* taxonomical classes.

In methods of the invention for producing a complex N-glycan, the methods include a step of culturing the host cell such that the fusion protein is expressed. For microbial hosts, this process entails culturing the cells in a suitable medium. Typically, cells are grown at 35° C. in appropriate media. Certain growth media in the present invention include, for example, common commercially-prepared media such as Luria-Bertani (LB) broth, Sabouraud Dextrose (SD) broth or Yeast medium (YM) broth. Other defined or synthetic growth media may also be used and the appropriate medium for growth of the particular host cell will be known by someone skilled in the art of microbiology or fermentation science. Temperature ranges and other conditions suitable for growth are known in the art (see, e.g., Bailey and Ollis 1986). In certain embodiments the pH of cell culture is between 3.5 and 7.5, between 4.0 and 7.0, between 4.5 and 6.5, between 5 and 5.5, or at 5.5.

The host cells used in the methods of producing a complex N-glycan contain a polynucleotide encoding any of the recombinant proteins of the invention as described in the section entitled "Recombinant Proteins of the Invention." In certain embodiments, the host cell contains a polynucleotide encoding a fusion protein comprising an N-acetylglucosaminyltransferase I catalytic domain and an N-acetylglucosaminyltransferase II catalytic domain, where the fusion protein catalyzes the transfer of N-acetylglucosamine to a terminal Manα3 residue and N-acetylglucosamine to a terminal Manα6 residue of an acceptor glycan to produce a complex N-glycan.

In certain embodiments, the host cell contains a polynucleotide encoding a UDP-GlcNAc transporter. The polynucleotide encoding the UDP-GlcNAc transporter may be endogenous (i.e., naturally present) in the host cell, or it may be heterologous to the host cell.

In certain embodiments, the host cell contains a polynucleotide encoding a α-1,2-mannosidase. The polynucleotide encoding the α-1,2-mannosidase may be endogenous in the host cell, or it may be heterologous to the host cell. These polynucleotides are especially useful for a host cell expressing high-mannose glycans transferred from the Golgi to the ER without effective exo-α-2-mannosidase cleavage. The α-1,2-mannosidase may be a mannosidase I type enzyme belonging to the glycoside hydrolase family 47 (cazy.org/GH47_all.html). In certain embodiments the α-1,2-mannosidase is an enzyme listed at cazy.org/GH47_characterized.html. In particular, the α-1,2- mannosidase may be an ER-type enzyme that cleaves glycoproteins such as enzymes in the subfamily of ER α-mannosidase I EC 3.2.1.113 enzymes. Examples of such enzymes include human α-2-mannosidase 1B (AAC26169), a combination of mammalian ER mannosidases, or a filamentous fungal enzyme such as α-1,2-mannosidase (MDS1) (*T. reesei* AAF34579; Maras M et al J. Biotech. 77, 2000, 255). For cytoplasmic expression the catalytic domain of the mannosidase is typically fused with a targeting peptide, such as HDEL, KDEL, or part of an ER or early Golgi protein, or expressed with an endogenous ER targeting structures of an animal or plant mannosidase I enzyme.

In certain embodiments, the host cell contains a polynucleotide encoding a galactosyltransferase. Galactosyltransferases transfer β-linked galactosyl residues to terminal N-acetylglucosaminyl residue. In certain embodiments the galactosyltransferase is a β-4-galactosyltransferase. Generally, β-4-galactosyltransferases belong to the CAZy glycosyltransferase family 7 (cazy.org/GT7_all.html) and include β-N-acetylglucosaminyl-glycopeptide β-1,4-galactosyltransferase (EC 2.4.1.38), which is also known as N-acetyllactosamine synthase (EC 2.4.1.90). Useful subfamilies include β4-GalT1, β4-GalT-II, -III, -IV, -V, and -VI, such as mammalian or human β4-GalT-1I, -III, -IV, -V, and -VI or any combinations thereof β4-GalT1, β4-GalTII, or β4-GalTIII are especially useful for galactosylation of terminal GlcNAcβ2-structures on N-glycans such as GlcNAc-Man3, GlcNAc2Man3, or GlcNAcMan5 (Guo S. et al. Glycobiology 2001, 11:813-20). The three-dimensional structure of the catalytic region is known (e.g. (2006) J. Mol. Biol. 357: 1619-1633), and the structure has been represented in the PDB database with code 2FYD. The CAZy database includes examples of certain enzymes. Characterized enzymes are also listed in the CAZy database at cazy.org/GT7_characterized.html. Examples of useful β4GalT enzymes include β4GalT1, e.g. bovine *Bos taurus* enzyme AAA30534.1 (Shaper N. L. et al Proc. Natl. Acad. Sci. U.S.A. 83 (6), 1573-1577 (1986)), human enzyme (Guo S. et al. Glycobiology 2001, 11:813-20), and *Mus musculus* enzyme AAA37297 (Shaper, N. L. et al. 1998 J. Biol. Chem. 263 (21), 10420-10428); β4GalTII enzymes such as human β4GalTII BAA75819.1, Chinese hamster *Cricetulus griseus* AAM77195, *Mus musculus* enzyme BAA34385, and Japanese Medaka fish *Oryzias latipes* BAH36754; and β4GalTIII enzymes such as human β4GalTIII BAA75820.1, Chinese hamster *Cricetulus griseus* AAM77196 and *Mus musculus* enzyme AAF22221.

The galactosyltransferase may be expressed in the cytoplasm of the host cell. A heterologous targeting peptide, such as a Kre2 peptide described in Schwientek J. Biol. Chem. 1996 3398, may be used. Promoters that may be used for expression of the galactosyltransferase include constitutive promoters such as gpd, promoters of endogenous glycosylation enzymes and glycosyltransferases such as mannosyltransferases that synthesize N-glycans in the Golgi or ER, and inducible promoters of high-yield endogenous proteins such as the cbh1 promoter.

In certain embodiments of the invention where the host cell contains a polynucleotide encoding a galactosyltransferase, the host cell also contains a polynucleotide encoding a UDP-Gal and/or UDP-Gal transporter. In certain embodiments of the invention where the host cell contains a polynucleotide encoding a galactosyltransferase, lactose may be used as the carbon source instead of glucose when culturing the host cell. The culture medium may be between pH 4.5 and 7.0 or between 5.0 and 6.5. In certain embodiments of the invention where the host cell contains a polynucleotide encoding a galactosyltransferase and a polynucleotide encoding a UDP-Gal and/or UDP-Gal transporter, a divalent cation such as $Mn^{2+}$, $Ca^{2+}$ or $Mg^{2+}$ may be added to the cell culture medium.

In certain embodiments, the host cell contains a polynucleotide encoding a sialyltransferase. A sialyltransferase transfers α3- or α6-linked sialic acid, such as Neu5Ac, to the terminal Gal of galactosylated complex glycans. Examples of suitable sialyltransferases can be found in the glycosylation protein family 29 (cazy.org/GT29.html). Useful α3- or α6-sialyltransferases include β-galactoside α-2,6-sialyltransferase (EC 2.4.99.1) with a certain subfamily ST6Gal-I, and N-acetyllactosaminide α-2,3-sialyltransferase (EC 2.4.99.6) with possible cross-reactivity with 3-galactoside α-2,3-sialyltransferase (EC 2.4.99.4). Useful subtypes of α3-sialyltransferases include ST3Gal-III and ST3Gal-IV. Certain enzymatically characterized species of these are listed as characterized in the CAZy database of glycosylation enzymes (cazy.org/GT29_characterized.html). The polynucleotide encoding the α3- or α6-linked sialyltransferase may be endogenous to the host cell, or it may be heterologous to the host cell. Sialylation in the host cell may require expression of enzymes synthesizing the donor CMP-sialic acid such as CMP-Neu5Ac, especially in fungal, plant, nematode/parasite, or insect cells.

The host cell may have increased or reduced levels of activity of various endogenous enzymes. A reduced level of activity may be provided by inhibiting the activity of the endogenous enzyme with an inhibitor, an antibody, or the like. In certain embodiments, the host cell is genetically modified in ways to increase or reduce activity of various endogenous enzymes. "Genetically modified" refers to any recombinant DNA or RNA method used to create a prokaryotic or eukaryotic host cell that expresses a polypeptide at elevated levels, at lowered levels, or in a mutated form. In other words, the host cell has been transfected, transformed, or transduced with a recombinant polynucleotide molecule, and thereby been altered so as to cause the cell to alter expression of a desired protein.

Genetic modifications which result in a decrease in gene expression, in the function of the gene, or in the function of the gene product (i.e., the protein encoded by the gene) can be referred to as inactivation (complete or partial), deletion, interruption, blockage, silencing, or down-regulation, or attenuation of expression of a gene. For example, a genetic modification in a gene which results in a decrease in the function of the protein encoded by such gene, can be the result of a complete deletion of the gene (i.e., the gene does not exist, and therefore the protein does not exist), a mutation in the gene which results in incomplete or no translation of the protein (e.g., the protein is not expressed), or a mutation in the gene which decreases or abolishes the natural function of the protein (e.g., a protein is expressed which has decreased or no enzymatic activity or action). More specifically, reference to decreasing the action of proteins discussed herein generally refers to any genetic modification in the host cell in question, which results in decreased expression and/or functionality (biological activity) of the proteins and includes decreased activity of the proteins (e.g., decreased catalysis), increased inhibition or degradation of the proteins as well as a reduction or elimination of expression of the proteins. For example, the action or activity of a protein of the present invention can be decreased by blocking or reducing the production of the protein, reducing protein action, or inhibiting the action of the protein. Combinations of some of these modifications are also possible. Blocking or reducing the production of a protein can include placing the gene encoding the protein under the control of a promoter that requires the presence of an inducing compound in the growth medium. By establishing conditions such that the inducer becomes depleted from the medium, the expression of the gene encoding the protein (and therefore, of protein synthesis) could be turned off. Blocking or reducing the action of a protein could also include using an excision technology approach similar to that described in U.S. Pat. No. 4,743,546. To use this approach, the gene encoding the protein of interest is cloned between specific genetic sequences that allow specific, controlled excision of the gene from the genome. Excision could be prompted by, for example, a shift in the cultivation temperature of the culture, as in U.S. Pat. No. 4,743,546, or by some other physical or nutritional signal.

In general, according to the present invention, an increase or a decrease in a given characteristic of a mutant or modified protein (e.g., enzyme activity) is made with reference to the same characteristic of a wild-type (i.e., normal, not modified) protein that is derived from the same organism (from the same source or parent sequence), which is measured or established under the same or equivalent conditions. Similarly, an increase or decrease in a characteristic of a genetically modified host cell (e.g., expression and/or biological activity of a protein, or production of a product) is made with reference to the same characteristic of a wild-type host cell of the same species, and preferably the same strain, under the same or equivalent conditions. Such conditions include the assay or culture conditions (e.g., medium components, temperature, pH, etc.) under which the activity of the protein (e.g., expression or biological activity) or other characteristic of the host cell is measured, as well as the type of assay used, the host cell that is evaluated, etc. As discussed above, equivalent conditions are conditions (e.g., culture conditions) which are similar, but not necessarily identical (e.g., some conservative changes in conditions can be tolerated), and which do not substantially change the effect on cell growth or enzyme expression or biological activity as compared to a comparison made under the same conditions.

Preferably, a genetically modified host cell that has a genetic modification that increases or decreases the activity of a given protein (e.g., an enzyme) has an increase or decrease, respectively, in the activity or action (e.g., expression, production and/or biological activity) of the protein, as compared to the activity of the wild-type protein in a wild-type host cell, of at least about 5%, and more preferably at least about 10%, and more preferably at least about 15%, and more preferably at least about 20%, and more preferably at least about 25%, and more preferably at least about 30%, and more preferably at least about 35%, and more preferably at least about 40%, and more preferably at least about 45%, and more preferably at least about 50%, and more preferably at least about 55%, and more preferably at least about 60%, and more preferably at least about 65%, and more preferably at least about 70%, and more preferably at least about 75%, and more preferably at least about 80%, and more preferably at least about 85%, and more preferably at least about 90%, and more preferably at least about 95%, or any percentage, in whole integers between 5% and 100% (e.g., 6%, 7%, 8%, etc.). The same differences are certain when comparing an isolated modified nucleic acid molecule or protein directly to the isolated wild-type nucleic acid molecule or protein (e.g., if the comparison is done in vitro as compared to in vivo).

In another aspect of the invention, a genetically modified host cell that has a genetic modification that increases or decreases the activity of a given protein (e.g., an enzyme) has an increase or decrease, respectively, in the activity or action (e.g., expression, production and/or biological activity) of the protein, as compared to the activity of the wild-type protein in a wild-type host cell, of at least about 2-fold, and more preferably at least about 5-fold, and more preferably at least about 10-fold, and more preferably about 20-fold, and more preferably at least about 30-fold, and more preferably at least about 40-fold, and more preferably at least about 50-fold, and more preferably at least about 75-fold, and more preferably at least about 100-fold, and more preferably at least about 125-fold, and more preferably at least about 150-fold, or any whole integer increment starting from at least about 2-fold (e.g., 3-fold, 4-fold, 5-fold, 6-fold, etc.).

In certain embodiments, the host cell has a reduced level of activity of a dolichyl-P-Man:Man(5)GlcNAc(2)-PP-dolichyl mannosyltransferase compared to the level of activity in a wild-type host cell. Dolichyl-P-Man:Man(5)GlcNAc(2)-PP-dolichyl mannosyltransferase (EC 2.4.1.130) transfers an alpha-D-mannosyl residue from dolichyl-phosphate D-mannose into a membrane lipid-linked oligosaccharide. Typically, the dolichyl-P-Man:Man(5)GlcNAc(2)-PP-dolichyl mannosyltransferase enzyme is encoded by an alg3 gene. In certain embodiments, the host cell has a reduced level of expression of an alg3 gene compared to the level of expression in a wild-type host cell. In certain embodiments, the alg3 gene is deleted from the host cell.

In certain embodiments, the host cell has a reduced level of activity of a alpha-1,6-mannosyltransferase compared to the level of activity in a wild-type host cell. Alpha-1,6-mannosyltransferase (EC 2.4.1.232) transfers an alpha-D-mannosyl residue from GDP-mannose into a protein-linked oligosaccharide, forming an elongation initiating alpha-(1->6)-D-mannosyl-D-mannose linkage in the Golgi apparatus. Typically, the alpha-1,6-mannosyltransferase enzyme is encoded by an och1 gene. In certain embodiments, the host cell has a reduced level of expression of an och1 gene compared to the level of expression in a wild-type host cell. In certain embodiments, the och1 gene is deleted from the host cell.

In certain embodiments, the host cell has a reduced level of protease activity. In certain embodiments, genes encoding various proteases are deleted from the host cell. These genes include, for example, genes encoding proteases such as pep1 (pepA in *Aspergillus*) and cellulolytic enzymes, such as cellobiohydrolase1 (cbh1).

In certain embodiments, the host cell may have a reduced level of activity of proteins involved in non-homologous end joining (NHEJ) in order to enhance the efficiency of homologous recombination. In certain embodiments, genes encoding these proteins are deleted from the host cell. The genes and their homologues include, but are not limited to, Ku70, Ku80, Lig4, Rad50, Xrs2, Sir4, Lift, or Neil as described in, for example, Ninomiya et al. 2004, Ishibashi et al. 2006, Villalba et al. 2008, and Mizutani et al. 2008.

In certain embodiments of methods of producing a complex N-glycan, the host cell is a *Trichoderma* cell that has a reduced level of activity of a dolichyl-P-Man:Man(5)GlcNAc(2)-PP-dolichyl mannosyltransferase compared to the level of activity in a wild-type *Trichoderma* cell.

In other certain embodiments of methods of producing a complex N-glycan, the host cell is a yeast cell that has a reduced level of activity of a dolichyl-P-Man:Man(5)GlcNAc(2)-PP-dolichyl mannosyltransferase and a reduced level of activity of an alpha-1,6-mannosyltransferase compared to the levels of activity in a wild-type yeast cell and further comprises a polynucleotide encoding a α-1,2-mannosidase.

In Vitro Methods of Producing Complex N-Glycans

In another aspect, the invention provides a method of producing a complex N-glycan, including a step of incubating a fusion protein comprising an N-acetylglucosaminyltransferase I catalytic domain and an N-acetylglucosaminyltransferase II catalytic domain, an acceptor glycan, and an N-acetylglucosamine donor together in a buffer, where the fusion protein catalyzes the transfer of N-acetylglucosamine to a terminal Manα3 residue and N-acetylglucosamine to a terminal Manα6 residue of an acceptor glycan to produce a complex N-glycan. In certain embodiments the acceptor glycan is attached to an amino acid, a peptide, or a polypeptide. In certain embodiments the acceptor glycan is attached to a heterologous polypeptide. In certain embodiments, the acceptor glycan is Man$_3$. In certain embodiments the N-acetylglucosamine donor is a UDP-GlcNAc transporter. Typically the buffer contains a divalent cation such as Mn$^{2+}$, Ca$^{2+}$, or Mg$^{2+}$ at concentrations of 1 µM to 100 mM, 100 µM to 50 mM, or 0.1 mM to 25 mM. The N-acetylglucosamine donor is typically used in molar excess, such as 1.1-100 fold excess with regard to the reactive acceptor sites on the acceptor glycan. The concentration of the acceptor glycan is typically between 1 µM to 100 mM, 100 µM to 50 mM, or 1 to 25 mM. Where the acceptor glycan is attached to a polypeptide, the concentration ranges are typically at the lower end because of higher molecular weights. The concentrations of the components of the reaction may be adjusted based on their solubilities in the buffer. The amount of enzyme activity (units) may be adjusted to allow an effective reaction within a reasonable reaction time. A reasonable reaction time is typically from a few minutes to several days. In certain embodiments the reaction time will be from about 0.5 hours to one day or from 1 to 6 hours.

Useful buffers include buffers suitable for the fusion protein such as TRIS, HEPES, MOPS in pH ranges of about 5 to 8.5, 5.5. to 8.0, or 6.0 and 7.5. Typically concentrations of TRIS, HEPES, or MOPS buffers will be between 5 to 150 mM, between 10-100 mM, or 10-60 mM adjusted to maintain the pH. The reaction may be optimized by adding salt such as NaCl at 10-200 mM and/or an enzyme stabilizing but not glycosylatable protein (e.g., a pure non-glycosylated or non-acceptor glycan containing albumin. In a certain embodiment the in vitro reaction is adjusted to be performed in cell culture medium. Phosphate buffers may be used to reduce reaction speed.

Cells and Methods for Production of Man$_3$GlcNAc$_2$ Glycans

In another aspect, the present invention provides filamentous fungal cells containing a mutation of alg3 and Man3GlcNAc2, where the Man3GlcNAc2 includes at least 50%, at least 60%, at least 70%, at least 80%, at least 90%, or 100% (mol %) of neutral N-glycans secreted by the cells. The neutral N-glycans may be attached to an amino acid, a peptide, or a polypeptide. The alg3 gene may be mutated by any means known in the art, such as point mutations or deletion of the entire alg3 gene. Preferably, the function of the alg3 protein is reduced or eliminated by the mutation of alga. The filamentous fungal cell may be an *Acremonium, Aspergillus, Aureobasidium, Cryptococcus, Chrysosporium, Chrysosporium lucknowense, Filibasidium, Fusarium, Gibberella, Humicola, Magnaporthe, Mucor, Myceliophthora, Myrothecium, Neocallimastix, Neurospora, Paecilomyces, Penicillium, Piromyces, Schizophyllum, Scytalidium, Talaromyces, Thermoascus, Thielavia, Tolypocladium*, or *Trichoderma* cell. In certain embodiments, the filamentous fungal cell is a *T. reesei* cell. In certain embodiments, the filamentous fungal cell further contains one or more polynucleotides encoding any of the recombinant proteins of the invention. For example, the filamentous fungal cell may further contain a first polynucleotide encoding an N-acetylglucosaminyltransferase I catalytic domain and a second polynucleotide encoding an N-acetylglucosaminyltransferase II catalytic domain. Alternatively, the filamentous fungal cell may further contain a polynucleotide encoding a fusion protein including an N-acetylglucosaminyltransferase I catalytic domain and an N-acetylglucosaminyltransferase II catalytic domain.

In yet another aspect, the present invention provides methods of producing a Man$_3$GlcNAc$_2$ glycan in a host cell, including the steps of providing a host cell with a reduced level of activity of a mannosyltransferase compared to the level of activity in a wild-type host cell, and culturing the host cell to produce a Man$_3$GlcNAc$_2$ glycan, where the Man$_3$GlcNAc$_2$ glycan makes up at least 50%, at least 60%, at least 70%, at least 80%, at least 90%, or 100% (mol %) of the neutral N-glycans secreted by the host cell.

The Man$_3$GlcNAc$_2$ glycan may be attached to a molecule such as an amino acid, a peptide, or a polypeptide. In certain embodiments, the amino acid is an asparagine residue. The asparagine residue may be in aminoglycosidic linkage from the side-chain amide (a biologic mammalian protein N-glycan linkage structure) and may be part of a peptide chain such as a dipeptide, an oligopeptide, or a polypeptide. The glycan may be a reducing end derivative such as an N-, O-, or C-linked, preferably glycosidic, derivative of the reducing GlcNAc or Man, such as a spacer or terminal organic residue with a certain glycan-linked structure selected from the group of an amino acid, alkyl, heteroalkyl, acyl, alkyloxy, aryl, arylalkyl, and heteroarylalkyl. The spacer may be further linked to a polyvalent carrier or a solid phase. In certain embodiments, alkyl-containing structures include methyl, ethyl, propyl, and C4-C26 alkyls, lipids such as glycerolipids, phospholipids, dolichol-phospholipids and ceramides and derivatives. The reducing end may also be derivatized by reductive amination to a secondary amine linkage or a derivative structure. Certain carriers include biopoly- or oligomers such as (poly)peptides, poly(saccharides) such as dextran, cellulose, amylose, or glycosaminoglycans, and other organic polymers or oligomers such as plastics including polyethylene, polypropylene, polyamides (e.g., nylon or polystyrene), polyacrylamide, and polylactic acids, dendrimers such as PAMAM, Starburst or Starfish dendrimers, or polylysine, and polyalkylglycols such as polyethylene glycol (PEG). Solid phases may include microtiter wells, silica particles, glass, metal including steel, gold and silver, polymer beads such as polystyrene or resin beads, polylactic acid beads, polysaccharide beads or organic spacers containing magnetic beads.

In certain embodiments, the Man$_3$GlcNAc$_2$ glycan is attached to a heterologous polypeptide. In certain embodiments, the heterologous polypeptide is a therapeutic protein. Therapeutic proteins may include monoclonal antibodies, erythropoietins, interferons, growth hormones, enzymes, or blood-clotting factors and may be useful in the treatment of humans or animals. For example, the Man$_3$GlcNAc$_2$ glycan may be attached to a therapeutic protein such as rituximab. Typically, the Man$_3$GlcNAc$_2$ glycan will be further modified to become a complex glycan. Such modification may take place in vivo in the host cell or by in vitro methods.

In certain embodiments, the mannosyltransferase is a dolichyl-P-Man:Man(5)GlcNAc(2)-PP-dolichyl mannosyltransferase. Typically, the dolichyl-P-Man:Man(5)GlcNAc(2)-PP-dolichyl mannosyltransferase enzyme is encoded by an alg3 gene. In certain embodiments, the host cell has a reduced level of expression of an alg3 gene compared to the level of expression in a wild-type host cell. In certain embodiments, the alg3 gene is deleted from the host cell. SEQ ID NOs: 97 and 98 provide the nucleic acid and amino acid sequences of the alg3 gene in *T. reesei*, respectively.

In certain embodiments, the level of activity of alpha-1,6-mannosyltransferase in the host cell is not reduced compared to the level of activity in a wild-type host cell. Typically, the alpha-1,6-mannosyltransferase enzyme is encoded by an och1 gene. In certain embodiments, the host cell contains an endogenous polynucleotide encoding an α-1,2-mannosidase.

In certain embodiments, the host cell is a *Trichoderma* cell, and in certain embodiments, the host cell is a *Trichoderma reesei* cell.

Filamentous Fungal Cells of the Invention

In a further aspect, the present invention provides filamentous fungal cells having a reduced level of expression of an alg3 gene of the invention, compared to the level of expression of the alg3 gene in a wild-type filamentous fungal cell, where the filamentous fungal cell also contains any of the recombinant proteins of the invention as described in the section entitled "Recombinant Proteins of the Invention.". For example, in certain embodiments the filamentous fungal cell further contains a polynucleotide encoding a fusion protein including an N-acetylglucosaminyltransferase I catalytic domain and an N-acetylglucosaminyltransferase II catalytic domain. The expression of the fusion protein may be controlled by a promoter that is operably linked to the polynucleotide. The promoter may be a constitutive promoter or an inducible promoter. In certain preferred embodiments, the promoter is an inducible promoter, such as the cbh1 inducible promoter.

In another aspect, the present invention provides filamentous fungal cells having a reduced level of expression of an alg3 gene of the invention, compared to the level of expression of the alg3 gene in a wild-type filamentous fungal cell, where the filamentous fungal cell also contains a first polynucleotide encoding a recombinant N-acetylglucosaminyltransferase I catalytic domain and a second polynucleotide encoding a recombinant N-acetylglucosaminyltransferase II catalytic domain. In such embodiments, the expression of the recombinant N-acetylglucosaminyltransferase I catalytic domain is controlled by a promoter that is operably linked to the first polynucleotide and the expression of the recombinant N-acetylglucosaminyltransferase II catalytic domain is controlled by a promoter that is operably linked to the second polynucleotide. The promoter may be a constitutive promoter or an inducible promoter. In certain preferred embodiments, the promoter is an inducible promoter, such as the cbh1 inducible promoter.

In other embodiments, a single polynucleotide may encode both the recombinant N-acetylglucosaminyltransferase I catalytic domain and the recombinant N-acetylglucosaminyltransferase II catalytic domain such that they are expressed as separate polypeptides. In such embodiments, the polynucleotide may contain an internal ribosome entry site that allows for the separate translation of each catalytic domain from the polynucleotide. In such embodiments, the expression of the recombinant N-acetylglucosaminyltransferase I catalytic domain is controlled by a promoter that is operably linked to the portion of the polynucleotide that encodes the N-acetylglucosaminyltransferase I catalytic domain and the expression of the recombinant N-acetylglucosaminyltransferase II catalytic domain is controlled by a promoter that is operably linked to the portion of the polynucleotide that encodes the N-acetylglucosaminyltransferase II catalytic domain. The promoter may be a constitutive promoter or an inducible promoter. In certain preferred embodiments, the promoter is an inducible promoter, such as the cbh1 inducible promoter.

As disclosed herein, N-acetylglucosaminyltransferase I (GlcNAc-TI; GnTI; EC 2.4.1.101) catalyzes the reaction UDP-N-acetyl-D-glucosamine+3-(alpha-D -mannosyl)-beta-D-mannosyl-R<=>UDP+3-(2-(N-acetyl-beta-D-glucosaminyl)-alpha-D -mannosyl)-beta-D-mannosyl-R, where R represents the remainder of the N-linked oligosaccharide in the glycan acceptor. An N-acetylglucosaminyltransferase I catalytic domain is any portion of an N-acetylglucosaminyltransferase I enzyme that is capable of catalyzing this reaction. Amino acid sequences for N-acetylglucosaminyltransferase I enzymes from various organisms are listed in SEQ ID NOs: 1-19. Additional GnTI enzymes are listed in the CAZy database in the glycosyltransferase family 13 (cazy.org/GT13 all). Enzymatically characterized species includes *A. thaliana* AAR78757.1 (U.S. Pat. No. 6,653,459), *C. elegans* AAD03023.1 (Chen S. et al J. Biol. Chem. 1999; 274(1):288-97), *D. melanogaster* AAF57454.1 (Sarkar & Schachter Biol. Chem. 2001 February; 382(2):209-17); *C. griseus* AAC52872.1 (Puthalakath H. et al J. Biol. Chem. 1996 271 (44):27818-22); *H. sapiens* AAA52563.1 (Kumar R. et al Proc Natl Acad Sci U S A. 1990 December; 87(24):9948-52); *M. auratus* AAD04130.1 (Opat As et al Biochem J. 1998 Dec. 15; 336 (Pt 3):593-8), (including an example of deactivating mutant), Rabbit, *O. cuniculus* AAA31493.1 (Sarkar M et al. Proc Natl Acad Sci USA. 1991 Jan. 1; 88(1):234-8). Additional examples of characterized active enzymes can be found at cazy.org/GT13_characterized. The 3D structure of the catalytic domain of rabbit GnTI was defined by X-ray crystallography in Unligil U M et al. EMBO J. 2000 Oct. 16; 19(20):5269-80. The Protein Data Bank (PDB) structures for GnTI are 1FO8, 1FO9, 1FOA, 2AM3, 2AM4, 2AM5, and 2APC. In certain embodiments, the N-acetylglucosaminyltransferase I catalytic domain is from the human N-acetylglucosaminyltransferase enzyme (SEQ ID NO: 1), or variants thereof. In certain embodiments, the N-acetylglucosaminyltransferase I catalytic domain contains a sequence that is at least 70%, at least 75%, at least 80%, at least 85%, at least 90%, at least 95%, at least 96%, at least 97%, at least 98%, at least 99%, or 100% identical to amino acid residues 84-445 of SEQ ID NO: 1. In some embodiments, a shorter sequence can be used as a catalytic domain (e.g. amino acid residues 105-445 of the human enzyme or amino acid residues 107-447 of the rabbit enzyme; Sarkar et al. (1998) Glycoconjugate J 15:193-197). Additional sequences that can be used as the GnTI catalytic domain include amino acid residues from about amino acid 30 to 445 of the human enzyme or any C-terminal stem domain starting between amino acid residue 30 to 105 and continuing to about amino acid 445 of the human enzyme, or corresponding homologous sequence of another GnTI or a catalytically active variant or mutant thereof. The catalytic domain may include N-terminal parts of the enzyme such as all or part of the stem domain, the transmembrane domain, or the cytoplasmic domain.

As disclosed herein, N-acetylglucosaminyltransferase II (GlcNAc-TII; GnTII; EC 2.4.1.143) catalyzes the reaction UDP-N-acetyl-D-glucosamine+6-(alpha-D -mannosyl)-beta-D-mannosyl-R<=>UDP+6-(2-(N-acetyl-beta-D-glucosaminyl)-alpha -D-mannosyl)-beta-D-mannosyl-R, where R represents the remainder of the N-linked oligosaccharide in the glycan acceptor. An N-acetylglucosaminyltransferase II catalytic domain is any portion of an N-acetylglucosaminyltransferase II enzyme that is capable of catalyzing this reaction. Amino acid sequences for N-acetylglucosaminyltransferase II enzymes from various organisms are listed in SEQ ID NOs: 20-33. In certain embodiments, the N-acetylglucosaminyltransferase II catalytic domain is from the human N-acetylglucosaminyltransferase II enzyme (SEQ ID NO: 20), or variants thereof. Additional GnTII species are listed in the CAZy database in the glycosyltransferase family 16 (cazy.org/GT16_all). Enzymatically characterized species include GnTII of *C. elegans, D. melanogaster, Homo sapiens, Rattus norvegigus, Sus scrofa* (cazy.org/GT16_characterized). In certain embodiments, the N-acetylglucosaminyltransferase II catalytic domain contains a sequence that is at least 70%, at least 75%, at least 80%, at least 85%, at least 90%, at least 95%, at least 96%, at least 97%, at least 98%, at least 99%, or 100% identical to amino acid residues from about 30 to about 447 of SEQ ID NO: 21. The catalytic domain may include N-terminal parts of the enzyme such as all or part of the stem domain, the transmembrane domain, or the cytoplasmic domain.

In embodiments where the filamentous fungal cell contains a fusion protein of the invention, the fusion protein may further contain a spacer in between the N-acetylglucosaminyltransferase I catalytic domain and the N-acetylglucosaminyltransferase II catalytic domain. Any of the spacers of the invention as described in the section entitled "Spacers" may be used. In certain preferred embodiments, the spacer is an EGIV spacer, a 2×G4S spacer, a 3×G4S spacer, or a CBHI spacer. In other embodiments, the spacer contains a sequence from a stem domain.

For ER/Golgi expression the N-acetylglucosaminyltransferase I and/or N-acetylglucosaminyltransferase II catalytic domain is typically fused with a targeting peptide or a part of an ER or early Golgi protein, or expressed with an endogenous ER targeting structures of an animal or plant N-acetylglucosaminyltransferase enzyme. In certain preferred embodiments, the N-acetylglucosaminyltransferase I and/or N-acetylglucosaminyltransferase II catalytic domain contains any of the targeting peptides of the invention as described in the section entitled "Targeting peptides." Preferably, the targeting peptide is linked to the N-terminal end of the catalytic domain. In some embodiments, the targeting peptide contains any of the stem domains of the invention as described in the section entitled "Targeting peptides." In certain preferred embodiments, the targeting peptide is a Kre2 targeting peptide. In other embodiments, the targeting peptide further contains a transmembrane domain linked to the N-terminal end of the stem domain or a cytoplasmic domain linked to the N-terminal end of the stem domain. In embodiments where the targeting peptide further contains a transmembrane domain, the targeting peptide may further contain a cytoplasmic domain linked to the N-terminal end of the transmembrane domain.

The level of expression of an alg3 gene of the invention may be reduced by any suitable method known in the art, including, without limitation, mutating the alg3 gene. The alg3 may be mutated by, for example, point mutations or deletion of the entire alg3 gene. Preferably, the function of the alg3 protein is reduced or eliminated by the mutation of alga. The alg3 gene encodes a dolichyl-P-Man:Man(5)GlcNAc(2)-PP-dolichyl alpha-1,3-mannosyltransferase. As disclosed herein, a dolichyl-P-Man:Man(5)GlcNAc(2)-PP-dolichyl mannosyltransferase of the invention transfers an alpha-D-mannosyl residue from dolichyl-phosphate D-mannose into a membrane lipid-linked oligosaccharide.

In certain embodiments, the filamentous fungal cell may contain a polynucleotide encoding a UDP-GlcNAc transporter. The polynucleotide encoding the UDP-GlcNAc transporter may be endogenous (i.e., naturally present) in the filamentous fungal cell, or it may be heterologous to the filamentous fungal cell.

In other embodiments, the filamentous fungal cell may also contain a polynucleotide encoding a α-1,2-mannosidase of the invention as described in the section entitled "Host Cells." The polynucleotide encoding the α-1,2-mannosidase may be endogenous in the filamentous fungal cell, or it may be heterologous to the filamentous fungal cell. These polynucleotides are especially useful for a filamentous fungal cell expressing high-mannose glycans transferred from the Golgi to the ER without effective exo-α-2-mannosidase cleavage. For cytoplasmic expression the catalytic domain of the mannosidase is typically fused with a targeting peptide, such as HDEL, KDEL, or part of an ER or early Golgi protein, or expressed with an endogenous ER targeting structures of an animal or plant mannosidase I enzyme.

In further embodiments, the filamentous fungal cell may also contain a polynucleotide encoding a galactosyltransferase of the invention as described in the section entitled "Host Cells." Galactosyltransferases transfer β-linked galactosyl residues to terminal N-acetylglucosaminyl residue. In certain embodiments the galactosyltransferase is a β-4-galactosyltransferase. The galactosyltransferase may be expressed in the cytoplasm of the filamentous fungal. A heterologous targeting peptide, such as a Kre2 peptide described in Schwientek J. Biol. Chem. 1996 3398, may be used. Promoters that may be used for expression of the galactosyltransferase include constitutive promoters such as gpd, promoters of endogenous glycosylation enzymes and glycosyltransferases such as mannosyltransferases that synthesize N-glycans in the Golgi or ER, and inducible promoters of high-yield endogenous proteins such as the cbh1 promoter. In embodiments of the invention where the host cell contains a polynucleotide encoding a galactosyltransferase, the host cell also contains a polynucleotide encoding a UDP-Gal and/or UDP-Gal transporter. In certain embodiments of the invention where the filamentous fungal cell contains a polynucleotide encoding a galactosyltransferase, lactose may be used as the carbon source instead of glucose when culturing the filamentous fungal cell. The culture medium may be between pH 4.5 and 7.0 or between 5.0 and 6.5. In certain embodiments of the invention where the filamentous fungal cell contains a polynucleotide encoding a galactosyltransferase and a polynucleotide encoding a UDP-Gal and/or UDP-Gal transporter, a divalent cation such as $Mn^{2+}$, $Ca^{2+}$ or $Mg^{2+}$ may be added to the cell culture medium.

In other embodiments, the filamentous fungal cell may also contain a polynucleotide encoding a sialyltransferase of the invention as described in the section entitled "Host Cells.". A sialyltransferase transfers α3- or α6-linked sialic acid, such as Neu5Ac, to the terminal Gal of galactosylated complex glycans. The polynucleotide encoding the α3- or α6-linked sialyltransferase may be endogenous to the filamentous fungal cell, or it may be heterologous to the filamentous fungal cell. Sialylation in the filamentous fungal cell may require expression of enzymes synthesizing the donor CMP-sialic acid such as CMP-Neu5Ac, especially in fungal, plant, nematode/parasite, or insect cells.

Additionally, the filamentous fungal cell may have increased or reduced levels of activity of various additional endogenous enzymes. A reduced level of activity may be provided by inhibiting the activity of the endogenous enzyme with an inhibitor, an antibody, or the like. In certain embodiments, the filamentous fungal cell is genetically modified in ways to increase or reduce activity of one or more endogenous enzymes. Methods of genetically modifying a filamentous fungal cell to increase or reduce activity of one or more endogenous enzymes are well known in the art and include, without limitation, those described in the section entitled "Host Cells." In certain embodiments, the filamentous fungal cell has a reduced level of activity of a alpha-1,6-mannosyltransferase compared to the level of activity in a wild-type filamentous fungal cell. Alpha-1,6-mannosyltransferase (EC 2.4.1.232) in the Golgi apparatus transfers an elongation initiating alpha-D-mannosyl residue from GDP-mannose into a protein-linked N-glycan oligosaccharide, forming an alpha-(1->6)-D-mannosyl-D-mannose linkage. Typically, the alpha-1,6-mannosyltransferase enzyme is encoded by an och1 gene. In certain embodiments, the filamentous fungal cell has a reduced level of expression of an och1 gene compared to the level of expression in a wild-type filamentous fungal cell. In certain embodiments, the och1 gene is deleted from the filamentous fungal cell.

The filamentous fungal cell may be, for example, an *Acremonium, Aspergillus, Aureobasidium, Cryptococcus, Chrysosporium, Chrysosporium lucknowense, Filibasidium, Fusarium, Gibberella, Humicola, Magnaporthe, Mucor, Myceliophthora, Myrothecium, Neocallimastix, Neurospora, Paecilomyces, Penicillium, Piromyces, Schizophyllum, Scytalidium, Talaromyces, Thermoascus, Thielavia, Tolypocladium,* or *Trichoderma* cell. In certain embodiments, the filamentous fungal cell is a *T. reesei* cell.

Pharmaceutical Compositions Containing Complex N-Glycans Produced by the Methods of the Invention In another aspect, the present invention provides a composition, e.g., a pharmaceutical composition, containing one or more complex N-glycans attached to a heterologous molecule produced by the methods of the invention, formulated together with a pharmaceutically acceptable carrier. Pharmaceutical compositions of the invention also can be administered in combination therapy, i.e., combined with other agents. For example, the combination therapy can include an complex N-glycans attached to a heterologous molecule according to the present invention combined with at least one other therapeutic agent.

As used herein, "pharmaceutically acceptable carrier" includes any and all solvents, dispersion media, coatings, antibacterial and antifungal agents, isotonic and absorption delaying agents, and the like that are physiologically compatible. Preferably, the carrier is suitable for intravenous, intramuscular, subcutaneous, parenteral, spinal or epidermal administration (e.g., by injection or infusion). Depending on the route of administration, the active compound, i.e., the complex N-glycan attached to a heterologous molecule according to the invention, may be coated in a material to protect the compound from the action of acids and other natural conditions that may inactivate the compound.

The pharmaceutical compositions of the invention may include one or more pharmaceutically acceptable salts. A "pharmaceutically acceptable salt" refers to a salt that retains the desired biological activity of the parent compound and does not impart any undesired toxicological effects (see e.g., Berge, S. M., et al. (1977) J. Pharm. Sci. 66:1-19). Examples of such salts include acid addition salts and base addition salts. Acid addition salts include those derived from nontoxic inorganic acids, such as hydrochloric, nitric, phosphoric, sulfuric, hydrobromic, hydroiodic, phosphorous and the like, as well as from nontoxic organic acids such as aliphatic mono- and dicarboxylic acids, phenyl-substituted alkanoic acids, hydroxy alkanoic acids, aromatic acids, aliphatic and aromatic sulfonic acids and the like. Base addition salts include those derived from alkaline earth metals, such as sodium, potassium, magnesium, calcium and the like, as well as from nontoxic organic amines, such as N,N'-dibenzylethylenediamine, N-methylglucamine, chloroprocaine, choline, diethanolamine, ethylenediamine, procaine and the like.

A pharmaceutical composition of the invention also may include a pharmaceutically acceptable antioxidant. Examples of pharmaceutically acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Examples of suitable aqueous and nonaqueous carriers that may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of presence of microorganisms may be ensured both by sterilization procedures, and by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

Pharmaceutically acceptable carriers include sterile aqueous solutions or dispersions and sterile powders for the extemporaneous preparation of sterile injectable solutions or dispersion. The use of such media and agents for pharmaceutically active substances is known in the art. Except insofar as any conventional media or agent is incompatible with the active compound, use thereof in the pharmaceutical compositions of the invention is contemplated. Supplementary active compounds can also be incorporated into the compositions.

Therapeutic compositions typically must be sterile and stable under the conditions of manufacture and storage. The composition can be formulated as a solution, microemulsion, liposome, or other ordered structure suitable to high drug concentration. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. In many cases, it will be preferable to include isotonic agents, for example, sugars, polyalcohols such as mannitol, sorbitol, or sodium chloride in the composition. Prolonged absorption of the injectable compositions can be brought about by including in the composition an agent that delays absorption, for example, monostearate salts and gelatin.

Sterile injectable solutions can be prepared by incorporating the active compound in the required amount in an appropriate solvent with one or a combination of ingredients enumerated above, as required, followed by sterilization microfiltration. Generally, dispersions are prepared by incorporating the active compound into a sterile vehicle that contains a basic dispersion medium and the required other ingredients from those enumerated above. In the case of sterile powders for the preparation of sterile injectable solutions, the certain methods of preparation are vacuum drying and freeze-drying (lyophilization) that yield a powder of the active ingredient plus any additional desired ingredient from a previously sterile-filtered solution thereof.

The amount of active ingredient which can be combined with a carrier material to produce a single dosage form will vary depending upon the subject being treated, and the particular mode of administration. The amount of active ingredient which can be combined with a carrier material to produce a single dosage form will generally be that amount of the composition which produces a therapeutic effect. Generally, out of one hundred percent, this amount will range from about 0.01 percent to about ninety-nine percent of active ingredient, preferably from about 0.1 percent to about 70 percent, most preferably from about 1 percent to about 30 percent of active ingredient in combination with a pharmaceutically acceptable carrier.

Dosage regimens are adjusted to provide the optimum desired response (e.g., a therapeutic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier. The specification for the dosage unit forms of the invention are dictated by and directly dependent on (a) the unique characteristics of the active compound and the particular therapeutic effect to be achieved, and (b) the limitations inherent in the art of compounding such an active compound for the treatment of sensitivity in individuals.

For administration of the complex N-glycan attached to a heterologous molecule, in particular where the heterologous molecule is an antibody, the dosage ranges from about 0.0001 to 100 mg/kg, and more usually 0.01 to 5 mg/kg, of the host body weight. For example, dosages can be 0.3 mg/kg body weight, 1 mg/kg body weight, 3 mg/kg body weight, 5 mg/kg body weight or 10 mg/kg body weight or within the range of 1-10 mg/kg. An exemplary treatment regime entails administration once per week, once every two weeks, once every three weeks, once every four weeks, once a month, once every 3 months or once every three to 6 months. Certain dosage regimens for a complex N-glycan attached to a heterologous antibody include 1 mg/kg body weight or 3 mg/kg body weight via intravenous administration, with the antibody being given using one of the following dosing schedules: (i) every four weeks for six dosages, then every three months; (ii) every three weeks; (iii) 3 mg/kg body weight once followed by 1 mg/kg body weight every three weeks.

Alternatively a complex N-glycan attached to a heterologous molecule according to the invention can be administered as a sustained release formulation, in which case less frequent administration is required. Dosage and frequency vary depending on the half-life of the administered substance in the patient. In general, human antibodies show the longest half life, followed by humanized antibodies, chimeric antibodies, and nonhuman antibodies. The dosage and frequency of administration can vary depending on whether the treatment is prophylactic or therapeutic. In prophylactic applications, a relatively low dosage is administered at relatively infrequent intervals over a long period of time. Some patients continue to receive treatment for the rest of their lives. In therapeutic applications, a relatively high dosage at relatively short intervals is sometimes required until progression of the disease is reduced or terminated, and preferably until the patient shows partial or complete amelioration of symptoms of disease. Thereafter, the patient can be administered a prophylactic regime.

Actual dosage levels of the active ingredients in the pharmaceutical compositions of the present invention may be varied so as to obtain an amount of the active ingredient which is effective to achieve the desired therapeutic response for a particular patient, composition, and mode of administration, without being toxic to the patient. The selected dosage level will depend upon a variety of pharmacokinetic factors including the activity of the particular compositions of the present invention employed, or the ester, salt or amide thereof, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts.

A "therapeutically effective dosage" of immunoglobulin of the invention preferably results in a decrease in severity of disease symptoms, an increase in frequency and duration of disease symptom-free periods, or a prevention of impairment or disability due to the disease affliction. For example, for the treatment of tumors, a "therapeutically effective dosage" preferably inhibits cell growth or tumor growth by at least about 20%, more preferably by at least about 40%, even more preferably by at least about 60%, and still more preferably by at least about 80% relative to untreated subjects. The ability of a compound to inhibit tumor growth can be evaluated in an animal model system predictive of efficacy in human tumors. Alternatively, this property of a composition can be evaluated by examining the ability of the compound to inhibit, such inhibition in vitro by assays known to the skilled practitioner. A therapeutically effective amount of a therapeutic compound can decrease tumor size, or otherwise ameliorate symptoms in a subject. One of ordinary skill in the art would be able to determine such amounts based on such factors as the subject's size, the severity of the subject's symptoms, and the particular composition or route of administration selected.

A composition of the present invention can be administered via one or more routes of administration using one or more of a variety of methods known in the art. As will be appreciated by the skilled artisan, the route and/or mode of administration will vary depending upon the desired results. Certain routes of administration for binding moieties of the invention include intravenous, intramuscular, intradermal, intraperitoneal, subcutaneous, spinal or other parenteral routes of administration, for example by injection or infusion. The phrase "parenteral administration" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion.

Alternatively, a complex N-glycan attached to a heterologous molecule according to the invention can be administered via a nonparenteral route, such as a topical, epidermal or mucosal route of administration, for example, intranasally, orally, vaginally, rectally, sublingually or topically.

The active compounds can be prepared with carriers that will protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art. See, e.g., Sustained and Controlled Release Drug Delivery Systems, J. R. Robinson, ed., Marcel Dekker, Inc., New York, 1978.

Therapeutic compositions can be administered with medical devices known in the art. For example, in a certain embodiment, a therapeutic composition of the invention can be administered with a needleless hypodermic injection device, such as the devices disclosed in U.S. Pat. Nos. 5,399,163; 5,383,851; 5,312,335; 5,064,413; 4,941,880; 4,790,824; or 4,596,556. Examples of well-known implants and modules useful in the present invention include: U.S. Pat. No. 4,487,603, which discloses an implantable micro-infusion pump for dispensing medication at a controlled rate; U.S. Pat. No. 4,486,194, which discloses a therapeutic device for administering medicants through the skin; U.S. Pat. No. 4,447,233, which discloses a medication infusion pump for delivering medication at a precise infusion rate; U.S. Pat. No. 4,447,224, which discloses a variable flow implantable infusion apparatus for continuous drug delivery; U.S. Pat. No. 4,439,196, which discloses an osmotic drug delivery system having multi-chamber compartments; and U.S. Pat. No. 4,475,196, which discloses an osmotic drug delivery system.

In certain embodiments, the use of the complex N-glycan attached to a heterologous molecule according to the invention is for the treatment of any disease that may be treated with therapeutic antibodies.

It is to be understood that, while the invention has been described in conjunction with the certain specific embodiments thereof, the foregoing description is intended to illustrate and not limit the scope of the invention. Other aspects, advantages, and modifications within the scope of the invention will be apparent to those skilled in the art to which the invention pertains.

The invention having been described, the following examples are offered to illustrate the subject invention by way of illustration, not by way of limitation.

EXAMPLES

Example 1

Host Strain Selection for Glycoengineering

The aim of this example was to identify optimal *T. reesei* strains for glycoengineering. An optimal strain produces high amounts of Man5 N-glycans and low amounts of acidic glycans.

Samples

Different *T. reesei* strains including M44 (VTT-D-00775; Selinheimo et al., FEBS J. 2006, 273(18): 4322-35), M81, M84, M109, M110, M131, M132, M133, M134 and M124 (a *mus*53-deleted strain of M44) were analyzed. Each of the ten strains was grown in shake flask cultures. Samples were taken at three different time points: 3 days, 5 days, and 7 days. Both supernatants (secreted proteins) and cell pellets were collected and stored frozen at −20° C. until glycan analysis was conducted.

N-glycans were isolated from secreted proteins from the indicated time points followed by matrix-assisted laser desorption/ionization-time-of-flight (MALDI-TOF) glycan profiling. Cell pellets from the 5 days time point were subjected to N-glycan profiling. A total of 80 samples (30 each of neutral- and acidic supernatant fractions, and 10 each of neutral- and acidic pellet fractions) were subjected to analysis.

Strain M44 was also subjected to batch and fed-batch fermentor cultivation in order to assess the difference on glycan profile between shake flask and fermentor culture. For glycan analysis, samples from three different time points were analyzed for a total of 12 samples (6 neutral and 6 acidic fractions). As a control, culture medium was analyzed.

Mass Spectrometry Methods

MALDI-TOF mass spectrometry was performed with a Bruker Ultraflex TOF/TOF instrument (Bruker Daltonics, Germany). Neutral N-glycans were detected in positive ion reflector mode as $[M+Na]^+$ ions, and acidic N-glycans were detected in negative ion linear mode as $[M-H]^-$ ions. The relative molar abundance of neutral N-glycan components was assigned based on their relative signal intensities in the spectra. The resulting glycan signals in the presented glycan profiles were normalized to 100% to allow comparison between samples.

Protein-Specific Glycosylation Methods

Proteins from a fermentor-cultured sample were separated with SDS-PAGE and blotted to a PVDF membrane. The protein bands of interest were excised, and N-glycans were liberated by enzymatic release with PNGase F.

Neutral N-glycan Profile of *T. reesei* Strains

The desired Man5 structure can be observed as a $[M+Na]^+$ signal at m/z value of 1257.4 in the mass spectra presented in FIG. 1. The neutral glycome of the analyzed *T. reesei* strains were found to have either Man5 or Man8 as the main neutral glycan species ($H_5N_2$ and $H_8N_2$ in Table 2).

TABLE 2

The percentage of different neutral N-glycan signals of analyzed *T. reesei* strains.

| | | Strain | | | | | | | | | |
|---|---|---|---|---|---|---|---|---|---|---|---|
| Composition | m/z | M44 % | M81 % | M84 % | M109 % | M110 % | M131 % | M132 % | M133 % | M134 % | M124 % |
| H3N2 | 933 | 0.0 | 0.0 | 0.0 | 0.0 | 0.0 | 0.0 | 0.0 | 0.0 | 0.0 | 0.0 |
| H4N2 | 1095 | 1.2 | 0.0 | 0.0 | 1.8 | 0.9 | 0.0 | 2.3 | 0.0 | 2.3 | 4.1 |
| H5N2 | 1257 | 81.0 | 70.8 | 4.0 | 78.9 | 5.8 | 78.8 | 84.1 | 10.7 | 73.2 | 77.9 |
| H6N2 | 1419 | 5.8 | 5.3 | 0.0 | 5.3 | 0.9 | 4.8 | 4.6 | 0.9 | 6.0 | 7.3 |
| H7N2 | 1581 | 4.8 | 7.3 | 1.5 | 4.7 | 3.0 | 4.8 | 3.9 | 3.8 | 5.8 | 4.8 |
| H8N2 | 1743 | 3.7 | 8.6 | 81.5 | 5.1 | 68.2 | 5.9 | 2.6 | 68.1 | 6.3 | 3.3 |
| H9N2 | 1905 | 2.9 | 8.0 | 9.0 | 3.4 | 16.0 | 4.6 | 2.0 | 12.8 | 5.7 | 2.3 |
| H10N2 | 2067 | 0.5 | 0.0 | 2.5 | 0.8 | 3.7 | 1.1 | 0.4 | 2.5 | 0.7 | 0.4 |
| H11N2 | 2229 | 0.0 | 0.0 | 1.5 | 0.0 | 1.4 | 0.0 | 0.0 | 1.2 | 0.0 | 0.0 |
| H12N2 | 2391 | 0.0 | 0.0 | 0.0 | 0.0 | 0.0 | 0.0 | 0.0 | 0.0 | 0.0 | 0.0 |

Some acidic N-glycans were observed in neutral N-glycan fractions. This may have been due to specific properties of the phosphorylated glycans, e.g. presence of phosphodiester structures, or other properties of the phosphoglycans which could lead to leakage of acidic species to neutral fraction under the experimental conditions used in this study. To check the corresponding structure, the signal of interest was subjected to MS/MS analysis. Mass spectrometric fragmentation of glycans was performed using Bruker Ultraflex TOF/TOF in MS/MS analysis mode (FIG. 2). Because the glycans were not permethylated, definitive structural assignment based on the MS/MS data could not be obtained.

Acidic N-glycan Profiles of *T. reesei* Strains

Figure 3:
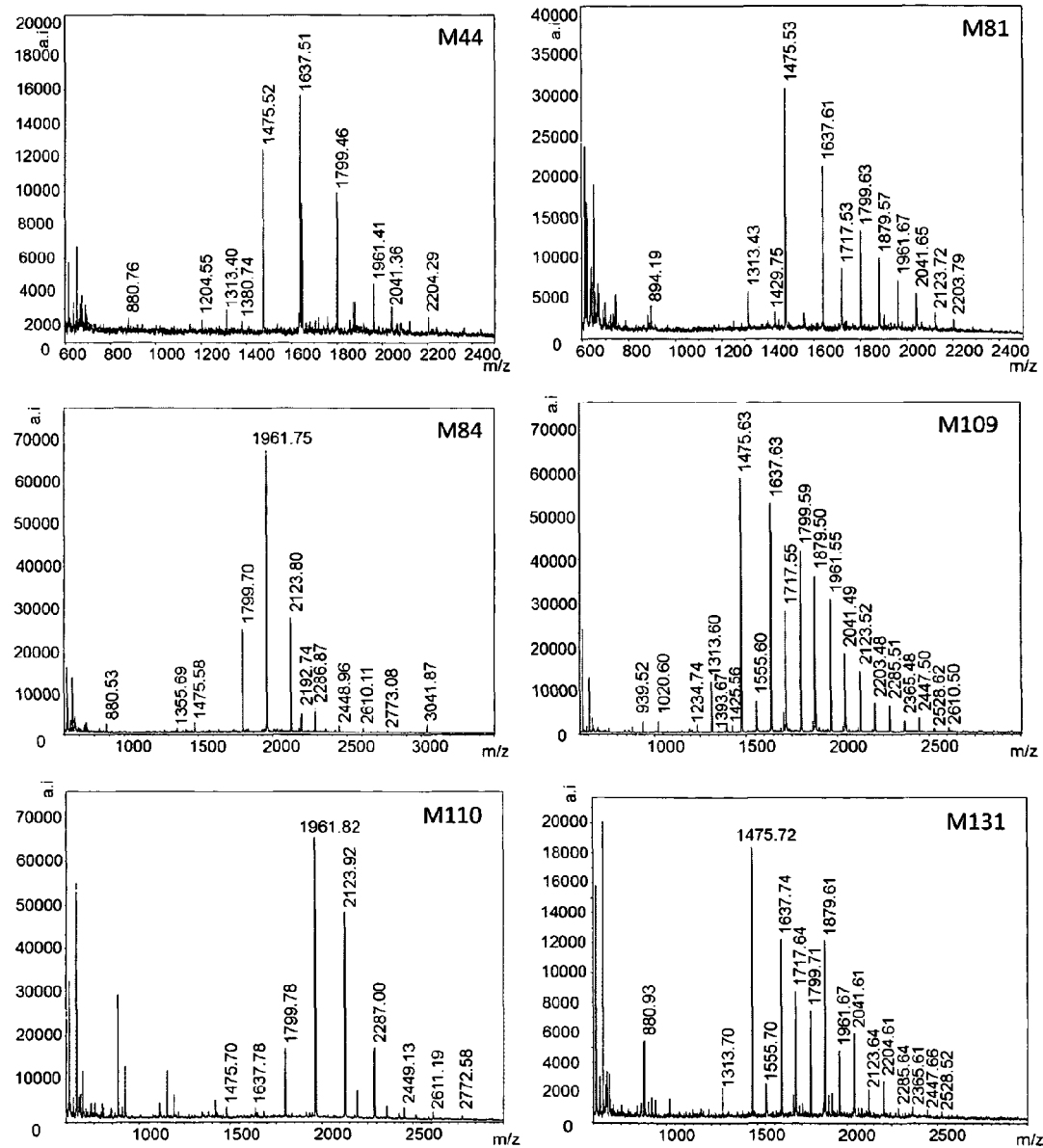
FIG. 3 shows mass spectrometric acidic glycan profiles of *T. reesei* strains M44, M81, M84, M109, M110, M131, M132, M133, M134, and M124.

For glycoengineering purposes it was useful to have strains with a minimum amount of acidic N-glycans. Therefore, acidic N-glycan profiles were analyzed from the strains used for screening. The acidic N-glycan spectra of analyzed strains are shown in FIG. 3 and below in Table 3.

TABLE 3

The percentage of different acidic N-glycan signals of analyzed *T. reesei* strains.

|  | m/z | M44 % | M81 % | M84 % | M109 % | M110 % | M131 % | M132 % | M133 % | M134 % | M124 % |
|---|---|---|---|---|---|---|---|---|---|---|---|
| Hex3HexNAc2SP | 989 | 0.0 | 0.0 | 0.0 | 0.0 | 0.0 | 0.0 | 0.0 | 0.0 | 0.0 | 0.0 |
| Hex4HexNAc2SP | 1151 | 0.0 | 0.0 | 0.0 | 0.0 | 0.0 | 0.0 | 0.0 | 0.0 | 0.0 | 0.0 |
| Hex5HexNAc2SP | 1313 | 4.0 | 5.2 | 0.0 | 3.7 | 0.0 | 2.8 | 7.4 | 0.0 | 5.2 | 2.8 |
| Hex5HexNAc2SP2 | 1393 | 0.0 | 0.0 | 0.0 | 0.7 | 0.0 | 0.0 | 0.0 | 0.0 | 0.9 | 0.0 |
| Hex6HexNAc2SP | 1475 | 23.7 | 27.3 | 2.2 | 18.1 | 2.1 | 22.4 | 21.0 | 3.9 | 25.9 | 26.3 |
| Hex6HexNAc2SP2 | 1555 | 0.0 | 2.8 | 0.0 | 2.4 | 0.0 | 3.2 | 1.1 | 0.0 | 3.6 | 1.7 |
| Hex7HexNAc2SP | 1637 | 30.3 | 18.8 | 1.1 | 16.2 | 2.0 | 14.9 | 24.7 | 0.0 | 17.2 | 23.3 |
| Hex7HexNAc2SP2 | 1717 | 0.0 | 7.7 | 0.0 | 8.6 | 0.0 | 10.7 | 2.5 | 0.0 | 10.4 | 7.0 |
| Hex8HexNAc2SP | 1799 | 18.4 | 11.8 | 17.9 | 12.8 | 9.7 | 9.1 | 19.7 | 14.5 | 8.8 | 11.2 |
| Hex8HexNAc2SP2 | 1879 | 5.1 | 8.8 | 0.0 | 11.0 | 0.0 | 14.8 | 4.0 | 0.0 | 12.4 | 10.0 |
| Hex9HexNAc2SP | 1961 | 7.3 | 6.4 | 49.1 | 9.5 | 37.9 | 5.9 | 6.1 | 53.9 | 4.1 | 3.5 |
| Hex9HexNAc2SP2 | 2041 | 4.2 | 5.0 | 0.0 | 5.7 | 0.0 | 7.3 | 5.1 | 0.0 | 5.9 | 7.2 |
| Hex10HexNAc2SP | 2123 | 2.8 | 2.9 | 19.7 | 4.5 | 28.1 | 2.6 | 2.3 | 19.3 | 2.1 | 1.6 |
| Hex10HexNAc2SP | 2203 | 2.8 | 2.1 | 0.0 | 2.2 | 0.0 | 2.7 | 3.6 | 0.0 | 1.9 | 3.3 |
| Hex11HexNAc2SP | 2285 | 1.5 | 1.3 | 3.7 | 2.1 | 9.5 | 1.2 | 0.9 | 5.0 | 1.0 | 0.8 |
| Hex11HexNAc2SP2 | 2365 | 0.0 | 0.0 | 0.0 | 0.9 | 0.0 | 1.3 | 1.5 | 0.0 | 0.8 | 1.3 |
| Hex12HexNAc2SP | 2447 | 0.0 | 0.0 | 1.3 | 1.0 | 1.6 | 1.0 | 0.0 | 0.0 | 0.5 | 0.0 |
| Hex12HexNAc2SP2 | 2527 | 0.0 | 0.0 | 0.0 | 0.4 | 0.0 | 0.0 | 0.0 | 0.0 | 0.3 | 0.0 |
| Hex13HexNAc2SP | 2609 | 0.0 | 0.0 | 1.2 | 0.4 | 1.1 | 0.0 | 0.0 | 0.0 | 0.0 | 0.0 |
| Hex14HexNAc2SP | 2771 | 0.0 | 0.0 | 0.6 | 0.0 | 0.9 | 0.0 | 0.0 | 0.0 | 0.0 | 0.0 |

N-glycan Profile from Fermentor Cultured Strain M44

Figure 4:
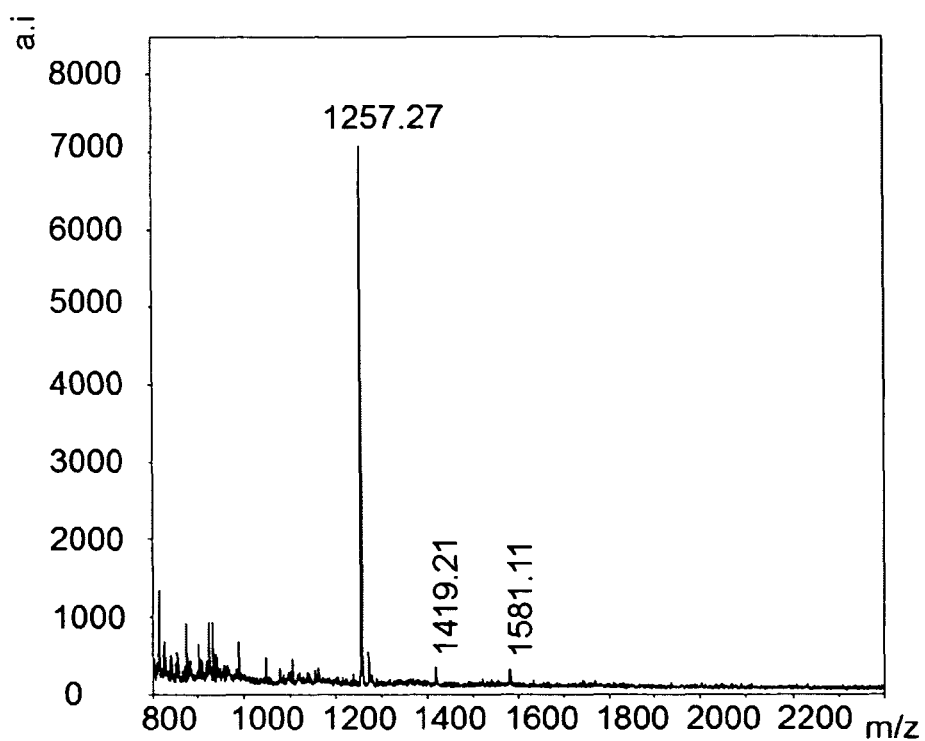
FIG. 4 shows neutral (a) and acidic (b) N-glycan profiles of *T. reesei* strain M44 cultured in a fermentor for 131.4 hours (fed batch).
Figure 4:
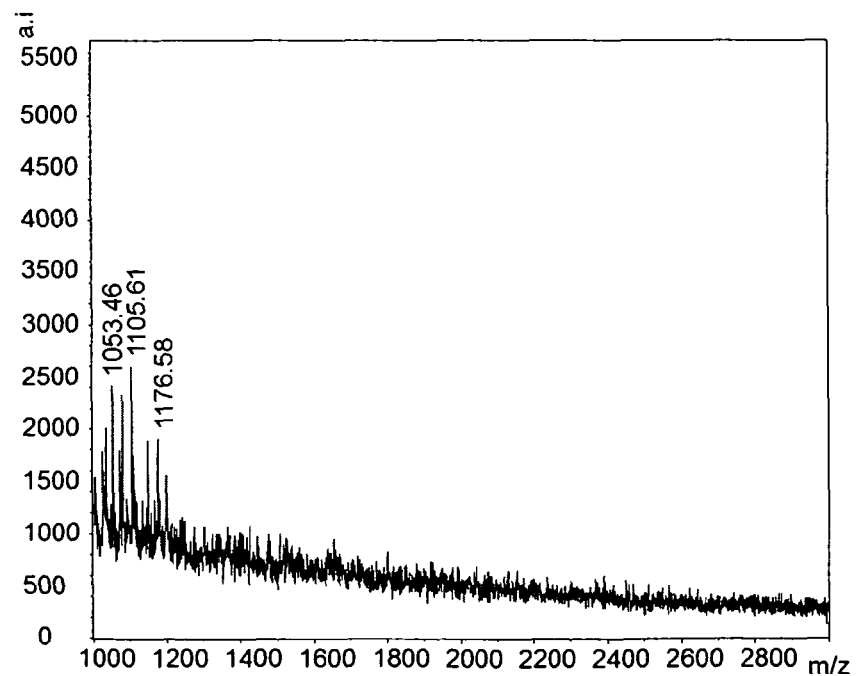

Strain M44 was cultivated in a fermentor in order to find out if different culture conditions can cause changes in its glycan profile. N-glycan analysis was performed for samples cultured in a fermentor (Batch; 41:10, 88:45 and 112:50 hours, and Fed batch; 45:50, 131:40 and 217:20 hours) and compared to that of shake flask culture. Neutral and acidic N-glycans of secreted proteins of *T. reesei* strain M44 cultured in fermentor are shown in FIG. 4. Comparison between the N-glycan percentages from flask and fermentor cultures is presented below in Table 4.

TABLE 4

The percentage of N-glycan signals of *T. reesei* strain M44 cultured in flask and in fermentor.

| Composition | m/z | flask % | fermentor % |
|---|---|---|---|
| H3N2 | 933 | 0.0 | 0.0 |
| H4N2 | 1095 | 1.2 | 0.0 |
| H5N2 | 1257 | 81.0 | 91.3 |

TABLE 4-continued

The percentage of N-glycan signals of *T. reesei* strain M44 cultured in flask and in fermentor.

| Composition | m/z | flask % | fermentor % |
|---|---|---|---|
| H6N2 | 1419 | 5.8 | 4.5 |
| H7N2 | 1581 | 4.8 | 4.2 |
| H8N2 | 1743 | 3.7 | 0.0 |
| H9N2 | 1905 | 2.9 | 0.0 |
| H10N2 | 2067 | 0.5 | 0.0 |
| H11N2 | 2229 | 0.0 | 0.0 |
| H12N2 | 2391 | 0.0 | 0.0 |

N-glycan Analysis of Shake Flask Culture Medium

Figure 5:
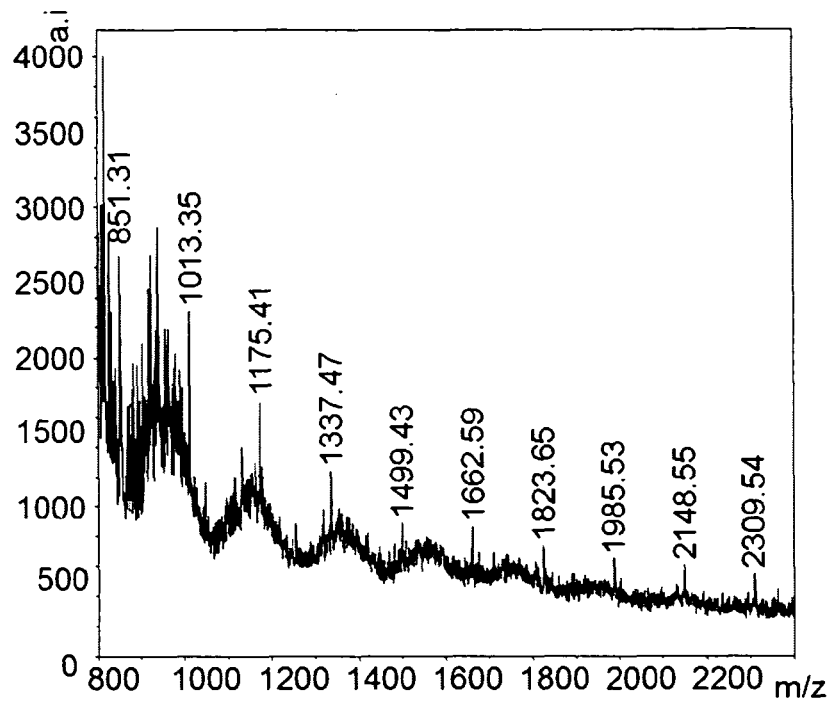
FIG. 5 shows mass spectrometric neutral (a) and acidic (b) N-glycan profiles of *T. reesei* culture medium.
Figure 5:
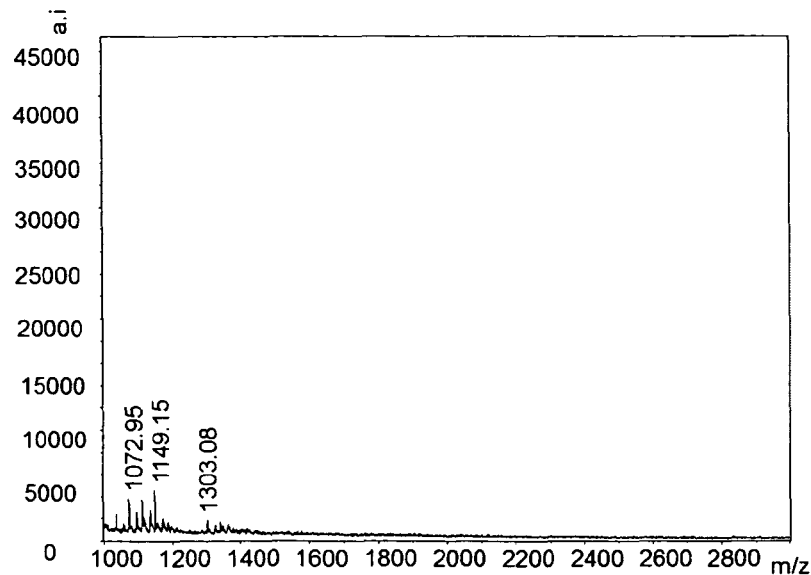

As a control experiment, culture medium (without contact with fungus) of *T. reesei* was analyzed. FIG. 5a shows neutral N-glycan analysis in which no N-glycans were observed. Only minor signals of hexose oligomers, most likely derived from the plant material used in the medium, were visible above the baseline. In FIG. 5b (acidic glycans), no signals corresponding to N-glycans were observed.

N-glycosylation of Secreted Proteins

Figure 6:
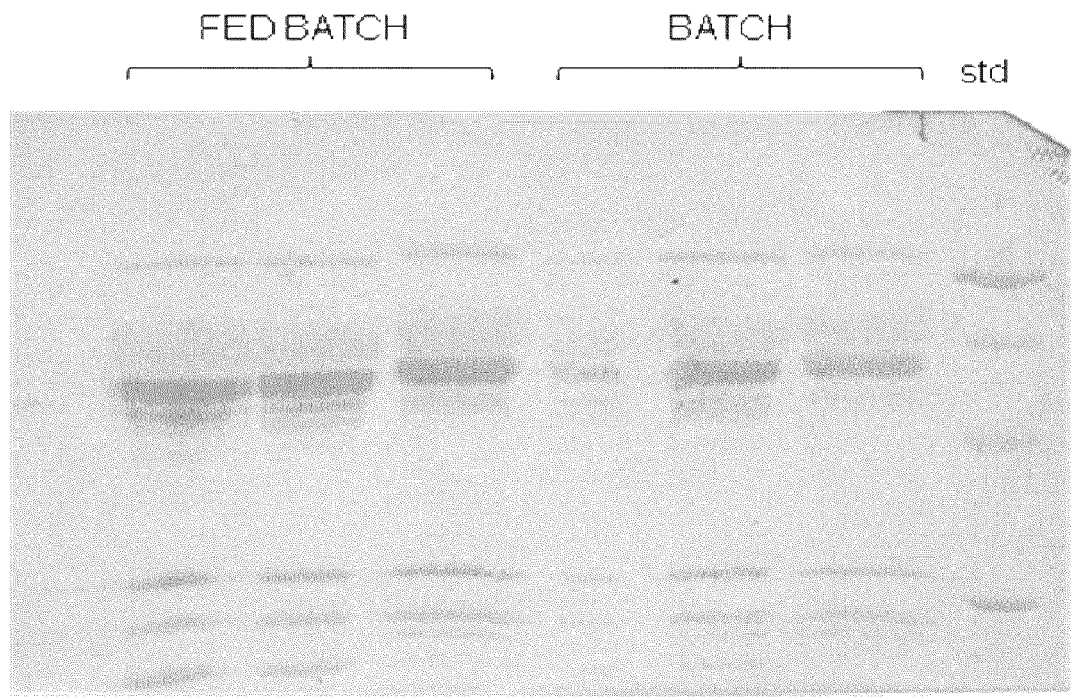
FIG. 6 shows a membrane blot of *T. reesei* M44 secreted proteins.
Figure 7:
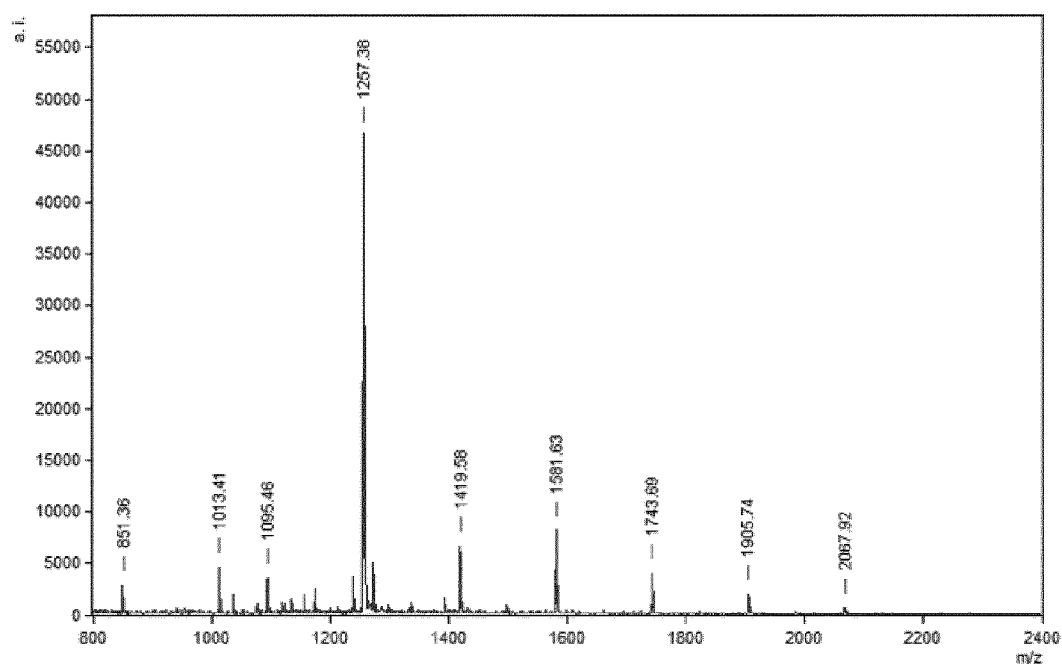
FIG. 7 shows an example of analyzed protein bands of *T. reesei* M44 cultivated in a fermentor. The glycosylation of proteins did not differ significantly from average glycosylation in *T. reesei*. The spectrum was focused to the minor base line signals, and the major signal of the spectrum was not quantitative in comparison to other signals.

To check whether there is variation in glycosylation between individual secreted proteins, the samples from fermentation culture supernatants were separated with SDS-PAGE and blotted to PVDF membrane. The N-glycans of selected bands were then detached with on-membrane enzymatic release. Results are shown in FIGS. 6 and 7.

Conclusions: Neutral Glycans

The purpose of this study was to identify *T. reesei* strains for glycoengineering with the highest amount of Man5 N-glycans and the lowest amount of acidic glycans. Strains which have Man5 as a main peak in mass spectrometry analysis can have higher endogenous α-1,2-mannosidase activity. Based on the background information on *T. reesei* N-glycosylation, the likely structure for Man5 is Manα3[Manα3(Manα6)Manα6]Manβ4GlcNAcβ4GlcNAc (Salovuori et al. 1987; Stals et al. Glycobiology 14, 2004, page 725).

Some strains contained $H_8N_2$ as a major neutral glycoform. Based on the literature, this glycoform is most likely to be a Glcα3Manα2Manα2Man5 structure (Stals et al. Glycobiology 14, 2004, page 725). It is possible that glucosidase deficiency in these strains prevents the trimming of the glycans to the smaller glycoforms.

In some strains, acidic N-glycans were observed in neutral spectra. This situation may have been due to a higher proportion of acidic N-glycans or to leakage of specific structures into the neutral fraction during the separation of neutral glycans from acidic glycans.

The glycan profile of strains was a bit more favorable for glycoengineering when cultivated in a fermentor compared to in shake flasks. The glycosylation of individual proteins from fermentor-cultured samples didn't differ significantly from average glycosylation. All analyzed proteins contained Man5 as a main glycoform. This observation suggested that all secreted proteins go through similar glycan processing. Thus it appeared that the majority of secreted proteins were glycosylated similarly by the $T.$ $reesei$ host cells, which is not always the case with mammalian cells.

Acidic Glycans

The phosphorylation of N-glycan is not generally desired for glycoengineering because the terminal phosphate residue is not present in regular therapeutic proteins, including antibodies. Some exceptions to this rule are a few specialized proteins used for lysosomal glycosylation storage disorders. Phosphorylation of N-glycans may be protein-specific in fungi. In animals, mannose phosphorylation is a conserved lysosomal targeting signal.

To date there have been no reports of sulfation of $T.$ $reesei$ N-glycans. Therefore, the acidic structures referred to in this report were likely to be phosphorylated glycans.

Phosphorylation is more common when $T.$ $reesei$ is cultivated in low pH values, as is the case in flask cultures, which may be related to low pH stress and mycelia breakage (Stals et al., 2004, $Glycobiology$ 14:713-724). In this study a clear difference was observed between flask and fermentor cultured samples. Acidic N-glycans, all phosphorylated, were observed in shake flask culture samples. The amount of acidic N-glycans in fermentor samples may have been below the detection limit, or, because of higher pH there may have been no significant phosphorylation of glycans. The proportion of acidic N-glycans to the total amount of N-glycans could not be verified with the method used in this study due to the different ionization efficiencies between neutral and acidic glycan species.

In order to determine phosphorylation levels, N-glycans were released by N-glycanase from 10 μg of $T.$ $reesei$ secreted protein cultured in batch and fed batch fermentor. Protein concentration was measured using a Bradford-based method with BSA as a standard. One pmol of standard molecule NeuAcHex4HexNAc2 was added to acidic N-glycans samples prior to MALDI-TOF analysis. Amounts of major glycoforms (Hex7HexNAc2P for fermentor and Hex6-8HexNAc2P for flask culture) were 0.9 pmol/10 pg of secreted protein of batch culture, 0.6 pmol/10 pg of secreted protein of fed batch culture, and 160 pmol/10 pg of secreted protein of flask culture when the pH of the culture was allowed to drop. The amount of neutral N-glycans was measured using 10 pmol of standard glycan Hex2HexNAc4 added to neutral N-glycan samples, prior to MALDI-TOF analysis. The amount of major glycoform Hex5HexNAc2 was 87 pmol/10 pg of secreted protein in batch and fed-batch cultures and 145 pmol/10 pg of secreted protein in flask culture. Thus, the proportion of acidic N-glycans to total amount of N-glycans was 1% in batch culture, 0.7% in fed-batch culture and 52% in flask culture. Quantitation was based only on signal intensity comparison using MALDI-TOF data.

N-glycans were also larger in acidic fraction. This may have been due to phospho-mannosylation reactions in which phosphorus with one hexose unit is attached to a glycan backbone. Some diphosphorylated structures were seen in acidic spectra. This explanation is in agreement with the previously published data on phosphorylated glycans found in $T.$ $reesei$ (Stals et al. 2004, Glycobiology 14:725-737). When cultured in a fermentor, the proportion of acidic N-glycans was very low, below the detection limit.

The N-glycan spectra of $T.$ $reesei$ culture media did not reveal contamination of the $T.$ $reesei$ N-glycome with glycans derived from plant material containing medium.

In conclusion, N-glycan analysis of different $T.$ $reesei$ strains revealed that the major glycoform in strains M44, M109, M131, M132 and M124 is Man5 or Manα3[Manα3(Manα6)Manα6]Manβ4GlcNAcβ4GlcNAc. The possible presence of glucose, including H8N2 as a minor component in Man5-producing strains was considered. Two strains (M109 and M131) contained a larger amount of H8N2 than H7N2. The enrichment of H8N2 could have indicated partial glucosidase deficiency.

Strain M44 contained almost no phosphorylated glycans. Leaking acidic glycans observed in neutral glycan fraction as signals at m/z 1521 and m/z 1683 were observed in samples from strains M131, M109, M132 and M124, which indicated higher phosphorylation levels and the presence of potential phosphodiester structures.

The aim of this study was to find a strain with maximal production of Man5Gn2 structure and low-level production of acidic (phosphorylated) N-glycans. The best strains had over 80% of Man5 under pH-controlled shake flask culture conditions. The best strains also had reduced production of di-phosphorylated glycans and/or larger phosphorylated structures (see Table 3).

Example 2

Generation of an Alg3-Deficient $Trichoderma$ Strain

Vector Construction and Strain Generation

The gene encoding the ALG3 mannosyltransferase was identified in the $Trichoderma$ $reesei$ genome sequence. A disruption construct was designed to insert the acetamidase selection marker between 1000 by 5' and 3' flanking region fragments of the alg3 gene. The flanking region fragments were amplified by PCR, and the construct was made by homologous recombination cloning in $Saccharomyces$ $cerevisiae$. The disruption cassette was released from its backbone vector by digestion and transformed into the $T.$ $reesei$ strain M124. Transformants were selected on acetamidase medium and screened by PCR with a forward primer outside the 5' flanking region fragment of the construct and the reverse primer inside the AmdS selection marker.

Screening of Transformants

Figure 8:
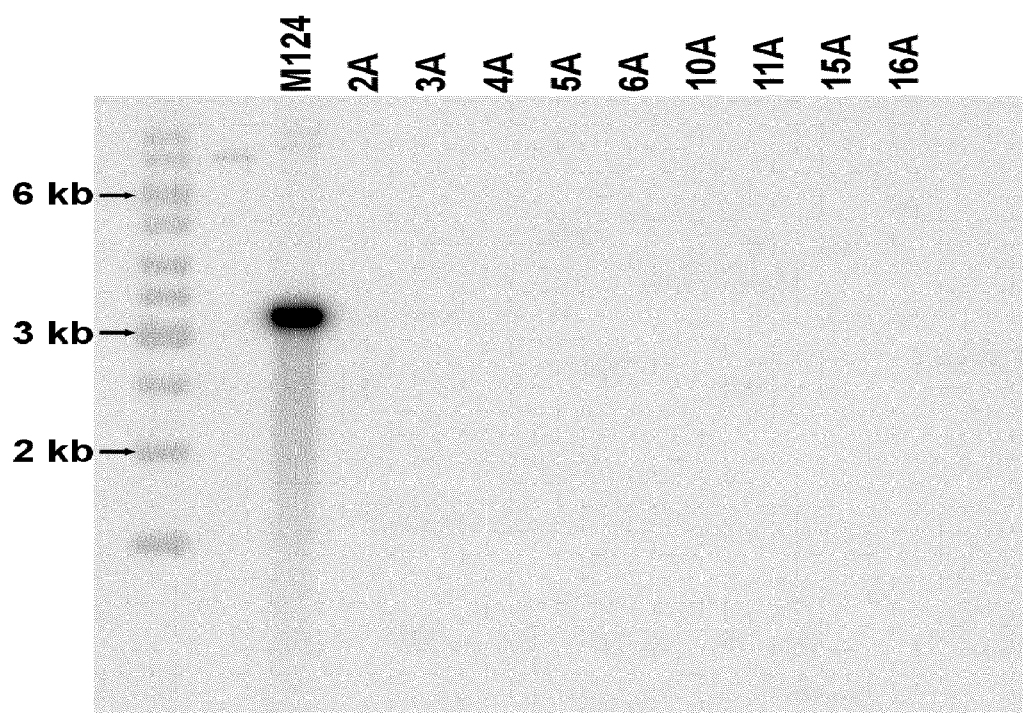
FIG. 8 shows a Southern blot of DNA from the parental strain and from Alg3 knockout strains with an alg3 probe.

Fifty-eight out of 62 screened transformants gave a PCR product of the size expected for integration of the construct to the alg3 locus. Nine PCR-positive transformants were purified to uninuclear clones through single spore cultures, and spore suspensions were made from them. These nine clones were analyzed for the correct integration of the disruption cassette by Southern hybridization. EcoRI-digested genomic DNA from the parental strain and from nine clones was hybridized with an alg3 probe under standard hybridization conditions. The probe hybridized with DNA from the parental strain, but not with DNA from any of the clones, indicating successful deletion of alg3 (FIG. 8).

Figure 9:
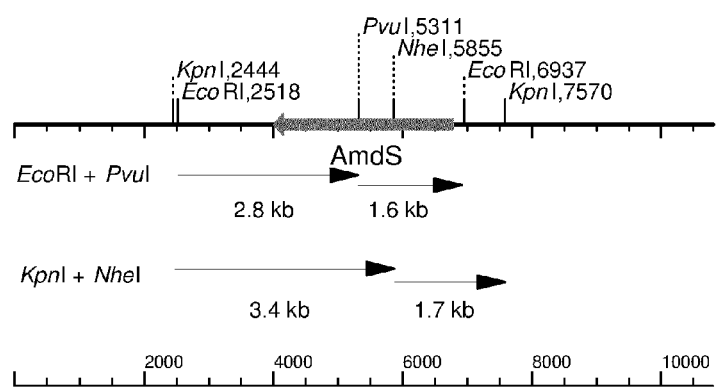
FIG. 9A shows a restriction enzyme map of a section of the pTTv38 construct with sizes of predicted restriction products.
FIG. 9B shows a Southern blot of genomic DNA from the parental strain and the Alg3 knockout strains digested with EcoRI+PvuI (E+P) or KpnI+NheI (K+N). The control DNA was pTTv38 plasmid DNA digested with NotI. The blot was probed with an AmdS probe.
Figure 9:
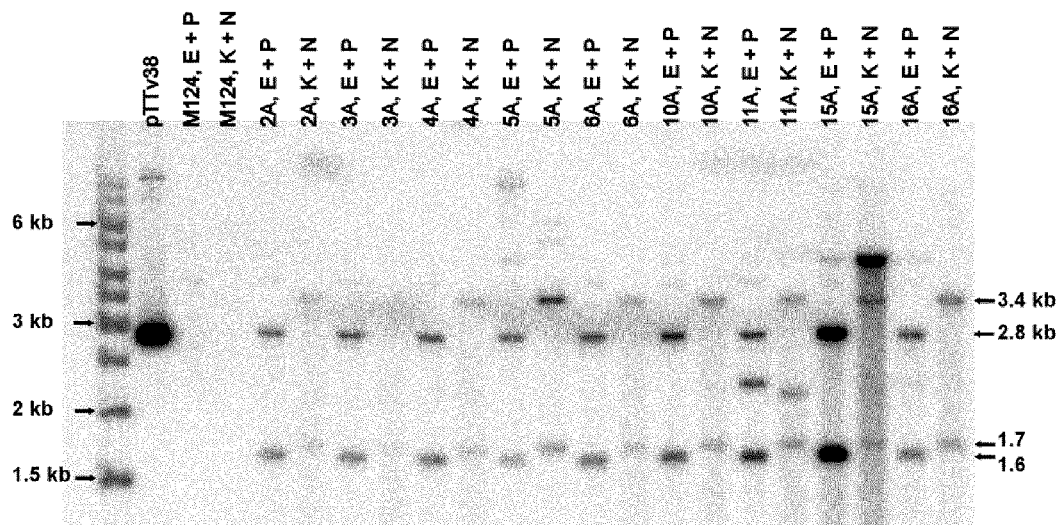

Further analysis was made by Southern hybridization with an AmdS probe. The AmdS gene was included in the deletion cassette and was predicted to be detectable in DNA from the transformants, but not in DNA from the parental strain. Genomic DNA of parental strain M124 and nine transformants was digested with EcoRI+PvuI (E+P) and KpnI+NheI (K+ N). NotI digested plasmid carrying the alg3-AmdS deletion cassette was used as a positive control. The probe recognized the expected ~2.7 kb fragment (AmdS) from the positive control but did not hybridize with the parental strain. All transformants gave the expected signals (1.6+2.8 kb for E+P and 1.7+3.4 kb for K+N, shown with arrows in FIG. 9B) indicating correct integration of the deletion cassette. Clones 11A and 15A also showed hybridization of some additional fragments suggesting unspecific integration of the deletion cassette to the genome (FIG. 9B).

N-glycan Analytics

Shake-flask cultures of five different Alg3 knockout strains (4A, 5A, 6A, 10A and 16A) and parental strain M124 were analyzed for N-glycans. Samples were collected from time points of 3, 5, 7, and 9 days. All cultures were grown as duplicates.

The protein concentration of secreted proteins from a randomly selected knockout strain (4A) from all time points was measured using a Bradford-based assay against a BSA standard curve. The highest protein concentration was detected on day 5. Therefore, day 5 samples were used for N-glycan analysis for all five knockout strains. All samples, including the duplicate cultures, were analyzed as triplicates. Ten pg was used for N-glycan analysis. Both neutral and acidic N-glycans were analyzed by MALDI-TOF.

Figure 10:
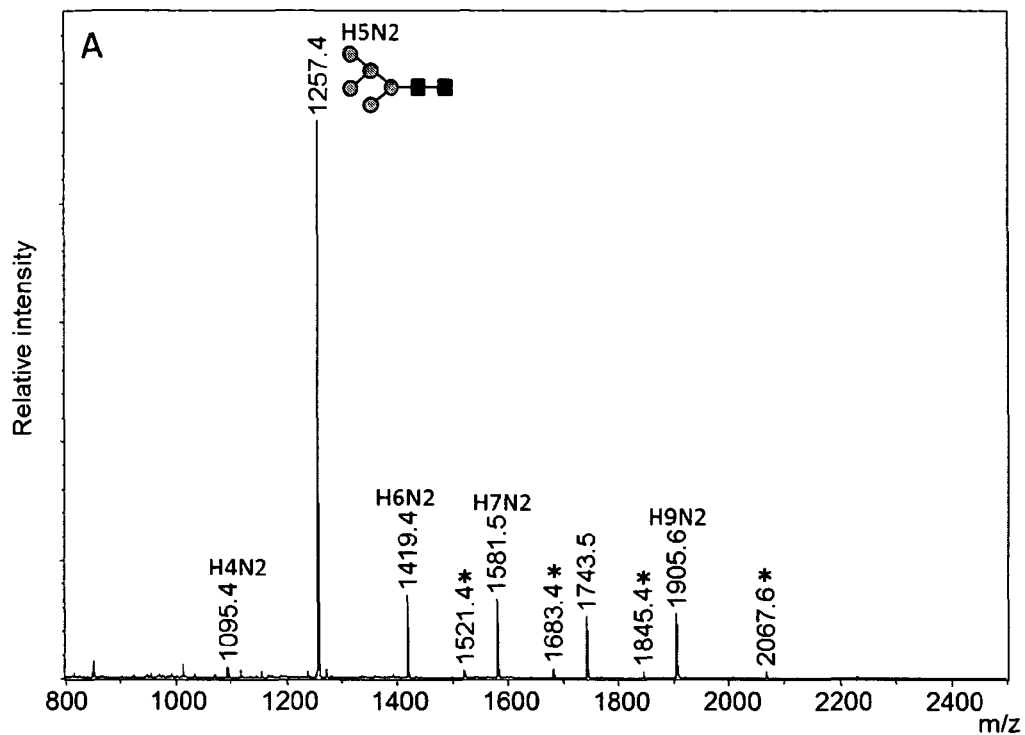
FIG. 10 shows MALDI analysis of neutral N-glycans. Part A shows the parental strain M124. Part B shows the Alg3 knockout 4A. Squares represent N-acetylglucosamine, and circles represent mannose, except for the one labeled glucose.
Figure 10:
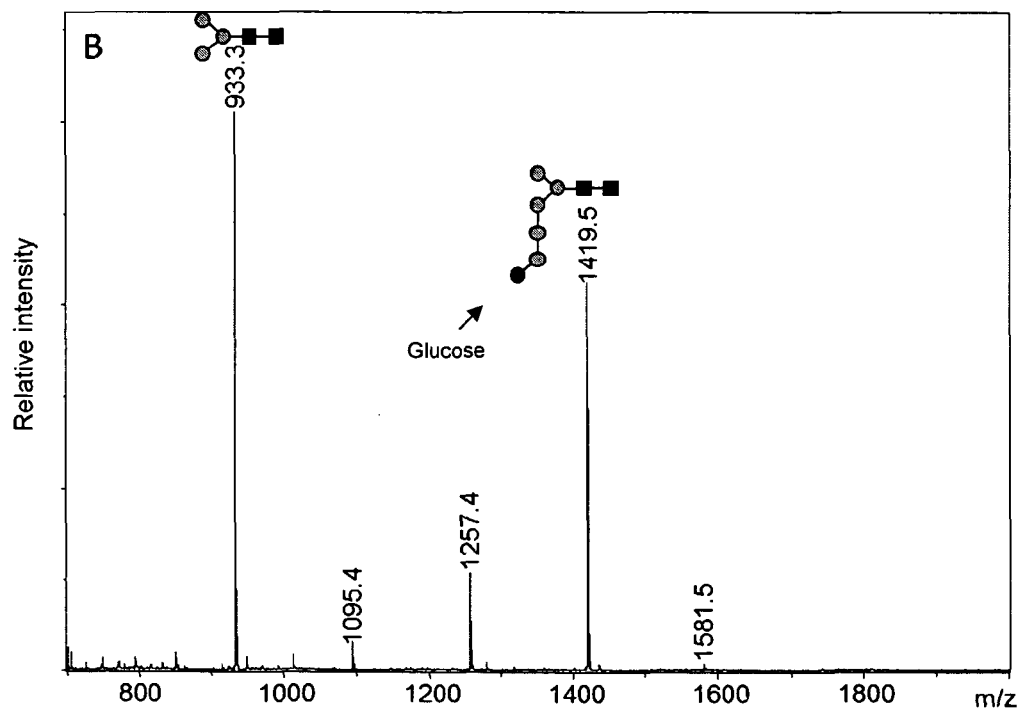
Figure 11:
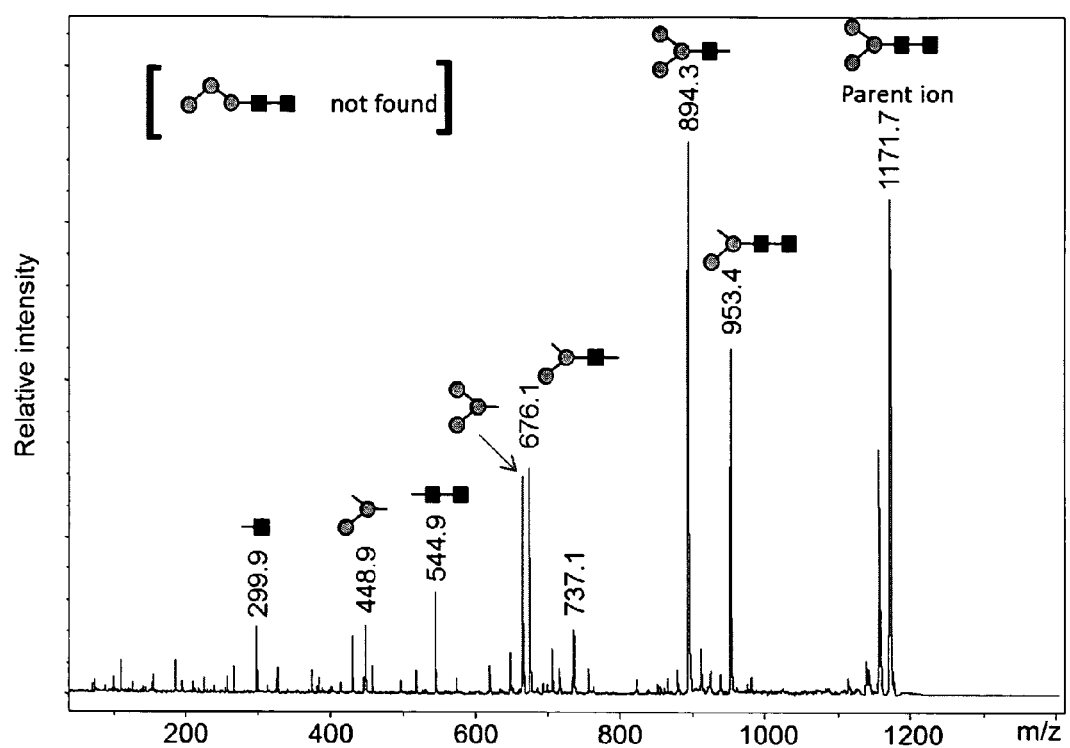
FIG. 11 shows fragmentation analysis of Man3Gn2 from the 4A Alg3 knockout strain.
Figure 12:
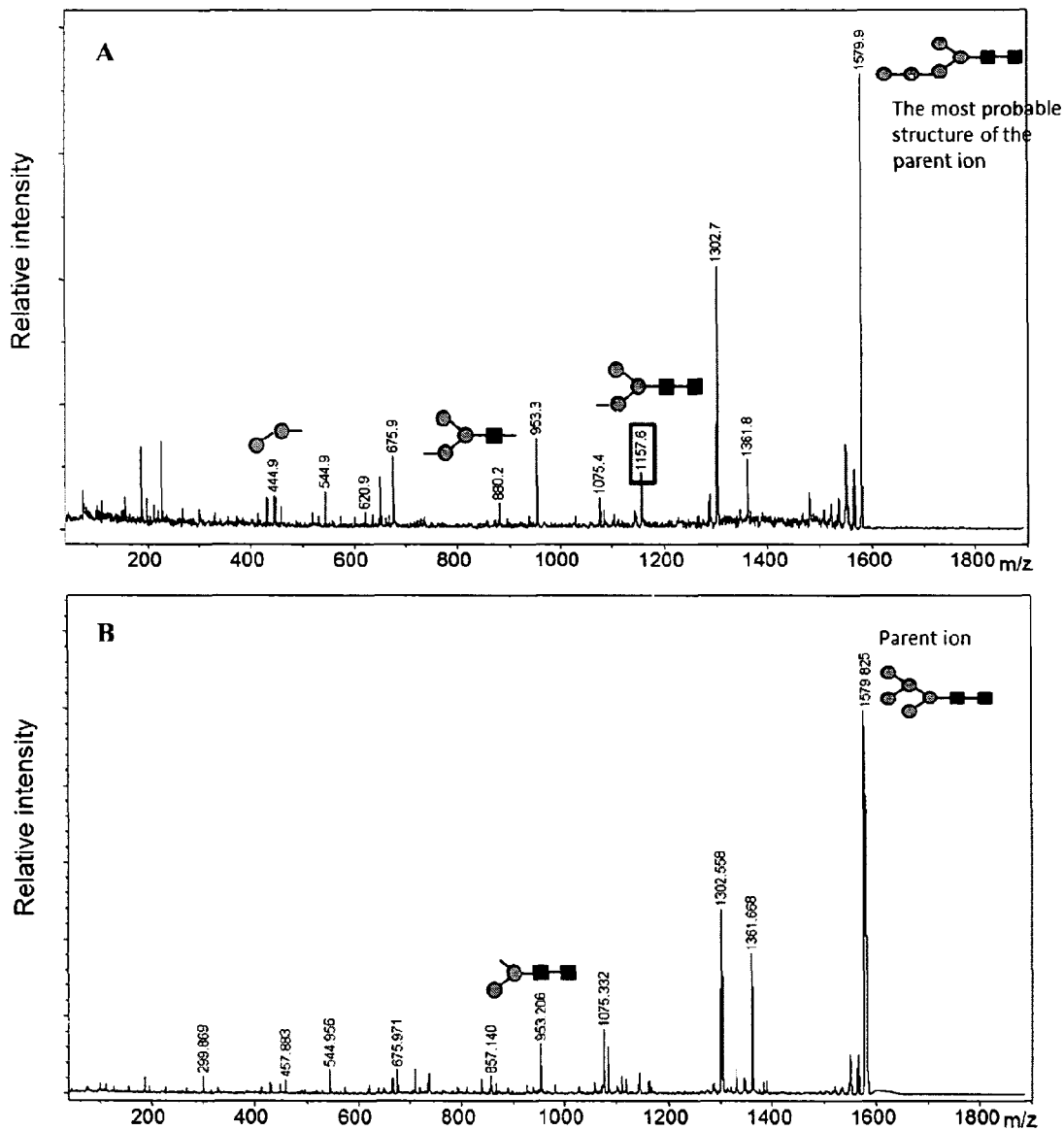
FIG. 12 shows fragmentation analysis of Hex5Gn2 from Alg3 knockout strain 4A (part A) and parental strain M124 (part B). The signal marked with a box exists only as an isomer from the Alg3 knockout strain.

The major glycoform in parental strain M124 was Man5Gn2. In all Alg3 knockout strains the major glycoform was Man3 (FIG. 10). No Man3 was found in the parental strain M124. In different Alg3 knockout strains the amount of Man3 ranged between 49.7%-55.2% in the shake-flask cultures allowing pH drop. Hex6Gn2 was increased in the parental strain. Signal intensities as percentages of observed neutral N-glycan signals are presented in Table 5 below.

mentation using the Bruker Ultraflex III TOF/TOF instrument according to the manufacturer's instructions (FIGS. 11 and 12).

Figure 13:
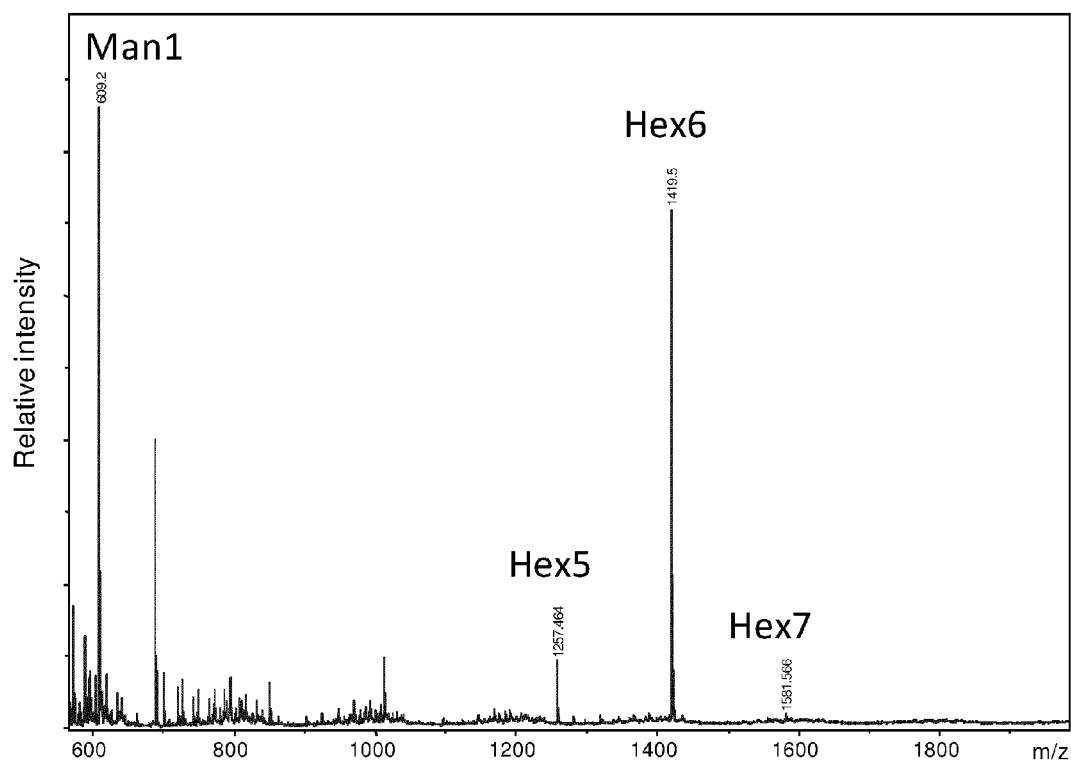
FIG. 13 shows neutral N-glycans from Alg3 knockout strain 4A after α-mannosidase digestion.

Next, it was determined whether the hexose unit on the non-reducing end of the Hex6Gn2 structure is a mannose or a glucose. Alpha-mannosidase digestion was performed on all knockout strains and the parental strain (FIG. 13). Jack bean mannosidase, which cleaves α-mannoses and leaves the β-mannose from backbone untouched, was used. The resulting structure was expected to be Man1Gn2.

Due to low molecular weight range effects in MALDI, the relative intensity of the Man1GlcNAc2 glycan may have been somewhat reduced, which explained a small increase in the relative amount of Hex6. After α-mannosidase digestion, Man3 and Man4 glycoforms disappeared. No Man2 structure was observed. However, Hex6 (m/z 1419) was not digested (Table 6) indicating that there was a glucose unit on the non-reducing end of the structure. Some non-digestible Hex5 was also present, likely produced by a weak reaction removing the sterically hindered Man6-branch of Hex6.

TABLE 6

Neutral N-glycans of Alg3 knockout strain 4A before (native) and after α-mannosidase digestion.

| | | 4A | |
| --- | --- | --- | --- |
| Composition | m/z | Native Average | a-Man'ase % |
| Hex1HexNAc2 | 609.21 | 0.0 | 53.2 |
| Hex2HexNAc2 | 771.26 | 0.0 | 0.0 |
| Hex3HexNAc2 | 933.31 | 47.5 | 0.0 |
| Hex4HexNAc2 | 1095.37 | 3.8 | 0.0 |
| Hex5HexNAc2 | 1257.42 | 11.7 | 5.0 |
| Hex6HexNAc2 | 1419.48 | 36.8 | 41.0 |
| Hex7HexNAc2 | 1581.53 | 0.2 | 0.8 |
| Hex8HexNAc2 | 1743.58 | 0.0 | 0.0 |
| Hex9HexNAc2 | 1905.63 | 0.0 | 0.0 |
| Hex10HexNAc2 | 2067.69 | 0.0 | 0.0 |

For the final analysis of different structures found in the Alg3 knockout strains, a large-scale PNGase F digestion was

TABLE 5

Neutral N-glycan content of Alg3 knockout strains.

| | | Strain | | | | | | | | | | |
| --- | --- | --- | --- | --- | --- | --- | --- | --- | --- | --- | --- | --- |
| | | Parental M124 | | 4A | | 5A | | 6A | | 10A | | 16A | |
| Composition | m\z | Average | STDEV | Average | STDEV | Average | STDEV | Average | STDEV | Average | STDEV | Average | STDEV |
| Hex3HexNAc2 | 933.31 | 0.0 | 0.0 | 53.6 | 0.2 | 55.2 | 4.2 | 49.7 | 0.5 | 53.3 | 0.9 | 53.4 | 0.9 |
| Hex4HexNAc2 | 1095.37 | 1.6 | 0.1 | 2.7 | 0.0 | 2.9 | 0.7 | 3.4 | 0.1 | 3.2 | 0.4 | 3.4 | 0.4 |
| Hex5HexNAc2 | 1257.42 | 70.2 | 3.3 | 8.5 | 0.2 | 7.3 | 1.1 | 10.4 | 0.5 | 8.6 | 0.9 | 9.7 | 0.9 |
| Hex6HexNAc2 | 1419.48 | 7.9 | 1.1 | 35.0 | 0.3 | 34.4 | 1.9 | 36.1 | 0.6 | 34.9 | 0.5 | 33.2 | 0.7 |
| Hex7HexNAc2 | 1581.53 | 7.8 | 0.6 | 0.3 | 0.4 | 0.3 | 0.4 | 0.3 | 0.4 | 0.0 | 0.0 | 0.3 | 0.4 |
| Hex8HexNAc2 | 1743.58 | 5.9 | 0.7 | 0.0 | 0.0 | 0.0 | 0.0 | 0.0 | 0.0 | 0.0 | 0.0 | 0.0 | 0.0 |
| Hex9HexNAc2 | 1905.63 | 6.0 | 0.9 | 0.0 | 0.0 | 0.0 | 0.0 | 0.0 | 0.0 | 0.0 | 0.0 | 0.0 | 0.0 |
| Hex10HexNAc2 | 2067.69 | 0.7 | 0.1 | 0.0 | 0.0 | 0.0 | 0.0 | 0.0 | 0.0 | 0.0 | 0.0 | 0.0 | 0.0 |

Figure 14:
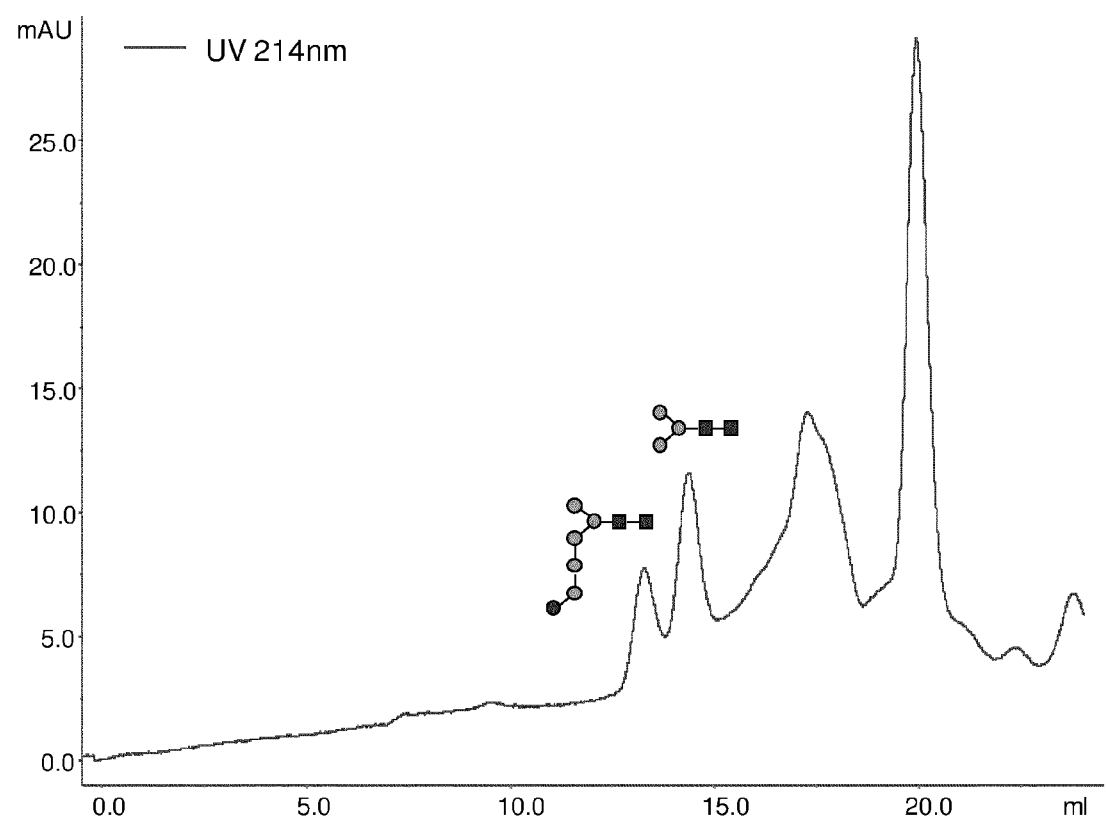
FIG. 14 shows the separation of two major glycans from the Alg3 knockout strain by liquid chromatography.
Figure 15:
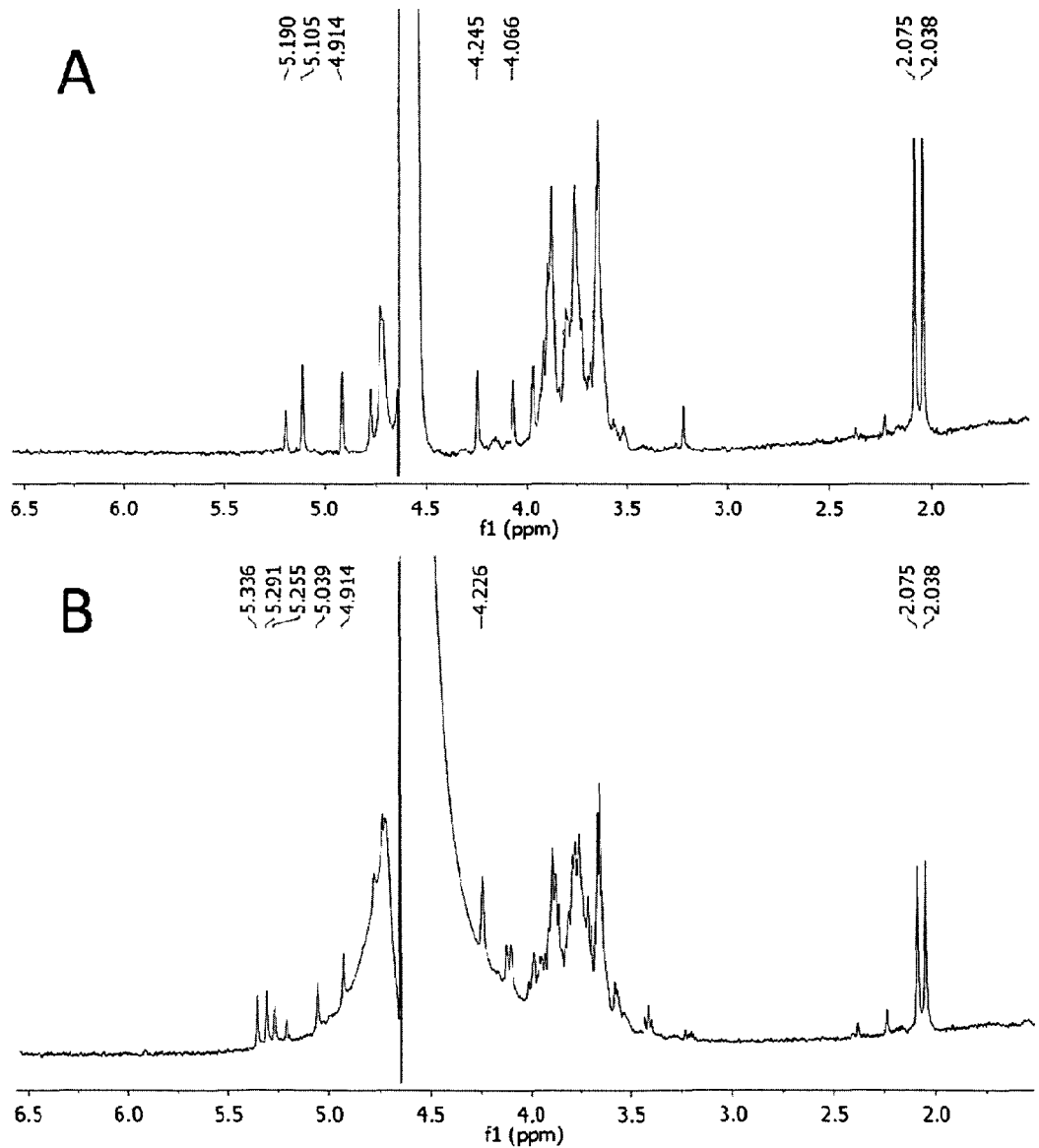
FIG. 15 shows proton NMR spectra of Hex3HexNAc2 (part A) and Hex6HexNAc2 (part B) fractions. Spectra were collected at 40° C. using a Varian Unity INOVA 600 MHz spectrometer equipped with a cryoprobe.

The presence of different isomers of each glycoform cannot be observed by MALDI MS analysis, so further tandem mass spectrometry studies were performed. First, the Man3 and Hex5Gn2 structures were investigated. For Man3 it was asked whether the Man3 structure is branched or linear. For this analysis, a sample containing both these structures was permethylated and analyzed with mass spectrometric fragperformed to Alg3 knockout strain 4A. Two major glycans were purified with HPLC (FIG. 14) and analyzed by NMR (FIG. 15).

Based on the data presented in FIG. 15A, the Hex3HexNAc2 species was unambiguously identified as Manα1-3(Manα1-6)Manβ1-4GlcNAcβ1-4GlcNAc. The Manα3 and Manα6 H-1 units resonated at 5.105 and 4.914 ppm, respectively. The Manβ4 H-2 unit was observed at 4.245 ppm. This signal was very characteristic, due to the neighboring Manα 3-OH substitution. The N-acetyl group —CH₃ signals of the core GlcNAc units were observed at 2.038 and 2.075. These values agreed well with those reported for this pentasaccharide in the Sugabase-database (www.boc-.chem.uu.nl/sugabase/sugabase.html). Moreover, the proton-NMR spectrum was measured for a commercially produced Manα1-3(Manα1-6)Manβ1-4GlcNAcβ1-4GlcNAc (Glycoseparations, Inc.) in identical experimental conditions, and nearly identical chemical shifts were obtained.

The NMR spectrum of the Hex6HexNAc2 component is shown in FIG. 15B. The data implied that this component represents the octasaccharide Glcα1-3Manα1-2Manα1-2Manα1-3 (Manα1-6)Manβ1-4GlcNAcβ1-4GlcNAc. The presence of a glucose unit was evident from the 5.255 signal showing a typical αGlc 2.4 Hz coupling. All Man signals typically show <1 Hz coupling due to the equatorial H-2 configuration. Small differences were observed compared to the Sugabase data (Table 7), which may be ascribed to the different temperature used in the present NMR measurement (40° C. vs. 26° C.).

TABLE 7

Published NMR data of Glcα1-3Manα1-2Manα1-2Manα1-3(Manα1-6)Manβ1-4G1cNAcβ1-4G1cNAc.
Data was obtained from Sugabase (found at boc.chem.uu.nl/sugabase/sugabase).

a-D-Manp-(1-6) +
|
b-D-Manp-(1-4)-b-D-GlcpNAc-(1-4)-D-GlcNAc
|
a-D-Glcp-(1-3)-a-D-Manp-(1-2)-a-D-Manp-(1-2)-a-D-Manp-(1-3) +

| Residue | Linkage | Proton | PPM | J Hz |
|---|---|---|---|---|
| D-GlcNAc |  | H-1a | 5.189 |  |
|  |  | H-1b | 4.694 |  |
|  |  | H-2a | 3.867 |  |
|  |  | H-2b | 3.692 |  |
|  |  | NAc | 2.038 |  |
| b-D-GlcpNAc | 4 | H-1 | 4.606 |  |
|  |  | H-2 | 3.792 |  |
|  |  | NAc | 2.077 |  |
| b-D-Manp | 4, 4 | H-1 | 4.773 |  |
|  |  | H-2 | 4.237 |  |
| a-D-Manp | 6, 4, 4 | H-1 | 4.913 |  |
|  |  | H-2 | 3.964 |  |
| a-D-Manp | 3, 4, 4 | H-1 | 5.346 |  |
|  |  | H-2 | 4.080 |  |
| a-D-Manp | 2, 3, 4, 4 | H-1 | 5.304 |  |
|  |  | H-2 | 4.103 |  |
| a-D-Manp | 2, 2, 3, 4, 4 | H-1 | 5.038 |  |
|  |  | H-2 | 4.224 |  |
| a-D-Glcp | 3, 2, 2, 3, 4, 4 | H-1 | 5.247 |  |
|  |  | H-2 | 3.544 |  |

Finally, the N-glycan profiles of randomly selected knock-out strain 4A were analyzed at different time points (days 3, 5, 7 and 9). The shake flask culture pH was 4.8 at the starting time point and 2.6 at the ending time point. Triplicate samples from every time point of duplicate cultures were analyzed. It was observed that in both duplicates, the relative amount of Man3Gn2 signal decreased as a function of growth time because of the reduction of pH. However, the amount of Hex6Gn2 signal increased as a function of growth time (Table 8).

TABLE 8

The percentages of signal intensities from observed neutral glycan signals of Alg3 4A knockout strain. Duplicate cultures (3A and 4A) from four different time points (days 3, 5, 7 and 9) were analyzed.

| | | Alg3 knock out strain 4A (flask 3A) | | | | | | | |
|---|---|---|---|---|---|---|---|---|---|
| | | Day 3, 3A | | Day 5, 3A | | Day 7, 3A | | Day 9, 3A | |
| Composition | m/z | average | stdev | average | stdev | average | stdev | average | stdev |
| Hex3HexNAc | 730.24 | 0.0 | 0.0 | 0.0 | 0.0 | 0.0 | 0.0 | 0.0 | 0.0 |
| Hex2HexNAc2 | 771.26 | 0.0 | 0.0 | 0.0 | 0.0 | 0.0 | 0.0 | 0.0 | 0.0 |
| Hex3HexNAc2 | 933.31 | 61.7 | 3.7 | 61.3 | 0.8 | 61.1 | 1.9 | 52.7 | 7.7 |
| Hex4HexNAc2 | 1095.37 | 2.6 | 0.2 | 2.5 | 0.1 | 2.1 | 0.4 | 3.7 | 1.0 |

TABLE 8-continued

The percentages of signal intensities from observed neutral glycan signals of Alg3 4A knockout strain. Duplicate cultures (3A and 4A) from four different time points (days 3, 5, 7 and 9) were analyzed.

| Hex5HexNAc2 | 1257.42 | 4.3  | 0.6 | 6.5  | 0.4 | 5.7  | 0.6 | 6.4  | 1.0 |
| Hex6HexNAc2 | 1419.48 | 31.4 | 3.5 | 29.8 | 0.4 | 31.1 | 1.6 | 37.2 | 5.7 |

Alg3 knock out strain 4A (flask 4A)

| Composition | m/z | Day 3, 4A average | stdev | Day 5, 4A average | stdev | Day 7, 4A average | stdev | Day 9, 4A average | stdev |
| --- | --- | --- | --- | --- | --- | --- | --- | --- | --- |
| Hex3HexNAc  | 730.24  | 0.0  | 0.0 | 0.0  | 0.0 | 0.0  | 0.0 | 0.7  | 1.2 |
| Hex2HexNAc2 | 771.26  | 0.0  | 0.0 | 0.0  | 0.0 | 0.0  | 0.0 | 0.3  | 0.5 |
| Hex3HexNAc2 | 933.31  | 61.7 | 3.2 | 58.6 | 1.1 | 55.6 | 1.9 | 54.8 | 5.9 |
| Hex4HexNAc2 | 1095.37 | 3.4  | 1.0 | 2.6  | 0.2 | 3.1  | 0.2 | 2.6  | 0.5 |
| Hex5HexNAc2 | 1257.42 | 5.2  | 1.5 | 6.7  | 0.4 | 7.1  | 0.4 | 7.6  | 3.7 |
| Hex6HexNAc2 | 1419.48 | 29.7 | 0.9 | 32.1 | 0.8 | 34.3 | 1.5 | 34.0 | 3.6 |

A difference between these two analyses (Tables 4 and 7) concerning the percentage of Man3 in clone 4A (Day 5) were noted. This difference may have been due to differences in the analyses procedures. Some lability of the heterogenous culture medium protein preparations was observed after freeze-thaw cycle(s), likely due to glycan and/or protein degradation, resulting in reduced amounts of larger glycans. Generation of the data in Table 5 included additional freeze thaw-cycles.

Figure 16:
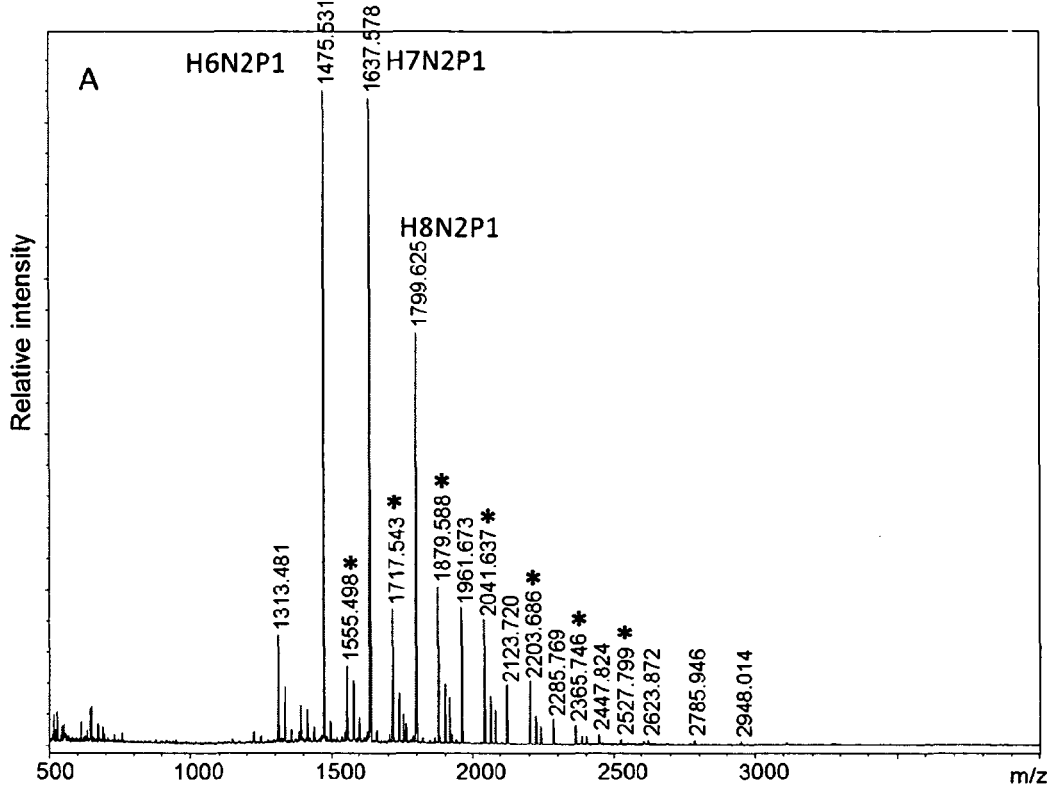
FIG. 16 shows the acidic fraction of parental strain M124 (part A) and Alg3 knockout strain 4A (B). N-glycans with two phosphate units are marked with an asterisk.
Figure 16:
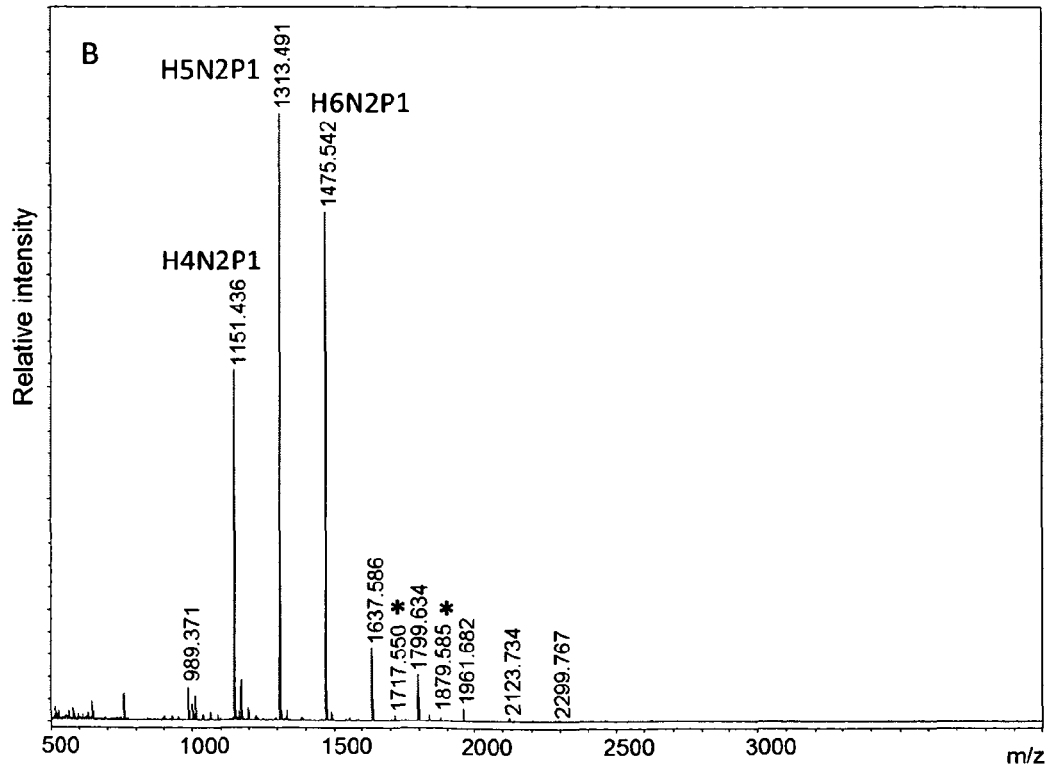

Acidic N-glycan fractions were also analyzed by MALDI (FIG. 16). The abundance of different acidic compounds in parental strain M124 differed from all Alg3 knockout strains, among which the acidic fraction seemed to be very similar.

Three major glycans in the parental strain were H6N2P1, H7N2P1 and H8N2P1. In the Alg3 knockout the size shifted into smaller glycans: H5N2P1, H6N2P1 and H4N2P1. Additionally, diphosphorylated glycans were more abundant in the parental strain. This may have been due to a lack of a suitable substrate for the particular enzyme that attaches phosphorylated mannose to a glycan. The phosphorylated mannose can be further elongated by other mannose residues. Phosphorylation was not substantially present in glycans of the parent M124 strain produced under fermentation conditions.

Comparison of Fermentor and Shake Flask Grown Samples

Figure 17:
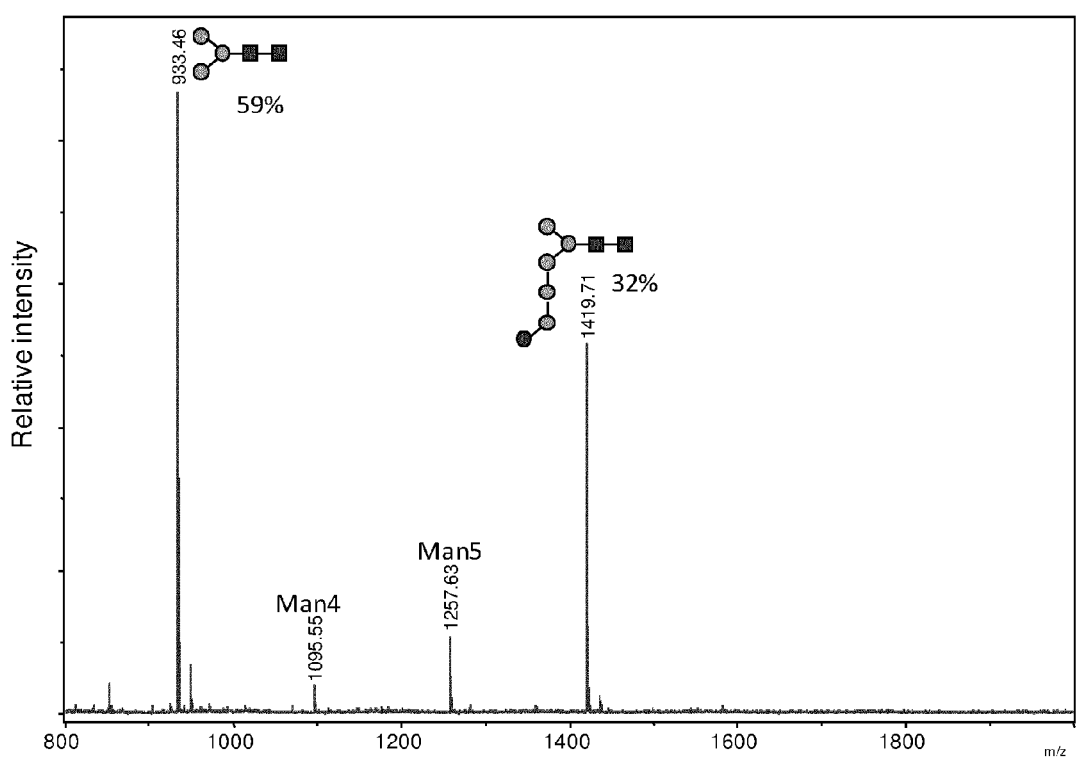
FIG. 17 shows neutral N-glycans from supernatant of *T. reesei* Alg3 knockout strain 4A that was cultured in a flask for 5 days.
Figure 18:
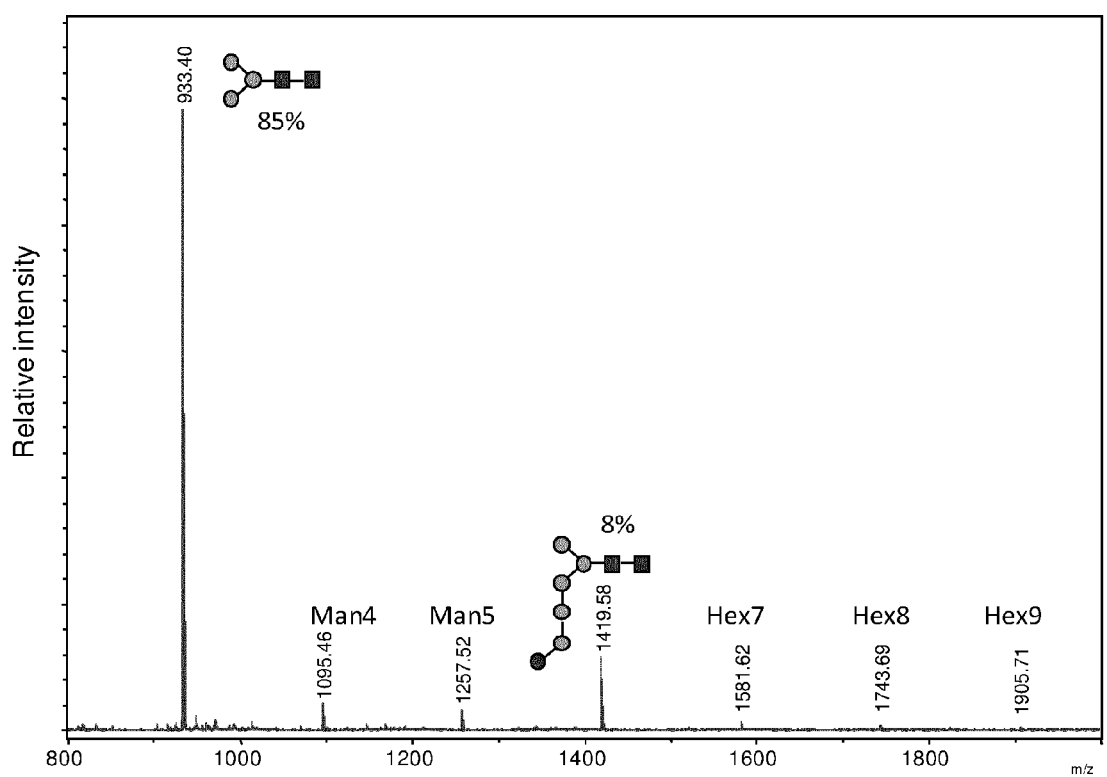
FIG. 18 shows neutral N-glycans from supernatant of *T. reesei* Alg3 knockout strain 4A that was cultured in a fermentor for 10 days.

One Alg3 knockout strain (transformant 4A) was grown in batch fermentation on lactose and spent grain extract medium. The medium was 60 g/l lactose with 20 g/l spent grain extract with a volume of 7 liters (fermentor run bio01616) after inoculation. Other medium components were $KH_2PO_4$ and $(NH_4)_2SO_4$. Culture pH was controlled between 5.5 and 5.8. Biomass and culture supernatant samples were taken during the course of the run and stored at −20° C. Mycelial samples were also collected for possible RNA analysis and were frozen immediately in liquid nitrogen and transferred to −70° C. Samples collected from the whole course of these fermentations were analyzed for N-glycan composition. N-glycan analysis was carried out for fermentor run bio01616) and for the 5 days time point sample from the shake flask culture of transformant 4A (FIGS. 17 and 18). The main signal in the shake flask culture was Man3 (59%). In the fermentor culture, the main signal was Man3 (85%), and the proportion of Hex6 was decreased to 8%.

Conclusions

The Alg3 knockout was successful in producing 50% or more of the expected Man3 glycoform. The desired branched structure of Manα3(Manα6)Manβ- was verified by fragmentation mass spectrometry and NMR spectroscopy.

The other products of the Alg3 knockout included Man4 (mannose-containing minor product), Hex5 (a degradation product of Hex6 as indicated in FIG. 13) and Hex6, which was the second largest component. The Hex6 component was characterized to contain terminal Glc by mannosidase resistance and specific NMR signals including Glcα3Man-terminal. It was considered that the glycan structure could be further optimized by methods for reducing the amount of the terminal Glc, which was likely causing suboptimal efficacy of glucosidase II with the glycan devoid of mannoses on the Manα6-arm of the molecule. Further optimization of fermentation conditions may reduce the amount of terminal Glc.

This data indicated better glycosylation results in the *T. reesei* Alg3 knockout compared to earlier data for Alg3 knockouts in *Aspergillus* (Kainz et al., Appl Environ Microb. 2008 1076-86) and *P. pastoris* (Davidson et al., Glycobiology 2004, 399-407). In the works of Kainz et al. and Davidson et al., similar or higher Hex6 corresponding product levels were reported. Those studies also reported additional problems with α2-Mannose, $OCH_1$ products and larger size, and cell type-specific glycans produced by *P. pastoris*. In conclusion, N-glycan analysis of *T. reesei* Alg3 knockouts revealed that the major glycoform in the knockout strains is Man3Gn2, a desired starting point for efficient generation of mammalian-type N-glycans.

Example 3

Purification and Activity of Individual GnTI and GnTII Enzymes

Human GnTI and GnTII (N-acetylglucosaminyltransferase I and N-acetylglucosaminyltransferase II) were expressed as soluble, secreted proteins in *Pichia pastoris* in order to study their acceptor specificity and activity.

Generation of GnTI Construct for Production in *P. Pastoris*

Human GnTI (P26572) sequence was obtained as a full-length sequence and subcloned into *Trichoderma reesei* overexpression vectors. Protein coding sequences (CDS) encoding the soluble part of human GnTI were cloned to the pBLARG-SX expression vector in order to produce a secreted form of the protein in *Pichia pastoris* for enzymatic studies. During the cloning procedure, a His tag encoding sequence was added to 5' end of the frame to obtain a tag at the N-terminus of the truncated protein. The sequence was verified by sequencing analysis. Resulting vector pTTg5 was linearized and transformed by electroporation to *P. pastoris* GY190 cells to yield strain GY4. Arg$^+$ transformants were picked and screened by PCR. GY4 clones containing the integrated plasmid were tested for protein expression.

Expression and Purification of Soluble GnTI

*P. pastoris* strain GY4 expressing soluble GnTI was first grown overnight with shaking at +30° C. in BMGY medium (1% yeast extract, 2% peptone, 100 mM potassium phosphate pH 6.0, 1.34% yeast nitrogen base, 4×10-5% biotin, 1% glycerol) to $OD_{600}$ 2-6. The cells were then harvested by centrifugation and resuspended to $OD_{600}$ of 1 in BMMY medium (like BMGY, but with 0.5% methanol instead of 1% glycerol). The culture was placed in a baffled flask and returned to a shaking incubator at +16° C. 100% methanol was added to a final concentration of 0.5% every 24 h to maintain induction. 1 ml samples of the expression culture were taken 0, 24, 48, and 72 hours after induction, and both the cell pellets and the supernatants were stored for analysis. After 3 days of induction, the cells from the whole culture were harvested by centrifugation, and the supernatant was collected for further purification of GnTI.

Preparation of Crude GnTI Sample for Activity Assay

*Pichia pastoris* cell culture, which contained soluble His-tagged GnTI was processed for activity assay by concentration and buffer exchange. In brief, 40 ml of *P. pastoris* supernatant from shake flask culture was harvested at day 3 after induction with MeOH by pelleting the cells in 50 ml Falcon tube (Eppendorf 5810R, 3220 rcf, 5 min at +4° C.) and collecting the supernatant. The supernatant was then concentrated to <2.5 ml by sequential centrifugations (Eppendorf 5810R or comparable, 3220 rcf, 10 min at +4° C.) with Millipore Amicon Ultracel 30K concentrator. The volume of the concentrate was adjusted to 2.5 ml with 100 mM MES, pH 6.1. Concentrate was subjected to buffer exchange with a PD-10 gel filtration column (GE Healthcare 17-0851-01). The column was first equilibrated with 100 mM MES, pH 6.1 and then the sample (2.5 ml) was added, flow-through was discarded and elution with 2.25 ml of MES buffer was collected. Finally, 500 μl of the eluate was concentrated to 100 μl with Millipore Biomax 30K concentrator (Eppendorf 5417, 12 000 rcf, 5 min+4° C.) and used directly in activity assays.

Activity Assay of GnTI Enzyme

Manα1-6(Manα1-3)Manβ1-4GlcNAc (Man$_3$Gn) was used as an acceptor for GnTI in the GnTI activity assay. The GnTI reaction was carried out by incubating the reaction mixture, which contained 0.1 mM acceptor Man$_3$GlcNAc, 20 mM UDP-GlcNAc, 50 mM GlcNAc, 100 mM MnCl$_2$, 0.5% BSA and 8 μl GnTI in 100 mM MES, pH 6.1, in a total volume of 10 μl at room temperature overnight. The reaction was stopped by incubating the reaction at 100° C. for 5 min.

In parallel to the GnTI activity assay, the possible HexNAc'ase activity in the crude enzyme preparation was controlled. GlcNAcβ1-2Manα1-6(GlcNAcβ1-2Manα1-3) Manβ1-4GlcNAcβ1-4GlcNAc-Asn (=Gn$_2$Man$_3$Gn$_2$-Asn) was used as a substrate for HexNAc'ase. The reaction was carried out in a similar way as for GnTI, except 100 pmol of Gn$_2$Man$_3$Gn$_2$-Asn was added instead of Man$_3$Gn and UDP-GlcNAc. No HexNAc'ase activity was detected.

The reaction mixture was purified for MALDI analysis by sequential Hypersep C18 (100 mg, Thermo Scientific, cat no: 60300-428) and Hypercarb (10 mg/96 well plate/1 PKG, cat no 60302-606) chromatography on HyperSep 96-well Vacuum Manifold, Thermo Scientific. Hypersep $C_{18}$ was prepared with 300 μl EtOH and 300 μl MQ water, the collection plate was then put under, and samples were loaded and eluted with 150 μl MQ water. Hypercarb was prepared with 300 μl MeOH and 300 μl MQ water. Eluates from Hypersep C18 were loaded, salts were removed with 150 μl 0.5 M NH$_4$Ac, and wells were washed with 2×300 μl MQ water. GnTI reaction products were eluted with 150 μl 25% ACN, and HexNAc'ase reaction products were eluted with 25% ACN and 0.05% TFA. Samples were dried in a Speedvac.

Figure 19:
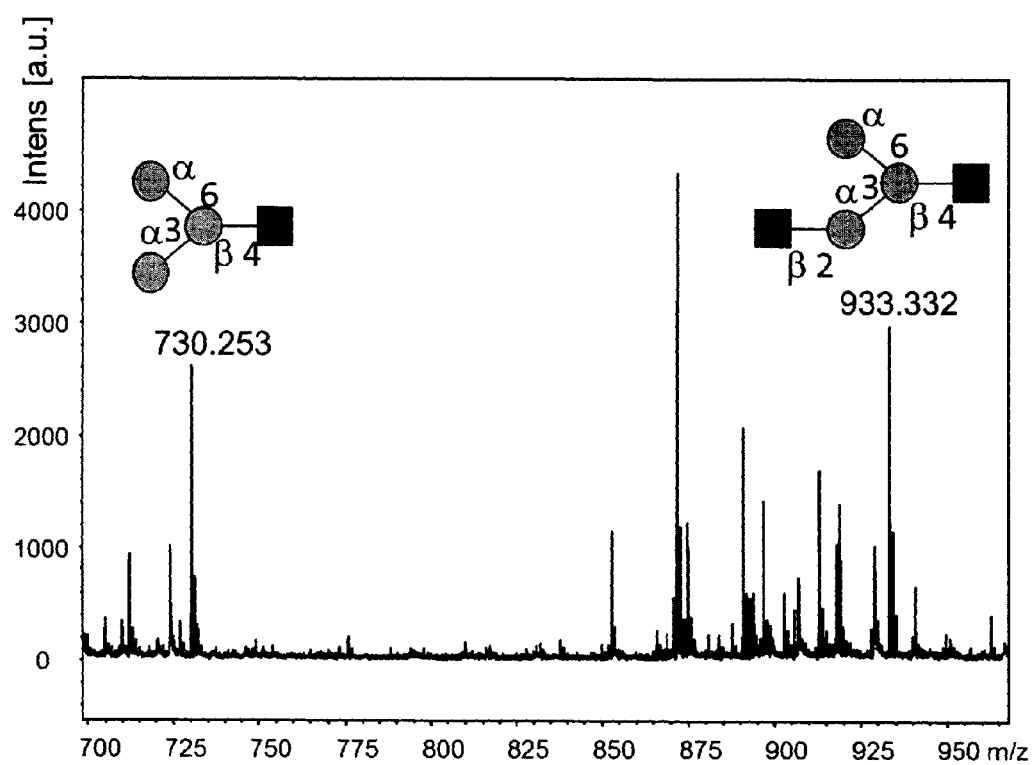
FIG. 19 shows a MALDI spectrum of GnTI reaction mixture. GnTI has converted 54% of the acceptor to the product with one additional HexNAc.

Matrix-assisted laser desorption-ionization time-of-light (MALDI-TOF) mass spectrometry (MS) was performed with a Bruker Ultraflex TOF/TOF instrument (Bruker Daltonics, Germany). Acceptor saccharide and product were detected in positive ion reflector mode as [M+Na]+ ions. Calculated m/z values for [M+Na]+-signals of Hex$_3$HexNAc$_1$ and Hex$_3$ HexNAc$_2$ were 733.238 and 933.318, respectively. The percent ratio of the acceptor and the product was calculated from the signals corresponding to Hex$_3$HexNAc$_1$ and Hex$_3$ HexNAc$_2$ (FIG. 19).

Generation of GnTII Construct for Production in *P. pastoris*

Figure 20:
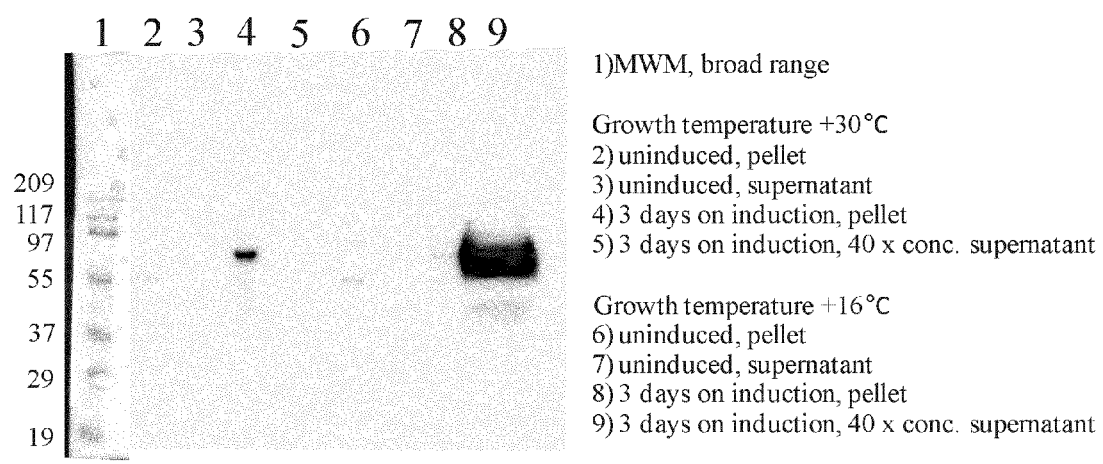
FIG. 20 shows Western blot analysis of GnTII expression. Samples were run in 12% SDS-PAGE gel and blotted on nitrocellulose membrane. Histidine-tagged GnTII was detected on the membrane using mouse α-HIS monoclonal antibodies. Numbers shown on the left are the sizes of molecular weight marker proteins (kDa).

The nucleotide sequence encoding human GnTII was PCR-amplified with primers GP3 and GP13, which contained KpnI and EcoRI restriction sites, respectively. The EcoRI/KpnI-digested PCR fragment was ligated to a similarly digested pBLARG-SX cloning vector. After verifying the sequence, the final construct was transformed to *P. pastoris* strain GS190 to yield strain GY22. Positive yeast transformants were screened by PCR. Two clones (only one of which is shown in FIG. 20) were studied for expression of GnTII under the control of the methanol-inducible AOX1 promoter at +16° C. and at +30° C.

Expression of Soluble GnTII

According to Western blot analysis (FIG. 20), *P. pastoris* strain GY22 produced soluble recombinant GnTII enzyme. GnTII has a calculated molecular mass of 49049.0 Da and two predicted N-glycosylation sites. The recombinant GnTII was secreted into the culture medium at +16° C. (lane 9). When grown at +30° C., the recombinant GnTII was arrested inside the cells (lane 4).

Activity Assays of Soluble GnTII

*P. pastoris* cell culture containing soluble His-tagged GnTII was processed for an activity assay as described for GnTI above. Cell culture was centrifuged, supernatant was harvested and concentrated, buffer exchange to 100 mM MES, pH 6.1 was conducted, and the resulting sample was further concentrated prior to activity testing.

The activity assay was carried out similarly as for GnTI. GnMan3Gn was used as a GnTII acceptor.

The GnTII reaction was carried out in the presence of 0.1 mM acceptor GnMan3Gn, 20 mM UDP-GlcNAc, 50 mM GlcNAc, 100 mM MnCl$_2$, 0.5% BSA, and GnTII in 100 mM MES, pH 6.1. Purification of the reaction mixture for MALDI-TOF MS analysis was performed by sequential Hypersep C18 and Hypercarb chromatography on a 96-well plate on vacuum manifold as described for GnTI above.

MALDI-TOF MS was performed with a Bruker Ultraflex TOF/TOF instrument (Bruker Daltonics, Germany). Acceptor saccharide and product were detected in positive ion reflector mode as [M+Na]+ ions. Ratio of the product and acceptor at the end of the reaction was calculated from their signal intensities (calculated m/z values for [M+Na]+ signals of GnMan3Gn acceptor and product with one GlcNAc addition are 933.318 and 1136.397, respectively).

Cultivation of *P. pastoris* producing GnTII was repeated, and GnTII concentrate (60×) from supernatant was prepared and its activity measured according to the methods described above. MALDI spectrum of time point samples at 2.5 h, 5 h, and overnight showed that 80%, 83%, and 82% of the acceptor was converted to product, respectively. The close-to-maximum reaction was reached in 2.5 hours.

Figure 21:
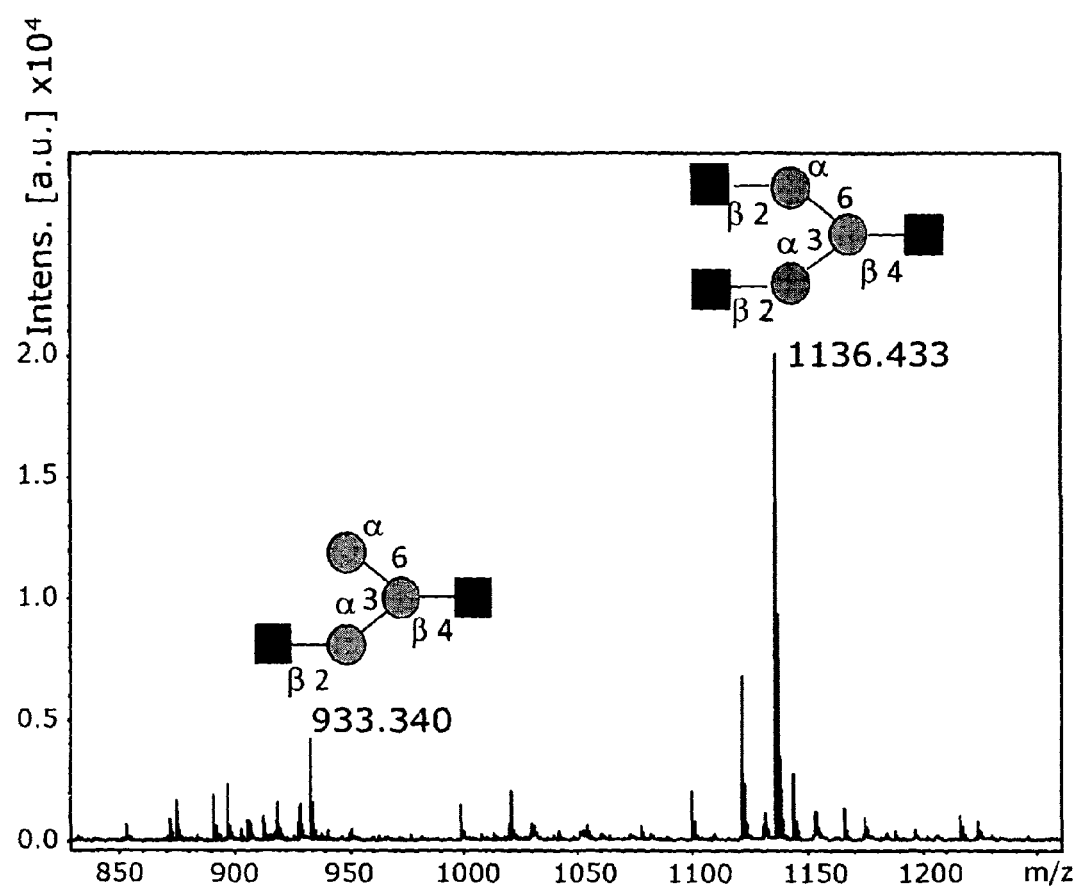
FIG. 21 shows a MALDI spectrum of GnTII reaction mixture. 83% of the acceptor (m/z 913.340) was converted to product (m/z 1136.433).

In addition, a crude GnTII sample was prepared, and the activity assay was carried out as described above for the crude GnTI sample. The reaction mixture was incubated overnight, purified, and subjected to MALDI analysis. MALDI spectra revealed GnTII activity (FIG. 21). HexNAc'ase activity was not detected in the crude GnTII sample.

The methods used to synthesize a GnTII acceptor for use in the above-described GnTII activity assays were as follows. A GnTI sample was prepared from a *P. pastoris* cultivation medium as described above. This GnTI sample showed high GnTI activity and, therefore, it could be used in conversion of about 40 nmol of Man3Gn to GnMan3Gn. The reaction was carried out in the presence of 0.5 mM Man3Gn, 20 mM UDP-GlcNAc, 50 mM GlcNAc, 100 mM $MnCl_2$, 0.5% BSA, and GnTI sample. The reaction mixture was incubated three days at room temperature. A sample of ~1% was subjected to purification by Hypercarb chromatography and MALDI analysis. The GnTI reaction converted almost all of Man3Gn acceptor to GnMan3Gn product according to MALDI spectrum. Only 2.8% of the acceptor was not converted.

Example 4

GnTI/GnTII Fusion Protein

Generation of GnTI/GnTII Expression Construct

A recombinant GnTI/II fusion protein was constructed by amplifying a 1313 by GnTII fragment with a 65-mer fusion primer at the 5'-end, which contained an in-frame fusion site (a short sequence from GnTI containing a naturally occurring AleI restriction site with the stop-codon removed and overlapped with GnTII sequence) and 3'-end primers homologous to GntII containing either SpeI or NdeI restriction sites. This fusion site allowed the cloning of a fusion fragment directly to a *T. reesei* overexpression vector with wild type GnTI under the control of the cbh1 promoter (cloning with AleI/NdeI) or with wild type GnTI under the control of the gpd promoter (cloning with AleI/SpeI). High-fidelity Phusion polymerase (Finnzymes) and standard amplification and cloning procedures were used. The sequence was verified by sequencing directly from expression vectors. The resulting vector was used to express the fusion as a transmembrane protein in *T. reesei*.

To gain more information on the functionality of the fusion proteins, fusion GnTI/II proteins were also expressed as soluble proteins in *P. pastoris*. CDS of the GnTI/II fusion encoding the soluble part of the protein was cloned to the pBLARG-SX expression vector in order to produce protein for enzymatic studies. During the cloning procedure, His tag encoding sequence was added to the 5'-end of the frame to obtain a tag at the N-terminus of the truncated protein. The sequence was verified by sequencing analysis. The resulting vector was linearized and transformed by electroporation to *P. pastoris* strain GS190 to yield strain GY6. Arg$^+$ transformants were picked and screened by PCR. *P. pastoris* clones containing the integrated plasmid were tested for protein expression.

Purification of Soluble GnTI/II Produced in *P. pastoris*

Expression in *P. pastoris* and purification procedures were carried out as described above with recombinant GnTI protein.

Enzyme Activity Tests of GnTI/II Fusion Protein

Figure 22:
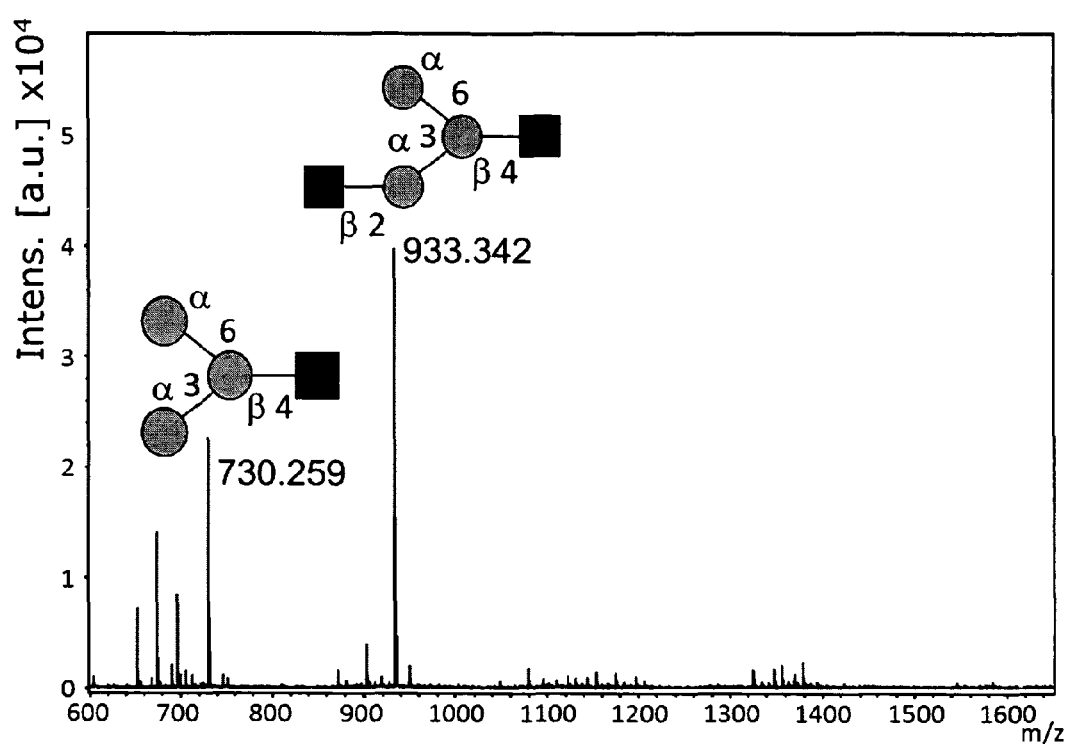
FIG. 22 shows GnTI activity observed for the GnTI/GnTII fusion protein.

Activity assays were carried out as described above for GnTI assays using Man3Gn oligosaccharide as an acceptor and UDP-GlcNAc donor. The products of the reaction were analyzed by MALDI-TOF mass spectrometry. Only GnTI activity was observed for the GnTI/GnTII fusion protein (FIG. 22).

Transformation of *T. reesei* with GnTI/GnTII Construct by Random Integration

A chimeric human GnTI/GnTII plasmid with a gpdA promoter was co-transformed into the *T. reesei* M124 strain with random integration. Selection was obtained by co-transformation of a plasmid containing an acetamidase marker gene. Twenty PCR positive transformants were purified to uninuclear clones and grown in shake flask cultures for glycan analysis. All transformants and the parental strain M124 were cultivated in *Trichoderma* minimal medium (TrMM), pH 4.8, supplemented with 4% lactose and 2% spent grain extract. Supernatant and mycelia samples were collected on days 3, 5, and 7, and were stored frozen until analysis. In addition, as a control, *T. reesei* was transformed with a GnTI construct by random integration.

Glycan Analysis of *T. reesei* GnTI/GnTII Strains Obtained by Random Integration Samples from 20 different clones at three different time points (days 3, 5 and 7) from *T. reesei* strain M124 GnTI/GnTII transformants were analyzed. Samples from two parental M124 strains were analyzed for controls. N-glycanase reactions without SDS denaturation were performed in 96-well plates in triplicate for 5 µg of supernatant protein. The protein concentration of the supernatants was measured by Bradford-based assay (Bio-Rad Quick Start Bradford Protein Assay) using BSA as a standard. Both neutral and acidic N-glycans were analyzed by MALDI-TOF MS. No Go product was detected using the GnTI/GnTII construct in any of the clones at any time point as well as in clones of GnTI transformants with gpdA promoter.

Transformation of *T. reesei* with GnTI/GnTII Construct by Targeted Integration

A chimeric GnTI/GnTII sequence was subcloned into a pTTv38 backbone, a vector that contains an acetamidase marker gene and 5'- and 3'-flanking sequence sites for alg3 locus integration. The vector was transformed into *T. reesei* M124 strain as a digested fragment. From this transformation, 18 PCR positive transformants, yielding PCR fragments indicating correct integration to the alg3 locus, were detected. These transformants were cultured in shake flasks after a single spore purification step and were analyzed as described below.

Glycan Analysis of *T. reesei* GnTI/GnTII Strains Obtained by Targeting to alg3 Locus Supernatant samples of 10 different clones at three different time points (days 3, 5 and 7) of Δalg3 *T. reesei* GnTI/GnTII transformants were obtained. Clones had been cultivated in shake flasks with two different media compositions. TrMM, pH 5.5, with 2% spent grain extract, 4% lactose, and K-phthalate buffering was used for all clones and, in parallel, TrMM, pH 5.5, with 2% spent grain extract, 4% lactose, 1% casamino acids, and K-phthalate buffering was used for five of the clones. Cultivation was continued for 7 days: 5 days at +28° C. and days 6 and 7 at +24° C.

N-glycan analyses were made in triplicate in 96-well plates for 5 µg of supernatant protein. Samples were analyzed from days 3, 5, and 7. The protein concentration of the supernatants was measured by Bradford-based assay (Bio-Rad Quick Start Bradford Protein Assay) using BSA as a standard. Both neutral and acidic N-glycans were analyzed by MALDI-TOF MS.

Figure 23:
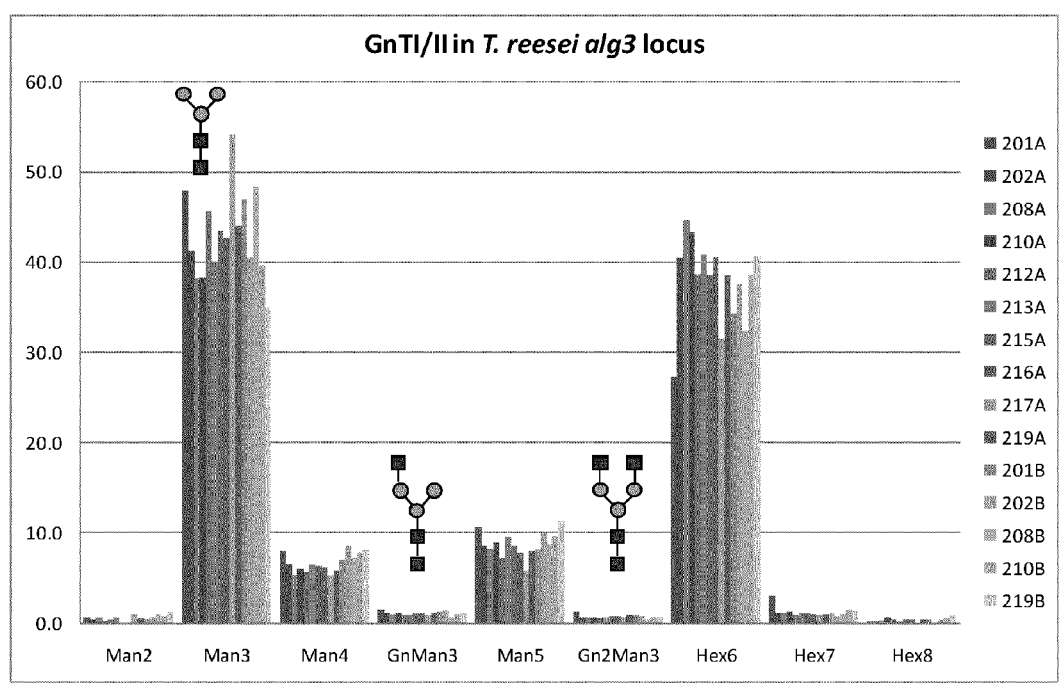
FIG. 23 shows the N-glycans present in GnTI/GnTII *T. reesei* transformants obtained by targeting to the alg3 locus.

Detectable amounts of glycoform G0 were found in every clone. Clone 201A contained the most with 1.2% of Gn2Man3 (FIG. 23 and Table 9). In addition, the amount of Hex6 was lowest in this particular clone. The second medium with 1% casamino acids did not give any extra production of G0/GlcNAcβ2Manα3(GlcNAcβ2-GlcNAcβ2Manα6)Manβ4GlcNAcβ4GlcNAcβ. The results of the days 3 and 7 samples were essentially the same as for the day 5 sample.

TABLE 9

The signal intensity percentages of observed N-glycans from secreted proteins of T. reesei GnTI/II transformants (GnTI/II integrated into the alg3 locus). Clones with letter A in their name were cultivated in medium A) and clones with B in medium B), which had an extra 1% casamino acids compared to medium A).

| | | clone 201A, day 5 | | | | | clone 202A, day 5 | | | | | clone 208A, day 5 | | | | |
|---|---|---|---|---|---|---|---|---|---|---|---|---|---|---|---|---|
| Composition | m\z | Average | SD | RSD | MIN | MAX | Average | SD | RSD | MIN | MAX | Average | SD | RSD | MIN | MAX |
| Man2 | 771.3 | 0.6 | 0.5 | 86.8 | 0.0 | 1.0 | 0.4 | 0.7 | 173.2 | 0.0 | 1.1 | 0.6 | 0.6 | 92.3 | 0.0 | 1.1 |
| Man3 | 933.3 | 47.9 | 14.5 | 30.2 | 39.0 | 64.6 | 41.3 | 0.2 | 0.4 | 41.1 | 41.5 | 38.2 | 1.1 | 2.8 | 37.0 | 38.9 |
| Man4 | 1095.4 | 7.9 | 2.9 | 36.5 | 5.9 | 11.3 | 6.4 | 0.6 | 8.7 | 6.0 | 7.0 | 5.3 | 0.2 | 4.0 | 5.0 | 5.5 |
| GnMan3 | 1136.4 | 1.4 | 0.7 | 46.9 | 1.0 | 2.2 | 1.1 | 0.3 | 23.5 | 0.8 | 1.3 | 1.0 | 0.2 | 17.0 | 0.9 | 1.2 |
| Man5 | 1257.4 | 10.5 | 2.5 | 23.5 | 8.7 | 13.3 | 8.6 | 0.8 | 9.7 | 7.7 | 9.4 | 8.2 | 0.3 | 4.0 | 7.8 | 8.5 |
| Gn2Man3 | 1339.5 | 1.2 | 0.8 | 69.1 | 0.6 | 2.2 | 0.6 | 0.1 | 21.0 | 0.5 | 0.8 | 0.6 | 0.1 | 21.5 | 0.5 | 0.7 |
| Hex6 | 1419.5 | 27.3 | 23.7 | 86.7 | 0.0 | 42.0 | 40.5 | 0.6 | 1.5 | 39.9 | 41.1 | 44.7 | 0.7 | 1.6 | 43.9 | 45.2 |
| Hex7 | 1581.5 | 2.9 | 3.0 | 103.3 | 1.1 | 6.4 | 1.0 | 0.1 | 11.0 | 1.0 | 1.2 | 1.1 | 0.1 | 11.7 | 1.0 | 1.2 |
| Hex8 | 1743.6 | 0.1 | 0.2 | 173.2 | 0.0 | 0.4 | 0.2 | 0.3 | 173.2 | 0.0 | 0.5 | 0.3 | 0.2 | 87.0 | 0.0 | 0.4 |

| | | clone 210A, day 5 | | | | | clone 212A, day 5 | | | | | clone 213A, day 5 | | | | |
|---|---|---|---|---|---|---|---|---|---|---|---|---|---|---|---|---|
| Composition | m\z | Average | SD | RSD | MIN | MAX | Average | SD | RSD | MIN | MAX | Average | SD | RSD | MIN | MAX |
| Man2 | 771.3 | 0.1 | 0.2 | 173.2 | 0.0 | 0.4 | 0.4 | 0.4 | 86.8 | 0.0 | 0.7 | 0.6 | 0.6 | 94.4 | 0.0 | 1.1 |
| Man3 | 933.3 | 38.2 | 1.1 | 3.0 | 37.5 | 39.5 | 45.6 | 1.3 | 2.8 | 44.2 | 46.8 | 40.0 | 2.8 | 7.0 | 37.3 | 42.9 |
| Man4 | 1095.4 | 6.0 | 0.4 | 6.6 | 5.5 | 6.2 | 5.6 | 0.3 | 5.1 | 5.4 | 5.9 | 6.5 | 0.6 | 8.8 | 6.0 | 7.1 |
| GnMan3 | 1136.4 | 1.1 | 0.1 | 8.9 | 1.0 | 1.2 | 0.9 | 0.2 | 22.4 | 0.7 | 1.1 | 0.9 | 0.1 | 8.5 | 0.8 | 1.0 |
| Man5 | 1257.4 | 8.9 | 0.3 | 3.7 | 8.6 | 9.3 | 7.2 | 0.5 | 7.0 | 6.8 | 7.7 | 9.5 | 0.4 | 3.8 | 9.1 | 9.8 |
| Gn2Man3 | 1339.5 | 0.6 | 0.1 | 17.5 | 0.6 | 0.8 | 0.5 | 0.1 | 11.9 | 0.5 | 0.6 | 0.6 | 0.1 | 18.3 | 0.5 | 0.7 |
| Hex6 | 1419.5 | 43.2 | 0.7 | 1.6 | 42.7 | 44.0 | 38.6 | 1.2 | 3.0 | 37.4 | 39.7 | 40.7 | 2.5 | 6.1 | 38.2 | 43.2 |
| Hex7 | 1581.5 | 1.2 | 0.0 | 3.7 | 1.2 | 1.2 | 0.8 | 0.0 | 4.1 | 0.8 | 0.8 | 1.0 | 0.1 | 10.8 | 0.9 | 1.2 |
| Hex8 | 1743.6 | 0.6 | 0.3 | 57.0 | 0.3 | 1.0 | 0.4 | 0.1 | 34.8 | 0.3 | 0.5 | 0.1 | 0.2 | 173.2 | 0.0 | 0.3 |

| | | clone 215A, day 5 | | | | | clone 216A, day 5 | | | | | clone 217A, day 5 | | | | |
|---|---|---|---|---|---|---|---|---|---|---|---|---|---|---|---|---|
| Composition | m\z | Average | SD | RSD | MIN | MAX | Average | SD | RSD | MIN | MAX | Average | SD | RSD | MIN | MAX |
| Man2 | 771.3 | 0.0 | 0.0 | 0.0 | 0.0 | 0.0 | 0.0 | 0.0 | 0.0 | 0.0 | 0.0 | 0.9 | 0.0 | 5.0 | 0.9 | 1.0 |
| Man3 | 933.3 | 43.4 | 1.9 | 4.4 | 41.3 | 45.1 | 42.6 | 2.0 | 4.6 | 40.5 | 44.4 | 54.1 | 1.1 | 1.9 | 53.0 | 55.0 |
| Man4 | 1095.4 | 6.3 | 0.5 | 8.5 | 5.7 | 6.8 | 6.1 | 0.6 | 10.3 | 5.4 | 6.7 | 5.2 | 0.3 | 6.5 | 4.9 | 5.5 |
| GnMan3 | 1136.4 | 1.1 | 0.1 | 6.9 | 1.0 | 1.2 | 1.1 | 0.2 | 14.1 | 0.9 | 1.2 | 0.9 | 0.2 | 17.4 | 0.7 | 1.0 |
| Man5 | 1257.4 | 8.5 | 0.4 | 4.2 | 8.2 | 8.9 | 7.7 | 0.6 | 8.4 | 7.0 | 8.3 | 5.8 | 0.1 | 2.6 | 5.6 | 5.9 |
| Gn2Man3 | 1339.5 | 0.7 | 0.2 | 29.3 | 0.6 | 1.0 | 0.7 | 0.2 | 26.4 | 0.5 | 0.9 | 0.7 | 0.1 | 14.7 | 0.6 | 0.7 |
| Hex6 | 1419.5 | 38.5 | 1.8 | 4.6 | 37.4 | 40.5 | 40.5 | 1.7 | 4.2 | 39.0 | 42.4 | 31.5 | 1.5 | 4.7 | 30.5 | 33.3 |
| Hex7 | 1581.5 | 1.1 | 0.1 | 4.5 | 1.1 | 1.2 | 1.0 | 0.1 | 6.4 | 0.9 | 1.0 | 0.9 | 0.1 | 12.9 | 0.8 | 1.0 |
| Hex8 | 1743.6 | 0.4 | 0.3 | 88.5 | 0.0 | 0.6 | 0.4 | 0.3 | 87.6 | 0.0 | 0.6 | 0.0 | 0.0 | 0.0 | 0.0 | 0.0 |

| | | clone 219A, day 5 | | | | | clone 201B, day 5 | | | | | clone 202B, day 5 | | | | |
|---|---|---|---|---|---|---|---|---|---|---|---|---|---|---|---|---|
| Composition | m\z | Average | SD | RSD | MIN | MAX | Average | SD | RSD | MIN | MAX | Average | SD | RSD | MIN | MAX |
| Man2 | 771.3 | 0.5 | 0.4 | 96.7 | 0.0 | 0.9 | 0.4 | 0.7 | 173.2 | 0.0 | 1.1 | 0.6 | 1.1 | 173.2 | 0.0 | 1.8 |
| Man3 | 933.3 | 44.0 | 1.8 | 4.1 | 42.4 | 45.9 | 46.9 | 0.2 | 0.5 | 46.6 | 47.1 | 40.6 | 1.7 | 4.3 | 38.6 | 41.8 |
| Man4 | 1095.4 | 5.7 | 0.1 | 1.5 | 5.6 | 5.8 | 6.9 | 0.9 | 12.7 | 6.0 | 7.8 | 8.5 | 0.9 | 10.0 | 7.7 | 9.4 |
| GnMan3 | 1136.4 | 1.0 | 0.2 | 16.6 | 0.9 | 1.2 | 1.2 | 0.4 | 32.1 | 0.9 | 1.6 | 1.3 | 0.4 | 0.0 | 0.9 | 1.8 |
| Man5 | 1257.4 | 8.0 | 1.2 | 15.6 | 6.7 | 9.2 | 8.1 | 0.5 | 5.7 | 7.8 | 8.6 | 10.0 | 0.6 | 6.2 | 9.5 | 10.6 |
| Gn2Man3 | 1339.5 | 0.9 | 0.1 | 14.2 | 0.8 | 1.0 | 0.8 | 0.1 | 7.1 | 0.8 | 0.9 | 0.7 | 0.5 | 70.8 | 0.3 | 1.3 |
| Hex6 | 1419.5 | 38.5 | 1.1 | 2.8 | 37.3 | 39.2 | 34.2 | 0.7 | 2.1 | 33.8 | 35.1 | 37.5 | 1.1 | 2.8 | 36.7 | 38.7 |
| Hex7 | 1581.5 | 1.0 | 0.2 | 15.4 | 0.8 | 1.1 | 1.1 | 0.1 | 5.2 | 1.0 | 1.2 | 0.8 | 0.7 | 86.9 | 0.0 | 1.2 |
| Hex8 | 1743.6 | 0.4 | 0.1 | 17.9 | 0.3 | 0.5 | 0.4 | 0.3 | 90.7 | 0.0 | 0.7 | 0.0 | 0.0 | 0.0 | 0.0 | 0.0 |

| | | clone 208B, day 5 | | | | | clone 210B, day 5 | | | | | clone 219B, day 5 | | | | |
|---|---|---|---|---|---|---|---|---|---|---|---|---|---|---|---|---|
| Composition | m\z | Average | SD | RSD | MIN | MAX | Average | SD | RSD | MIN | MAX | Average | SD | RSD | MIN | MAX |
| Man2 | 771.3 | 0.9 | 0.8 | 87.1 | 0.0 | 1.5 | 0.8 | 0.7 | 86.7 | 0.0 | 1.2 | 1.2 | 0.1 | 10.3 | 1.0 | 1.3 |
| Man3 | 933.3 | 48.4 | 1.2 | 2.4 | 47.3 | 49.6 | 39.6 | 1.1 | 2.7 | 38.6 | 40.8 | 34.9 | 1.8 | 5.2 | 33.2 | 36.8 |
| Man4 | 1095.4 | 7.2 | 0.2 | 2.2 | 7.0 | 7.3 | 7.9 | 0.6 | 8.0 | 7.3 | 8.5 | 8.1 | 0.3 | 4.1 | 7.8 | 8.4 |
| GnMan3 | 1136.4 | 0.6 | 0.6 | 92.1 | 0.0 | 1.1 | 1.0 | 0.1 | 12.7 | 0.9 | 1.1 | 1.1 | 0.1 | 12.1 | 1.0 | 1.2 |
| Man5 | 1257.4 | 8.7 | 0.7 | 7.6 | 7.9 | 9.1 | 9.6 | 0.2 | 2.0 | 9.4 | 9.8 | 11.3 | 0.8 | 7.5 | 10.7 | 12.3 |
| Gn2Man3 | 1339.5 | 0.4 | 0.2 | 44.3 | 0.2 | 0.6 | 0.6 | 0.2 | 32.4 | 0.4 | 0.8 | 0.6 | 0.1 | 13.9 | 0.5 | 0.6 |
| Hex6 | 1419.5 | 32.4 | 0.4 | 1.4 | 32.1 | 32.9 | 38.5 | 0.3 | 0.8 | 38.3 | 38.9 | 40.6 | 0.7 | 1.8 | 39.8 | 41.1 |
| Hex7 | 1581.5 | 1.0 | 0.2 | 15.5 | 0.8 | 1.1 | 1.5 | 0.1 | 8.2 | 1.4 | 1.6 | 1.4 | 0.2 | 13.5 | 1.2 | 1.5 |
| Hex8 | 1743.6 | 0.4 | 0.4 | 87.7 | 0.0 | 0.7 | 0.5 | 0.5 | 92.4 | 0.0 | 0.9 | 0.8 | 0.1 | 16.3 | 0.7 | 0.9 |

Example 5

GnTII/GnTI Fusion Protein

Generation of GnTII/GnTI Expression Construct

A GnTII/GnTI fusion expression construct was generated by applying PCR overlap techniques. Fusion fragments were amplified from GnTII and GnTI templates separately with primers containing 50 bp in-frame overlaps at the fusion site. Fragments were purified from an agarose gel and used as PCR template for amplification of the fusion construct according to standard procedures. The fusion construct was cloned into a vector with ApaI/SpeI restriction sites. The resulting construct was verified by sequencing analysis. A vector was generated for expressing the soluble form of GnTII/GnTI in *P. pastoris* with His tagging at the N-terminus of the target protein. This vector was generated in a similar manner as described above for the GnTI/II fusion construct.

Purification of Soluble GnTII/GnTI Produced in *P. pastoris*

Expression in *P. pastoris* and purification procedures were carried out as described above for recombinant GnTI protein.

Enzyme Activity Tests of GnTII/GnTI Fusion Protein

Figure 24:
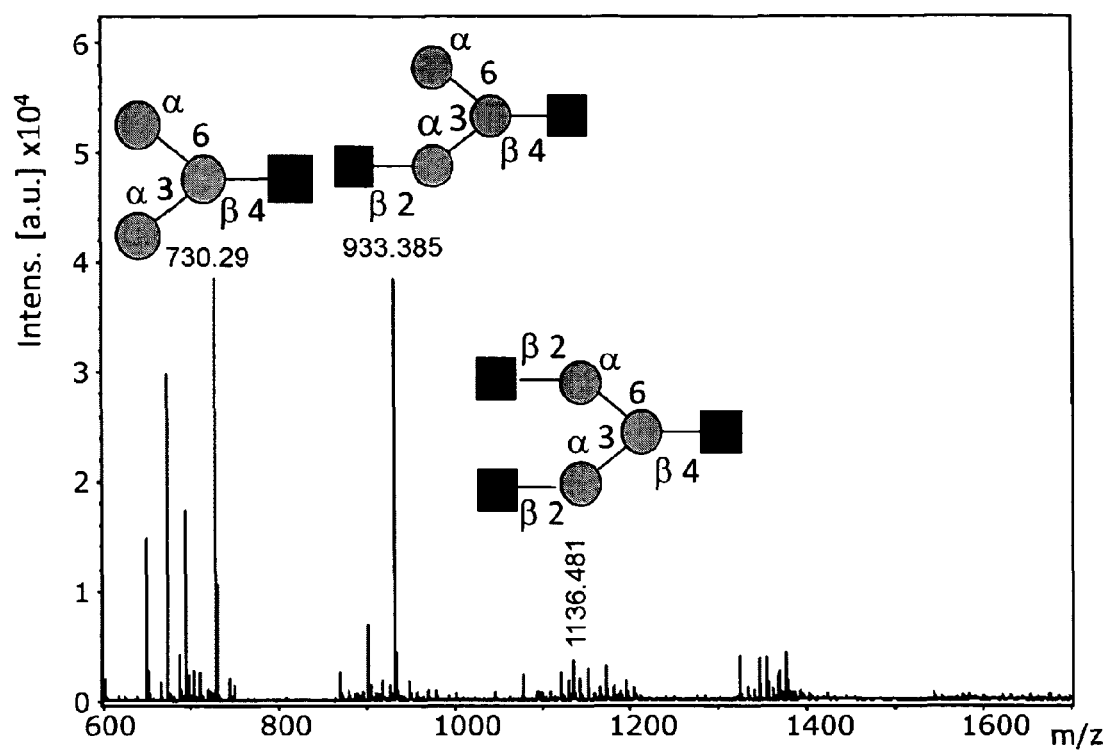
FIG. 24 shows a MALDI spectrum of the purified reaction mixture from the enzyme activity test of the GnTII/GnTI fusion protein.

Activity assays were carried out as described above for GnTI using Man3Gn oligosaccharide as an acceptor. A MALDI spectrum of the purified reaction mixture from the GnTII/GnTI reaction showed that two GlcNAcβ-residues were transferred to the acceptor (FIG. 24).

and 2% spent grain extract. In addition, seven transformants and the parental strain were cultivated in TrMM, pH 5.5, with 4% lactose, 2% spent grain extract, and 1% casamino acids, buffered with 100 mM PIPPS (piperazine1, 4bis2propanesulfonic acid). pH measurements were used to monitor the growth rate of the strains. Supernatant and mycelia samples were collected on days 3, 5, and 7, stored frozen, and analyzed for glycan structures. The GnTII/GnTI sequence was also cloned into a plasmid containing the cbh1 promoter. In addition, as a control, *T. reesei* was transformed with a GnTI construct by random integration.

Glycan Analysis of *T. reesei* GnTII/GnTI Strains Obtained by Random Integration 156 supernatant samples of *T. reesei* strain M124 GnTII/GnTI transformants and parental M124 strain cultivated in two different media were analyzed. The first medium was TrMM, pH 4.8, supplemented with 2% spent grain extract and 4% lactose, and the second medium was TrMM, pH 5.5, supplemented with 2% spent grain extract, 4% lactose, 100 mM PIPPS, and 1% casamino acids. Cells were grown in both types of media for 3, 5 and 7 days.

N-glycanase reactions without SDS denaturation were carried out in 96-well plates in triplicate for 5 µg of supernatant protein for samples from time points of 3 and 5 days. The protein concentration of the supernatants was measured by Bradford-based assay (Bio Rad Quick Start Bradford Protein Assay) using BSA as a standard. Both neutral and acidic N-glycans were analyzed by MALDI-TOF MS.

TABLE 10

Summary of GnTII/GnTI fusion protein activities.

| GnTII/GnTI transformant | Acceptor concentration | Products formed (Gn1Man3Gn) | Products formed (Gn2Man3Gn) |
|---|---|---|---|
| Transformant 1 | 0.5 mM | 47% | 5% |
| Transformant 1 | 0.1 mM | — | 11% |
| Transformant 2 | 0.5 mM | 3% | 2.4% |

Characterization by β-N-acetylglucosaminidase

Figure 25:
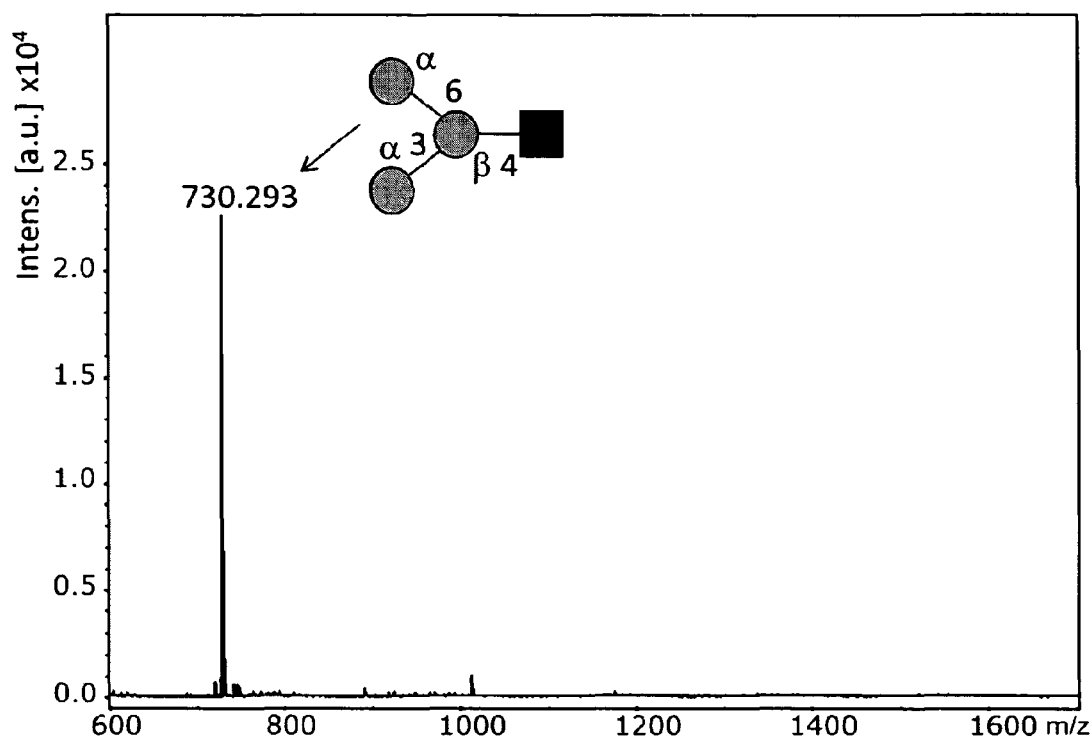
FIG. 25 shows a spectrum of the β1-2,3,4,6-N-acetylglucosaminidase reaction mixture.

The mixture formed in the GnTII/GnTI activity reaction was treated with β1-2,3,4,6-N-acetylglucosaminidase from *Streptococcus pneumoniae*. MALDI MS analysis was used to determine that both transferred β-linked GlcNAc residues were cleaved (FIG. 25).

Galactosylation by β1-4GalT

Figure 26:
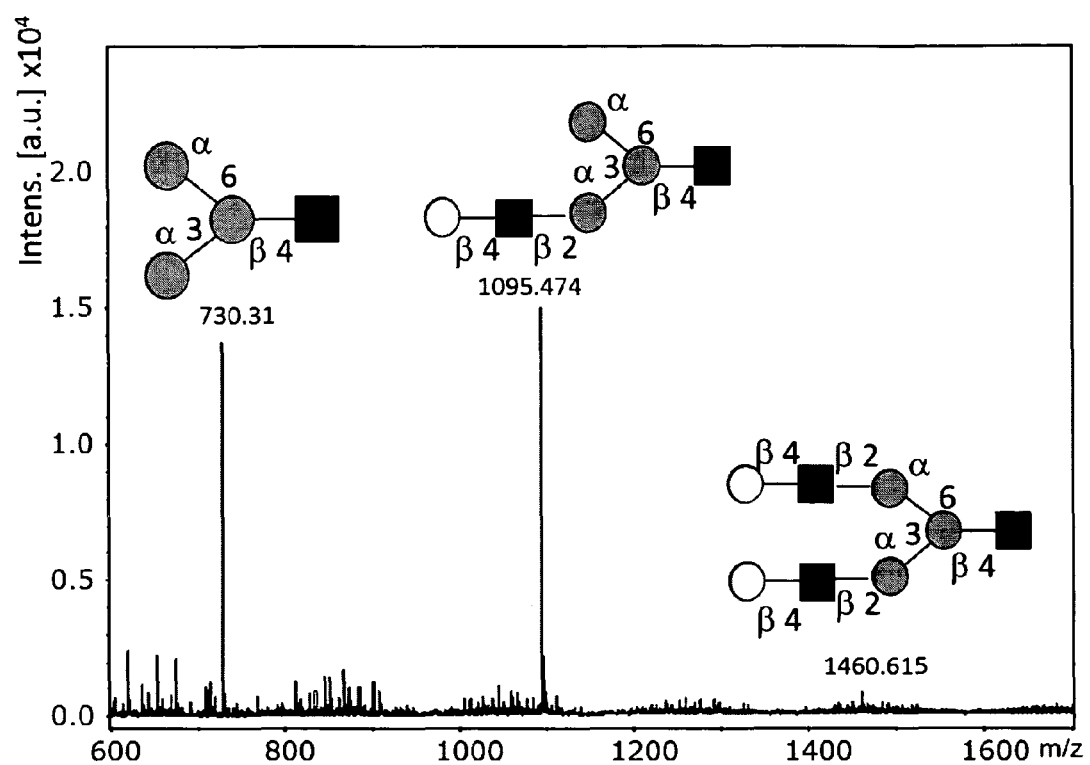
FIG. 26 shows a MALDI spectrum of β1-4GalT reaction mixture.

The mixture formed in the GnTII/GnTI activity reaction was treated with β1-4GalT from bovine milk. β1-4GalT was expected to galactosylate the terminal GlcNAc residues in the product mixture. According to MALDI spectrum of the β1-4GalT reaction mixture, both products were galactosylated. Two galactoses were transferred to the Gn2Man3Gn product, which indicated that the GlcNAc residues were linked to separate mannose branches (FIG. 26).

Transformation of *T. reesei* with GnTII/GnTI Construct by Random Integration

A chimeric GnTII/GnTI sequence was designed and cloned into a vector containing the gpdA promoter. After verification of the plasmid sequence, it was co-transformed into the *T. reesei* M124 strain with the hygromycin marker gene. Thirteen PCR positive transformants were identified. All positive transformants and the parental strain M124 were cultivated in TrMM, pH 4.8, supplemented with 4% lactose No sign of the expected GnTII/GnTI product was visible in any of the clones from time points of 3 and 5 days. In addition, no product was observed from GnTI and GnTI/II transformants with gpdA promoters that were generated by random integration.

Transformation of *T. reesei* with GnTII/GnTI Construct by Targeted Integration

A vector having the chimeric GnTII/GnTI sequence under the control of the cbh1 promoter was constructed with a pyr4 gene loopout marker and subcloned into a backbone vector between alg3 flanking region fragments for targeted integration. A PmeI-digested expression cassette was transformed into *T. reesei* strain M127 (pyr4⁻ strain of M124). After plate selection, the clones were PCR-screened and purified through single spores. To obtain material for glycan analyses, shake flask cultivations were performed as described. Five PCR positive transformants indicating correct integration to the alg3 locus in the M127 transformation were cultivated in a 300 ml volume for seven days at +28° C. in a media containing TrMM, pH 5.5, supplemented with 40 g/l lactose, 20 g/l spent grain extract, and 100 mM PIPPS. To avoid bacterial contamination, 100 mg/l ampicillin was added into the flasks at the time of inoculation. Samples for glycan analyses were collected on days 3, 5 and 7.

Glycan Analysis of *T. reesei* GnTII/GnTI Strains Obtained by Targeting to alg3 Locus Supernatant samples of *T. reesei* strain M124 (control), five different clones of M127 GnTII/GnTI transformants, and control medium samples were prepared in triplicate on 96-well plates for 5 μs of supernatant protein. The protein concentrations of the supernatants were measured by Bradford-based assay (Bio-Rad Quick Start Bradford Protein Assay) using BSA as a standard. PNGase F reactions were performed as described, but without SDS denaturation. The released N-glycans were first purified with Hypersep C-18 and then with Hypersep Hypercarb (both from Thermo Scientific) where neutral and acidic glycans were separated. Both purifications were performed in 96-well format. Neutral N-glycans were analyzed by MALDI-TOF MS.

Figure 27:
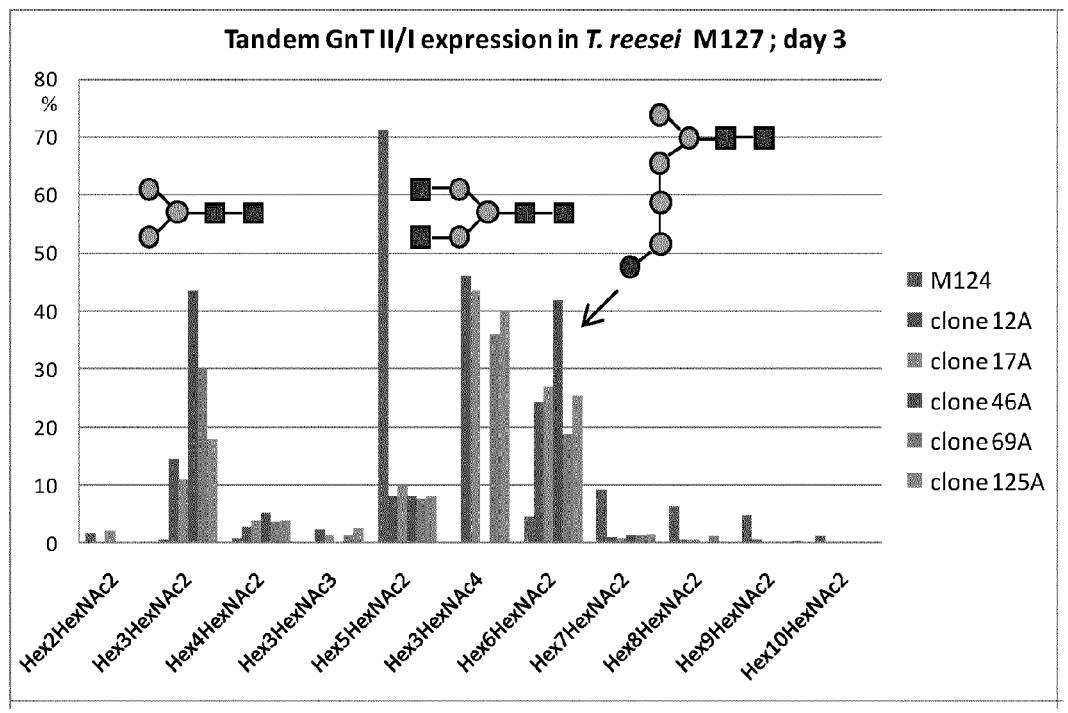
FIG. 27 shows diagrams of observed N-glycans from supernatant proteins of *T. reesei* M127 pTTv110 transformants (gnt II/I in alg3 locus) on days 3 (A), 5 (B) and 7 (C and D). The clone 17A produced the most G0 on day 7. (E) Mass spectrum of neutral N-glycans of supernatant proteins from *T. reesei* strain M127 GnT II/I transformant clone 17A cultivated for 7 days in shake flasks. Signals marked with asterisks originated from the culture medium.
Figure 27:
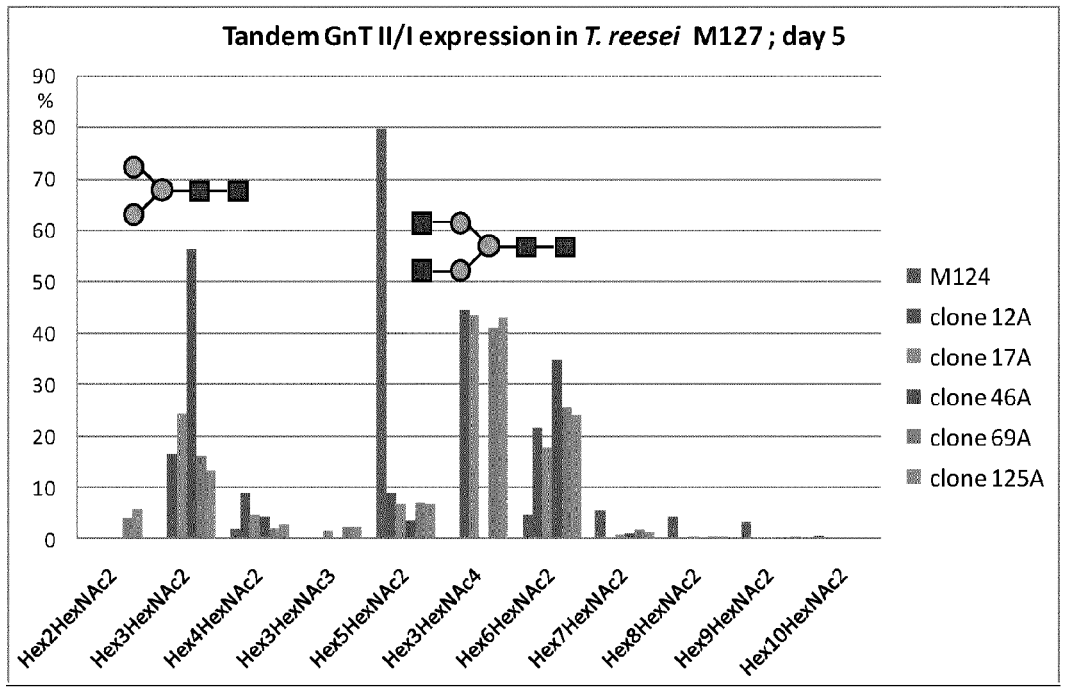
Figure 27:
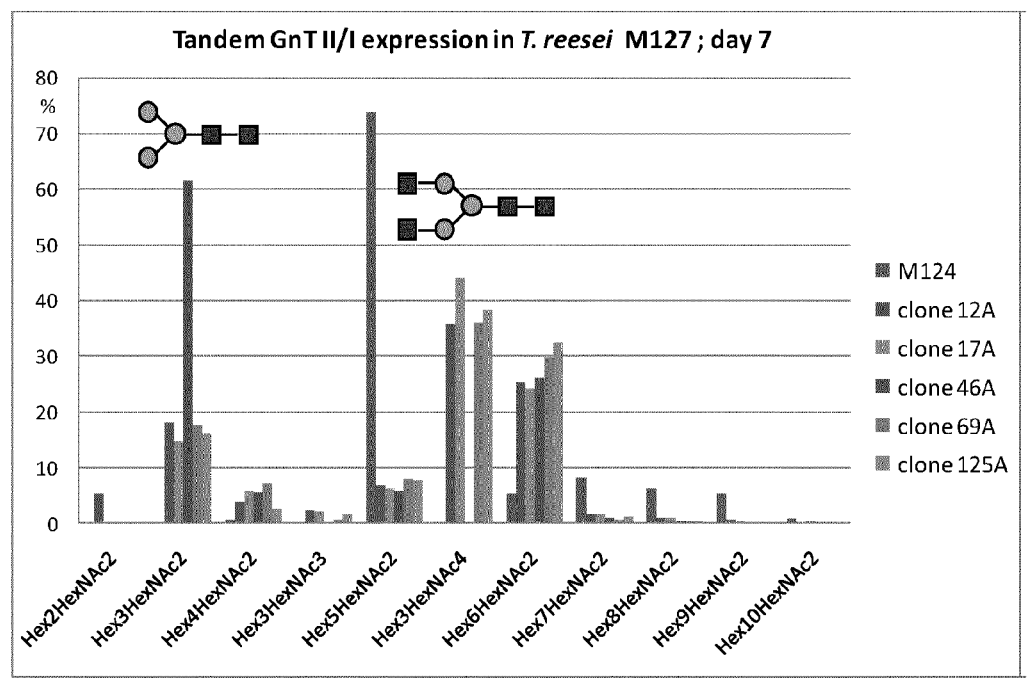
Figure 27:
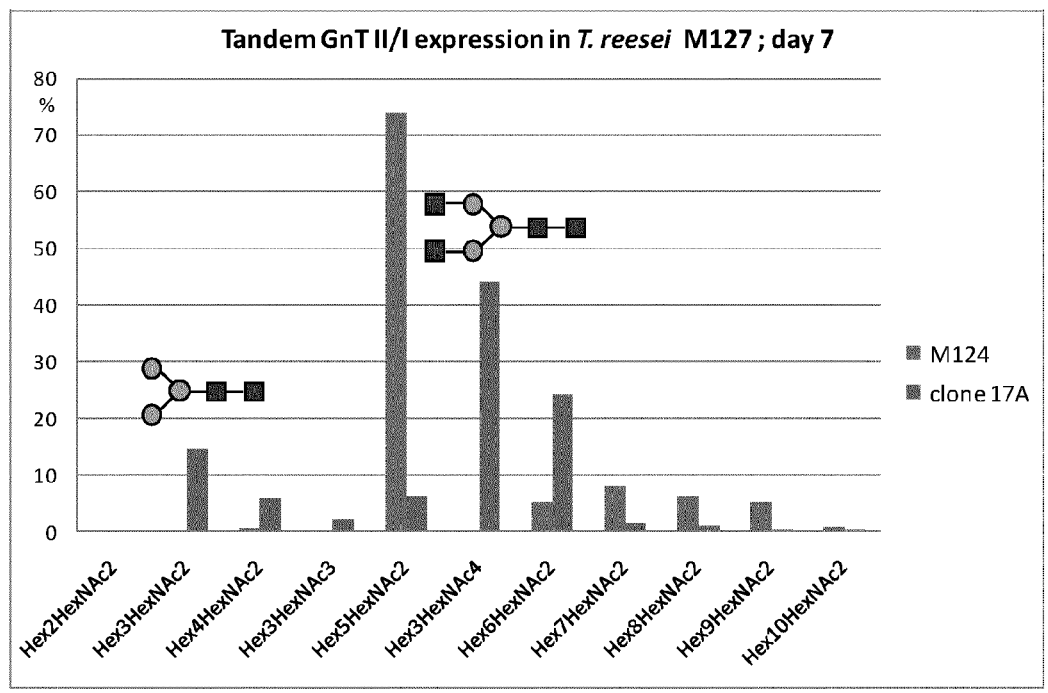
Figure 27:
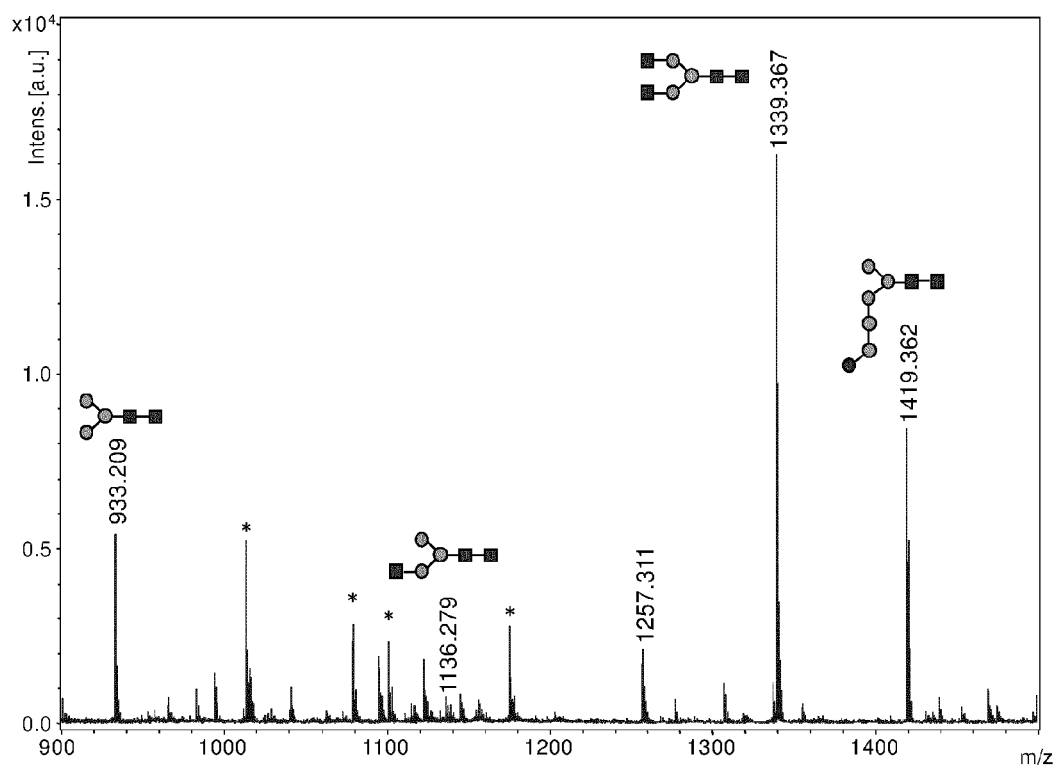

The proportions of neutral N-glycans from *T. reesei* M127 GnTII/GnTI transformants were compared to proportions from strain M124, which was otherwise the same as strain M127 but pyr4 positive. Four of the five GnTII/GnTI transformants produced G0 as a main glycoform at all time points (3, 5 and 7 days). Only clone 46A was G0 negative (FIG. 27). The proportion of Man3Gn was small in every clone at all time points, but the proportion of Hex6 was still quite large. On day 7, clone 17A produced the most G0 and the least Hex6 in comparison to other clones (FIG. 27). Four clones of the GnTII/GnTI transformants produced around 40% of glycoform G0 on day 5 in shake flask conditions (FIG. 27). Fermentation conditions with controlled pH can increase the amount of G0 product and reduce the amount of Hex6 in alg3 knock-outs.

In the medium sample, a series of plant-type N-glycans were observed, but no signals corresponding to G0 were observed.

Transformation of Rituximab-Producing *T. reesei* with GnTII/GnTI Construct by Targeted Integration The expression cassette described in the section entitled "Transformation of *T. reesei* with GnTII/GnTI Construct by Targeted Integration" was transformed into *T. reesei* strain M279 (pyr4⁻ strain of the strain M202). M202 was obtained by deleting pep1 protease in M124 and introducing rituximab heavy and light chain (with Kex2 cleavage site). After plate selection, the clones were PCR-screened and purified through single spores. To obtain material for glycan analyses, shake flask cultivations were performed as described in the section entitled "Transformation of *T. reesei* with GnTII/GnTI Construct by Targeted Integration" and, in addition, some culture media were supplemented with 0.3 mg/ml soybean trypsin inhibitor (SBTI) and 1% casamino acids. SBTI was added first at inoculation and then daily on days 3-6. PMSF and Pepstatin A were added to all samples before freezing.

Figure 28:
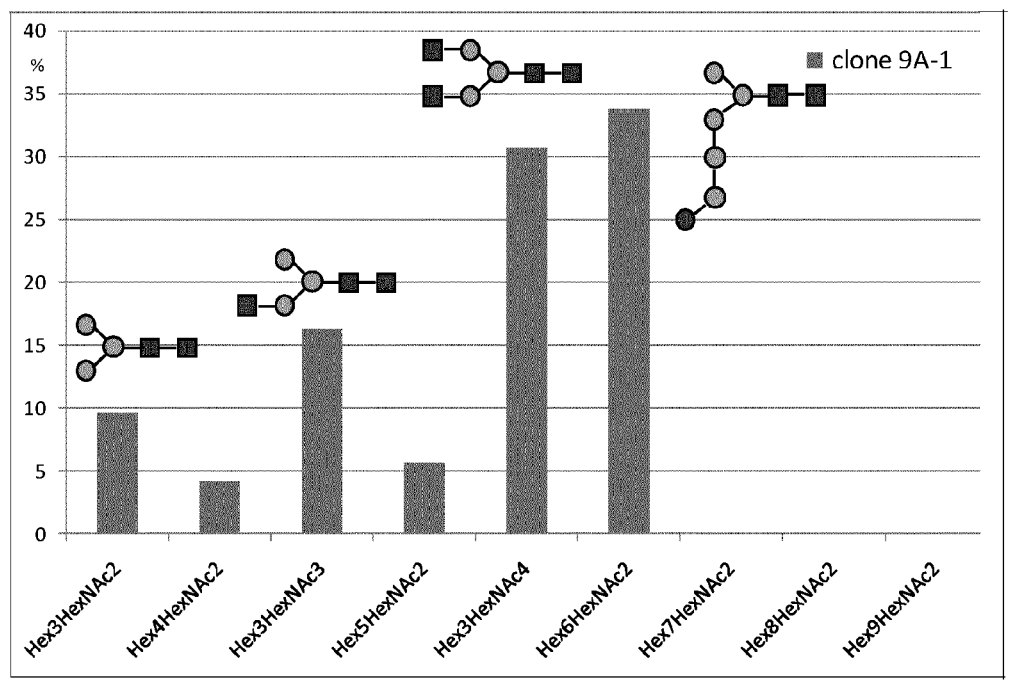
FIG. 28 shows neutral N-glycans of rituximab from *T. reesei* M202 GnT II/I transformant clones (A) 9A-1 and (B) 31A-1, both cultivated with soybean trypsin inhibitor, and (C) mass spectrum of neutral N-glycans of rituximab purified from *T. reesei* strain M202 GnT II/I transformant clone 9A-1 cultivated for 5 days in shake flasks in the presence of soybean trypsin inhibitor.
Figure 28:
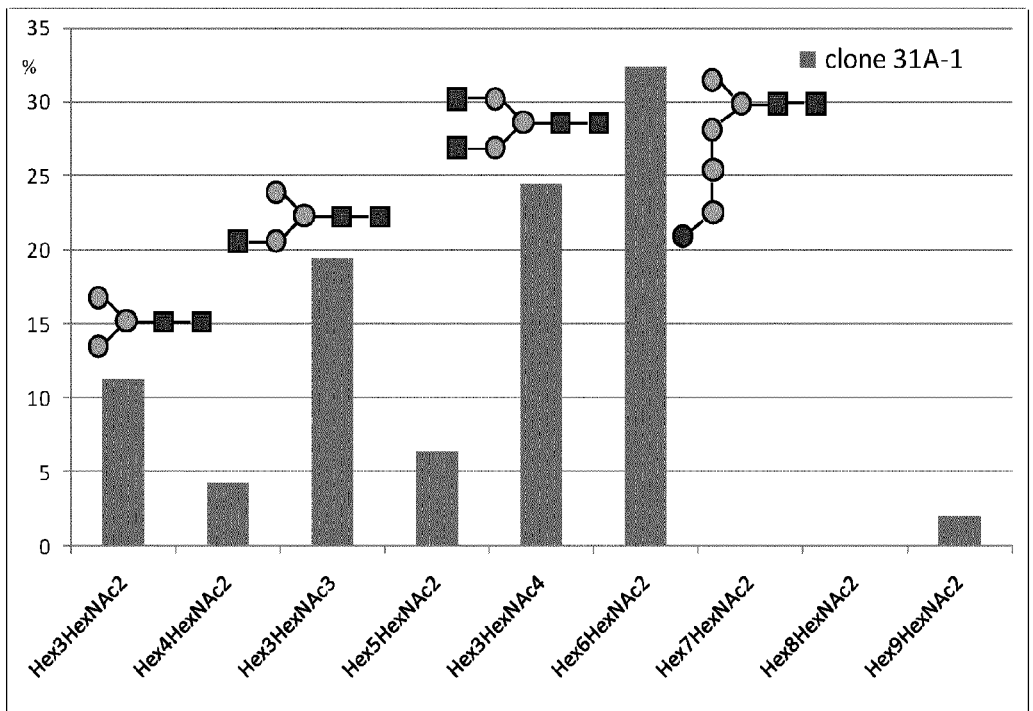
Figure 28:
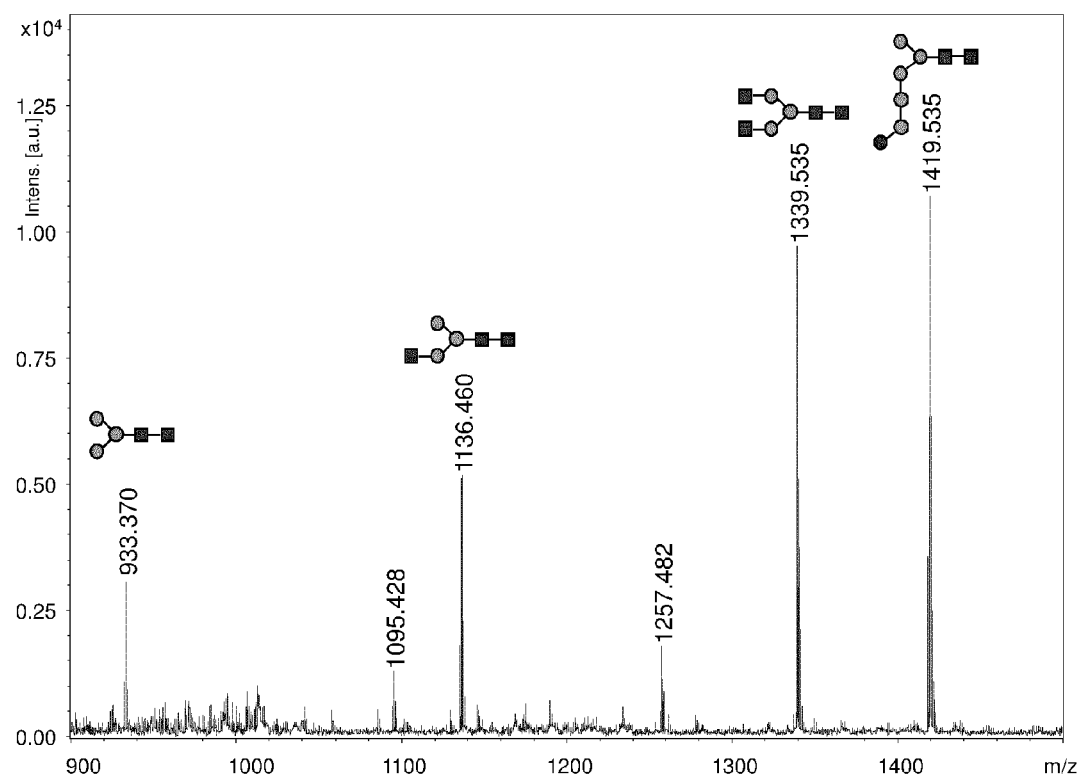

Glycan Analysis of Rituximab-Producing *T. reesei* GnTII/GnTI Strains Obtained by Targeting to alg3 Locus Rituximab was purified with Protein G affinity chromatography from day 5 supernatant samples with SBTI and from day 5 and 7 samples without SBTI. PNGase F reactions were performed for ~10 μg of denatured protein. The released N-glycans were first purified with Hypersep C-18 and then with Hypersep Hypercarb (both from Thermo Scientific) where neutral and acidic glycans were separated. The purification steps were performed in 96-well format. Neutral and acidic N-glycans were analyzed by MALDI-TOF MS. Two of the GnTII/GnTI transformant clones, 9A-1 and 31A-1, produced G0 glycoform at ~30% and ~24%, respectively. However, reasonable quantities of Hex6 and GnMan3 were still observed (FIG. 28). Rituximab from the other clones contained little or no G0.

Optimization of Spacers

A series of spacer modifications for GnTII/GnTI fusion proteins were constructed. These variants were produced in *Pichia* and studied in vitro for enzyme stability and activity.

The materials and methods for cloning the GnTI/GnTI fusion proteins are described here. T45 sequence was amplified in two parts by using PCR overlapping strategy. First, a fragment was amplified with GP13 5' primer and GP93 3' primer, and a second fragment was amplified with GP92 5' primer and GP2 3' primer. Amplification was carried out with Phusion high-fidelity PCR polymerase (Finnzymes) under the standard conditions provided by the supplier. Cycling conditions were as follows: initial denaturation at 98° C. for 30 seconds, denaturation at 98° C. for 5 seconds, annealing at 65° C. for 30 seconds, extension at 72° C. for 45 seconds, repeat 20 times, and final extension at 72° C. for 20 minutes. The resulting PCR products were purified from the agarose gel with a Fermentas GeneJET gel extraction kit. These fragments with overlapping, modified sequences were combined in the same reaction mixture with standard conditions without primers. Ten annealing/extension cycles were carried out as follows: initial denaturation at 98° C. for 30 seconds, denaturation at 98° C. for 5 seconds, annealing at 65° C. for 30 seconds, extension at 72° C. for 45 seconds, repeat 10 times, and final extension at 72° C. for 20 minutes. Primers GP13 (5') and GP2 (3') were added, and cycling was continued as described above for 20 amplification cycles. The amplified T45 fragment was purified with a Fermentas GeneJET PCR purification kit, digested with EcoRI/KpnI (New England Biolabs) according to standard protocols, and cloned into EcoRI/KpnI digested yeast expression vector pBLARG-SX. The resulting vector was sequenced with primers 3'AOX, 5'AOX, GP9, GP37, GP38 and GP122. The sequence was found to be correct.

This resulting plasmid was used as a template for the 3×G4S spacer modification. Cloning of the T46 sequence was done as described above with T45. GP13 5'-primer and GP95 3'-primer were used for first fragment synthesis, and GP94 5'-primer and GP2 3'-primer were used for second fragment synthesis. Fragments were combined, and primers GP13 (5') and GP2 (3') were added for amplification. Amplified fragment T46 was then digested with EcoRI/KpnI and cloned into yeast expression vector pBLARG-SX. The resulting vector was sequenced with the primers described above, and the sequence was found to be correct.

Cellulase-related natural spacers were constructed with a similar PCR overlap method. With the CBHI-related spacer, the first fragment was amplified with GP13 5'-primer and GP107 3'-primer. The second fragment was amplified with GP108 5'-primer and GP2 3'-primer (Table 11). With the EGIV-related spacer, the first fragment was amplified with GP13 5' primer and GP109 3' primer. The second fragment was amplified with GP110 5'-primer and GP2 3'-primer (Table 11). In both cases, PCR products were purified from agarose gel, combined, and used as a template for the next PCR reaction to amplify the sequences T50 and T51. T50 and T51 PCR products were then digested with EcoRI/KpnI and cloned into yeast expression vector pBLARG-SX.

All PCR amplifications were made with high-fidelity Phusion polymerase (Finnzymes). Primers (Table 11) were ordered from MWG Operon. Sequencing was performed by the DNA Sequencing Laboratory of the Institute of Biotechnology, University of Helsinki, as a commercial service.

TABLE 11

Primer sequences.

| Primer | Sequence 5'-3' |
|---|---|
| 3'AOX | GCAAATGGCATTCTGACATCC (SEQ ID NO: 99) |
| 5'AOX | GACTGGTTCCAATTGACAAGC (SEQ ID NO: 100) |
| GP2 | CAGTGGTACCCTAATTCCAGCTAGGATCATAGCCCTCCCACG (SEQ ID NO: 101) |
| GP9 | CGGACCACCGCAAGTTCC (SEQ ID NO: 102) |
| GP13 | ATGCGGAATTCTG<u>CATCATCATCATCATCAT</u>TCGCCAGCGTAAGAACGAGGCCCT (6 × HIS) (SEQ ID NO: 103) |
| GP37 | CCTTTCTCTATCCAACTCTACC (SEQ ID NO: 104) |
| GP38 | GGAACTTGCGGTGGTCCG (SEQ ID NO: 105) |
| GP92 | CCGCCGGCTCCAGGGAGGTGGGGGCAGTGGAGGTGGCGGCAGTGGGAGGGTGCCCACC GCCGCCCC (SEQ ID NO: 106) |
| GP93 | GCGGTGGGCACCCTCCCACTGCCGCCACCTCCACTGCCCCCACCTCCCTGGAGCCGGCGG TAAGAC (SEQ ID NO: 107) |
| GP94 | AGGTGGGGGCAGTGGAGGTGGCGGCAGTGGCGGCGGTGGAAGTGGGAGGGTGCCCACC GCCGCCC (SEQ ID NO: 108) |
| GP95 | CGGTGGGCACCCTCCCACTTCCACCGCCGCCACTGCCGCCACCTCCACTGCCCCCACCTC CCTG (SEQ ID NO: 109) |
| GP107 | GTTTCCGCCGGGAGGGTTGCCGCCGCTAGGGTTGCCGGTGCTCTGGAGCCGGCGGTAAG ACTTGC (SEQ ID NO: 110) |
| GP108 | GCAACCCTCCCGGCGGAAACCCGCCTGGCAGCACCGGGAGGGTGCCCACCGCCGCCCCT CCCGCCC (SEQ ID NO: 111) |
| GP109 | CCGCCTCCAGGAACAGTGGCGCTGGCGGTGGCCGTCGCGGCGGAGCTCTGGAGCCGGCG GTAAGACTTGC (SEQ ID NO: 112) |
| GP110 | CGCCACTGTTCCTGGAGGCGGTAGCGGCCCCACCAGCGGGAGGGTGCCCACCGCCGCCC CTCCCGCCCAGC (SEQ ID NO: 113) |
| GP122 | CATTAGCGAGAAGTTTACGG (SEQ ID NO: 114) |

Figure 29:
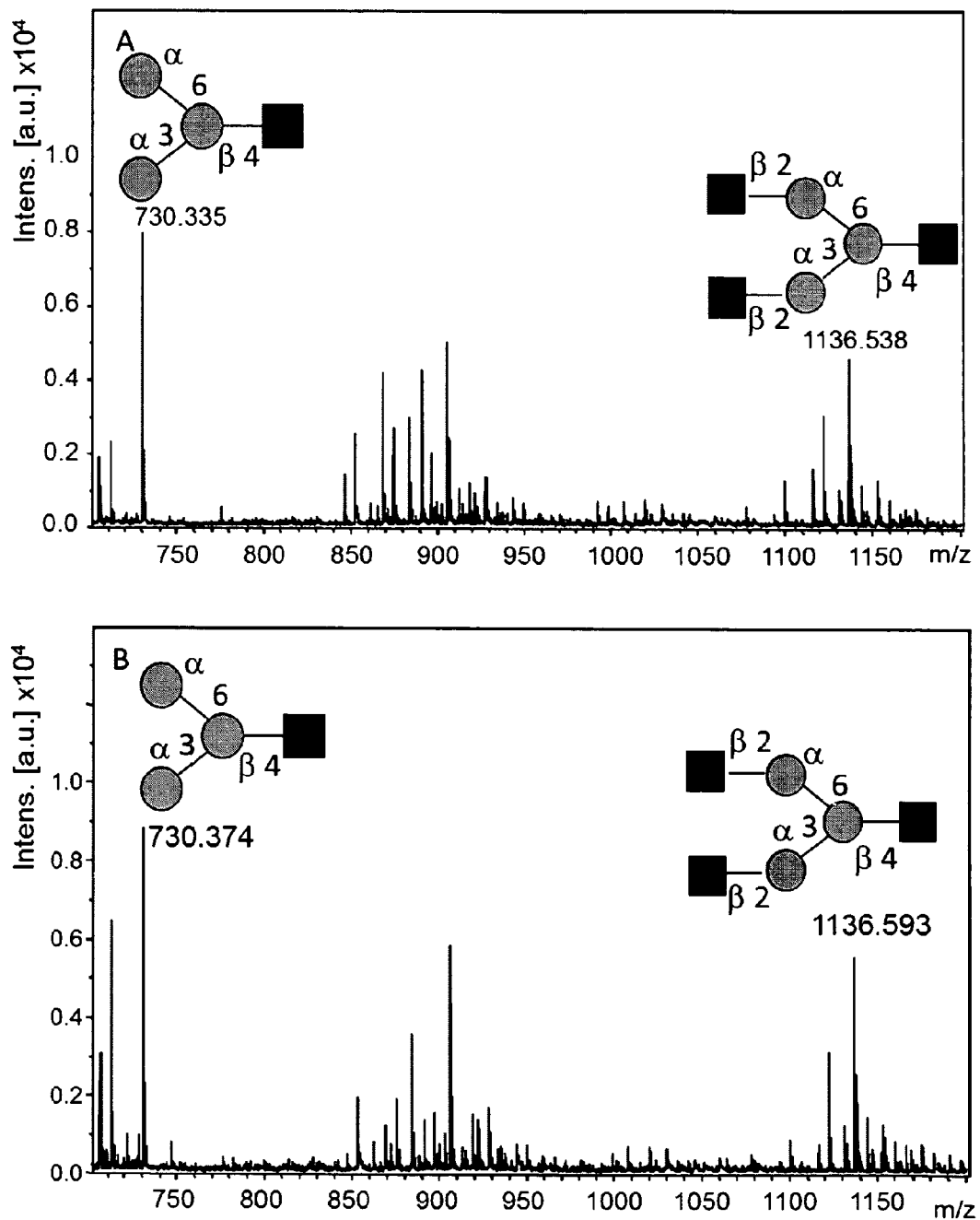
FIG. 29 shows MALDI spectra of spacer modified GnTII/GnTI fusion reaction mixtures. Part (A) shows a reaction mixture of GnTII/GnTI with 3×G4S spacer modification. 36% of the acceptor has been converted to product with two additional HexNAcs. Part (B) shows a reaction mixture of GnTII/GnTI with 2×G4S spacer modification. 38% of the acceptor has been converted to product with two additional HexNAcs. Calculated m/z values for [M+Na]+-signals of GnTI product, Hex3HexNAc2 (calc. m/z 933.318), was not detected in either spectra because all of the GnTI product was converted directly to Hex3HexNAc3, (calc. m/z 1136.318).

Spacer modified (3×G4S and 2×G4S) GnTII/GnTI fusion enzymes were processed for an activity assay by concentration and buffer exchange in a similar way as described for GnTI in Example 3. Activity assays were carried out with Man3Gn acceptor, and reaction mixtures were purified as described in the GnTI activity assay. MALDI analysis was also performed as described with the GnTI reaction mixture, but, in addition, formation of the GnTII product, Hex3HexNAc3, was followed. The calculated m/z values for the [M+Na]+ signal of Hex3HexNAc3 was 1136.318 (FIG. 29).

Spacer Variants

GnTII/I spacer variants were modified from the wild type spacer sequence of the GnTII/I fusion protein. The modified spacers are listed in Table 12. All four spacer variant strains (GY32, GY33, GY49, and GY50), wild-type GnTII/I fusion strain (GY7-2), and mock strain (GY3) were expressed at +16° C. with protease inhibitors. Strains were inoculated in 60 ml of BMGY-medium at +30° C., 220 rpm, over-night (o/n). Over-night cultures were pelleted and cells were resuspended in 60 ml of BMMY-medium. Protease inhibitors, 1 mM EDTA, 1.5 µM Pepstatin A (Sigma) and 1 Complete EDTA free protease inhibitor cocktail tablet (Roche) were added in cultures at the same time when MeOH induction was started and after that once in a day. 25 ml samples were taken from cultures on day 3 and day 4, and supernatant samples were concentrated using concentration tubes (Millipore), buffer was exchanged in PD-10 columns into 100 mM MES pH 6.1 and concentrated into final 50×. Cell pellets were resuspended in 500 µl of 1×PBS, except cell pellet of wild type ($3^{rd}$), which was resuspended in 500 µl of 100 mM MES pH 6.1 and complete (EDTA free) inhibitor cocktail.

The amino acid sequence of the GnTII/GnTI fusion protein containing the 3×G4S spacer is set forth in SEQ ID NO: 119. The nucleotide sequence of the GnTII/GnTI fusion protein containing the 3×G4S spacer is set forth in SEQ ID NO: 141. The amino acid sequence of the GnTII/GnTI fusion protein containing the 2×G4S spacer is set forth in SEQ ID NO: 121. The nucleotide sequence of the GnTII/GnTI fusion protein containing the 2×G4S spacer is set forth in SEQ ID NO: 139. The amino acid sequence of the GnTII/GnTI fusion protein containing the CBHI spacer is set forth in SEQ ID NO: 123. The nucleotide sequence of the GnTII/GnTI fusion protein containing the CBHI spacer is set forth in SEQ ID NO: 143. The amino acid sequence of the GnTII/GnTI fusion protein containing the EGIV spacer is set forth in SEQ ID NO: 125. The nucleotide sequence of the GnTII/GnTI fusion protein containing the EGIV spacer is set forth in SEQ ID NO: 145.

A 200 µl sample of cell suspension was washed by repeating centrifuging and resuspending cells in 100 mM MES pH 6.1 with complete (EDTA free) inhibitor cocktail. A cell lysate was prepared by taking 200 µl of washed cell sample, adding 50 µl glass beads and 2 µl Triton X-100 and putting in bead beater for 6 min. GnTI activity assays of 50× concentrated *P. pastoris* culture supernantants, cell sample and cell lysate were performed as above.

TABLE 12

Description of yeast strains.

| Yeast Strains | Description | Sequence of spacer variant |
|---|---|---|
| GY3 | Mock strain | |
| GY7-2 | Wild-type GnTII/I fusion | |
| GY32-5 GY32-9 | GnTII/I fusion 3×G4S spacer variant | SEQ ID NO: 118 |
| GY33-7 GY33-8 | GnTII/I fusion 2×G4S spacer variant | SEQ ID NO: 120 |
| GY49-3 | GnTII/I fusion CBHI spacer variant | SEQ ID NO: 122 |
| GY50-7 GY50-10 | GnTII/I fusion EGIV spacer variant | SEQ ID NO: 124 |

Figure 30:
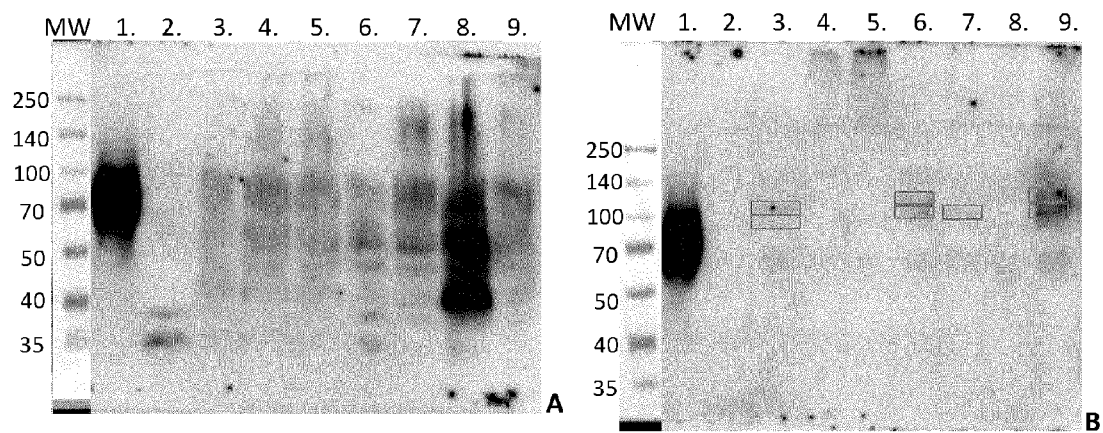
FIG. 30 shows Western blots of GnTII/I spacer variant cell pellets (A), and supernatants (B). Lanes 1. GnTII positive control, 2 GY3 mock strain, 3. GY7-2 wild type GnTII/I 4. GY32-5 3×G4S spacer, 5. GY32-9 3×G4S spacer, 6. GY33-7 2×G4S spacer, 7. GY33-8 2×G4S spacer, 8. GY49-3 CBHI spacer and 9. GY50-10 EGIV spacer.

Western blots analysis of cell pellets and 50× concentrated culture supernatants from day 3 are shown in FIG. 30. The CBHI spacer variant (GY49) gave a strong signal from the cell pellet sample but not from the supernatant. The EGIV spacer variant (GY50) was detected from the supernatant, but only faint signal was obtained. Faint signals from supernatant samples were also obtained with the wild-type GnTII/I fusion strain (GY7-2) and the 2×G4S spacer variant strains GY33-7 and GY33-8 (FIG. 30).

The activities of the GnTII/I fusion protein containing the spacer variants were then compared to the activity of the GnTII/I fusion protein containing the wild-type spacer.

Figure 31:
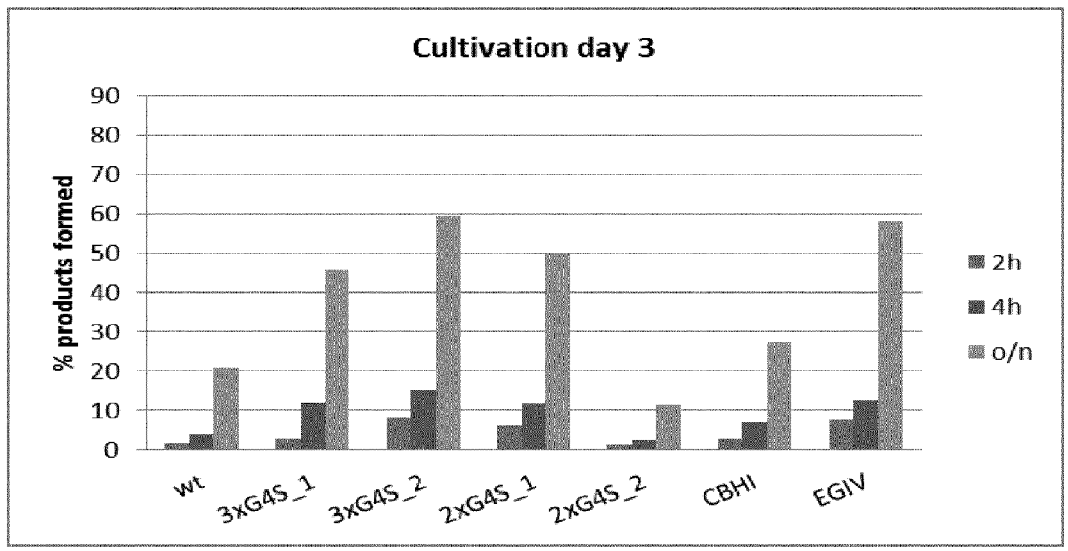
FIG. 31 shows GnT activities of wild-type GnII/I and spacer variants from supernatants and expressed in the presence of protease inhibitors after day 3 (A) expression phases and day 4 (B) expression phases. The x-axis depicts sample identity (wt=wild-type, _1, _2=parallel clones of the spacer variants), and the y-axis depicts percentage of products formed (GnTI and GnTII reaction products added together).
Figure 31:
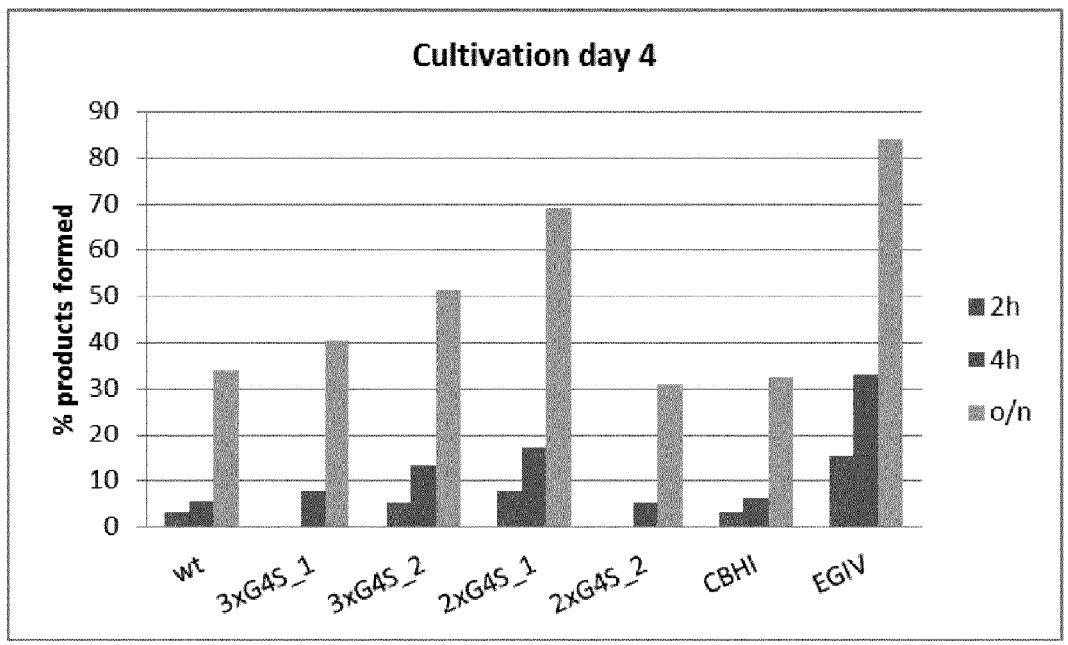

Fusion GnTII/I Activity in Supernatants.The GnTI substrate Man3Gn was provided and the reaction product, GnMan3Gn, acted as the acceptor for the GnTII activity of the fusion protein. Samples for activity assays were taken after day 3 and day 4 expression phases. FIG. 31 shows activity assay results of cultures of GnTII/I fusion proteins containing either the wild type spacer or the spacer variants. Sample cultivations were done in the presence of inhibitors (1.5 µM pepstatin A, 1 mM EDTA, 1 tablet/50 ml of complete EDTA free protease inhibitor cocktail tablet). For simplicity, the GnTI and GnTII reaction products were added together. All activity assay samples contained only minor amounts (<5%) of GnTI product GnMan3Gn, indicating that GnTII actively transformed the GnMan3Gn to Gn2Man3Gn.

All four spacer variants showed GnT activities, although there was some variability between clones and cultivation days. The GnTII/I fusion proteins containing the 2×G4S (clone_1), 3×G4S (clone_1 and clone 2), or EGIV spacer variants showed higher activity than the enzyme with the wild-type spacer (FIG. 31). The GnTII/I fusion protein containing the CBHI spacer variant showed comparable activity with the enzyme with the wild-type spacer (FIG. 31). The GnTII/I fusion protein containing the 2×G4S variant (clone 2) had lower activity than the enzyme with the wild-type spacer (FIG. 31). Day 4 samples had higher activities than day 3 samples, with the exception of the GnTII/I fusion protein containing the 3×G4S spacer variants (clone_1 and clone_2), which showed higher activity on day 3 (FIG. 31). The GnTII/I fusion protein containing the EGIV spacer variant had the highest activity on day 4 (FIG. 31).

Figure 32:
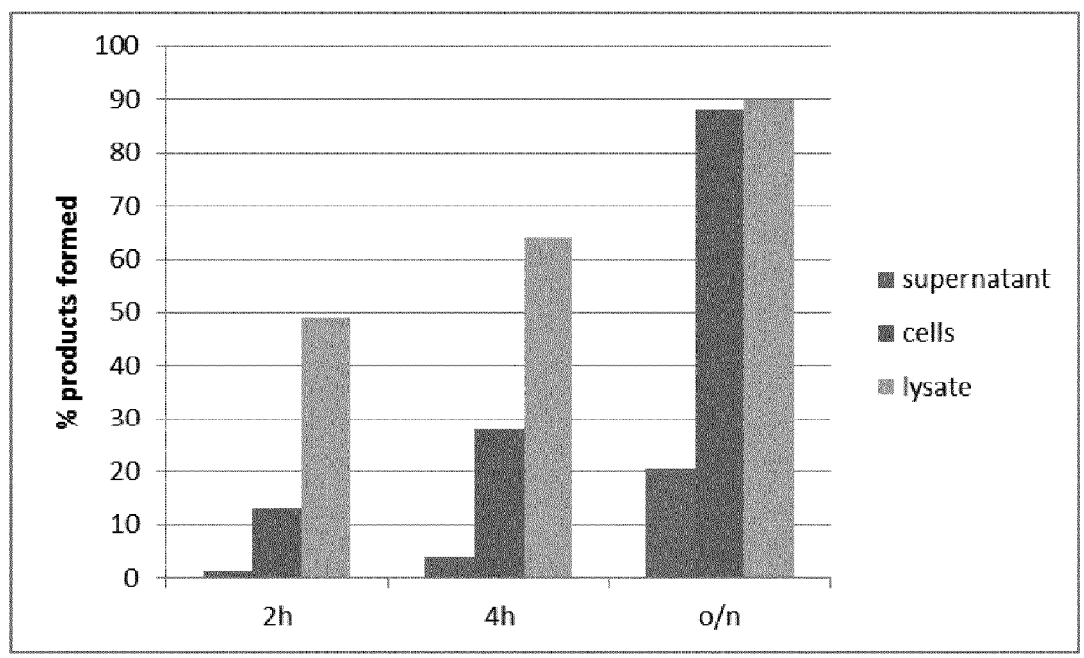
FIG. 32 shows GnT activities of GnTII/I fusion protein (with wild type spacer) in supernatant, cells and lysate. GnTI and GnTII products have been added together

Fusion GnTII/I Activity in Cells and Cell Lysates.Activity assays of cell, cell lysate, and supernatant samples from cells containing the GnTII/I fusion protein having the wild-type spacer indicated that lysate samples contained the highest activity (FIG. 32). The second highest activity was on the cell surface, and lowest activity was seen in the supernatant samples (FIG. 32). Accordingly, it appears that most of the GnTII/I fusion protein was localized in cells or on the cell surface, with only a small amount being secreted.

Figure 33:
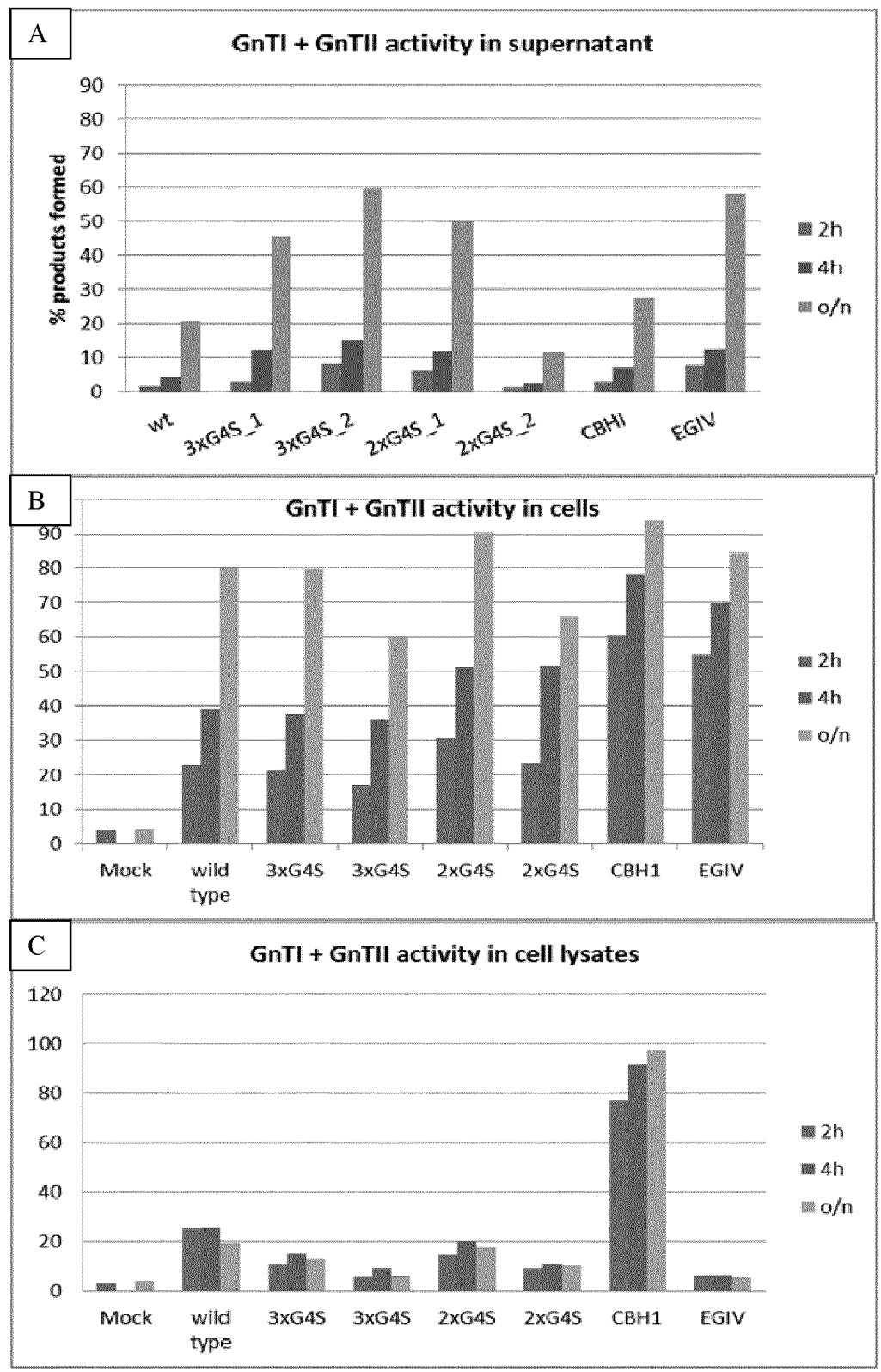
FIG. 33 shows GnT activities of GnTII/I wild-type and spacer variants in (A) supernatants, (B) cells, and (C) lysates.

GnT activities of cells containing GnTII/I fusion proteins having either the wild-type spacer or the spacer variants are shown in FIG. 33. The cells were resuspended in 500 µl of 100 mM MES, pH 6.1 with complete EDTA free inhibitor cocktail and spacer variants in 500 µl PBS and cells and lysates for activity testing were prepared as above.

As shown in FIG. 33, GnTII/I fusion proteins containing the spacer variants had much higher GnTII/I activity in cells than in supernatants. In lysates, the enzymes appeared to be inactive. It is believed that this lack of activity is due to the action of released proteases. The GnTII/I fusion protein containing the CBHI spacer variant showed a high activity in cells and lysates (FIG. 33), which correlates with Western blot analysis showing higher signal in the cell pellet sample (FIG. 30).

Discussion.In supernatants, the GnTII/I fusion proteins containing the 2×G4S and 3×G4S spacer variants had higher activity that the GnTII/I fusion protein containing the wild-type spacer, while the CBHI spacer variant had comparable activity to the GnTII/I fusion protein containing the wild-type spacer. Moreover, the GnTII/I fusion protein containing the EGIV spacer variant showed the highest GnT activity. Western blot analysis of day 3 samples had some correlation with the results of day 4 activities. Western blot analysis showed faint bands with supernatant samples of wild-type, both clones of 2×G4S and EGIV. The activities were detected in the following order: EGIV>2×G4S (clone_1)>3×G4S (clone_2)>3×G4S (clone_1)>CBHI=wild-type=2×G4S (clone 2).

Determination of GnTII/I fusion protein activity in supernatant, cell, and cell lysate samples of the GnTII/I fusion protein containing the wild-type spacer showed that most of the activity is associated within the cells and lower amount is secreted. It is believed that this explains why much better signals of His-tagged GnTII/I were seen in cell fractions rather than in supernatant fractions in Western blot analysis.

The inhibition of serine and cysteine proteases by complete EDTA free inhibitor tablet, metalloproteinases by EDTA and aspartic proteases by pepstatin A, improved the yield of GnTII/I fusion protein. This observation on the use of serine protease inhibitor is in accordance with the work of Salamin et al. (*Appl. Environ. Microbiol.*, 76 (2010) 4269-4276), which showed that serine type protease activity in the media of *P. pastoris* was completed inhibited with PMSF. In addition, Vad et al. (*J. Biotechnol.* 116 (2005) 251-260) reported high production, over 300 mg/l, of intact human parathyroid hormone in *P. pastoris* in the presence of 10 mM EDTA combined with co-expression of *Saccharomyces cerevisiae* protein disulphide isomerase.

All GnTII/I fusion proteins containing each of the four spacer variants possessed GnTII/I activity, and the activity of the enzymes having the 2×G4S and EGIV spacer variants had higher activities that the GnTII/I fusion protein containing the wild-type spacer.

Example 6

Use of Fusion Proteins with Man5 as the Acceptor Glycan

Construction of Rituximab-Expressing *T. reesei* Strain with Man5 Type N-Glycosylation The native rituximab sequence is codon harmonized. Original plasmids containing the synthesized rituximab light chain and heavy chain are generated. The antibody chains and CBHI fusion protein are designed with 40-nucleotide overlapping sequences as are the expression vectors pHHO1 (acetamidase selection marker, cbh1 flanks for integration into the cbh1 locus) for the heavy chain or pHHO2 (hygromycin selection marker, egl1 flanks for integration into the egl1 locus) for the light chain, to enable cloning using yeast homologous recombination.

The obtained gene plasmids are transformed into *E. coli*. DNA is prepared, and the synthetic genes are digested and isolated from the plasmid backbones. The expression vectors are constructed by yeast homologous recombination on the *T. reesei* expression vectors with the CBHI fusion protein and either heavy or light chain. The recombined plasmids are rescued from yeast and transformed into *E. coli*. After PCR screening, correct clones are isolated and sequenced. The expression cassette fragments are digested and isolated from the plasmid backbone resulting in around 10.2 kb fragments for the heavy chain constructs and 10.8 kb fragments for the light chain constructs. The heavy and light chain fragments are cotransformed into the *T. reesei* strain M124. Transformants are selected for hygromycin resistance and ability to grow on acetamide as a sole nitrogen source. Transformants are streaked on the double selective medium for two successive rounds and tested by PCR for integration of the expression constructs into the genome.

Introduction of GnTII/I Tandem Enzyme and Mannosidase II to *T. reesei* Strain Expressing Rituximab Antibody In addition to introducing a recombinant GnTII/I into a Man5-producing strain such as M124, a mannosidase II activity is further needed to remove two mannoses from the GlcNAcMan5 glycan structure so that GnTII/I can use GlcNAcMan3 as an acceptor molecule.

The GnTII/I expression cassette described in previous examples can be targeted to, for example, the cbh2 locus of *T. reesei*, using methods essentially as described above. To generate a GlcNAcMan3 acceptor molecule for GnTII/I fusion protein, mannosidase II activity is then introduced to the strain using transformation methods described above.

Mannosidase II activity is introduced to the rituximab antibody-expressing M124 strain by designing a desired mannosidase-containing expression cassette with a promoter for driving the mannosidase expression. Useful promoters are those from gpdA or cbh1. Mannosidase II activity can be transformed by random integration followed by screening of strains with most suitable expression level. The expression cassette is linked with a proprietary selection marker gene, or a selection marker is co-transformed as a separate expression cassette. Transformation is performed according methods described above.

A mannosidase II fusion construct can be derived from a *T. reesei* cytoplasmic, transmembrane and stem domain, or targeting peptide, of KRE2 and ligated in-frame to an N-terminal amino acid deletion of a human mannosidase II. The encoded fusion protein localizes in the ER/Golgi by means of the KRE2 targeting peptide sequence while retaining its mannosidase catalytic domain activity and is capable of hydrolyzing GlcNAcMan5GlcNAc2 into GlcNAcMan3GlcNAc2.

In certain embodiments, a full-length human mannosidase II can be expressed in an M124 strain.

The KRE2 targeting peptide comprises the amino acids from about 1 to about 106 or from about 1 to about 83 of KRE2.

```
Kre2 aa 1-106
                                           (SEQ ID NO: 115)
MASTNARYVRYLLIAFFTILVFYFVSNSKYEGVDLNKGTFTAPDSTKTTP

KPPATGDAKDFPLALTPNDPGFNDLVGIAPGPRMNATFVTLARNSDVWDI

ARSIRQ

Kre2 aa 1-83
                                           (SEQ ID NO: 116)
MASTNARYVRYLLIAFFTILVFYFVSNSKYEGVDLNKGTFTAPDSTKTTP

KPPATGDAKDFPLALTPNDPGFNDLVGIAPGPR
```

After transformation of *Trichoderma* with the mannosidase II construct described above, *Trichoderma* strains are selected, streaked on selective medium for two successive rounds, and tested by PCR for integration of the expression constructs into the genome. Selected transformants of *Trichoderma* strains producing Man5 and expressing the GnTII/I fusion protein, mannosidase II, and rituximab antibody are then cultured in shake flasks or fermentor conditions and analyzed for glycan content as described above.

Example 7

Expression of GnTI and GnTII in *T. reesei*

Transformation of *T. reesei* M124 with GnTI Construct by Random Integration

Codon optimized human GntI was transformed into the *T. reesei* M124 strain. The GntI gene was cloned into a vector under the control of two different promoters: (1) the inducible promoter of the cbh1 gene; and (2) the constitutively expressed promoter of the gpdA gene. The vectors containing GntI under either of the two promoters were each co-transformed into the *T. reesei* M124 strain with a plasmid containing either an acetamidase or a hygromycin resistance marker gene.

Thirty-four transformants with GntI under the gpdA promoter and under acetamide selection were screened by PCR, and all were positive for GntI. For transformants with GntI under the cbh1 promoter and under acetamide selection, 19 of 26 were PCR-positive for the GntI construct. In addition, initial DNA extraction was performed for five strains with GntI under the cbh1 promoter and under hygromycin selection. All of these strains were PCR-positive. Twenty-five gpdA promoter transformants and all of the cbh1 promoter transformants (14+5) were purified to uninuclear clones and spore suspensions were prepared.

For initial analysis purposes, 23 gpdA promoter transformants and 19 cbh1 promoter transformants (14 grown from acetamide and five from hygromycin selection), as well as the parental strain M124 were cultivated in 250 ml shake flasks with 50 ml of *Trichoderma* minimal medium supplied with 2% spent grain extract and 4% lactose. Growth of the strains was monitored by pH measurements. Samples (supernatants and mycelia) were collected on days 3, 5, and 7, stored frozen until used for glycan structure analysis.

Glycan analysis of *T. reesei* GnTI Strains Obtained by Random Integration

The protein concentration of all supernatant samples was measured by Bradford-based assay (BioRad Quickstart Bradford Protein Assay) using BSA as a standard. Secreted protein content of samples subjected to N-glycan analysis was adjusted to 5 µg or 10 µg. N-glycan analysis was performed either on 96-well plates for 5 µg of supernatant protein, or in 1.5 ml tubes for 10 µg of supernatant protein. All N-glycan analyses were performed in triplicate. Both neutral and acidic N-glycans were analyzed with MALDI-TOF MS.

To get more exact measurements of the amount of the GnT1 product Gn1Hex5 produced in four of GnT1 transformants (from days 3 and 5) and also of the amount of produced acidic N-glycans, the MALDI spectra was spiked with a known glycan. For neutral and acidic N-glycans, an internal calibrant of 2 pmol/spectrum Hex2HexNAc4 at the mass value of 1177 Da and 0.5 pmol of monosialylated Hex4HexNAc2 at the mass value of 1362 Da were used, respectively. Analyses were performed in triplicate.

Figure 34:
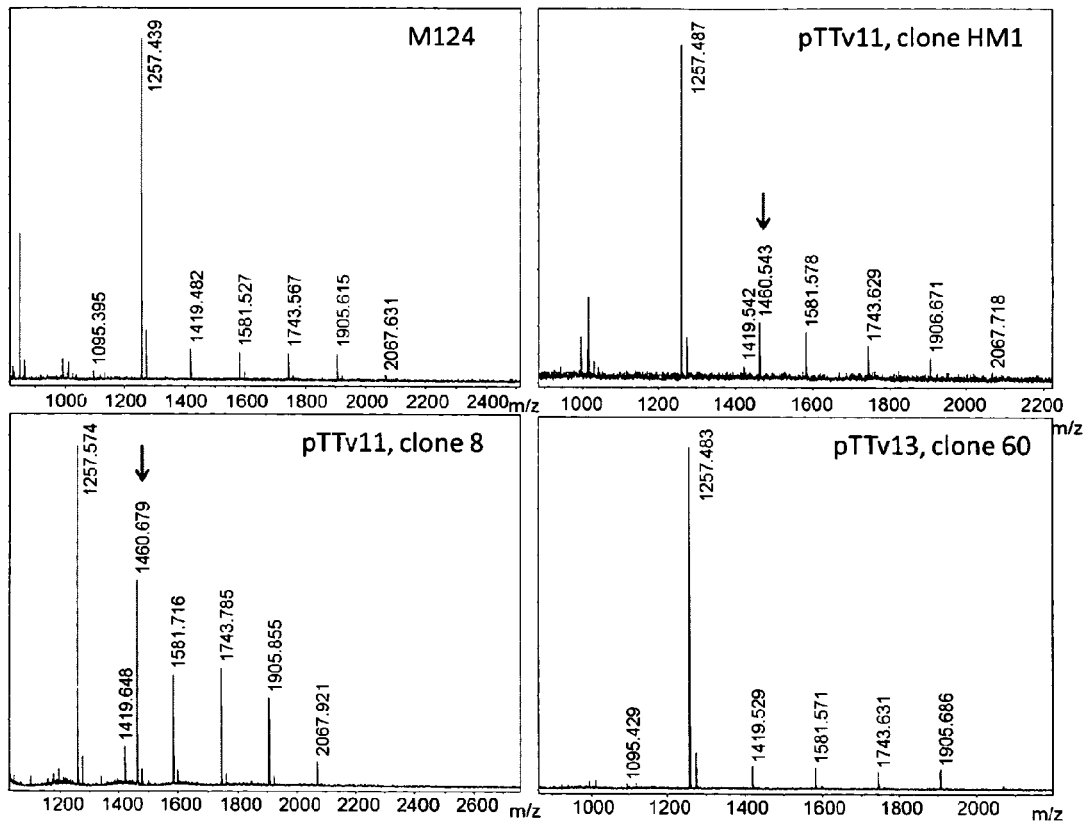
FIG. 34 shows example spectra of neutral N-glycans of parental strain M124 and GnT1 transformants on day 5. Signal with Gn addition (m/z 1460) is marked with an arrow. (pTTv11 with cbh1 promoter, pTTv13 with gpdA promoter).

No GnT1 product was observed in any of the gpdA promoter transformants. However, eight cbh1 promoter transformants produced the GnT1 product Gn1Man5 (FIGS. 34 and 35, and Table 13); five with hygromycin selection, three with acetamide selection.

Figure 36:
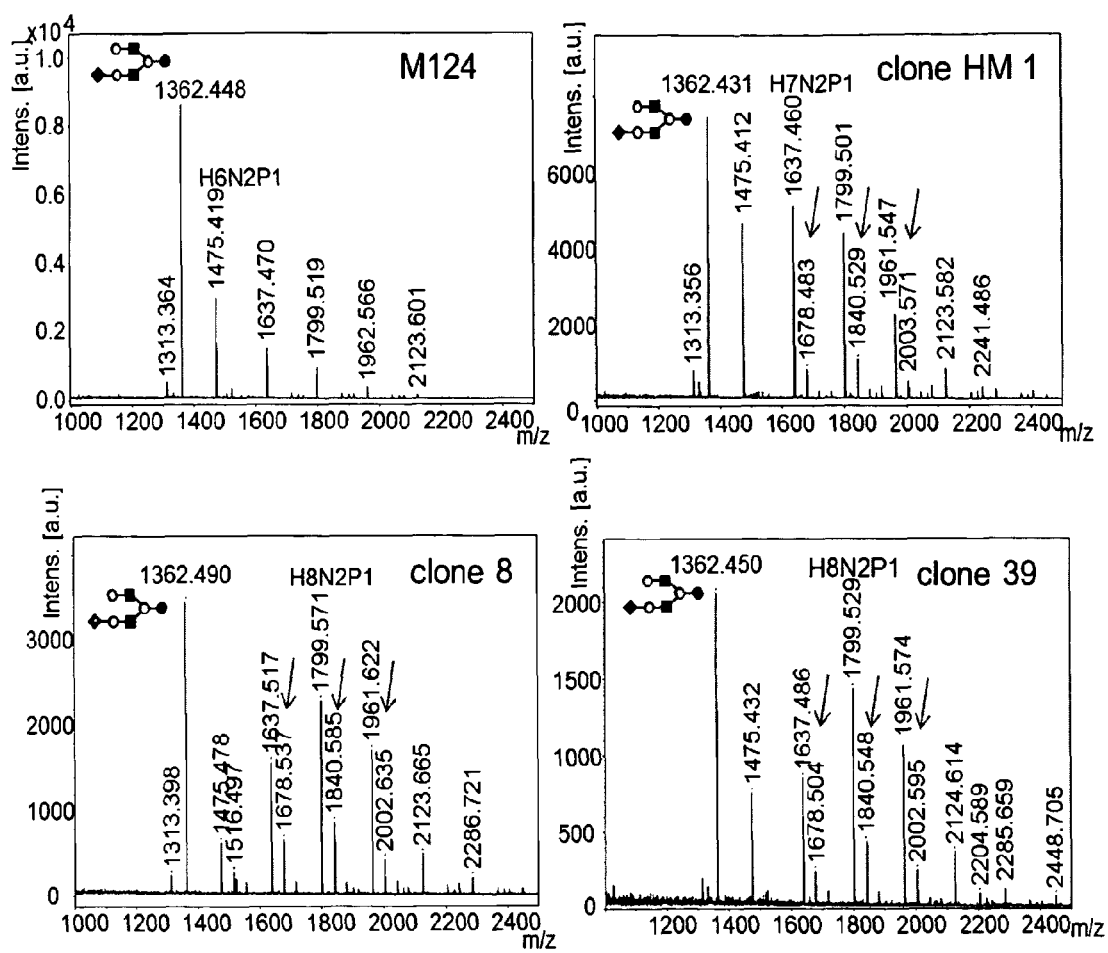
FIG. 36 shows example spectra of phosphorylated N-glycans of parental M124 strain and GnT1 transformants with internal calibrant (NeuAcHex4HexNAc2, 0.5 pmol.). GnT1 products are marked with an arrow.

The GnT1 products Gn1Man6P1, Gn1Man7P1, and Gn1Man8P1 were also found in phosphorylated N-glycans of all positive transformants. The amount of phosphorylated N-glycans had increased in GnT1 transformants, and the profile was biased toward larger N-glycans, with Man7P1 or Man8P1 having the strongest signal (Man6P1 in parental M124) (FIG. 36).

Figure 35:
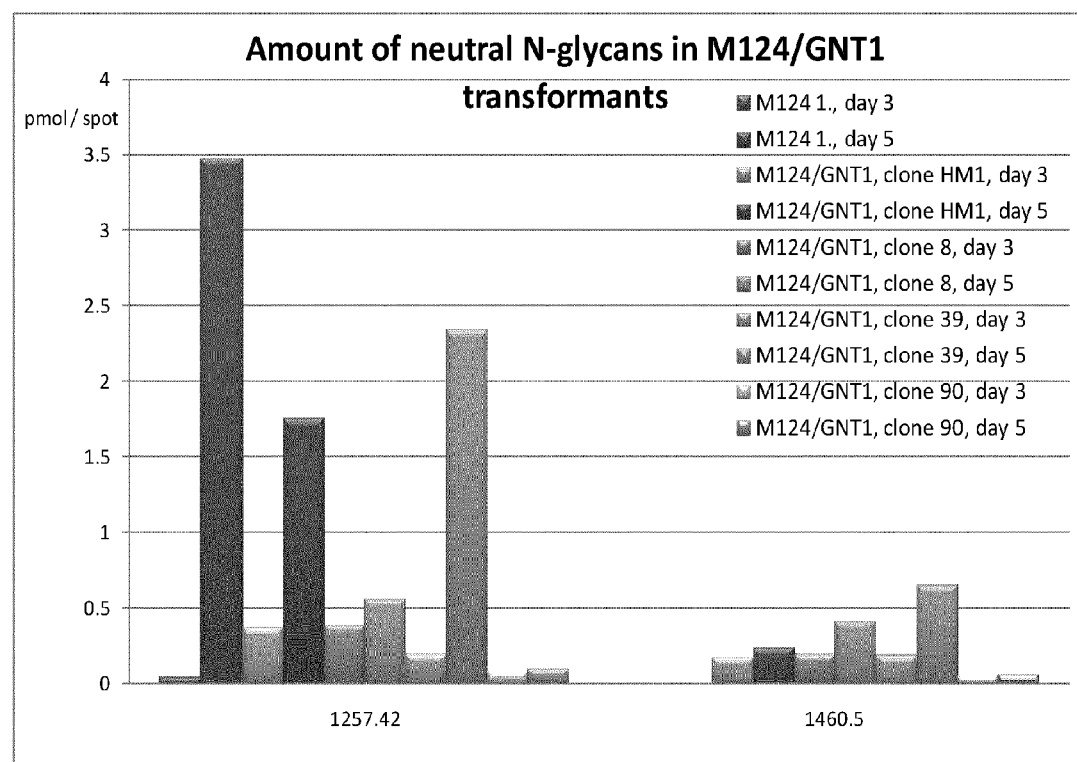
FIG. 35 shows the amounts of Man5 and Gn1Man5 in four positive GNT1 transformants on days 3 and 5. Quantitation was carried out against internal calibrant (Hex2HexNAc4, 2 pmol).

Eight GnTI transformants produced the Gn1Man5 structure. Gn1Man5 was most abundant in clone 39. However, the best clone appeared to be clone 8, which produced the second highest level of Gn1Man5, but had a high proportion of Man5 and Gn1Man5 (FIG. 35). Clone 8, which contains GnTI under the control of the cbhI promoter, was named strain M198, and was selected for continued analysis.

Transformation of *T. reesei* M198 Strain with GnTII Construct by Targeted Integration Five GnTII-harboring vectors were created (Table 14). Two of the vectors contained the native mammalian Golgi targeting peptide in GNTII. In the three other vectors, the mammalian targeting peptide was replaced by a *T. reesei* MNT1 ($\alpha$-1,2-mannosyltransferase) targeting peptide. All five vectors contained either a cbh1 promoter or a gpdA promoter, and a pyr4 loop-out marker. Additionally, all five vectors were targeted to integrate into the alg3 locus, thus deleting the alg3 gene. In the MNT1/GnTII constructs under the cbh1 promoter, two different sized GnTII sequence deletions were tested.

TABLE 13

The percentages of signal intensities of Man5 and Gn1Man5 compared to internal calibrant Hex2HexNAc4 in four positive GnT1 transformants and parental M124 strain on days 3 and 5. Man5 is the main glycoform in parental M124 strain.

| | | M1241., day 3 | | | | | M1241., day 5 | | | | |
|---|---|---|---|---|---|---|---|---|---|---|---|
| Composition | m\z | Average | SD | RSD | MIN | MAX | Average | SD | RSD | MIN | MAX |
| Hex2HexNAc4 | 1177.42 | 97.7 | 0.5 | 0.5 | 97.1 | 98.0 | 36.5 | 0.8 | 2.3 | 35.9 | 37.1 |
| Hex5HexNAc2 | 1257.42 | 2.3 | 0.5 | 22.5 | 2.0 | 2.9 | 63.5 | 0.8 | 1.3 | 62.9 | 64.1 |
| Hex5HexNAc3 | 1460.5 | 0.0 | 0.0 | 0.0 | 0.0 | 0.0 | 0.0 | 0.0 | 0.0 | 0.0 | 0.0 |
| | | M124/GNT1, clone HM1, day 3 | | | | | M124/GNT1, clone HM1, day 5 | | | | |
| Composition | m\z | Average | SD | RSD | MIN | MAX | Average | SD | RSD | MIN | MAX |
| Hex2HexNAc4 | 1177.42 | 78.5 | 14.5 | 18.4 | 68.2 | 88.7 | 50.1 | 10.6 | 21.2 | 42.6 | 57.6 |
| Hex5HexNAc2 | 1257.42 | 14.5 | 9.9 | 68.0 | 7.5 | 21.5 | 44.0 | 9.6 | 21.9 | 37.2 | 50.8 |
| Hex5HexNAc3 | 1460.5 | 7.1 | 4.6 | 65.6 | 3.8 | 10.3 | 5.9 | 1.0 | 16.7 | 5.2 | 6.6 |
| | | M124/GNT1, clone 8, day 3 | | | | | M124/GNT1, clone 8, day 5 | | | | |
| Composition | m\z | Average | SD | RSD | MIN | MAX | Average | SD | RSD | MIN | MAX |
| Hex2HexNAc4 | 1177.42 | 77.3 | 7.6 | 9.8 | 72.0 | 82.7 | 67.3 | 10.0 | 14.9 | 56.5 | 76.3 |
| Hex5HexNAc2 | 1257.42 | 15.0 | 5.2 | 34.4 | 11.4 | 18.7 | 18.9 | 6.2 | 32.5 | 12.8 | 25.1 |
| Hex5HexNAc3 | 1460.5 | 7.6 | 2.4 | 31.6 | 5.9 | 9.3 | 13.8 | 4.0 | 29.1 | 10.8 | 18.3 |
| | | M124/GNT1, clone 39, day 3 | | | | | M124/GNT1, clone 39, day 5 | | | | |
| Composition | m\z | Average | SD | RSD | MIN | MAX | Average | SD | RSD | MIN | MAX |
| Hex2HexNAc4 | 1177.42 | 83.7 | 1.5 | 1.8 | 82.7 | 84.8 | 40.0 | 1.9 | 4.6 | 37.9 | 41.1 |
| Hex5HexNAc2 | 1257.42 | 8.3 | 1.0 | 11.7 | 7.6 | 8.9 | 46.9 | 1.8 | 3.8 | 45.6 | 49.0 |
| Hex5HexNAc3 | 1460.5 | 8.0 | 0.6 | 6.9 | 7.6 | 8.4 | 13.1 | 0.3 | 2.1 | 12.7 | 13.3 |
| | | M124/GNT1, clone 90, day 3 | | | | | M124/GNT1, clone 90, day 5 | | | | |
| Composition | m\z | Average | SD | RSD | MIN | MAX | Average | SD | RSD | MIN | MAX |
| Hex2HexNAc4 | 1177.42 | 93.8 | 1.6 | 1.7 | 92.4 | 95.6 | 92.6 | 2.7 | 2.9 | 89.8 | 95.3 |
| Hex5HexNAc2 | 1257.42 | 3.7 | 1.0 | 25.9 | 2.6 | 4.5 | 4.7 | 1.4 | 30.9 | 3.2 | 6.0 |
| Hex5HexNAc3 | 1460.5 | 2.5 | 0.7 | 26.2 | 1.8 | 3.1 | 2.7 | 1.3 | 47.8 | 1.5 | 4.1 |

TABLE 14

Constructed GNT2 vectors.

| Plasmid name | Promoter | Targeting peptide | N-terminal deletion (GnTII) |
|---|---|---|---|
| pTTv140 | cbh1 | mammalian | N/A |
| pTTv141 | gpdA | mammalian | N/A |
| pTTv142 | cbh1 | Trichoderma MNT1 | 74 amino acids |
| pTTv143 | cbh1 | Trichoderma MNT1 | 104 amino acid |
| pTTv144 | gpdA | Trichoderma MNT1 | 74 amino acids |

These vectors, except for the pTTv144 vector, were transformed into the best py4-negative GnTI producing strain M198 (M319) as PmeI fragments. Transformants were purified to uninuclear clones and PCR screened. Clones showing the correct integration at both ends were then selected for continued analysis.

To study the growth characteristics of the generated GNTII-expressing strains, large shake flask cultures were prepared. Shake flask culture were prepared in two separate batches. The first batch contained pTTv140, pTTv142, and pTTv143. The second batch contained pTTv141. The parental strain M198 was used as a control strain. The cells were grown in TrMM medium supplemented with 40 g/l lactose, 20 g/l spent grain extract, and 100 mM PIPPS, pH 5.5. Five transformants per construct were cultured. The pTTv140, pTTv142, and pTTv143 cultures were sampled on days 3, 5, 7, and 9. The pTTv141 cultures were sampled on days 3, 5, 7, and 10. The pH and cell dry weight of each sample were measured and culture supernatant samples were used for glycan structure analysis.

Glycan Analysis of T. reesei Strains Obtained by Targeting GnTII to alg3 Locus of T. reesei M198 Strain Five different clones containing the pTTv140 vector (containing the native targeting peptide and the cbhI promoter), the pTTv142 vector (containing the MNT1 targeting peptide, the GNTII 74 aa N-terminal deletion, and the cbhI promoter), the pTTv143 vector (containing the MNT1 targeting peptide, the GNTII 110 aa N-terminal deletion, and the cbhI promoter), and the pTTv141 vector (containing the targeting peptide and the gpdA promoter) were analyzed.

N-glycan analyses were prepared in triplicate for day 5 samples, and in duplicate for day 3 and 7 samples on 96-well plates for 5 μg of supernatant protein. The protein concentrations of the supernatants were measured by Bradford-based assay (BioRad Quickstart Bradford Protein Assay) using BSA as a standard. PNGase F reactions were performed as described. The released N-glycans were first purified with Hypersep C-18 100 mg and then with Hypersep Hypercarb 10 mg (both from Thermo Scientific) where neutral and acidic glycans were separated. Both purifications were performed in 96-well format. Neutral N-glycans were analyzed by MALDI-TOF MS.

Figure 37:
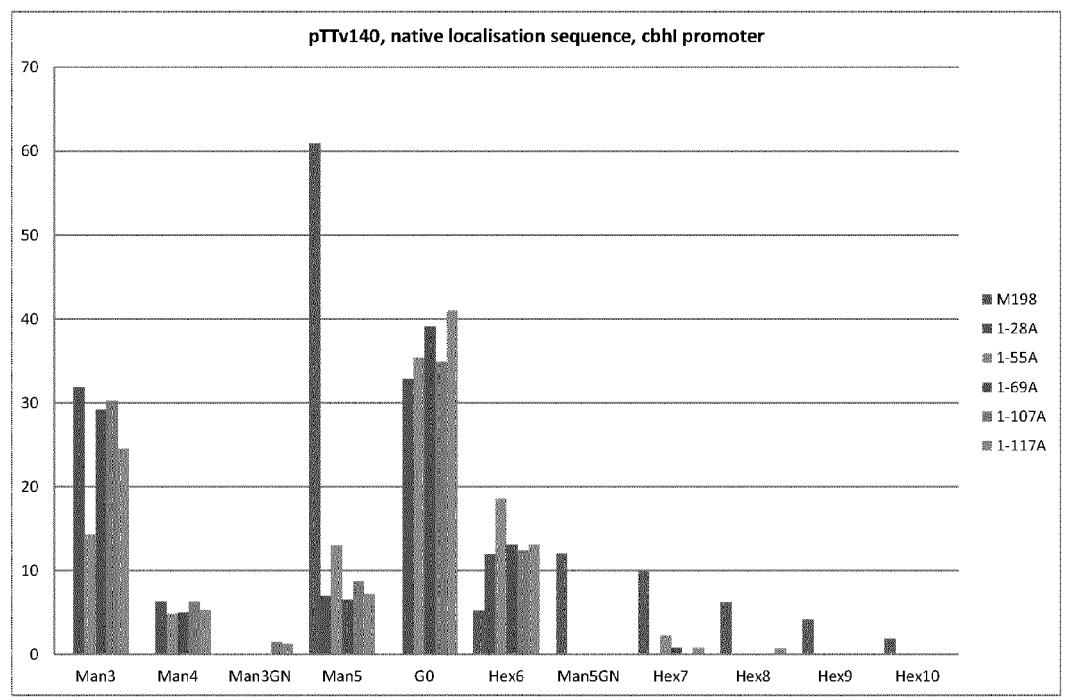
FIG. 37 shows diagrams of neutral N-glycans of different GnTII strains/clones from day 5. Part (A) show the pTTv140 clone. Part (B) shows the pTTv142 clone. Part (C) shows the pTTv143 clone. Part (D) shows the pTTv141 clone.
Figure 37:
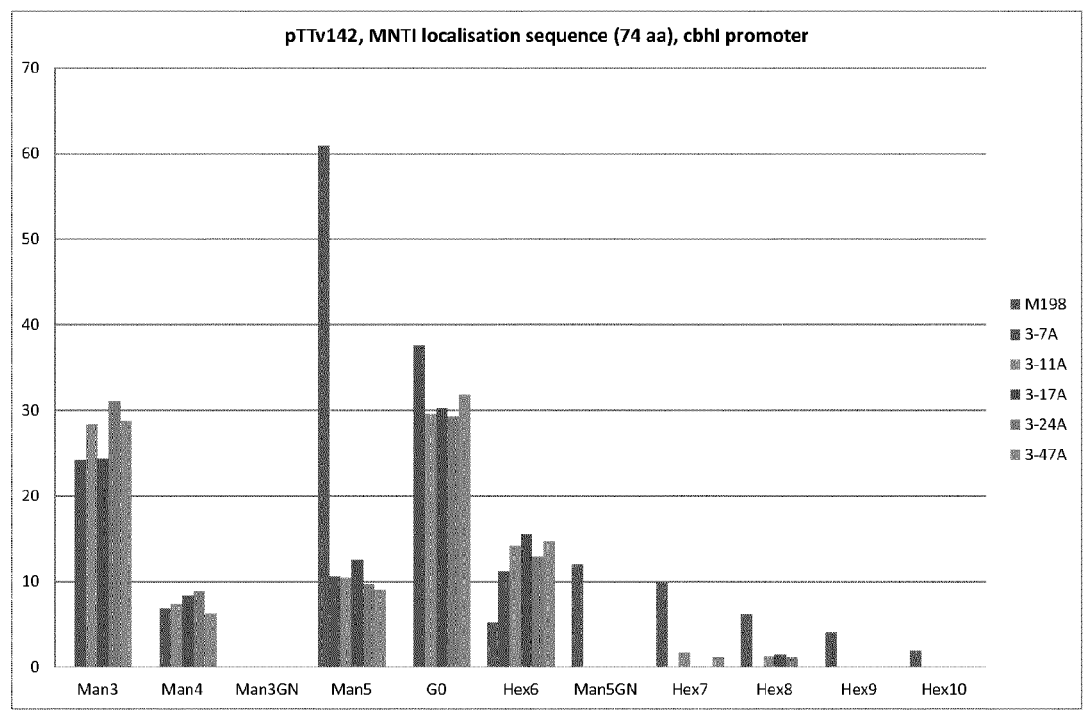
Figure 37:
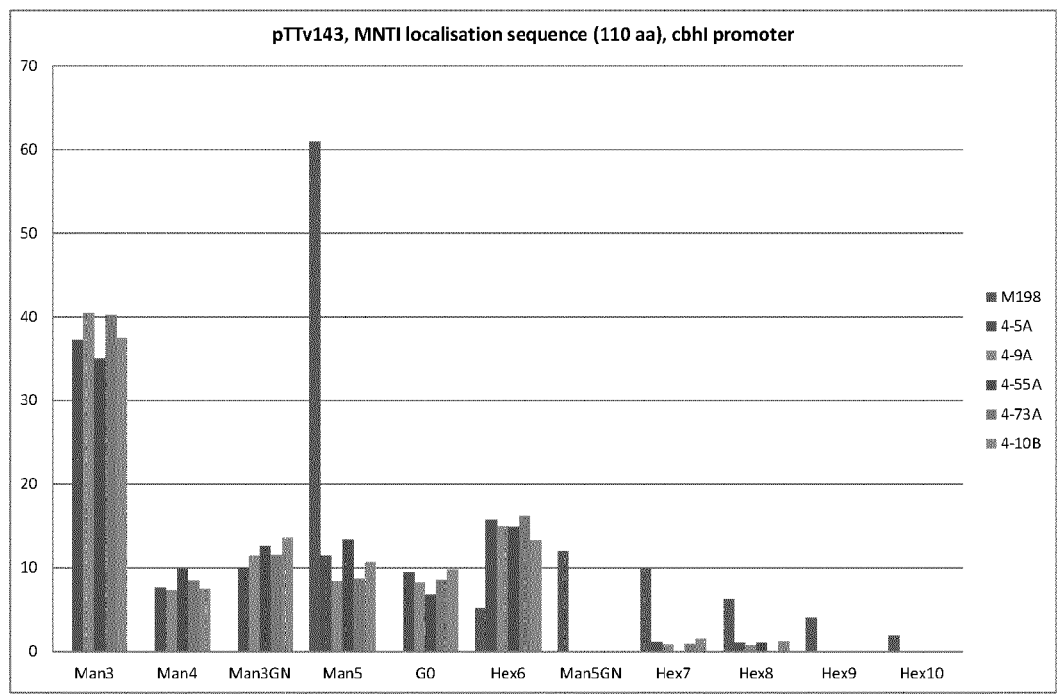
Figure 37:
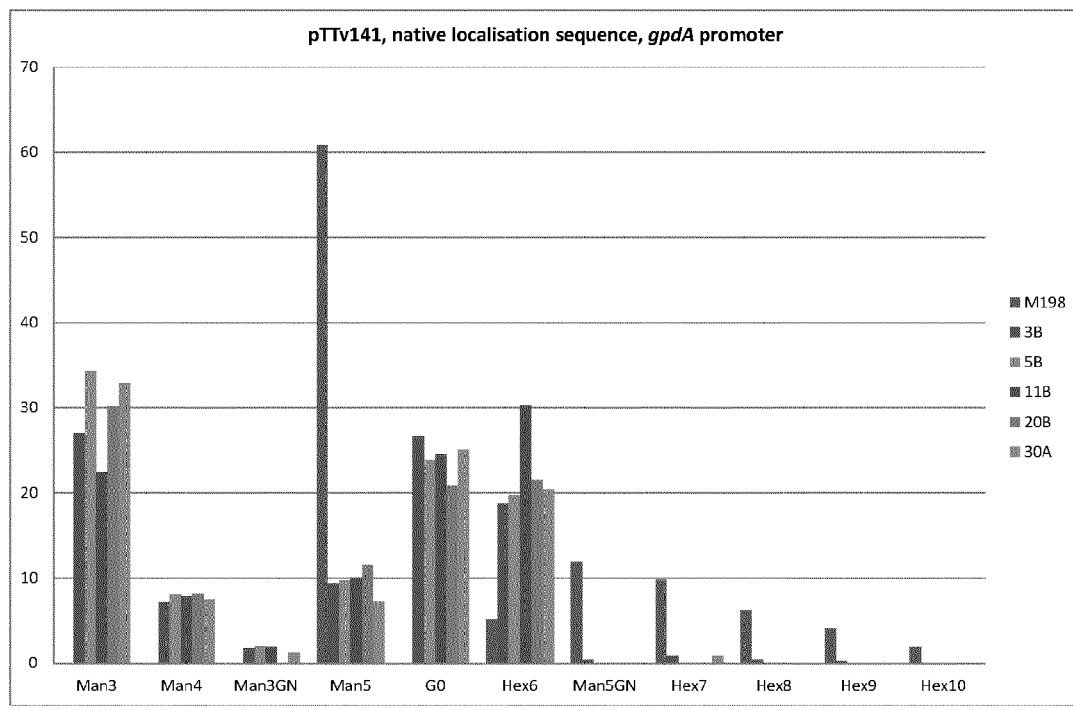

N-glycans of four different strains transformed with GnTII were analyzed. Clone 1-117A, which was transformed with the pTTv140 vector, and thus contained the native targeting peptide and the cbhI promoter, produced about 40% of G0 and about 13% of Hex6 (FIG. 37A). Clones transformed with the pTTv143 vector, thus containing the MNT1 targeting peptide, the GnTII 110 aa N-terminal deletion, and the cbhI promoter, produced about 10% of G0 (FIG. 37C). Clone 3B, which contained the gbdA promoter produced about 28% of G0 and about 19% of Hex6 (FIG. 37D).

Figure 38:
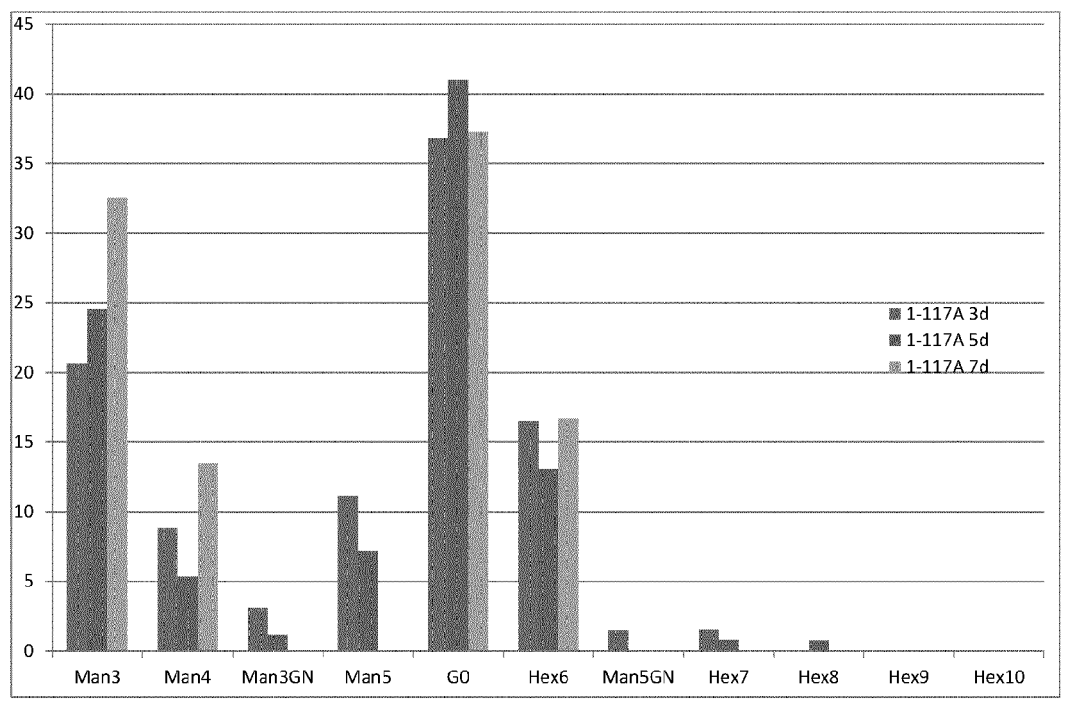
FIG. 38 shows an example of neutral N-glycans of different GnTII strains/clones and the parental strain M198 from days 3, 5, and 7. Part (A) shows clone 1-117A. Part (B) shows clone 3-11A. Part (C) shows clone 30A. Part (D) shows parental stain M198.
Figure 38:
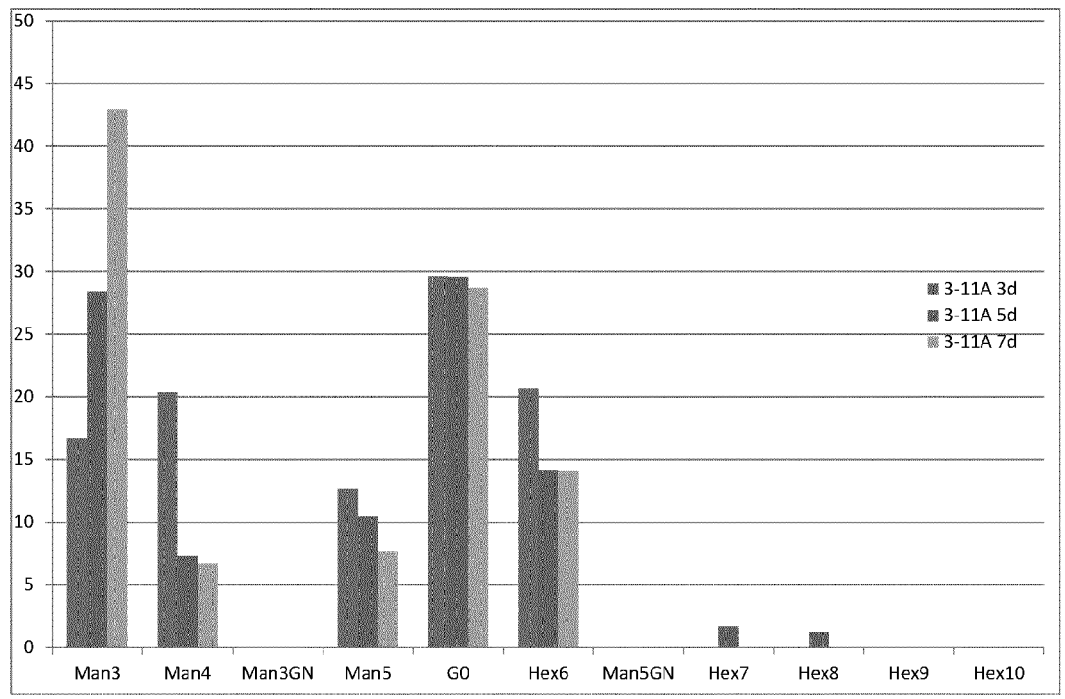
Figure 38:
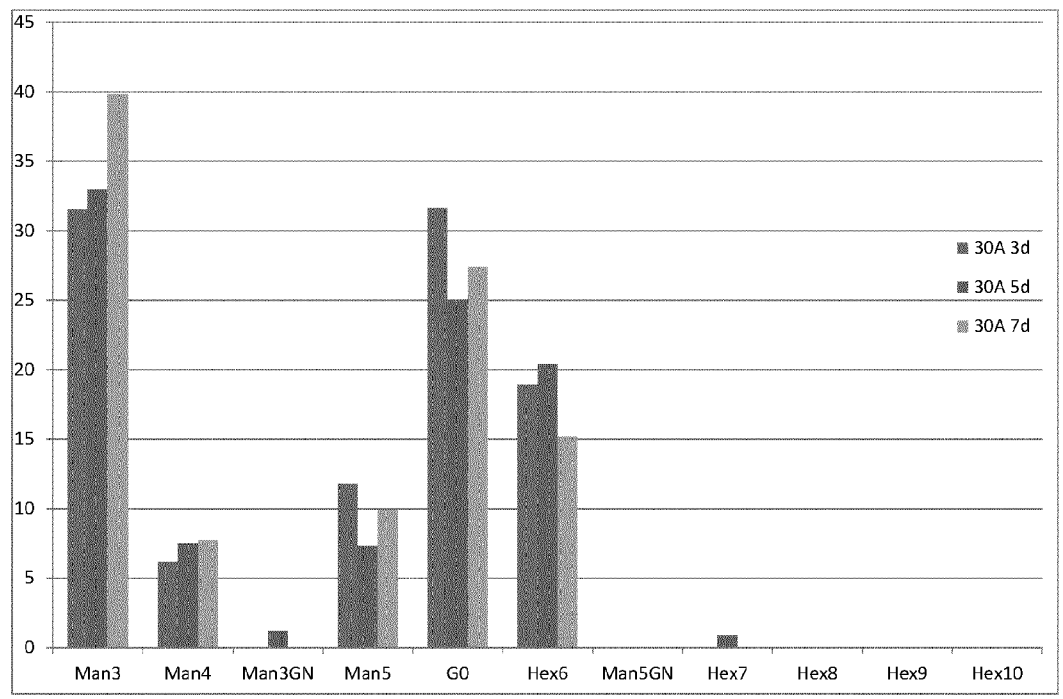
Figure 38:
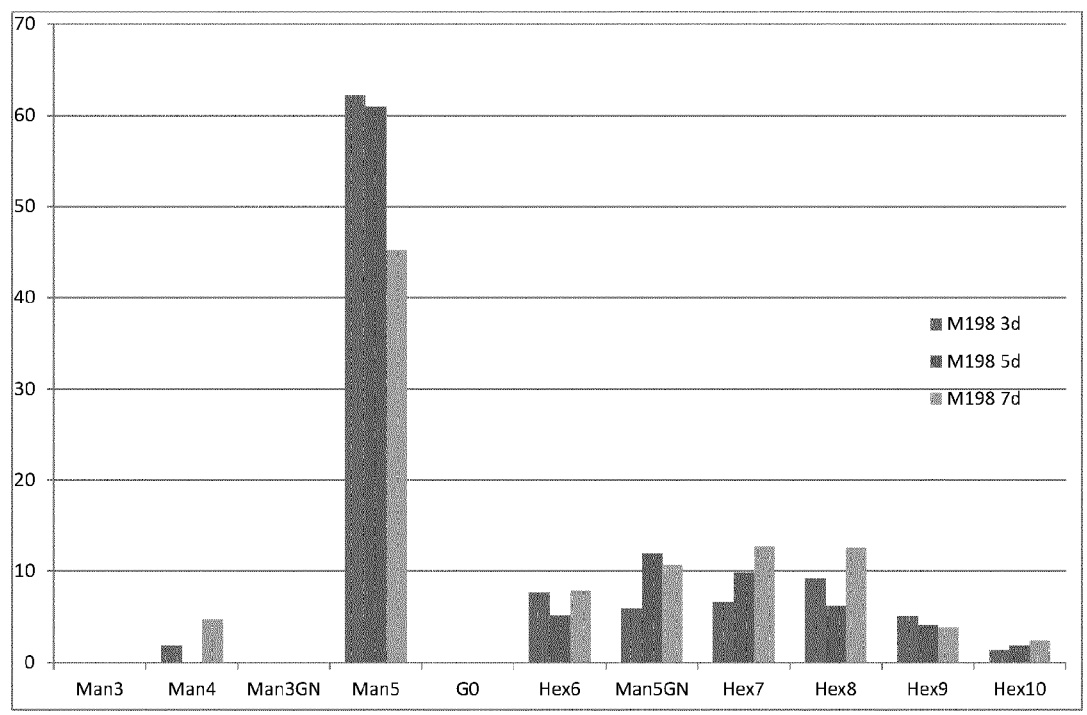

The glycosylation patterns of representative clones containing the pTTv140, pTTv141, and pTTv142 vectors were also shown to be stable as function of time (FIG. 38).

Protein Specific Glycosylation

Figure 39:
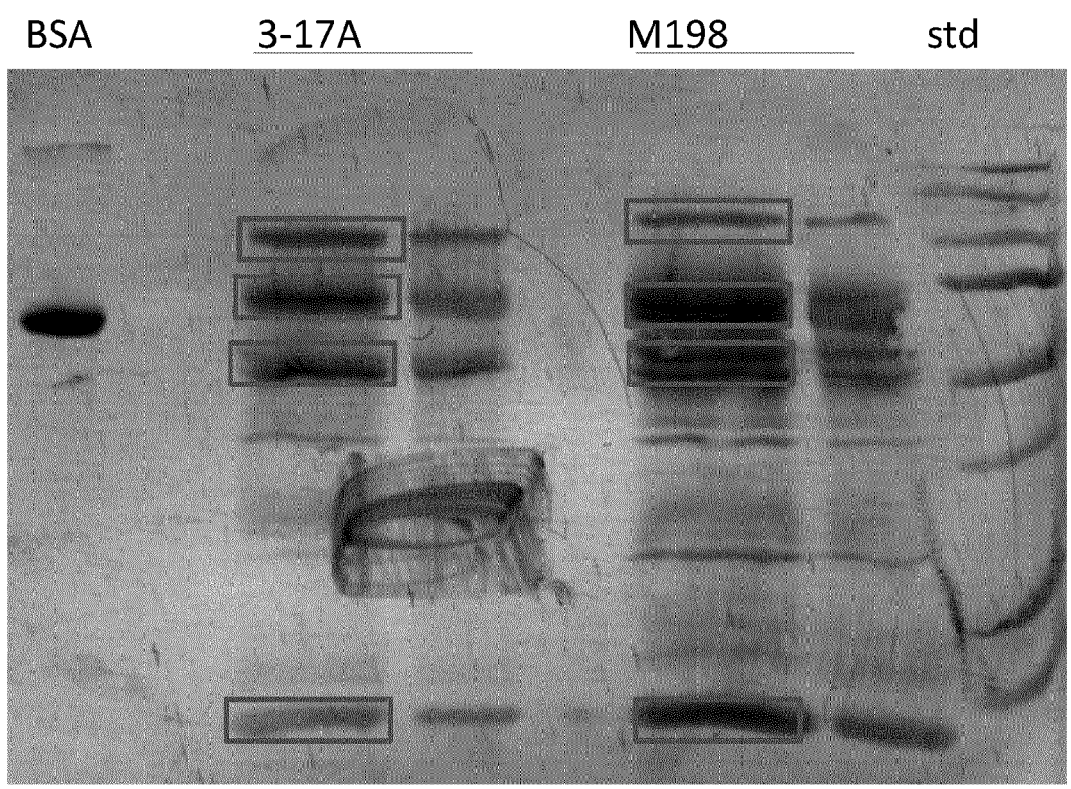
FIG. 39 shows the membrane of separated proteins of *T. reesei* strain M198 and GnTII clone 3-17A. The 50 kDA protein is marked with an arrow.

To analyze protein specific changes in glycosylation, samples from the pTTv142 vector-containing clone 3-17A and from the parental strain M198 were separated with SDS-PAGE and blotted to a PVDF membrane. The protein bands of interest (four bands of M198 and four of the 3-17A clone) were excised, and the N-glycans were liberated with on-membrane enzymatic release with PNGase F (FIG. 39).

Figure 40:
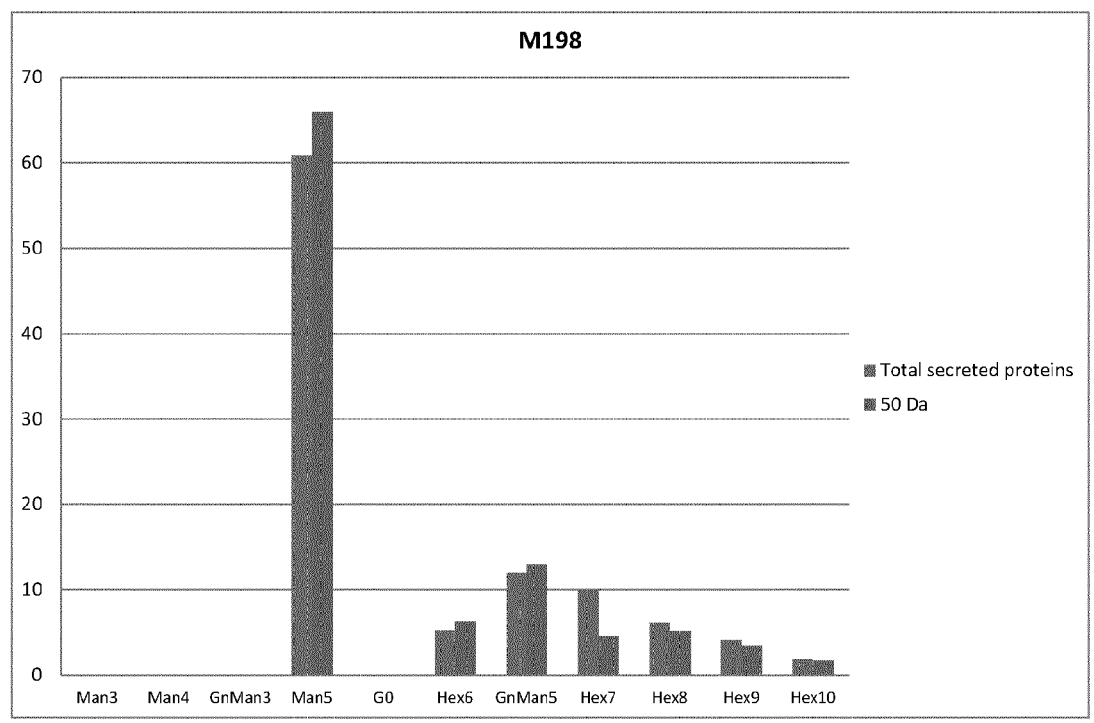
FIG. 40 shows column diagrams of total secreted proteins versus individual secreted protein(s) of parental strain M198 (A) and the GnTII clone 3-17A (B).
Figure 40:
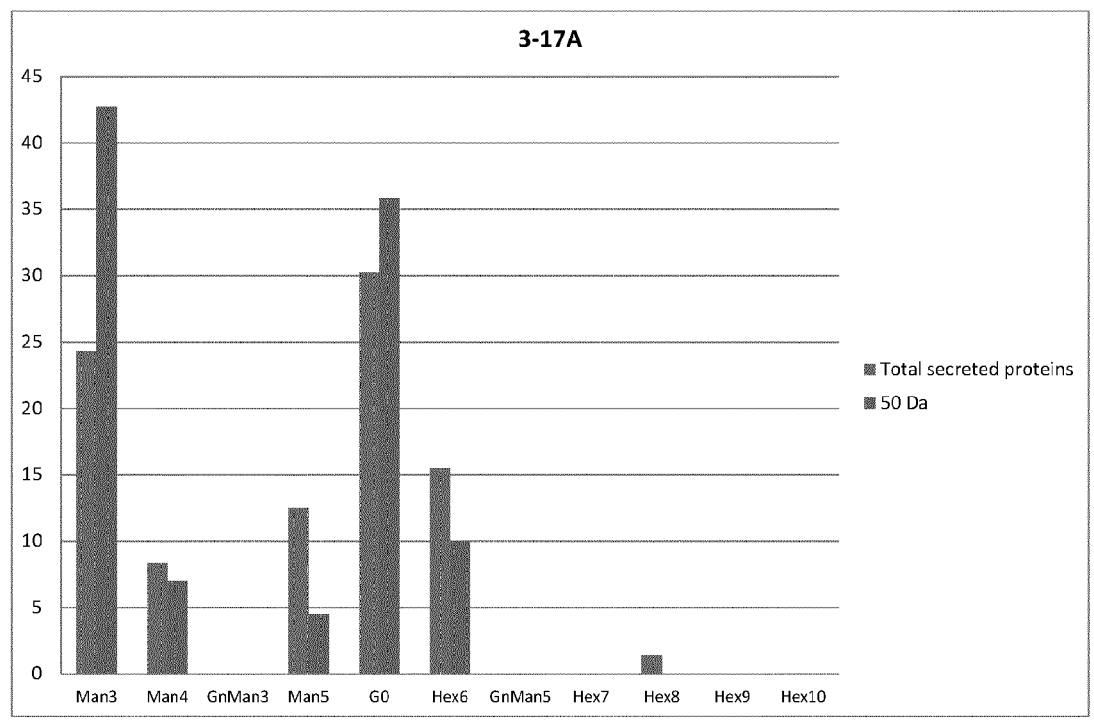

Detached and purified neutral N-glycans were analyzed using MALDI-TOF MS. The glycosylation pattern of total secreted proteins was similar to a separated 50 kDa protein of the M198 parental strain (FIG. 40). The smallest size protein band was unglycosylated.

In the GnTII clone 3-17A, most of the untypical signals had disappeared, confirming their origin from the medium. Additionally, the glycosylation pattern of clone 3-17A differed from the glycan patterns of total secreted proteins (FIG. 40B). The amount of G0 from clone 3-17A was about 35 to 36% (FIG. 40B).

Fermenter Cultivation of GnTII Strain

Figure 41:
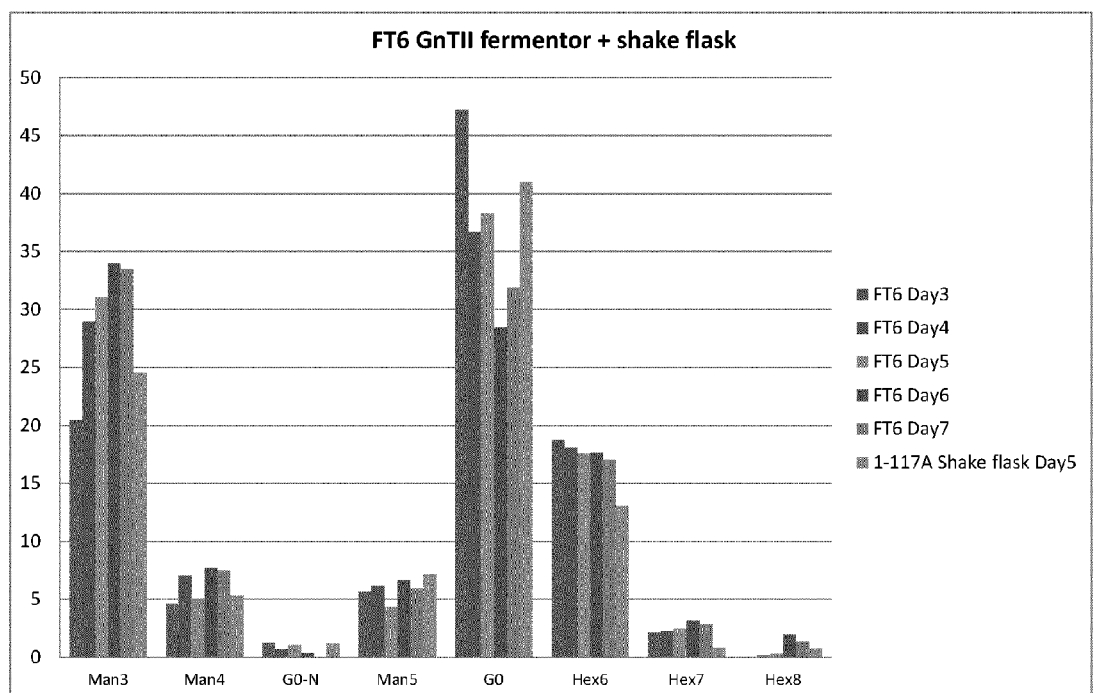
FIG. 41 shows a column diagram of fermentor cultured GnTII strain M329 from day 3 to day 7, and shake flask culture of strain M329 from day 5.

Fermenter cultivation of the GnTII strain 1-117A M329 (which contains the pTTv140 vector) was fermented in TrMM pH 5.5+2% Spent grain extract+6% lactose+0.5% KH$_2$PO$_4$+0.5% (NH$_4$)$_2$SO$_4$ at +28° C. (pH 5.5). N-glycan analysis was performed in triplicate to 5 μg of the secreted proteins described in the "Protein specific glycosylation" section above on samples taken on day 3. The amount of G0 was about 48% and the amount of Hex6 was about 19% on day 3 (FIG. 41).

Example 8

T. reesei ALG3 Homologs

Transformation of T. reesei M124 with GnTI Construct by Random Integration

T. reesei ALG3 homologs were identified from other organisms. These homologs can be used to design ALG3 deletion constructs for filamentous fungal cells other than T. reesei. The ALG3 homologs are listed in Table 15. A multiple amino acid sequence alignment of T. reesei ALG3 and ALG3 homologs are shown in FIG. 42.

TABLE 15

ALG3 Homologs.

| Reference sequence | Organism | SEQ ID NO: |
|---|---|---|
| Trire2\|104121\|fgenesh5_pg.C_scaffold_3000076 | Trichoderma reesei | 126 |
| Triat2\|270085\|fgenesh1_pg.contig_14_#_149 | Trichoderma atroviride | 127 |
| TriviGv29_8_2\|194462\|fgenesh1_pm.87_#_115 | Trichoderma virens | 128 |
| EGU81920.1 | Fusarium oxysporum Fo5176 | 129 |
| XP_389829.1 | Gibberella zeae PH-1 | 130 |
| AEO60805.1 | Myceliophthora thermophila | 131 |

TABLE 15-continued

ALG3 Homologs.

| Reference sequence | Organism | SEQ ID NO: |
|---|---|---|
| XP_962259.1 | *Neurospora crassa* OR74A | 132 |
| XP_001824044.1 | *Aspergillus oryzae* RIB40 | 133 |
| XP_001259497.1 | *Neosartorya fischeri* NRRL 181 | 134 |
| XP_001398696.2 | *Aspergillus niger* CBS 513.88 | 135 |
| XP_362427.2 | *Magnaporthe oryzae* 70-15 | 136 |
| NP_593853.1 | *Schizosaccharomyces pombe* 972h | 137 |

Example 9

GnTII/GnTI Fusion Protein Variants

Generation of GnTII/GnTI Expression Construct

A recombinant GnTI/II fusion protein under the control of the inducible promoter cbh1 and containing 1 of 4 spacer variants is constructed as described in Examples 4 and 5. The four spacer variants are the 2×G4S spacer, the 3×G4S spacer, the CBHI spacer, and the EGIV spacer.

Briefly, the fusion fragments are amplified from GnTII and GnTI templates separately with primers containing 50 by in-frame overlaps at the fusion site. Fragments are purified from an agarose gel and used as PCR template for amplification of the fusion construct according to standard procedures. The fusion construct is cloned into a vector with ApaI/SpeI restriction sites, under the control of the inducible promoter cbh1. Additionally, the native mammalian Golgi targeting peptide in the GNTII domain was replaced by a *T. reesei* MNT1 (α-1,2-mannosyltransferase) targeting peptide.

To introduce the 2×G4S spacer variants into the fusion protein, T45 sequence is amplified in two parts by using PCR overlapping strategy. First, a fragment is amplified with AKT1-6-1 5' primer (GGTACCGGGCCCACTGCGCAT-CATGCGCTTCCGAATCTACAAGCG (SEQ ID NO: 146)) and GP93 3' primer, and a second fragment is amplified with GP92 5' primer and AKT1-6-4 3' primer (GGCGCGCCAC-TAGTCTAATTCCAGCTGGGATCATAGCC (SEQ ID NO: 147)). Amplification is carried out with Phusion high-fidelity PCR polymerase (Finnzymes) under the standard conditions provided by the supplier. Cycling conditions are as described in Example 5. The resulting PCR product is purified from the agarose gel, and the fragments with overlapping, modified sequences are combined in the same reaction mixture with standard conditions without primers. Ten annealing/extension cycles are carried out as described in Example 5. Primers AKT1-6-1 (5') and AKT1-6-4 (3') are added, and cycling is continued as described in Example 5 for 20 amplification cycles. The amplified T45 fragment is then purified, digested with ApaI/SpeI (New England Biolabs) according to standard protocols, and cloned into the *Trichoderma reesei* expression vector. The cloned fragment is then verified by sequencing with appropriate set of primers and the generated sequence is used for construction of *T. reesei* expression vector with 2×G4S promoter and alg3 targeting.

The resulting plasmid is used as a template for the 3×G4S spacer modification. Cloning of the T46 sequence is done as described above with T45. AKT1-6-1 5'-primer and GP95 3'-primer are used for first fragment synthesis, and GP94 5'-primer and AKT1-6-4 3'-primer are used for second fragment synthesis. Fragments are combined, and primers AKT1-6-1 (5') and AKT1-6-4 (3') are added for amplification. Amplified fragment T46 is then digested with ApaI/SpeI and cloned into the *Trichoderma reesei* expression vector. The cloned fragment is then verified by sequencing with an appropriate set of primers and the generated sequence is used for construction of *T. reesei* expression vector with 3×G4S promoter and alg3 targeting.

The CBHI and EGIV spacers are constructed with a similar PCR overlap method. For the CBHI spacer, the first fragment is amplified with AKT1-6-1 5'-primer and GP107 3'-primer. The second fragment is amplified with GP108 5'-primer and AKT1-6-4 3'-primer (Table 11). For the EGIV spacer, the first fragment is amplified with AKT1-6-1 5' primer and GP109 3' primer. The second fragment is amplified with GP110 5'-primer and AKT1-6-4 3'-primer (Table 11). In both cases, the PCR products are purified from agarose gel, combined, and used as a template for the next PCR reaction to amplify the sequences T50 and T51. T50 and T51 PCR products are then digested with ApaI/SpeI and cloned into the *Trichoderma reesei* expression vector. The cloned fragments are then verified by sequencing with appropriate sets of primers and the generated sequences are used for construction of *T. reesei* expression vectors with either CBHI or EGIV promoter and alg3 targeting.

All PCR amplifications are made with high-fidelity Phusion polymerase (Finnzymes). Primers (Table 11) are ordered from MWG Operon. Sequencing is performed by the DNA Sequencing Laboratory of the Institute of Biotechnology, University of Helsinki, as a commercial service.

The *Trichoderma reesei* expression vectors with the described chimeric GnTII/GnTI sequences with spacer variations (2×G4S, 3×G4S, CBHI, and EGIV) are subcloned under the control of the cbh1 promoter, with a pyr4 gene loopout marker and alg3 flanking region fragments for targeted integration in the backbone are then constructed. Expression cassettes are transformed into *T. reesei* strain M279 (pyr4⁻ strain of M202). After plate selection, the clones are PCR-screened and purified through single spores. To obtain material for glycan analyses, shake flask cultivations are performed as described.

Introduction of GnTII/I Fusion Protein Variants to *T. reesei* Strain Expressing Rituximab Antibody The recombinant GnTII/I fusion protein variants are introduced into the rituximab-expressing *T. reesei* strain M279 described in Example 5.

Briefly, the vectors having the GnTII/GnTI fusion protein under the control of the cbh1 promoter, the MNTI targeting peptide, the pyr4 loop-out marker, and each of the 4 spacer variants are each subcloned into a backbone vector between alg3 flanking region fragments for targeted integration, thus deleting the alg3 gene. A PmeI-digested expression cassette is transformed into *T. reesei* strain M279 (a pyr4⁻ strain). After plate selection, the clones are PCR-screened and purified through single spores.

Glycan Analysis of Rituximab-Producing *T. reesei* GnTII/GnTI Variant Strains Obtained by Targeting to alg3 Locus To obtain material for glycan analysis, shake flask cultivations are performed as described in Example 5 and, in addition, some culture media are supplemented with 0.3 mg/ml soybean trypsin inhibitor (SBTI) and 1% casamino acids. SBTI is added first at inoculation and then daily on days 3-6. PMSF and Pepstatin A is added to all samples before freezing.

Rituximab is purified with Protein G affinity chromatography from day 5 supernatant samples with SBTI and from day 5 and 7 samples without SBTI. PNGase F reactions are performed for ~10 µg of denatured protein. The released N-glycans are first purified with Hypersep C-18 and then with Hypersep Hypercarb (both from Thermo Scientific) where neutral and acidic glycans are separated. The purification steps are performed in 96-well format. Neutral and acidic N-glycans are analyzed by MALDI-TOF MS to test for the presence of the G0 glycoform on the rituximab antibody.

We claim:

1. A method of producing a complex N-glycan, comprising:
   (1) providing a filamentous fungal or yeast host cell, wherein the host cell comprises a polynucleotide encoding a fusion protein comprising an N-acetylglucosaminyltransferase I catalytic domain and an N-acetylglucosaminyltransferase II catalytic domain, wherein the N-acetylglucosaminyltransferase II catalytic domain is positioned N-terminal to the N-acetylglucosaminyltransferase I catalytic domain, and wherein the alg3 gene is deleted from the host cell; and
   (2) culturing the filamentous fungal or yeast host cell such that the fusion protein is expressed, wherein the fusion protein catalyzes the transfer of N-acetylglucosamine to a terminal Manα3 residue and N-acetylglucosamine to a terminal Manα6 residue of an acceptor glycan to produce a complex N-glycan.

2. The method of claim 1, wherein the acceptor glycan is attached to a heterologous polypeptide.

3. The method of claim 1, wherein the complex N-glycan is GlcNAcβ2Manα3(GlcNAcβ2Manα6)Manβ4GlcNAcβ4GlcNAc.

4. The method of claim 1, wherein the host cell is a filamentous fungal cell selected from the group consisting of *Trichoderina* sp., *Acremonium, Aspergillus, Aureobasidium, Cryptococcus, Chrysosporium, Chrysosporiunz lucknowense, Filibasidiunz, Fusarium, Gibberella, Magnaporthe, Mucor, Mycellophthora, Myrothecium, Neocallimastix, Neurospora, Paecilomyces, Piromyces, Schizophyllum, Talaromyces, Thermoascus, Thielavia*, and *Tolypocladium*.

5. The method of claim 1, wherein the host cell further comprises a polynucleotide encoding a UDP-GlcNAc transporter.

6. The method of claim 1, wherein the host cell is a *Trichoderma* cell.

7. The method of claim 1, wherein the recombinant fusion protein comprises:
   a spacer sequence comprising sequence from a human N-acetylglucosaminyltransferase I stem domain located in between the catalytic domains, and
   a targeting peptide located N-terminal to the N-acetylglucosaminyltransferase II catalytic domain wherein the targeting peptide comprises a cytoplasmic domain, a transmembrane domain, and a stem domain from human N-acetylglucosaminyltransferase II.

8. The method of claim 1, wherein the recombinant protein comprises:
   a spacer sequence located in between the catalytic domains, wherein the spacer sequence is at least 5 amino acids in length of
   a) a sequence selected from the group consisting of SEQ ID NO: 118, SEQ ID NO: 120, SEQ ID NO: 122, and SEQ ID NO: 124,
   b) a sequence that is at least 70% identical to SEQ ID NOs: 118, 120, 122or 124,
   c) a sequence $\{(Yyy)_n Xxx\}_m$ where n is 2 to 10, m is 2 to 10, and Xxx and Yyy are selected from Ser, Thr, Gly, Pro and Ala, with the proviso that Xxx and Yyy are not the same amino acid residue, or
   d) a sequence $\{(Gly)_n Xxx\}_m$ where n is 2 to 10, m is 2 to 10, and Xxx is selected from Ser, Thr, Gly, Pro and Ala; and
   a targeting peptide located N-terminal to the N-acetylglucosaminyltransferase II catalytic domain wherein the targeting peptide comprises a cytoplasmic domain, a transmembrane domain, and a stem domain from human N-acetylglucosaminyltransferase II.

9. The method of claim 1, wherein the recombinant protein comprises
   a spacer sequence located in between the catalytic domains, wherein the spacer sequence is at least 5 amino acids in length of
   a) a sequence selected from the group consisting of SEQ ID NO: 118, SEQ ID NO: 120, SEQ ID NO: 122, and SEQ ID NO: 124,
   b) a sequence that is at least 70% identical to SEQ ID NOs: 118, 120, 122, or 124,
   c) a sequence $\{(Yyy)_n Xxx\}_m$, where n is 2 to 10, m is 2 to 10, and Xxx and Yyy are selected from Ser, Thr, Gly, Pro and Ala, with the proviso that Xxx and Yyy are not the same amino acid residue, or
   d) a sequence $\{(Gly)_n Xxx\}_m$ where n is 2 to 10, m is 2 to 10, and Xxx is selected from Ser, Thr, Gly, Pro and Ala; and
   a targeting peptide located N-terminal to the N-acetylglucosaminyltransfease II catalytic domain wherein the targeting peptide comprises:

a cytoplasmic domain selected from the group consisting of SEQ ID NO: 39, SEQ ID NO: 42, SEQ ID NO: 45, SEQ ID NO: 48, SEQ ID NO: 51, SEQ ID NO: 54, SEQ ID NO: 57, SEQ ID NO: 60, SEQ ID NO: 63, SEQ ID NO: 66, SEQ ID NO: 69, SEQ ID NO: 72, SEQ ID NO: 75, SEQ ID NO: 80, SEQ ID NO: 83, SEQ ID NO: 86, SEQ ID NO: 89, and SEQ ID NO: 92, a transmembrane domain selected from the group consisting of SEQ ID NO: 40, SEQ ID NO: 43, SEQ ID NO: 46, SEQ ID NO: 49, SEQ ID NO: 52, SEQ ID NO: 55, SEQ ID NO: 58, SEQ ID NO: 61, SEQ ID NO: 64, SEQ ID NO: 67, SEQ ID NO: 70, SEQ ID NO: 73, SEQ ID NO: 76, SEQ ID NO: 78, SEQ ID NO: 81, SEQ ID NO: 84, SEQ ID NO: 87, SEQ ID NO: 90, and SEQ ID NO: 93, and a stem domain selected from the group consisting of SEQ ID NO: 41, SEQ ID NO: 44, SEQ ID NO: 47, SEQ ID NO: 50, SEQ ID NO: 53, SEQ ID NO: 56, SEQ ID NO: 59, SEQ ID NO: 62, SEQ ID NO: 65, SEQ ID NO: 68, SEQ ID NO: 71, SEQ ID NO: 74, SEQ ID NO: 77, SEQ ID NO: 79, SEQ ID NO: 82, SEQ ID NO: 85, SEQ ID NO: 88, SEQ ID NO: 91, and SEQ ID NO: 94.

10. The method of claim 1, wherein the recombinant protein comprises a spacer sequence located in between the catalytic domains, wherein the spacer sequence is at least 5 amino acids in length of:
 a) a sequence selected from the group consisting of SEQ ID NO: 118, SEQ ID NO: 120, SEQ ID NO: 122, and SEQ ID NO: 124,
 b) a sequence that is at least 70% identical to SEQ ID NOs: 118, 120, 122, or 124,
 c) a sequence $\{(Yyy)_n Xxx\}_m$ where n is 2 to 10, m is 2 to 10, and Xxx and Yyy are selected from Ser, Thr, Gly, Pro and Ala, with the proviso that Xxx and Yyy are not the same amino acid residue, or
 d) a sequence $\{(Gly)_n Xxx\}_m$ where n is 2 to 10, m is 2 to 10, and Xxx is selected from Ser, Thr, Gly, Pro and Ala; and a targeting peptide located N-terminal to the N-acetylglucosaminyltransferase II catalytic domain wherein the targeting peptide consists of SEQ ID NO: 115, SEQ ID NO: 116, or amino acids 1-85 of *T. reesei* MNT1 fused to the human N-acetylglucosaminyltransferase II catalytic domain.

11. The method of claim 1, wherein the recombinant protein is at least 90% identical to SEQ ID NO: 95.

12. The method of claim 1, wherein the recombinant protein is SEQ ID NO: 95.

13. The method of claim 1, wherein the recombinant protein is at least 90% identical to SEQ ID NO: 119.

14. The method of claim 1, wherein the recombinant protein is SEQ ID NO: 119.

15. The method of claim 1, wherein the recombinant protein is at least 90% identical to SEQ ID NO: 121.

16. The method of claim 1, wherein the recombinant protein is SEQ ID NO: 121.

17. The method of claim 1, wherein the recombinant protein is at least 90% identical to SEQ ID NO: 123.

18. The method of claim 1, wherein the recombinant protein is SEQ ID NO: 123.

19. The method of claim 1, wherein the recombinant protein is at least 90% identical to SEQ ID NO: 125.

20. The method of claim 1, wherein the recombinant protein is SEQ ID NO: 125.

21. The method of claim 1, wherein the polynucleotide is integrated at the the alg3 locus of the host cell.

* * * * *

SEQUENCE LISTING

```
<160> NUMBER OF SEQ ID NOS: 147

<210> SEQ ID NO 1
<211> LENGTH: 445
<212> TYPE: PRT
<213> ORGANISM: Homo sapiens

<400> SEQUENCE: 1

Met Leu Lys Lys Gln Ser Ala Gly Leu Val Leu Trp Gly Ala Ile Leu
 1               5                  10                  15

Phe Val Ala Trp Asn Ala Leu Leu Leu Phe Phe Trp Thr Arg Pro
             20                  25                  30

Ala Pro Gly Arg Pro Pro Ser Val Ser Ala Leu Asp Gly Asp Pro Ala
             35                  40                  45

Ser Leu Thr Arg Glu Val Ile Arg Leu Ala Gln Asp Ala Glu Val Glu
     50                  55                  60

Leu Glu Arg Gln Arg Gly Leu Leu Gln Gln Ile Gly Asp Ala Leu Ser
 65                  70                  75                  80

Ser Gln Arg Gly Arg Val Pro Thr Ala Ala Pro Pro Ala Gln Pro Arg
                 85                  90                  95

Val Pro Val Thr Pro Ala Pro Ala Val Ile Pro Ile Leu Val Ile Ala
                100                 105                 110

Cys Asp Arg Ser Thr Val Arg Arg Cys Leu Asp Lys Leu Leu His Tyr
            115                 120                 125

Arg Pro Ser Ala Glu Leu Phe Pro Ile Ile Val Ser Gln Asp Cys Gly
    130                 135                 140

His Glu Glu Thr Ala Gln Ala Ile Ala Ser Tyr Gly Ser Ala Val Thr
145                 150                 155                 160

His Ile Arg Gln Pro Asp Leu Ser Ser Ile Ala Val Pro Pro Asp His
                165                 170                 175

Arg Lys Phe Gln Gly Tyr Tyr Lys Ile Ala Arg His Tyr Arg Trp Ala
            180                 185                 190

Leu Gly Gln Val Phe Arg Gln Phe Arg Phe Pro Ala Ala Val Val Val
        195                 200                 205

Glu Asp Asp Leu Glu Val Ala Pro Asp Phe Phe Glu Tyr Phe Arg Ala
    210                 215                 220

Thr Tyr Pro Leu Leu Lys Ala Asp Pro Ser Leu Trp Cys Val Ser Ala
225                 230                 235                 240

Trp Asn Asp Asn Gly Lys Glu Gln Met Val Asp Ala Ser Arg Pro Glu
                245                 250                 255

Leu Leu Tyr Arg Thr Asp Phe Phe Pro Gly Leu Gly Trp Leu Leu Leu
            260                 265                 270

Ala Glu Leu Trp Ala Glu Leu Glu Pro Lys Trp Pro Lys Ala Phe Trp
        275                 280                 285

Asp Asp Trp Met Arg Arg Pro Glu Gln Arg Gln Gly Arg Ala Cys Ile
    290                 295                 300
```

```
Arg Pro Glu Ile Ser Arg Thr Met Thr Phe Gly Arg Lys Gly Val Ser
305                 310                 315                 320

His Gly Gln Phe Phe Asp Gln His Leu Lys Phe Ile Lys Leu Asn Gln
                325                 330                 335

Gln Phe Val His Phe Thr Gln Leu Asp Leu Ser Tyr Leu Gln Arg Glu
            340                 345                 350

Ala Tyr Asp Arg Asp Phe Leu Ala Arg Val Tyr Gly Ala Pro Gln Leu
        355                 360                 365

Gln Val Glu Lys Val Arg Thr Asn Asp Arg Lys Glu Leu Gly Glu Val
    370                 375                 380

Arg Val Gln Tyr Thr Gly Arg Asp Ser Phe Lys Ala Phe Ala Lys Ala
385                 390                 395                 400

Leu Gly Val Met Asp Asp Leu Lys Ser Gly Val Pro Arg Ala Gly Tyr
                405                 410                 415

Arg Gly Ile Val Thr Phe Gln Phe Arg Gly Arg Val His Leu Ala
            420                 425                 430

Pro Pro Pro Thr Trp Glu Gly Tyr Asp Pro Ser Trp Asn
        435                 440                 445

<210> SEQ ID NO 2
<211> LENGTH: 445
<212> TYPE: PRT
<213> ORGANISM: Pan troglodytes

<400> SEQUENCE: 2

Met Leu Lys Lys Gln Ser Ala Gly Leu Val Leu Trp Gly Ala Ile Leu
1               5                   10                  15

Phe Val Ala Trp Asn Ala Leu Leu Leu Phe Phe Trp Thr Arg Pro
            20                  25                  30

Ala Pro Gly Arg Pro Ser Val Ser Ala Leu Asp Asp Pro Ala
        35                  40                  45

Ser Leu Thr Arg Glu Val Ile Arg Leu Ala Gln Asp Ala Glu Val Glu
    50                  55                  60

Leu Glu Arg Gln Arg Gly Leu Leu Gln Gln Ile Gly Asp Ala Leu Ser
65                  70                  75                  80

Ser Gln Arg Gly Arg Val Pro Thr Ala Ala Pro Ala Gln Pro Arg
                85                  90                  95

Val Pro Val Thr Pro Ala Pro Ala Val Ile Pro Ile Leu Val Ile Ala
            100                 105                 110

Cys Asp Arg Ser Thr Val Arg Arg Cys Leu Asp Lys Leu Leu His Tyr
            115                 120                 125

Arg Pro Ser Ala Glu Leu Phe Pro Ile Ile Val Ser Gln Asp Cys Gly
        130                 135                 140

His Glu Glu Thr Ala Gln Ala Ile Ala Ser Tyr Gly Ser Ala Val Thr
145                 150                 155                 160

His Ile Arg Gln Pro Asp Leu Ser Ser Ile Ala Val Pro Pro Asp His
            165                 170                 175

Arg Lys Phe Gln Gly Tyr Tyr Lys Ile Ala Arg His Tyr Arg Trp Ala
            180                 185                 190

Leu Gly Gln Val Phe Arg Gln Phe Gly Phe Pro Ala Ala Val Val Val
        195                 200                 205

Glu Asp Asp Leu Glu Val Ala Pro Asp Phe Phe Glu Tyr Phe Gln Ala
    210                 215                 220

Thr Tyr Pro Leu Leu Lys Ala Asp Pro Ser Leu Trp Cys Val Ser Ala
```

```
                225                 230                 235                 240
Trp Asn Asp Asn Gly Lys Glu Gln Met Val Asp Ala Ser Arg Pro Glu
                245                 250                 255

Leu Leu Tyr Arg Thr Asp Phe Phe Pro Gly Leu Gly Trp Leu Leu Leu
            260                 265                 270

Ala Glu Leu Trp Ala Glu Leu Glu Pro Lys Trp Pro Lys Ala Phe Trp
        275                 280                 285

Asp Asp Trp Met Arg Arg Pro Glu Gln Arg Gly Arg Ala Cys Ile
    290                 295                 300

Arg Pro Glu Ile Ser Arg Thr Met Thr Phe Gly Arg Lys Gly Val Ser
305                 310                 315                 320

His Gly Gln Phe Phe Asp Gln His Leu Lys Phe Ile Lys Leu Asn Gln
                325                 330                 335

Gln Phe Val His Phe Thr Gln Leu Asp Leu Ser Tyr Leu Gln Arg Glu
            340                 345                 350

Ala Tyr Asp Arg Asp Phe Leu Ala Arg Val Tyr Gly Ala Pro Gln Leu
        355                 360                 365

Gln Val Glu Lys Val Arg Thr Asn Asp Arg Lys Glu Leu Gly Glu Val
    370                 375                 380

Arg Val Gln Tyr Thr Gly Arg Asp Ser Phe Lys Ala Phe Ala Lys Ala
385                 390                 395                 400

Leu Gly Val Met Asp Asp Leu Lys Ser Gly Val Pro Arg Ala Gly Tyr
                405                 410                 415

Arg Gly Ile Val Thr Phe Gln Phe Arg Gly Arg Val His Leu Ala
            420                 425                 430

Pro Pro Pro Thr Trp Glu Gly Tyr Asp Pro Ser Trp Asn
        435                 440                 445

<210> SEQ ID NO 3
<211> LENGTH: 445
<212> TYPE: PRT
<213> ORGANISM: Pongo abelii

<400> SEQUENCE: 3

Met Leu Lys Lys Gln Ser Ala Gly Leu Val Leu Trp Gly Ala Ile Leu
1               5                   10                  15

Phe Val Ala Trp Asn Ala Leu Leu Leu Leu Phe Phe Trp Thr Arg Pro
            20                  25                  30

Ala Pro Gly Arg Pro Pro Ser Val Ser Ala Leu Asp Asp Asp Pro Ala
        35                  40                  45

Ser Leu Thr Arg Glu Val Ile Arg Leu Ala Gln Asp Ala Glu Val Glu
    50                  55                  60

Leu Glu Arg Gln Arg Gly Leu Leu Gln Gln Ile Gly Asp Ala Leu Trp
65                  70                  75                  80

Ser Gln Arg Gly Arg Val Pro Thr Pro Ala Leu Pro Ala Gln Pro Arg
                85                  90                  95

Val Pro Ala Thr Pro Ala Pro Ala Val Ile Pro Ile Leu Val Ile Ala
            100                 105                 110

Cys Asp Arg Ser Thr Val Arg Arg Cys Leu Asp Lys Leu Leu Gln Tyr
        115                 120                 125

Arg Pro Ser Ala Glu Leu Phe Pro Ile Ile Val Ser Gln Asp Cys Gly
    130                 135                 140

His Glu Glu Thr Ala Gln Ala Ile Ala Ser Tyr Gly Ser Ala Val Thr
145                 150                 155                 160
```

His Ile Arg Gln Pro Asp Leu Ser Ser Ile Ala Val Pro Pro Asp His
                165                 170                 175

Arg Lys Phe Gln Gly Tyr Tyr Lys Ile Ala Arg His Tyr Arg Trp Ala
            180                 185                 190

Leu Gly Gln Ile Phe Gln Arg Phe Arg Phe Pro Ala Ala Val Val Val
        195                 200                 205

Glu Asp Asp Leu Glu Val Ala Pro Asp Phe Glu Tyr Phe Gln Ala
210                 215                 220

Thr Tyr Pro Leu Leu Lys Ala Asp Pro Ser Leu Trp Cys Val Ser Ala
225                 230                 235                 240

Trp Asn Asp Asn Gly Lys Glu Gln Met Val Asp Ala Ser Lys Pro Glu
                245                 250                 255

Leu Leu Tyr Arg Thr Asp Phe Phe Pro Gly Leu Gly Trp Leu Leu Leu
            260                 265                 270

Ala Glu Leu Trp Ala Glu Leu Glu Pro Lys Trp Pro Lys Ala Phe Trp
        275                 280                 285

Asp Asp Trp Met Arg Arg Pro Glu Gln Arg Lys Gly Arg Ala Cys Ile
    290                 295                 300

Arg Pro Glu Ile Ser Arg Thr Met Thr Phe Gly Arg Lys Gly Val Ser
305                 310                 315                 320

His Gly Gln Phe Phe Asp Gln His Leu Lys Phe Ile Lys Leu Asn Gln
                325                 330                 335

Gln Phe Val His Phe Thr Gln Leu Asp Leu Ser Tyr Leu Gln Arg Glu
            340                 345                 350

Ala Tyr Asp Arg Asp Phe Leu Ala Arg Val Tyr Gly Ala Pro Gln Leu
        355                 360                 365

Gln Val Glu Lys Val Arg Thr Asn Asp Arg Lys Glu Leu Gly Glu Val
    370                 375                 380

Arg Val Gln Tyr Thr Gly Arg Asp Ser Phe Lys Ala Phe Ala Lys Ala
385                 390                 395                 400

Leu Gly Val Met Asp Asp Leu Lys Ser Gly Val Pro Arg Ala Gly Tyr
                405                 410                 415

Arg Gly Ile Val Thr Phe Gln Phe Arg Gly Arg Val His Leu Ala
            420                 425                 430

Pro Pro Pro Thr Trp Glu Gly Tyr Asp Pro Ser Trp Asn
        435                 440                 445

<210> SEQ ID NO 4
<211> LENGTH: 445
<212> TYPE: PRT
<213> ORGANISM: Macaca mulatta

<400> SEQUENCE: 4

Met Leu Lys Lys Gln Ser Ala Gly Leu Val Leu Trp Gly Ala Ile Leu
 1               5                  10                  15

Phe Val Ala Trp Asn Ala Leu Leu Leu Phe Phe Trp Thr Arg Pro
            20                  25                  30

Ala Pro Gly Arg Pro Ser Val Ser Ala Leu Asn Asp Asp Pro Ala
        35                  40                  45

Ser Leu Thr Arg Glu Val Ile Arg Leu Ala Gln Asp Ala Glu Val Glu
    50                  55                  60

Leu Glu Arg Gln Arg Gly Leu Leu Gln Gln Ile Gly Asp Ala Leu Trp
65                  70                  75                  80

Ser Gln Arg Gly Arg Val Pro Thr Ala Gly Pro Ala Gln Pro His
                85                  90                  95

Val Pro Val Thr Pro Ala Pro Ala Val Ile Pro Ile Leu Val Ile Ala
            100                 105                 110

Cys Asp Arg Ser Thr Val Arg Arg Cys Leu Asp Lys Leu Leu His Tyr
            115                 120                 125

Arg Pro Ser Ala Glu Arg Phe Pro Ile Ile Val Ser Gln Asp Cys Gly
            130                 135                 140

His Glu Glu Thr Ala Gln Ala Ile Ala Ser Tyr Gly Ser Ala Val Thr
145                 150                 155                 160

His Ile Arg Gln Pro Asp Leu Ser Ser Ile Ala Val Pro Pro Asp His
                165                 170                 175

Arg Lys Phe Gln Gly Tyr Tyr Lys Ile Ala Arg His Tyr Arg Trp Ala
            180                 185                 190

Leu Gly Gln Val Phe His Arg Phe Arg Phe Pro Ala Ala Val Val Val
            195                 200                 205

Glu Asp Asp Leu Glu Val Ala Pro Asp Phe Phe Glu Tyr Phe Gln Ala
            210                 215                 220

Thr Tyr Pro Leu Leu Lys Ala Asp Pro Ser Leu Trp Cys Val Ser Ala
225                 230                 235                 240

Trp Asn Asp Asn Gly Lys Glu Gln Met Val Asp Ser Gly Lys Pro Glu
                245                 250                 255

Leu Leu Tyr Arg Thr Asp Phe Phe Pro Gly Leu Gly Trp Leu Leu Leu
            260                 265                 270

Ala Glu Leu Trp Ala Glu Leu Glu Pro Lys Trp Pro Lys Ala Phe Trp
            275                 280                 285

Asp Asp Trp Met Arg Arg Pro Glu Gln Arg Lys Gly Arg Ala Cys Ile
            290                 295                 300

Arg Pro Glu Ile Ser Arg Thr Met Thr Phe Gly Arg Lys Gly Val Ser
305                 310                 315                 320

His Gly Gln Phe Phe Asp Gln His Leu Lys Phe Ile Lys Leu Asn Gln
                325                 330                 335

Gln Phe Val His Phe Thr Gln Leu Asp Leu Ser Tyr Leu Gln Arg Glu
            340                 345                 350

Ala Tyr Asp Arg Asp Phe Leu Ala Arg Val Tyr Ala Ala Pro Gln Leu
            355                 360                 365

Gln Val Glu Lys Val Arg Thr Asn Asp Arg Lys Glu Leu Gly Glu Val
            370                 375                 380

Arg Val Gln Tyr Thr Gly Arg Asp Ser Phe Lys Ala Phe Ala Lys Ala
385                 390                 395                 400

Leu Gly Val Met Asp Asp Leu Lys Ser Gly Val Pro Arg Ala Gly Tyr
                405                 410                 415

Arg Gly Ile Val Thr Phe Gln Phe Arg Gly Arg Val His Leu Ala
            420                 425                 430

Pro Pro Pro Thr Trp Glu Gly Tyr Asp Pro Ser Trp Asn
            435                 440                 445

<210> SEQ ID NO 5
<211> LENGTH: 447
<212> TYPE: PRT
<213> ORGANISM: Cricetulus griseus

<400> SEQUENCE: 5

Met Leu Lys Lys Gln Ser Ala Gly Leu Val Leu Trp Gly Ala Ile Leu
1               5                   10                  15

Phe Val Gly Trp Asn Ala Leu Leu Leu Leu Phe Phe Trp Thr Arg Pro

```
            20                  25                  30
Ala Pro Gly Arg Pro Ser Asp Ser Ala Ile Asp Asp Pro Ala
             35                  40                  45
Ser Leu Thr Arg Glu Val Phe Arg Leu Ala Glu Asp Ala Glu Val Glu
 50                  55                  60
Leu Glu Arg Gln Arg Gly Leu Leu Gln Gln Ile Arg Glu His His Ala
 65                  70                  75                  80
Leu Trp Arg Gln Arg Trp Lys Val Pro Thr Val Ala Pro Pro Ala Trp
                     85                  90                  95
Pro Arg Val Pro Ala Thr Pro Ser Pro Ala Val Ile Pro Ile Leu Val
                    100                 105                 110
Ile Ala Cys Asp Arg Ser Thr Val Arg Arg Cys Leu Asp Lys Leu Leu
                115                 120                 125
His Tyr Arg Pro Ser Ala Glu His Phe Pro Ile Ile Val Ser Gln Asp
            130                 135                 140
Cys Gly His Glu Glu Thr Ala Gln Val Ile Ala Ser Tyr Gly Ser Ala
145                 150                 155                 160
Val Thr His Ile Arg Gln Pro Asp Leu Ser Asn Ile Ala Val Pro Pro
                165                 170                 175
Asp His Arg Lys Phe Gln Gly Tyr Tyr Lys Ile Ala Arg His Tyr Arg
                180                 185                 190
Trp Ala Leu Gly Gln Ile Phe Asn Lys Phe Lys Phe Pro Ala Ala Val
                195                 200                 205
Val Val Glu Asp Asp Leu Glu Val Ala Pro Asp Phe Phe Glu Tyr Phe
            210                 215                 220
Gln Ala Thr Tyr Pro Leu Leu Arg Thr Asp Pro Ser Leu Trp Cys Val
225                 230                 235                 240
Ser Ala Trp Asn Asp Asn Gly Lys Glu Gln Met Val Asp Ser Ser Lys
                245                 250                 255
Pro Glu Leu Leu Tyr Arg Thr Asp Phe Phe Pro Gly Leu Gly Trp Leu
                260                 265                 270
Leu Met Ala Glu Leu Trp Thr Glu Leu Glu Pro Lys Trp Pro Lys Ala
            275                 280                 285
Phe Trp Asp Asp Trp Met Arg Arg Pro Glu Gln Arg Lys Gly Arg Ala
            290                 295                 300
Cys Ile Arg Pro Glu Ile Ser Arg Thr Met Thr Phe Gly Arg Lys Gly
305                 310                 315                 320
Val Ser His Gly Gln Phe Phe Asp Gln His Leu Lys Phe Ile Lys Leu
                325                 330                 335
Asn Gln Gln Phe Val Ser Phe Thr Gln Leu Asp Leu Ser Tyr Leu Gln
                340                 345                 350
Arg Glu Ala Tyr Asp Arg Asp Phe Leu Ala Arg Val Tyr Ser Ala Pro
            355                 360                 365
Leu Leu Gln Val Glu Lys Val Arg Thr Asn Asp Gln Lys Glu Leu Gly
            370                 375                 380
Glu Val Arg Val Gln Tyr Thr Ser Arg Asp Ser Phe Lys Ala Phe Ala
385                 390                 395                 400
Lys Ala Leu Gly Val Met Asp Asp Leu Lys Ser Gly Val Pro Arg Ala
                405                 410                 415
Gly Tyr Arg Gly Val Val Thr Phe Gln Phe Arg Gly Arg Arg Val His
                420                 425                 430
Leu Ala Pro Pro Gln Thr Trp Glu Gly Tyr Asp Pro Ser Trp Asn
            435                 440                 445
```

<210> SEQ ID NO 6
<211> LENGTH: 447
<212> TYPE: PRT
<213> ORGANISM: Rattus norvegicus

<400> SEQUENCE: 6

```
Met Leu Lys Lys Gln Ser Ala Gly Leu Val Leu Trp Gly Ala Ile Ile
 1               5                  10                  15

Phe Val Gly Trp Asn Ala Leu Leu Leu Phe Phe Trp Thr Arg Pro
                20                  25                  30

Ala Pro Gly Arg Leu Pro Ser Asp Ser Ala Leu Gly Asp Asp Pro Ala
                35                  40                  45

Ser Leu Thr Arg Glu Val Ile His Leu Ala Glu Asp Ala Glu Ala Glu
50                  55                  60

Leu Glu Arg Gln Arg Gly Leu Leu Gln Gln Ile Lys Glu His Tyr Ser
65                  70                  75                  80

Leu Trp Arg Gln Arg Trp Arg Val Pro Thr Val Ala Pro Pro Ala Trp
                85                  90                  95

Pro Arg Val Pro Gly Thr Pro Ser Pro Ala Val Ile Pro Ile Leu Val
                100                 105                 110

Ile Ala Cys Asp Arg Ser Thr Val Arg Arg Cys Leu Asp Lys Leu Leu
                115                 120                 125

His Tyr Arg Pro Ser Ala Glu His Phe Pro Ile Ile Val Ser Gln Asp
130                 135                 140

Cys Gly His Glu Glu Thr Ala Gln Val Ile Ala Ser Tyr Gly Thr Ala
145                 150                 155                 160

Val Thr His Ile Arg Gln Pro Asp Leu Ser Asn Ile Ala Val Gln Pro
                165                 170                 175

Asp His Arg Lys Phe Gln Gly Tyr Tyr Lys Ile Ala Arg His Tyr Arg
                180                 185                 190

Trp Ala Leu Gly Gln Ile Phe Asn Lys Phe Lys Phe Pro Ala Ala Val
                195                 200                 205

Val Val Glu Asp Asp Leu Glu Val Ala Pro Asp Phe Phe Glu Tyr Phe
                210                 215                 220

Gln Ala Thr Tyr Pro Leu Leu Lys Ala Asp Pro Ser Leu Trp Cys Val
225                 230                 235                 240

Ser Ala Trp Asn Asp Asn Gly Lys Glu Gln Met Val Asp Ser Ser Lys
                245                 250                 255

Pro Glu Leu Leu Tyr Arg Thr Asp Phe Phe Pro Gly Leu Gly Trp Leu
                260                 265                 270

Leu Leu Ala Asp Leu Trp Ala Glu Leu Glu Pro Lys Trp Pro Lys Ala
                275                 280                 285

Phe Trp Asp Asp Trp Met Arg Arg Pro Glu Gln Arg Lys Gly Arg Ala
                290                 295                 300

Cys Ile Arg Pro Glu Ile Ser Arg Thr Met Thr Phe Gly Arg Lys Gly
305                 310                 315                 320

Val Ser His Gly Gln Phe Phe Asp Gln His Leu Lys Phe Ile Lys Leu
                325                 330                 335

Asn Gln Gln Phe Val Pro Phe Thr Gln Leu Asp Leu Ser Tyr Leu Gln
                340                 345                 350

Arg Glu Ala Tyr Asp Arg Asp Phe Leu Ala Gln Val Tyr Gly Ala Pro
                355                 360                 365

Gln Leu Gln Val Glu Lys Val Arg Thr Asn Asp Arg Lys Glu Leu Gly
```

```
            370                 375                 380
Glu Val Arg Val Gln Tyr Thr Ser Arg Asp Ser Phe Lys Ala Phe Ala
385                 390                 395                 400

Lys Ala Leu Gly Val Met Asp Asp Leu Lys Ser Gly Val Pro Arg Ala
                405                 410                 415

Gly Tyr Arg Gly Ile Val Thr Phe Gln Phe Arg Gly Arg Arg Val His
            420                 425                 430

Leu Ala Pro Pro Glu Thr Trp Asn Gly Tyr Asp Pro Ser Trp Asn
        435                 440                 445

<210> SEQ ID NO 7
<211> LENGTH: 447
<212> TYPE: PRT
<213> ORGANISM: Mus musculus

<400> SEQUENCE: 7

Met Leu Lys Lys Gln Thr Ala Gly Leu Val Leu Trp Gly Ala Ile Ile
1               5                   10                  15

Phe Val Gly Trp Asn Ala Leu Leu Leu Phe Phe Trp Thr Arg Pro
                20                  25                  30

Ala Pro Gly Arg Leu Pro Ser Asp Ser Ala Leu Gly Asp Asp Pro Ala
            35                  40                  45

Ser Leu Thr Arg Glu Val Ile His Leu Ala Glu Asp Ala Glu Ala Glu
50                  55                  60

Leu Glu Arg Gln Arg Gly Leu Leu Gln Gln Ile Lys Glu His Tyr Ala
65                  70                  75                  80

Leu Trp Arg Gln Arg Trp Arg Val Pro Thr Val Ala Pro Pro Ala Trp
                85                  90                  95

Pro Arg Val Pro Val Thr Pro Ser Pro Val Gln Ile Pro Ile Leu Val
            100                 105                 110

Ile Ala Cys Asp Arg Ser Thr Val Arg Arg Cys Leu Asp Lys Leu Leu
            115                 120                 125

His Tyr Arg Pro Ser Ala Glu Arg Phe Pro Ile Ile Val Ser Gln Asp
        130                 135                 140

Cys Gly His Glu Glu Thr Ala Gln Val Ile Ala Ser Tyr Gly Thr Ala
145                 150                 155                 160

Val Thr His Ile Arg Gln Pro Asp Leu Ser Asn Ile Ala Val Gln Pro
                165                 170                 175

Asp His Arg Lys Phe Gln Gly Tyr Tyr Lys Ile Ala Arg His Tyr Arg
            180                 185                 190

Trp Ala Leu Gly Gln Ile Phe Asn Lys Phe Lys Phe Pro Ala Ala Val
        195                 200                 205

Val Val Glu Asp Asp Leu Glu Val Ala Pro Asp Phe Phe Glu Tyr Phe
    210                 215                 220

Gln Ala Thr Tyr Pro Leu Leu Arg Thr Asp Pro Ser Leu Trp Cys Val
225                 230                 235                 240

Ser Ala Trp Asn Asp Asn Gly Lys Glu Gln Met Val Asp Ser Ser Lys
                245                 250                 255

Pro Glu Leu Leu Tyr Arg Thr Asp Phe Phe Pro Gly Leu Gly Trp Leu
            260                 265                 270

Leu Leu Ala Asp Leu Trp Ala Glu Leu Glu Pro Lys Trp Pro Lys Ala
        275                 280                 285

Phe Trp Asp Asp Trp Met Arg Arg Pro Glu Gln Arg Lys Gly Arg Ala
    290                 295                 300
```

```
Cys Ile Arg Pro Glu Ile Ser Arg Thr Met Thr Phe Gly Arg Lys Gly
305                 310                 315                 320

Val Ser His Gly Gln Phe Phe Asp Gln His Leu Lys Phe Ile Lys Leu
                325                 330                 335

Asn Gln Gln Phe Val Pro Phe Thr Gln Leu Asp Leu Ser Tyr Leu Gln
            340                 345                 350

Gln Glu Ala Tyr Asp Arg Asp Phe Leu Ala Gln Val Tyr Gly Ala Pro
        355                 360                 365

Gln Leu Gln Val Glu Lys Val Arg Thr Asn Asp Gln Lys Glu Leu Gly
    370                 375                 380

Glu Val Arg Val Gln Tyr Thr Ser Arg Asp Ser Phe Lys Ala Phe Ala
385                 390                 395                 400

Lys Ala Leu Gly Val Met Asp Asp Leu Lys Ser Gly Val Pro Arg Ala
                405                 410                 415

Gly Tyr Arg Gly Ile Val Thr Phe Gln Phe Arg Gly Arg Arg Val His
                420                 425                 430

Leu Ala Pro Pro Gln Thr Trp Thr Gly Tyr Asp Pro Ser Trp Asn
                435                 440                 445

<210> SEQ ID NO 8
<211> LENGTH: 447
<212> TYPE: PRT
<213> ORGANISM: Oryctolagus cuniculus

<400> SEQUENCE: 8

Met Leu Lys Lys Gln Ser Ala Gly Leu Val Leu Trp Gly Ala Ile Leu
1               5                   10                  15

Phe Val Ala Trp Asn Ala Leu Leu Leu Phe Phe Trp Thr Arg Pro
                20                  25                  30

Val Pro Ser Arg Leu Pro Ser Asp Asn Ala Leu Asp Asp Pro Ala
            35                  40                  45

Ser Leu Thr Arg Glu Val Ile Arg Leu Ala Gln Asp Ala Glu Val Glu
    50                  55                  60

Leu Glu Arg Gln Arg Gly Leu Leu Gln Gln Ile Arg Glu His His Ala
65                  70                  75                  80

Leu Trp Ser Gln Arg Trp Lys Val Pro Thr Ala Ala Pro Pro Ala Gln
                85                  90                  95

Pro His Val Pro Val Thr Pro Pro Ala Val Ile Pro Ile Leu Val
            100                 105                 110

Ile Ala Cys Asp Arg Ser Thr Val Arg Arg Cys Leu Asp Lys Leu Leu
            115                 120                 125

His Tyr Arg Pro Ser Ala Glu Leu Phe Pro Ile Ile Val Ser Gln Asp
130                 135                 140

Cys Gly His Glu Glu Thr Ala Gln Val Ile Ala Ser Tyr Gly Ser Ala
145                 150                 155                 160

Val Thr His Ile Arg Gln Pro Asp Leu Ser Asn Ile Ala Val Gln Pro
                165                 170                 175

Asp His Arg Lys Phe Gln Gly Tyr Tyr Lys Ile Ala Arg His Tyr Arg
            180                 185                 190

Trp Ala Leu Gly Gln Ile Phe His Asn Phe Asn Tyr Pro Ala Ala Val
        195                 200                 205

Val Val Glu Asp Asp Leu Glu Val Ala Pro Asp Phe Phe Glu Tyr Phe
    210                 215                 220

Gln Ala Thr Tyr Pro Leu Leu Lys Ala Asp Pro Ser Leu Trp Cys Val
225                 230                 235                 240
```

```
Ser Ala Trp Asn Asp Asn Gly Lys Glu Gln Met Val Asp Ser Ser Lys
                245                 250                 255

Pro Glu Leu Leu Tyr Arg Thr Asp Phe Phe Pro Gly Leu Gly Trp Leu
            260                 265                 270

Leu Leu Ala Glu Leu Trp Ala Glu Leu Glu Pro Lys Trp Pro Lys Ala
        275                 280                 285

Phe Trp Asp Asp Trp Met Arg Arg Pro Glu Gln Arg Lys Gly Arg Ala
    290                 295                 300

Cys Val Arg Pro Glu Ile Ser Arg Thr Met Thr Phe Gly Arg Lys Gly
305                 310                 315                 320

Val Ser His Gly Gln Phe Phe Asp Gln His Leu Lys Phe Ile Lys Leu
                325                 330                 335

Asn Gln Gln Phe Val Pro Phe Thr Gln Leu Asp Leu Ser Tyr Leu Gln
            340                 345                 350

Gln Glu Ala Tyr Asp Arg Asp Phe Leu Ala Arg Val Tyr Gly Ala Pro
        355                 360                 365

Gln Leu Gln Val Glu Lys Val Arg Thr Asn Asp Arg Lys Glu Leu Gly
    370                 375                 380

Glu Val Arg Val Gln Tyr Thr Gly Arg Asp Ser Phe Lys Ala Phe Ala
385                 390                 395                 400

Lys Ala Leu Gly Val Met Asp Asp Leu Lys Ser Gly Val Pro Arg Ala
                405                 410                 415

Gly Tyr Arg Gly Ile Val Thr Phe Leu Phe Arg Gly Arg Arg Val His
            420                 425                 430

Leu Ala Pro Pro Gln Thr Trp Asp Gly Tyr Asp Pro Ser Trp Thr
        435                 440                 445

<210> SEQ ID NO 9
<211> LENGTH: 447
<212> TYPE: PRT
<213> ORGANISM: Mesocricetus auratus

<400> SEQUENCE: 9

Met Leu Lys Lys Gln Ser Ala Gly Leu Val Leu Trp Gly Ala Ile Ile
1               5                   10                  15

Phe Val Gly Trp Asn Ala Leu Leu Leu Phe Phe Trp Thr Arg Pro
            20                  25                  30

Ala Pro Gly Arg Pro Pro Leu Asp Ser Ala Leu Asp Asp Pro Ala
        35                  40                  45

Ser Leu Thr Arg Glu Val Ile Arg Leu Ala Glu Asp Ala Glu Val Glu
    50                  55                  60

Leu Glu Arg Gln Arg Gly Leu Leu Gln Gln Ile Arg Glu His His Thr
65                  70                  75                  80

Leu Trp Asn Gln Arg Trp Lys Val Pro Thr Val Ala Pro Pro Ala Trp
                85                  90                  95

Pro Arg Val Pro Val Thr Pro Ser Pro Val Ile Pro Ile Leu Val
            100                 105                 110

Ile Ala Cys Asp Arg Ser Thr Val Arg Arg Cys Leu Asp Lys Leu Leu
        115                 120                 125

His Tyr Arg Pro Ser Ala Glu His Phe Pro Ile Ile Val Ser Gln Asp
    130                 135                 140

Cys Gly His Glu Glu Thr Ala Gln Val Ile Ala Ser Tyr Gly Ser Ala
145                 150                 155                 160

Val Thr His Ile Arg Gln Pro Asp Leu Ser Asn Ile Ala Val Gln Pro
```

```
                165                 170                 175
Asp His Arg Lys Phe Gln Gly Tyr Tyr Lys Ile Ala Arg His Tyr Arg
            180                 185                 190

Trp Ala Leu Gly Gln Ile Phe Asn Lys Phe Lys Phe Pro Ala Ala Val
        195                 200                 205

Val Val Glu Asp Asp Leu Glu Val Ala Pro Asp Phe Phe Glu Tyr Phe
    210                 215                 220

Gln Ala Thr Tyr Pro Leu Leu Arg Thr Asp Pro Ser Leu Trp Cys Val
225                 230                 235                 240

Ser Ala Trp Asn Asp Asn Gly Lys Glu Gln Met Val Asp Ser Ser Lys
                245                 250                 255

Pro Glu Leu Leu Tyr Arg Thr Asp Phe Phe Pro Gly Leu Gly Trp Leu
            260                 265                 270

Leu Leu Ala Glu Leu Trp Ala Glu Leu Glu Pro Lys Trp Pro Lys Ala
        275                 280                 285

Phe Trp Asp Asp Trp Met Arg Arg Pro Glu Gln Arg Lys Gly Arg Ala
    290                 295                 300

Cys Ile Arg Pro Glu Ile Ser Arg Thr Met Thr Phe Gly Arg Lys Gly
305                 310                 315                 320

Val Ser His Gly Gln Phe Phe Asp Gln His Leu Lys Phe Ile Lys Leu
                325                 330                 335

Asn Gln Gln Phe Val Ser Phe Thr Gln Leu Asp Leu Ser Tyr Leu Gln
            340                 345                 350

Arg Glu Ala Tyr Asp Arg Asp Phe Leu Ala Arg Val Tyr Gly Ala Pro
        355                 360                 365

Leu Leu Gln Val Glu Lys Val Arg Thr Asn Asp Gln Lys Glu Leu Gly
    370                 375                 380

Glu Val Arg Val Gln Tyr Thr Ser Arg Asp Ser Phe Lys Ala Phe Ala
385                 390                 395                 400

Lys Ala Leu Gly Val Met Asp Asp Leu Lys Ser Gly Val Pro Arg Ala
                405                 410                 415

Gly Tyr Arg Gly Ile Val Thr Phe Gln Phe Arg Gly Arg Arg Val His
            420                 425                 430

Leu Ala Pro Pro Arg Ser Trp Glu Gly Tyr Asp Pro Ser Trp Thr
        435                 440                 445

<210> SEQ ID NO 10
<211> LENGTH: 445
<212> TYPE: PRT
<213> ORGANISM: Ailuropoda melanoleuca

<400> SEQUENCE: 10

Met Leu Lys Lys Gln Ser Ala Gly Leu Val Leu Trp Gly Ala Ile Leu
1               5                   10                  15

Phe Val Ala Trp Asn Ala Leu Leu Leu Phe Phe Trp Thr Arg Pro
            20                  25                  30

Ser Pro Gly Arg Leu Pro Ser Glu Ser Ala Leu Asp Asp Pro Ala
        35                  40                  45

Val Leu Thr Arg Glu Val Ile Arg Leu Ala Glu Asp Ala Glu Val Glu
    50                  55                  60

Leu Glu Arg Gln Arg Gly Leu Leu Gln Gln Ile Arg Glu His His Ala
65                  70                  75                  80

Arg Trp Ser Gln Arg Trp Arg Ala Pro Thr Ala Thr Val Pro Ala Pro
                85                  90                  95
```

```
Ala Pro Ala Ser Asn Ala Pro Ala Val Ile Pro Ile Leu Val Ile Ala
            100                 105                 110

Cys Asp Arg Ser Thr Val Arg Arg Cys Leu Asp Lys Leu Leu His Tyr
        115                 120                 125

Arg Pro Ser Ala Glu His Phe Pro Ile Ile Val Ser Gln Asp Cys Gly
    130                 135                 140

His Glu Glu Thr Ala Gln Val Ile Ala Ser Tyr Gly Ser Ala Val Thr
145                 150                 155                 160

His Ile Arg Gln Pro Asp Leu Ser Ser Ile Ala Val Pro Pro Asp His
                165                 170                 175

Arg Lys Phe Gln Gly Tyr Tyr Lys Ile Ala Arg His Tyr Arg Trp Ala
            180                 185                 190

Leu Gly Gln Val Phe His Arg Phe Lys Phe Pro Ala Ala Val Val Val
        195                 200                 205

Glu Asp Asp Leu Glu Val Ala Pro Asp Phe Phe Glu Tyr Phe Gln Ala
    210                 215                 220

Thr Tyr Pro Leu Leu Arg Ala Asp Pro Ser Leu Trp Cys Val Ser Ala
225                 230                 235                 240

Trp Asn Asp Asn Gly Lys Glu Gln Met Val Asp Ser Ser Lys Pro Glu
                245                 250                 255

Leu Leu Tyr Arg Thr Asp Phe Phe Pro Gly Leu Gly Trp Leu Leu Leu
            260                 265                 270

Ala Glu Leu Trp Ala Glu Leu Glu Pro Lys Trp Pro Arg Ala Phe Trp
        275                 280                 285

Asp Asp Trp Met Arg Arg Pro Glu Gln Arg Gln Gly Arg Ala Cys Val
    290                 295                 300

Arg Pro Glu Ile Ser Arg Thr Met Thr Phe Gly Arg Lys Gly Val Ser
305                 310                 315                 320

His Gly Gln Phe Phe Asp Gln His Leu Lys Phe Ile Lys Leu Asn Gln
                325                 330                 335

His Phe Val Pro Phe Thr Gln Leu Asp Leu Ser Tyr Leu Arg Gln Glu
            340                 345                 350

Thr Tyr Asp Arg Asp Phe Leu Ala Arg Val Tyr Gly Ala Pro Leu Leu
        355                 360                 365

Gln Val Glu Lys Val Arg Thr Ser Glu Arg Asn Glu Leu Gly Glu Val
    370                 375                 380

Arg Val Gln Tyr Thr Gly Arg Asp Ser Phe Lys Ala Phe Ala Lys Ala
385                 390                 395                 400

Leu Gly Val Met Asp Asp Leu Lys Ser Gly Val Pro Arg Ala Gly Tyr
                405                 410                 415

Arg Gly Ile Val Ser Phe Leu Phe Arg Gly Arg Arg Val His Leu Ala
            420                 425                 430

Pro Pro Gln Thr Trp Asp Gly Tyr Asp Pro Ser Trp Asn
        435                 440                 445

<210> SEQ ID NO 11
<211> LENGTH: 447
<212> TYPE: PRT
<213> ORGANISM: Sus scrofa

<400> SEQUENCE: 11

Met Leu Lys Lys Gln Ser Ala Gly Leu Val Leu Trp Gly Ala Ile Leu
1               5                   10                  15

Phe Val Ala Trp Asn Ala Leu Leu Leu Leu Phe Phe Trp Thr Arg Pro
            20                  25                  30
```

```
Ala Pro Gly Arg Leu Pro Ser Asp Ser Ala Leu Asp Asp Pro Ala
         35                  40                  45
Ser Leu Thr Arg Glu Val Ile Arg Leu Ala Gln Asp Ala Glu Val Glu
 50                  55                  60
Leu Glu Arg Gln Arg Gly Leu Leu Gln Gln Ile Arg Glu His His Ala
 65                  70                  75                  80
Arg Trp Ser Gln Arg Trp Arg Val Pro Thr Val Ala Pro Pro Val Pro
                 85                  90                  95
Pro Arg Val Pro Val Thr Ser Ala Pro Thr Val Ile Pro Ile Leu Val
                100                 105                 110
Ile Ala Cys Asp Arg Ser Thr Val Arg Arg Cys Leu Asp Lys Leu Leu
                115                 120                 125
His Tyr Arg Pro Ser Ala Glu His Phe Pro Ile Ile Val Ser Gln Asp
        130                 135                 140
Cys Gly His Glu Glu Thr Ala Gln Val Ile Ala Ser Tyr Gly Ser Ala
145                 150                 155                 160
Val Thr His Ile Arg Gln Pro Asp Leu Ser Asn Ile Val Val Pro Pro
                165                 170                 175
Asp His Arg Lys Phe Gln Gly Tyr Tyr Lys Ile Ala Arg His Tyr Arg
                180                 185                 190
Trp Ala Leu Gly Gln Val Phe Glu Lys Phe Lys Phe Ser Ala Ala Val
        195                 200                 205
Val Val Glu Asp Asp Leu Glu Val Ala Pro Asp Phe Phe Glu Tyr Phe
210                 215                 220
Gln Ala Thr Tyr Pro Leu Leu Arg Ala Asp Pro Ser Leu Trp Cys Val
225                 230                 235                 240
Ser Ala Trp Asn Asp Asn Gly Lys Glu Gln Met Val Asp Ser Ser Lys
                245                 250                 255
Pro Glu Leu Leu Tyr Arg Thr Asp Phe Phe Pro Gly Leu Gly Trp Leu
                260                 265                 270
Leu Leu Ala Glu Leu Trp Ala Glu Leu Glu Pro Lys Trp Pro Lys Ala
        275                 280                 285
Phe Trp Asp Asp Trp Met Arg Arg Pro Glu Gln Arg Gln Gly Arg Ala
        290                 295                 300
Cys Val Arg Pro Glu Ile Ser Arg Thr Met Thr Phe Gly Arg Lys Gly
305                 310                 315                 320
Val Ser His Gly Gln Phe Phe Asp Gln His Leu Lys Phe Ile Lys Leu
                325                 330                 335
Asn Gln His Phe Val Pro Phe Thr Gln Leu Asp Leu Ser Tyr Leu Arg
                340                 345                 350
Arg Glu Ala Tyr Asp Arg Asp Phe Leu Ala Arg Val Tyr Gly Ala Pro
        355                 360                 365
Leu Leu Gln Val Glu Lys Val Arg Thr Ser Glu Arg Ser Glu Leu Gly
        370                 375                 380
Glu Val Arg Val Gln Tyr Thr Ser Arg Asp Ser Phe Lys Ala Phe Ala
385                 390                 395                 400
Lys Ala Leu Gly Val Met Asp Asp Leu Lys Ser Gly Val Pro Arg Ala
                405                 410                 415
Gly Tyr Arg Gly Ile Val Ser Phe Leu Phe Arg Gly Arg Arg Val Tyr
                420                 425                 430
Leu Ala Pro Pro Glu Thr Trp Asp Gly Tyr Asp Pro Ser Trp Asn
        435                 440                 445
```

<210> SEQ ID NO 12
<211> LENGTH: 447
<212> TYPE: PRT
<213> ORGANISM: Canis familiaris

<400> SEQUENCE: 12

Met Leu Lys Lys Gln Ser Ala Gly Leu Val Leu Trp Gly Ala Ile Leu
1               5                   10                  15

Phe Val Ala Trp Asn Ala Leu Leu Leu Phe Phe Trp Thr Arg Pro
            20                  25                  30

Ser Pro Ser Arg Leu Pro Ser Asp Ser Ala Leu Asp Asp Pro Ala
        35                  40                  45

Ser Leu Thr Arg Glu Val Ile Arg Leu Ala Glu Asp Ala Glu Val Glu
50                  55                  60

Leu Glu Arg Gln Arg Gly Leu Leu Gln Gln Ile Arg Glu His His Ala
65                  70                  75                  80

Arg Trp Ser Gln Arg Trp Arg Val Pro Thr Ala Ala Pro Pro Ala Pro
                85                  90                  95

Pro Arg Val Pro Val Ser Ser Pro Pro Ala Val Ile Pro Ile Leu Val
            100                 105                 110

Ile Ala Cys Asp Arg Ser Thr Val Arg Arg Cys Leu Asp Lys Leu Leu
        115                 120                 125

His Tyr Arg Pro Ser Ala Glu His Phe Pro Ile Ile Val Ser Gln Asp
130                 135                 140

Cys Gly His Glu Glu Thr Ala Gln Val Ile Ala Ser Tyr Gly Ser Ala
145                 150                 155                 160

Ile Thr His Ile Arg Gln Pro Asp Leu Ser Ser Ile Thr Val Pro Pro
                165                 170                 175

Asp His Arg Lys Phe Gln Gly Tyr Tyr Lys Ile Ala Arg His Tyr Arg
            180                 185                 190

Trp Ala Leu Gly Gln Val Phe His Lys Phe Lys Phe Pro Ala Ala Val
        195                 200                 205

Val Val Glu Asp Asp Leu Glu Val Ala Pro Asp Phe Phe Glu Tyr Phe
210                 215                 220

Gln Ala Thr Tyr Pro Leu Leu Arg Ala Asp Pro Ser Leu Trp Cys Val
225                 230                 235                 240

Ser Ala Trp Asn Asp Asn Gly Lys Glu Gln Met Val Asp Ser Ser Lys
                245                 250                 255

Pro Glu Leu Leu Tyr Arg Thr Asp Phe Phe Pro Gly Leu Gly Trp Leu
            260                 265                 270

Leu Leu Ala Glu Leu Trp Ala Glu Leu Glu Pro Lys Trp Pro Arg Ala
        275                 280                 285

Phe Trp Asp Asp Trp Met Arg Arg Pro Glu Gln Arg Gln Gly Arg Ala
290                 295                 300

Cys Val Arg Pro Glu Ile Ser Arg Thr Met Thr Phe Gly Arg Lys Gly
305                 310                 315                 320

Val Ser His Gly Gln Phe Phe Asp Gln His Leu Lys Phe Ile Lys Leu
                325                 330                 335

Asn Gln His Phe Val Pro Phe Thr Gln Leu Asp Leu Ser Tyr Leu Arg
            340                 345                 350

Gln Glu Thr Tyr Asp Arg Asp Phe Leu Ala Arg Val Tyr Gly Ala Pro
        355                 360                 365

Leu Leu Gln Val Glu Lys Val Arg Thr Ser Glu Arg Ser Glu Leu Gly
370                 375                 380

```
Glu Val Arg Val Gln Tyr Thr Gly Arg Asp Ser Phe Lys Ala Phe Ala
385                 390                 395                 400

Lys Ala Leu Gly Val Met Asp Asp Leu Lys Ser Gly Val Pro Arg Ala
            405                 410                 415

Gly Tyr Arg Gly Ile Val Ser Phe Leu Phe Arg Gly Arg Val His
        420                 425                 430

Leu Ala Pro Pro Gln Thr Trp Asp Gly Tyr Asp Pro Ser Trp Asn
        435                 440                 445

<210> SEQ ID NO 13
<211> LENGTH: 447
<212> TYPE: PRT
<213> ORGANISM: Bos taurus

<400> SEQUENCE: 13

Met Leu Lys Lys Gln Ser Ala Gly Leu Val Leu Trp Gly Ala Ile Leu
1               5                   10                  15

Phe Val Ala Trp Asn Ala Leu Leu Leu Phe Phe Trp Thr Arg Pro
            20                  25                  30

Ala Pro Gly Arg Leu Pro Ser Asp Ser Ala Leu Asp Asp Pro Ala
        35                  40                  45

Ser Leu Thr Arg Glu Val Ile Arg Leu Ala Gln Asp Ala Glu Val Glu
50                  55                  60

Leu Glu Arg Gln Arg Gly Leu Leu Gln Gln Ile Arg Glu His His Ala
65                  70                  75                  80

Arg Trp Ser Gln Arg Trp Arg Val Pro Thr Val Ala Pro Pro Val Pro
                85                  90                  95

Pro Arg Val Pro Val Thr Thr Pro Pro Ala Val Ile Pro Ile Leu Val
            100                 105                 110

Ile Ala Cys Asp Arg Ser Thr Val Arg Arg Cys Leu Asp Lys Leu Leu
        115                 120                 125

Asn Tyr Arg Pro Ser Ala Glu His Phe Pro Ile Ile Val Ser Gln Asp
    130                 135                 140

Cys Gly His Glu Glu Thr Ala Gln Val Ile Ala Ser Tyr Gly Ser Ala
145                 150                 155                 160

Val Met His Ile Arg Gln Pro Asp Leu Ser Thr Ile Ala Val Pro Pro
                165                 170                 175

Asp His Arg Lys Phe Gln Gly Tyr Tyr Lys Ile Ala Arg His Tyr Arg
            180                 185                 190

Trp Ala Leu Gly Gln Val Phe His Glu Phe Lys Phe Pro Ala Ala Val
        195                 200                 205

Val Val Glu Asp Asp Leu Glu Val Ala Pro Asp Phe Phe Glu Tyr Phe
    210                 215                 220

Gln Ala Thr Tyr Pro Leu Leu Arg Ala Asp Pro Ser Leu Trp Cys Val
225                 230                 235                 240

Ser Ala Trp Asn Asp Asn Gly Lys Glu Gln Met Val Asp Ser Ser Lys
                245                 250                 255

Pro Glu Leu Leu Tyr Arg Thr Asp Phe Phe Pro Gly Leu Gly Trp Leu
            260                 265                 270

Leu Leu Ala Glu Leu Trp Ala Glu Leu Glu Pro Lys Trp Pro Lys Ala
        275                 280                 285

Phe Trp Asp Asp Trp Met Arg Arg Pro Glu Gln Arg Gln Gly Arg Ala
    290                 295                 300

Cys Val Arg Pro Glu Ile Ser Arg Thr Met Thr Phe Gly Arg Lys Gly
```

```
                305                 310                 315                 320
Val Ser His Gly Gln Phe Phe Asp Gln His Leu Lys Phe Ile Lys Leu
                    325                 330                 335

Asn Gln His Phe Val Pro Phe Thr Gln Leu Asp Leu Ser Tyr Leu Arg
                340                 345                 350

Gln Glu Thr Tyr Asp Arg Asp Phe Leu Ala Arg Val Tyr Gly Ala Pro
                    355                 360                 365

Leu Leu Gln Val Glu Lys Val Arg Thr Ser Glu Arg Ser Glu Leu Gln
            370                 375                 380

Glu Val Arg Val Gln Tyr Thr Ser Arg Asp Ser Phe Lys Ala Phe Ala
385                 390                 395                 400

Lys Ala Leu Gly Val Met Asp Asp Leu Lys Ser Gly Val Pro Arg Ala
                        405                 410                 415

Gly Tyr Arg Gly Ile Val Ser Phe Leu Tyr Arg Gly Arg Val His
                    420                 425                 430

Leu Ala Pro Pro Gln Thr Trp Asp Gly Tyr Asp Pro Ser Trp Asn
                435                 440                 445
```

<210> SEQ ID NO 14
<211> LENGTH: 447
<212> TYPE: PRT
<213> ORGANISM: Equus caballus

<400> SEQUENCE: 14

```
Met Leu Lys Lys Gln Ser Ala Gly Leu Val Leu Trp Gly Ala Ile Leu
1               5                   10                  15

Phe Val Ala Trp Asn Ala Leu Leu Leu Leu Phe Phe Trp Met Arg Pro
                20                  25                  30

Ser Pro Ser Arg Leu Pro Ser Asp Gly Thr Leu Asp Asp Asp Pro Thr
            35                  40                  45

Gly Leu Thr Arg Lys Val Ile His Leu Ala Gln Asp Val Glu Val Glu
        50                  55                  60

Leu Glu Arg Gln Arg Gly Leu Leu Gln Gln Ile Arg Glu His His Ala
65                  70                  75                  80

Arg Trp Ser Gln Trp Trp Arg Val Pro Thr Val Pro Pro Val Pro
                85                  90                  95

Pro His Val Ser Val Thr Ser Leu Pro Ala Val Ile Pro Ile Leu Val
                100                 105                 110

Ile Ala Cys Asp Arg Ser Thr Val Arg Arg Cys Leu Asp Lys Leu Leu
                115                 120                 125

His Tyr Arg Pro Ser Ala Glu His Phe Pro Ile Ile Val Ser Gln Asp
                130                 135                 140

Cys Gly His Glu Glu Thr Ala Gln Val Ile Ala Ser Tyr Gly Ser Ala
145                 150                 155                 160

Val Thr His Ile Arg Gln Pro Asp Leu Ser Asn Ile Ala Val Pro Pro
                    165                 170                 175

Asp His Arg Lys Phe Gln Gly Tyr Tyr Lys Ile Ala Arg His Tyr Arg
                180                 185                 190

Trp Ala Leu Ala Gln Val Phe His Arg Phe Lys Phe Pro Ala Ala Val
            195                 200                 205

Val Val Glu Asp Asp Leu Glu Val Ala Pro Asp Phe Phe Glu Tyr Phe
        210                 215                 220

Gln Ala Thr Tyr Pro Leu Leu Arg Ala Asp Pro Ser Leu Trp Cys Val
225                 230                 235                 240
```

```
Ser Ala Trp Asn Asp Asn Gly Lys Glu Gln Met Val Asp Ser Ser Lys
            245                 250                 255

Pro Glu Leu Leu Tyr Arg Thr Asp Phe Phe Pro Gly Leu Gly Trp Leu
        260                 265                 270

Leu Leu Ala Glu Leu Trp Ala Glu Leu Glu Pro Lys Trp Pro Lys Ala
    275                 280                 285

Phe Trp Asp Asp Trp Met Arg Arg Pro Glu Gln Arg Gln Gly Arg Ala
290                 295                 300

Cys Val Arg Pro Glu Ile Ser Arg Thr Met Thr Phe Gly Arg Ile Gly
305                 310                 315                 320

Val Ser His Gly Gln Phe Phe Asp Gln His Leu Lys Phe Ile Lys Leu
            325                 330                 335

Asn Gln His Phe Val Pro Phe Thr Gln Leu Asp Leu Ser Tyr Leu Arg
        340                 345                 350

Gln Glu Ala Tyr Asp Lys Asp Phe Leu Ala Arg Val Tyr Gly Ala Pro
    355                 360                 365

Leu Leu Gln Val Glu Lys Val Arg Thr Gly Arg Ser Glu Leu Gly
370                 375                 380

Glu Val Arg Val Gln Tyr Thr Gly Arg Asp Ser Phe Lys Ala Phe Ala
385                 390                 395                 400

Lys Ala Leu Gly Val Met Asp Asp Leu Lys Ser Gly Val Pro Arg Ala
            405                 410                 415

Gly Tyr Arg Gly Ile Val Ser Phe Leu Phe Arg Gly Arg Val His
        420                 425                 430

Leu Ala Pro Pro Gln Thr Trp Glu Gly Tyr Asp Pro Ser Trp Asn
    435                 440                 445

<210> SEQ ID NO 15
<211> LENGTH: 447
<212> TYPE: PRT
<213> ORGANISM: Monodelphis domestica

<400> SEQUENCE: 15

Met Leu Lys Lys Gln Ser Ala Gly Leu Val Leu Trp Gly Ala Ile Leu
1               5                   10                  15

Phe Val Ala Trp Asn Ala Leu Leu Phe Phe Phe Trp Ala Arg Pro
            20                  25                  30

Leu Pro Gly Gly Pro Ser Ser Glu Asp Pro Phe Ala Asn Asp Pro Ala
        35                  40                  45

Ser Leu Ser Arg Arg Val Ile Arg Leu Ala Gln Glu Ala Glu Ile Glu
    50                  55                  60

Leu Glu Arg Gln His Val Leu Leu Gln Ile Gln Lys His Ser Val
65                  70                  75                  80

Leu Trp Asn Gln Arg Gln Gln Val Ala Thr Ala Gly Pro Pro Ala Val
            85                  90                  95

Ser His Pro Thr Val Ala Pro Thr Thr Phe Val Leu Pro Ile Leu Val
        100                 105                 110

Ile Ala Cys Asp Arg Ser Thr Val Arg Arg Cys Leu Asp Lys Leu Leu
    115                 120                 125

His Tyr Arg Pro Ser Ala Glu Arg Phe Pro Ile Ile Val Ser Gln Asp
130                 135                 140

Cys Gly His Lys Val Thr Ala Gln Val Ile Ala Ser Tyr Gly Asn Ala
145                 150                 155                 160

Ile Met His Ile Lys Gln Pro Asp Leu Ser Ser Ile Pro Val Pro Thr
            165                 170                 175
```

Glu His Arg Lys Phe Gln Gly Tyr Tyr Lys Ile Ala Arg His Tyr Arg
            180                 185                 190

Trp Ala Leu Asn Gln Val Phe Arg Thr Phe Lys Tyr Gln Ala Ala Val
        195                 200                 205

Val Val Glu Asp Asp Leu Glu Val Ala Pro Asp Phe Phe Glu Tyr Phe
    210                 215                 220

Gln Ala Thr Tyr Pro Leu Leu Arg Thr Asp Pro Ser Leu Trp Cys Val
225                 230                 235                 240

Ser Ala Trp Asn Asp Asn Gly Lys Glu Gln Met Val Asp Ala Lys Arg
                245                 250                 255

Pro Asp Leu Leu Tyr Arg Thr Asp Phe Pro Gly Leu Gly Trp Leu
            260                 265                 270

Leu Leu Ala Glu Leu Trp Asp Glu Leu Glu Pro Lys Trp Pro Lys Ala
        275                 280                 285

Phe Trp Asp Asp Trp Met Arg Gln Pro Glu Gln Arg Arg Asp Arg Ala
    290                 295                 300

Cys Leu Arg Pro Glu Ile Ser Arg Thr Met Thr Phe Gly Arg Lys Gly
305                 310                 315                 320

Val Ser Gln Gly Gln Phe Phe Asp Gln His Leu Lys Phe Ile Lys Leu
                325                 330                 335

Asn Gln Gly Phe Val Phe Phe Thr Gln Leu Asp Leu Ser Tyr Leu Lys
            340                 345                 350

Gln Glu Ala Tyr Asp Arg Asp Phe Ser Ala Arg Val Tyr Ala Ala Pro
        355                 360                 365

Gln Val Gln Val Glu Glu Leu Lys Ser Asn Gln Lys Gln Glu Leu Gly
    370                 375                 380

Glu Val Arg Val Gln Tyr Arg Gly Arg Asp Ser Phe Arg Ala Phe Ala
385                 390                 395                 400

Lys Ala Leu Gly Val Met Asp Asp Leu Lys Ser Gly Val Pro Arg Ala
                405                 410                 415

Ser Tyr Arg Gly Ile Val Ser Phe Leu Phe Arg Gly Arg Arg Val Tyr
            420                 425                 430

Leu Ala Pro Pro Gln Asp Trp Thr Gly Tyr Asp Pro Ser Trp Ser
        435                 440                 445

<210> SEQ ID NO 16
<211> LENGTH: 438
<212> TYPE: PRT
<213> ORGANISM: Salmo salar

<400> SEQUENCE: 16

Met Leu Arg Lys Arg Gly Ser Ala Ile Leu Cys Gly Ala Phe Leu Phe
1               5                   10                  15

Val Ala Trp Asn Ala Val Val Leu Tyr Leu Trp Gly Arg Pro Leu
            20                  25                  30

Ser Gly Arg Glu Glu Arg Glu Met Asp Gly Gly Arg Gly Gly Ala Asp
        35                  40                  45

Leu Ala Gly Asp Val Ile His Met Ala Glu Ala Phe Glu Ala Glu Leu
    50                  55                  60

Glu Met Gln Arg Lys Ile Leu Leu Gln Ile Gln Gly His Arg Ser Leu
65                  70                  75                  80

Trp Glu Gln Pro Asn Glu Asn Gly Ala Ser Arg Ile Gly Pro Pro Gln
                85                  90                  95

Val Val Ile Pro Ile Leu Val Ile Ala Cys Asn Arg Val Thr Val Lys

```
            100                 105                 110
Arg Cys Leu Asp Lys Leu Leu Glu Tyr Arg Pro Ser Ala Glu Leu Tyr
            115                 120                 125

Pro Ile Ile Val Ser Gln Asp Cys Gly His Ala Glu Thr Ala Gln Val
            130                 135                 140

Ile Gly Ser Tyr Gly Ser Gln Val Thr His Leu Lys Gln Pro Asp Leu
145                 150                 155                 160

Ser Asp Ile Ala Val Arg Pro Glu His Lys Lys Phe Gln Gly Tyr Tyr
                165                 170                 175

Lys Ile Ser Arg His Tyr Arg Trp Ala Leu Asn Gln Val Phe Asn Ser
                180                 185                 190

Leu Ser His Ser Ser Val Val Ile Val Glu Asp Asp Leu Glu Val Ala
            195                 200                 205

Pro Asp Phe Phe Glu Tyr Phe Arg Ser Leu His Pro Ile Leu Lys Ser
            210                 215                 220

Asp Leu Ser Leu Trp Cys Val Ser Ala Trp Asn Asp Asn Gly Arg Asp
225                 230                 235                 240

Gly Tyr Val Asp Pro Ala Lys Ala Asp Leu Leu Tyr Arg Thr Asp Phe
                245                 250                 255

Phe Pro Gly Leu Gly Trp Met Met Leu Lys Glu Leu Trp Val Glu Leu
                260                 265                 270

Glu Pro Lys Trp Pro Gly Ala Phe Trp Asp Asp Trp Met Arg Gln Pro
            275                 280                 285

Asp Gln Arg Arg Asp Arg Ala Cys Ile Arg Pro Glu Ile Ser Arg Thr
            290                 295                 300

Leu Thr Phe Gly Arg Lys Gly Val Ser Leu Gly Gln Phe Tyr Asp Lys
305                 310                 315                 320

Tyr Leu Arg Tyr Ile Lys Leu Asn Ser Glu Phe Val Pro Phe Thr Lys
                325                 330                 335

Leu Asp Leu Ala Tyr Leu Lys Glu Glu Lys Tyr Lys Glu Ile Phe Glu
                340                 345                 350

Lys Gln Val Tyr Ser Ala Pro Leu Val Lys Tyr Glu Glu Val Gln Arg
            355                 360                 365

Gly Gln Leu Lys Gly Ala Gly Pro Phe Cys Leu His Tyr Leu Ser Lys
            370                 375                 380

Asp Gly Phe Lys Val Leu Ala Lys Asn Leu Gly Val Met Glu Asp Leu
385                 390                 395                 400

Lys Ser Gly Val Pro Arg Thr Gly Tyr Arg Gly Val Val Ser Phe Leu
                405                 410                 415

Ser Arg Gly Arg Arg Ile Phe Leu Ala Pro Pro Gly Trp Ser Lys
                420                 425                 430

Tyr Asp Pro Thr Trp Ser
        435

<210> SEQ ID NO 17
<211> LENGTH: 452
<212> TYPE: PRT
<213> ORGANISM: Danio rerio

<400> SEQUENCE: 17

Met Leu Arg Lys Arg Ser Pro Leu Val Ile Cys Gly Ala Phe Ile Phe
1               5                   10                  15

Val Ala Trp Asn Val Val Leu Leu Phe Val Leu Met Arg Arg Pro Ser
            20                  25                  30
```

```
Ser Pro Gly Thr Phe Asn Asn Gln Asp Lys Pro Gly Thr Glu His
         35                  40                  45
Arg Ala Glu Gly Gly Lys Phe Gly Asn Ile Met Asn Glu Val Ile Arg
 50                      55                  60
Val Ala Asp Ala Phe Glu Ala Glu Leu Ala Ala Gln Lys Lys Ile Leu
 65                  70                  75                  80
Gln Gln Ile Gln Ser His Trp Ser Val Trp Asp Ser Lys Asp Gly Val
                 85                  90                  95
Ile Pro Glu Lys Ser Lys Ser Glu Val Glu His Thr Ala Pro Val Val
                100                 105                 110
Ile Pro Ile Leu Val Ile Ala Cys Asn Arg Val Thr Val Lys Arg Cys
                115                 120                 125
Leu Asp Lys Leu Ile Glu His Arg Pro Ser Ala Glu Leu His Pro Ile
130                 135                 140
Ile Val Ser Gln Asp Cys Gly His Arg Glu Thr Ser Asp Val Ile Gly
145                 150                 155                 160
Ser Tyr Gly Ser Gln Leu Thr His Ile Lys Gln Pro Asp Leu Ser Asp
                165                 170                 175
Val Ala Val Pro Pro Gln His Lys Lys Phe Gln Gly Tyr Tyr Lys Ile
                180                 185                 190
Ser Arg His Tyr Lys Trp Ala Leu Ser Gln Val Phe Asn Thr Phe Ser
                195                 200                 205
Tyr Ser Ser Val Val Val Glu Asp Asp Leu Glu Val Ala Pro Asp
                210                 215                 220
Phe Phe Glu Tyr Phe Arg Ala Leu His Pro Met Leu Lys Ser Asp Pro
225                 230                 235                 240
Thr Leu Trp Cys Val Ser Ala Trp Asn Asp Asn Gly Arg Asp Gly Phe
                245                 250                 255
Val Asp Pro Gly Lys Ala Ser Leu Leu Tyr Arg Thr Asp Phe Phe Pro
                260                 265                 270
Gly Leu Gly Trp Met Leu Thr Lys Asp Leu Trp Ala Glu Leu Glu Pro
                275                 280                 285
Lys Trp Pro Ala Ser Phe Trp Asp Asp Trp Met Arg His Pro Asp Gln
290                 295                 300
Arg Lys Asp Arg Ser Cys Ile Arg Pro Glu Ile Ser Arg Thr Leu Thr
305                 310                 315                 320
Phe Gly Arg Lys Gly Val Ser Leu Gly Gln Phe Tyr Asp Lys Tyr Leu
                325                 330                 335
Arg Phe Ile Lys Leu Asn Thr Glu Phe Val Pro Phe Thr Lys Met Asp
                340                 345                 350
Leu Ser Tyr Leu Glu Lys Glu Lys Tyr Asp Glu Ser Phe Glu Lys Glu
                355                 360                 365
Val Tyr Ala Ala Ser Leu Val Thr Leu Glu Asp Leu Lys Ser Gly Lys
370                 375                 380
Leu Ser Gly Ser Gly Pro Phe Arg Val Gln Tyr Ser Ser Pro Asp Ser
385                 390                 395                 400
Phe Lys Ser Leu Ala Arg Asn Leu Gly Val Met Asp Asp Leu Lys Ser
                405                 410                 415
Gly Val Pro Arg Ala Gly Tyr Arg Gly Ala Val Ser Phe Leu Leu Arg
                420                 425                 430
Gly Lys Arg Val Tyr Leu Ala Pro Pro Ala Gly Trp Ser Arg Tyr Asp
                435                 440                 445
Pro Ser Trp Ser
```

<210> SEQ ID NO 18
<211> LENGTH: 448
<212> TYPE: PRT
<213> ORGANISM: Xenopus laevis

<400> SEQUENCE: 18

```
Met Pro Arg Lys Val Ser Val Ala Ala Trp Gly Ala Ala Leu Phe Ile
 1               5                  10                  15

Ser Trp Asn Ala Ile Leu Leu Tyr Leu Met Ser Arg Ser Arg Gly
            20                  25                  30

Thr Asp His Ser Asp Leu Thr Ala His Val Ile Gln Leu Ala Glu Ala
                35                  40                  45

Ala Glu Ala Glu Leu Glu Lys Gln Lys Gly Leu Leu Gln Gln Ile His
        50                  55                  60

His Tyr Ser Gly Leu Leu Asn Gln Gln Gln Pro Ser Ser His Val Arg
 65                  70                  75                  80

Leu Ala Pro Leu Met Pro Ile Lys Asn Leu Asn Val Ser Ser Pro Phe
                85                  90                  95

Pro Ser Pro Val Gly Ser Gly Pro Leu Pro Leu Val Ile Pro Ile Leu
            100                 105                 110

Val Val Ala Cys Asp Arg Pro Ser Val Arg Arg Cys Leu Asp Ser Leu
        115                 120                 125

Leu Lys Tyr Arg Pro Ser Ala Glu Lys Phe Pro Ile Ile Val Ser Gln
130                 135                 140

Asp Cys Gly His Glu Glu Thr Gly Lys Val Ile Asp Ser Tyr Gly Asp
145                 150                 155                 160

Ala Val Thr His Ile Lys Gln Pro Asp Leu Ser Glu Val Ala Val Pro
                165                 170                 175

Pro Glu His Arg Lys Phe Gln Gly Tyr Tyr Lys Ile Ser Arg His Tyr
            180                 185                 190

Arg Trp Ala Leu Asn Gln Ile Phe Lys Ser Met Gly Tyr Lys Ala Ala
        195                 200                 205

Ile Val Val Glu Asp Asp Leu Glu Val Ala Pro Asp Phe Tyr Glu Tyr
    210                 215                 220

Phe Gln Ala Thr Leu Pro Leu Leu Gln Lys Asp Arg Met Leu Trp Cys
225                 230                 235                 240

Val Ser Ala Trp Asn Asp Asn Gly Lys Glu Ala Leu Ile Asp Pro Gly
                245                 250                 255

Gly Thr Ser Leu Leu Tyr Arg Ser Asp Phe Phe Pro Gly Leu Gly Trp
            260                 265                 270

Leu Leu Leu Arg Glu Leu Trp Glu Glu Leu Glu Pro Lys Trp Pro Ser
        275                 280                 285

Ala Phe Trp Asp Asp Trp Val Arg Arg Pro Glu Gln Arg Leu Asp Arg
    290                 295                 300

Ala Cys Val Arg Pro Glu Leu Ser Arg Thr Arg Thr Phe Gly Arg Lys
305                 310                 315                 320

Gly Val Ser Gln Gly Gln Phe Phe Asp Gln His Leu Arg Phe Ile Lys
                325                 330                 335

Leu Asn Gln Asp Leu Val Pro Phe Thr Lys Met Asp Leu Ser Tyr Leu
            340                 345                 350

Leu Lys Asp Thr Tyr Asp Pro Trp Phe Leu Glu Gln Val Tyr Gly Ala
        355                 360                 365
```

```
Pro Lys Ala Arg Ala Glu Glu Val Leu His Gly Gln Val Pro Gly Gly
    370                 375                 380

Arg Thr Val Arg Val Glu Tyr Thr Thr Lys Asp Thr Phe Lys Ala Met
385                 390                 395                 400

Ala Arg Ala Phe Gly Val Met Glu Asp Leu Lys Ser Gly Val Ala Arg
                405                 410                 415

Ala Ala Tyr Lys Gly Val Val Ser Phe Ser His Arg Gly Arg Arg Val
            420                 425                 430

Phe Leu Ala Pro Pro Lys Asp Trp Thr Gly Tyr Asp Pro Leu Trp Asn
        435                 440                 445

<210> SEQ ID NO 19
<211> LENGTH: 458
<212> TYPE: PRT
<213> ORGANISM: Drosophila melanogaster

<400> SEQUENCE: 19

Met Arg Thr Arg Lys Val Leu Leu Val Ile Gly Phe Leu Val Thr Trp
1               5                   10                  15

Thr Tyr Ala Thr Tyr Tyr Leu Leu Arg Gln Thr Gly Ile His Thr
            20                  25                  30

Ser Arg His Gln Ser Leu Gln Ala Tyr Lys Leu Asn Ser Gln Ala Arg
        35                  40                  45

Asp Ala Asn Met Gln Ser His His Leu Ala Lys Asn Val Phe Glu Phe
    50                  55                  60

Val Lys Leu Lys Tyr Leu Glu Lys Gln Pro Ser Val Ala Ser Thr
65                  70                  75              80

Pro Gln Ile Ser Ile Ile Ala Ala Glu Ile Ser Ala Glu Leu Pro Glu
                85                  90                  95

Gln His Val Ala Lys Ser Ala Thr Ala Arg Ile Pro Thr Lys Thr Tyr
            100                 105                 110

Leu Ala Asn Gly Glu Pro Val Phe Pro Val Val Phe Ala Cys Asn
        115                 120                 125

Arg Val Ser Val Lys Lys Cys Ile Asp Asn Leu Val Gln Tyr Arg Pro
130                 135                 140

Ser Val Glu Gln Phe Pro Ile Ile Val Ser Gln Asp Cys Gly Asp Glu
145                 150                 155                 160

Pro Thr Lys Glu Ala Ile Leu Ser Tyr Gly Lys Gln Val Thr Leu Ile
                165                 170                 175

Glu Gln Pro Asp Leu Ser Asp Ile Thr Val Leu Pro Lys Glu Lys Lys
            180                 185                 190

Phe Lys Gly Tyr Tyr Lys Ile Ala Arg His Tyr Gly Trp Ala Leu Asn
        195                 200                 205

Thr Thr Phe Ala Val Gly Phe Glu Phe Val Ile Ile Val Glu Asp Asp
    210                 215                 220

Leu Asn Val Ala Pro Asp Phe Phe Glu Tyr Phe Leu Gly Thr His Lys
225                 230                 235                 240

Leu Leu Lys Gln Asp Pro Ser Leu Trp Cys Val Ser Ala Trp Asn Asp
                245                 250                 255

Asn Gly Lys Ala Ala Val Val Asp Ala Ala Gln Pro Glu Leu Leu Tyr
            260                 265                 270

Arg Thr Asp Phe Phe Pro Gly Leu Gly Trp Met Leu Thr Lys Asp Leu
        275                 280                 285

Trp Ala Glu Leu Ser Val Lys Trp Pro Lys Ser Phe Trp Asp Asp Trp
    290                 295                 300
```

```
Ile Arg His Pro Ala Gln Arg Lys Asp Arg Val Cys Ile Arg Pro Glu
305                 310                 315                 320

Ile Ser Arg Thr Arg Thr Phe Gly Lys Ile Gly Val Ser Asn Gly Leu
            325                 330                 335

Phe Phe Asp Lys Tyr Leu Lys His Ile Lys Leu Ser Glu Asp Phe Val
        340                 345                 350

Gln Phe Thr Lys Ile Asn Met Ser Tyr Leu Leu Lys Asp Asn Tyr Asp
    355                 360                 365

Asn Thr Phe Leu Arg Arg Val Tyr Thr Tyr Pro Ile Val Thr Tyr Asp
370                 375                 380

Glu Leu Arg Arg Asn Leu Ile Arg Ile Glu Gly Pro Val Arg Ile Gln
385                 390                 395                 400

Tyr Thr Thr Arg Glu Gln Tyr Lys Arg Thr Thr Lys Met Leu Gly Leu
                405                 410                 415

Met Asp Asp Phe Lys Ser Gly Val Pro Arg Thr Ala Tyr His Gly Ile
            420                 425                 430

Val Ser Phe Tyr Tyr Asn Lys Arg Arg Val His Leu Ala Pro Asn Ala
        435                 440                 445

Asn Trp Lys Gly Tyr Glu Leu Ser Trp Ser
    450                 455

<210> SEQ ID NO 20
<211> LENGTH: 447
<212> TYPE: PRT
<213> ORGANISM: Homo sapiens

<400> SEQUENCE: 20

Met Arg Phe Arg Ile Tyr Lys Arg Lys Val Leu Ile Leu Thr Leu Val
1               5                   10                  15

Val Ala Ala Cys Gly Phe Val Leu Trp Ser Ser Asn Gly Arg Gln Arg
            20                  25                  30

Lys Asn Glu Ala Leu Ala Pro Pro Leu Leu Asp Ala Glu Pro Ala Arg
        35                  40                  45

Gly Ala Gly Gly Arg Gly Gly Asp His Pro Ser Val Ala Val Gly Ile
50                  55                  60

Arg Arg Val Ser Asn Val Ser Ala Ala Ser Leu Val Pro Ala Val Pro
65                  70                  75                  80

Gln Pro Glu Ala Asp Asn Leu Thr Leu Arg Tyr Arg Ser Leu Val Tyr
                85                  90                  95

Gln Leu Asn Phe Asp Gln Thr Leu Arg Asn Val Asp Lys Ala Gly Thr
            100                 105                 110

Trp Ala Pro Arg Glu Leu Val Leu Val Gln Val His Asn Arg Pro
        115                 120                 125

Glu Tyr Leu Arg Leu Leu Leu Asp Ser Leu Arg Lys Ala Gln Gly Ile
    130                 135                 140

Asp Asn Val Leu Val Ile Phe Ser His Asp Phe Trp Ser Thr Glu Ile
145                 150                 155                 160

Asn Gln Leu Ile Ala Gly Val Asn Phe Cys Pro Val Leu Gln Val Phe
                165                 170                 175

Phe Pro Phe Ser Ile Gln Leu Tyr Pro Asn Glu Phe Pro Gly Ser Asp
            180                 185                 190

Pro Arg Asp Cys Pro Arg Asp Leu Pro Lys Asn Ala Ala Leu Lys Leu
        195                 200                 205

Gly Cys Ile Asn Ala Glu Tyr Pro Asp Ser Phe Gly His Tyr Arg Glu
```

-continued

```
            210                 215                 220
Ala Lys Phe Ser Gln Thr Lys His His Trp Trp Lys Leu His Phe
225                 230                 235                 240

Val Trp Glu Arg Val Lys Ile Leu Arg Asp Tyr Ala Gly Leu Ile Leu
                245                 250                 255

Phe Leu Glu Glu Asp His Tyr Leu Ala Pro Asp Phe Tyr His Val Phe
            260                 265                 270

Lys Lys Met Trp Lys Leu Lys Gln Gln Glu Cys Pro Glu Cys Asp Val
                275                 280                 285

Leu Ser Leu Gly Thr Tyr Ser Ala Ser Arg Ser Phe Tyr Gly Met Ala
            290                 295                 300

Asp Lys Val Asp Val Lys Thr Trp Lys Ser Thr Glu His Asn Met Gly
305                 310                 315                 320

Leu Ala Leu Thr Arg Asn Ala Tyr Gln Lys Leu Ile Glu Cys Thr Asp
                325                 330                 335

Thr Phe Cys Thr Tyr Asp Asp Tyr Asn Trp Asp Trp Thr Leu Gln Tyr
            340                 345                 350

Leu Thr Val Ser Cys Leu Pro Lys Phe Trp Lys Val Leu Val Pro Gln
                355                 360                 365

Ile Pro Arg Ile Phe His Ala Gly Asp Cys Gly Met His His Lys Lys
            370                 375                 380

Thr Cys Arg Pro Ser Thr Gln Ser Ala Gln Ile Glu Ser Leu Leu Asn
385                 390                 395                 400

Asn Asn Lys Gln Tyr Met Phe Pro Glu Thr Leu Thr Ile Ser Glu Lys
                405                 410                 415

Phe Thr Val Val Ala Ile Ser Pro Pro Arg Lys Asn Gly Gly Trp Gly
                420                 425                 430

Asp Ile Arg Asp His Glu Leu Cys Lys Ser Tyr Arg Arg Leu Gln
                435                 440                 445

<210> SEQ ID NO 21
<211> LENGTH: 447
<212> TYPE: PRT
<213> ORGANISM: Pan troglodytes

<400> SEQUENCE: 21

Met Arg Phe Arg Ile Tyr Lys Arg Lys Val Leu Ile Leu Thr Leu Val
1               5                   10                  15

Val Ala Ala Cys Gly Phe Val Leu Trp Ser Ser Asn Gly Arg Gln Arg
                20                  25                  30

Lys Asn Glu Ala Leu Ala Pro Pro Leu Leu Asp Ala Glu Pro Ala Arg
            35                  40                  45

Gly Ala Gly Gly Arg Gly Gly Asp His Pro Ser Val Ala Val Gly Ile
        50                  55                  60

Arg Arg Val Ser Asn Val Ser Ala Ala Pro Leu Val Pro Ala Val Pro
65                  70                  75                  80

Gln Pro Glu Ala Asp Asn Leu Thr Leu Arg Tyr Arg Ser Leu Val Tyr
                85                  90                  95

Gln Leu Asn Phe Asp Gln Thr Leu Arg Asn Val Asp Lys Ala Gly Thr
            100                 105                 110

Trp Ala Pro Arg Glu Leu Val Leu Val Val Gln Val His Asn Arg Pro
        115                 120                 125

Glu Tyr Leu Arg Leu Leu Leu Asp Ser Leu Arg Lys Ala Gln Gly Ile
    130                 135                 140
```

```
Asp Asn Val Leu Val Ile Phe Ser His Asp Phe Trp Ser Thr Glu Ile
145                 150                 155                 160

Asn Gln Leu Ile Ala Gly Val Asn Phe Cys Pro Val Leu Gln Val Phe
                165                 170                 175

Phe Pro Phe Ser Ile Gln Leu Tyr Pro Asn Glu Phe Pro Gly Ser Asp
            180                 185                 190

Pro Arg Asp Cys Pro Arg Asp Leu Pro Lys Asn Ala Ala Leu Lys Leu
        195                 200                 205

Gly Cys Ile Asn Ala Glu Tyr Pro Asp Ser Phe Gly His Tyr Arg Glu
    210                 215                 220

Ala Lys Phe Ser Gln Thr Lys His His Trp Trp Trp Lys Leu His Phe
225                 230                 235                 240

Val Trp Glu Arg Val Lys Ile Leu Arg Asp Tyr Ala Gly Leu Val Leu
                245                 250                 255

Phe Leu Glu Glu Asp His Tyr Leu Ala Pro Asp Phe Tyr His Val Phe
            260                 265                 270

Lys Lys Met Trp Lys Leu Lys Gln Gln Glu Cys Pro Glu Cys Asp Val
        275                 280                 285

Leu Ser Leu Gly Thr Tyr Ser Ala Ser Arg Ser Phe Tyr Gly Met Ala
    290                 295                 300

Asp Lys Val Asp Val Lys Thr Trp Lys Ser Thr Glu His Asn Met Gly
305                 310                 315                 320

Leu Ala Leu Thr Arg Asn Ala Tyr Gln Lys Leu Ile Glu Cys Thr Asp
                325                 330                 335

Thr Phe Cys Thr Tyr Asp Asp Tyr Asn Trp Asp Trp Thr Leu Gln Tyr
            340                 345                 350

Leu Thr Val Ser Cys Leu Pro Lys Phe Trp Lys Val Leu Val Pro Gln
        355                 360                 365

Val Pro Arg Ile Phe His Ala Gly Asp Cys Gly Met His His Lys Lys
    370                 375                 380

Thr Cys Arg Pro Ser Thr Gln Ser Ala Gln Ile Glu Ser Leu Leu Asn
385                 390                 395                 400

Asn Asn Lys Gln Tyr Met Phe Pro Glu Thr Leu Thr Ile Ser Glu Lys
                405                 410                 415

Phe Thr Val Val Ala Ile Ser Pro Pro Arg Lys Asn Gly Gly Trp Gly
            420                 425                 430

Asp Ile Arg Asp His Glu Leu Cys Lys Ser Tyr Arg Arg Leu Gln
        435                 440                 445

<210> SEQ ID NO 22
<211> LENGTH: 447
<212> TYPE: PRT
<213> ORGANISM: Oryctolagus cuniculus

<400> SEQUENCE: 22

Met Arg Phe Arg Ile Tyr Lys Arg Lys Val Leu Ile Leu Thr Leu Val
1               5                   10                  15

Val Ala Ala Cys Gly Phe Val Leu Trp Ser Ser Asn Gly Arg Gln Arg
                20                  25                  30

Lys Asn Glu Ala Leu Ala Pro Pro Leu Leu Asp Ala Glu Pro Ala Arg
            35                  40                  45

Ala Ala Gly Gly Arg Gly Gly Asp His Pro Ala Val Ser Val Gly Ile
        50                  55                  60

Arg Arg Val Ser Asn Glu Ser Ala Ala Pro Leu Val Pro Ala Ala Ala
65                  70                  75                  80
```

Gln Pro Glu Ala Asp Asn Gln Thr Leu Arg Tyr Arg Ser Leu Val Tyr
                    85                  90                  95

Gln Leu Asn Phe Asp Gln Thr Leu Arg Asn Val Asp Lys Ala Gly Ser
                100                 105                 110

Trp Ala Pro Arg Glu Leu Val Leu Val Val Gln Val His Asn Arg Leu
            115                 120                 125

Glu Tyr Leu Arg Leu Leu Leu Asp Ser Leu Arg Lys Ala Gln Gly Ile
        130                 135                 140

Glu Asp Val Leu Val Ile Phe Ser His Asp Phe Trp Ser Pro Glu Ile
145                 150                 155                 160

Asn Gln Leu Ile Ala Gly Val Asp Phe Cys Pro Ile Leu Gln Val Phe
                165                 170                 175

Phe Pro Phe Ser Ile Gln Leu Tyr Pro Asn Glu Phe Pro Gly Ser Asp
            180                 185                 190

Pro Arg Asp Cys Pro Arg Asp Leu Gln Lys Asn Ala Ala Leu Lys Leu
        195                 200                 205

Gly Cys Ile Asn Ala Glu Tyr Pro Asp Ser Phe Gly His Tyr Arg Glu
    210                 215                 220

Ala Lys Phe Ser Gln Thr Lys His His Trp Trp Trp Lys Leu His Phe
225                 230                 235                 240

Val Trp Glu Arg Val Lys Val Leu Gln Asp Tyr Ala Gly Leu Ile Leu
                245                 250                 255

Phe Leu Glu Glu Asp His Tyr Leu Ala Pro Asp Phe Tyr His Val Phe
            260                 265                 270

Lys Lys Met Trp Lys Leu Lys Gln Gln Glu Cys Pro Glu Cys Asp Val
        275                 280                 285

Leu Ser Leu Gly Thr Tyr Thr Ala Ser Arg Ser Phe His Gly Ile Ala
    290                 295                 300

His Lys Val Asp Val Lys Thr Trp Lys Ser Thr Glu His Asn Met Gly
305                 310                 315                 320

Leu Ala Leu Thr Arg Asn Ala Tyr Gln Lys Leu Ile Glu Cys Thr Asp
                325                 330                 335

Thr Phe Cys Thr Tyr Asp Asp Tyr Asn Trp Asp Trp Thr Leu Gln Tyr
            340                 345                 350

Leu Thr Val Ser Cys Leu Pro Lys Leu Trp Arg Val Leu Val Pro Gln
        355                 360                 365

Val Pro Arg Val Phe His Ala Gly Asp Cys Gly Met His His Lys Lys
    370                 375                 380

Thr Cys Arg Pro Phe Thr Gln Ser Ala Gln Ile Glu Ser Leu Leu Asn
385                 390                 395                 400

Ser Asn Arg Gln Tyr Met Phe Pro Glu Thr Leu Ile Ile Ser Glu Lys
                405                 410                 415

Ser Pro Val Val Ser Ile Ala Ser Pro Arg Lys Asn Gly Gly Trp Gly
            420                 425                 430

Asp Ile Arg Asp His Glu Leu Cys Lys Ser Tyr Arg Leu Gln
        435                 440                 445

<210> SEQ ID NO 23
<211> LENGTH: 446
<212> TYPE: PRT
<213> ORGANISM: Ailuropoda melanoleuca

<400> SEQUENCE: 23

Met Arg Phe Arg Ile Tyr Lys Arg Lys Val Leu Ile Leu Thr Leu Val

-continued

```
1               5                   10                  15
Val Ala Ala Cys Gly Phe Val Leu Trp Ser Ser Asn Gly Arg Gln Arg
                20                  25                  30

Lys Asn Glu Ala Leu Ala Pro Pro Leu Leu Asp Ala Glu Pro Ala Arg
                35                  40                  45

Gly Ala Gly Arg Gly Gly Asp His Ser Ala Val Ser Ala Gly Ile
50                      55                  60

Arg Arg Val Ser Asn Asp Ser Ala Ala Pro Leu Val Pro Ala Ala Pro
65                  70                  75                  80

Gln Pro Glu Ala Asp Asn Leu Thr Leu Arg Tyr Arg Ser Leu Val Tyr
                85                  90                  95

Gln Leu Asn Phe Asp Gln Thr Leu Arg Asn Val Asp Lys Ala Gly Ser
                100                 105                 110

Trp Ala Pro Arg Glu Leu Val Leu Val Val Gln Val His Asn Arg Pro
                115                 120                 125

Asp Tyr Leu Arg Leu Leu Leu Asp Ser Leu Arg Lys Ala Gln Gly Ile
                130                 135                 140

Asp Asn Val Leu Val Ile Phe Ser His Asp Phe Trp Ser Thr Glu Ile
145                 150                 155                 160

Asn Gln Leu Ile Ala Gly Val Asp Phe Cys Pro Val Leu Gln Val Phe
                165                 170                 175

Phe Pro Phe Ser Ile Gln Leu Tyr Pro Asn Glu Phe Pro Gly Ser Asp
                180                 185                 190

Pro Arg Asp Cys Pro Arg Asp Leu Glu Lys Asn Ala Ala Leu Lys Met
                195                 200                 205

Gly Cys Ile Asn Ala Glu Tyr Pro Asp Ser Phe Gly His Tyr Arg Glu
                210                 215                 220

Ala Lys Phe Ser Gln Thr Lys His His Trp Trp Lys Leu His Phe
225                 230                 235                 240

Val Trp Glu Arg Val Lys Val Leu Arg Asp Tyr Ala Gly Leu Ile Leu
                245                 250                 255

Phe Leu Glu Glu Asp His Tyr Leu Ala Pro Asp Phe Tyr His Val Phe
                260                 265                 270

Lys Lys Met Trp Lys Leu Lys Gln Glu Glu Cys Thr Glu Cys Asp Val
                275                 280                 285

Leu Ser Leu Gly Thr Tyr Thr Ala Val Arg Ser Phe His Gly Ile Ala
                290                 295                 300

Asp Lys Val Asp Val Lys Thr Trp Lys Ser Thr Glu His Asn Met Gly
305                 310                 315                 320

Leu Ala Leu Thr Arg Asp Ala Tyr Gln Lys Leu Ile Glu Cys Thr Asp
                325                 330                 335

Thr Phe Cys Thr Tyr Asp Asp Tyr Asn Trp Asp Trp Thr Leu Gln Tyr
                340                 345                 350

Leu Thr Val Ser Cys Leu Pro Lys Phe Trp Lys Val Leu Val Pro Gln
                355                 360                 365

Val Pro Arg Ile Phe His Ala Gly Asp Cys Gly Met His His Lys Lys
                370                 375                 380

Thr Cys Arg Pro Ser Thr Gln Ser Ala Gln Ile Glu Ser Leu Leu Asn
385                 390                 395                 400

Asn Asn Lys Gln Tyr Leu Phe Pro Glu Thr Leu Ile Ile Ser Glu Lys
                405                 410                 415

Phe Val Ala Ala Ile Ser Pro Pro Arg Lys Asn Gly Gly Trp Gly Asp
                420                 425                 430
```

Ile Arg Asp His Glu Leu Cys Lys Ser Tyr Arg Arg Leu Gln
        435                 440                 445

<210> SEQ ID NO 24
<211> LENGTH: 446
<212> TYPE: PRT
<213> ORGANISM: Canis familiaris

<400> SEQUENCE: 24

Met Arg Phe Arg Ile Tyr Lys Arg Lys Val Leu Ile Leu Thr Leu Val
1               5                   10                  15

Val Ala Ala Cys Gly Phe Val Leu Trp Ser Ser Asn Gly Arg Gln Arg
            20                  25                  30

Lys Asn Glu Ala Leu Ala Pro Pro Leu Leu Asp Ala Glu Pro Ala Arg
        35                  40                  45

Gly Ala Gly Gly Arg Gly Gly Asp His Ser Ala Val Ser Val Gly Ile
    50                  55                  60

Arg Arg Gly Ser Asn Glu Ser Ala Ala Pro Leu Val Pro Ala Ala Pro
65                  70                  75                  80

Gln Pro Glu Ala Asp Asn Leu Thr Leu Arg Tyr Arg Ser Leu Val Tyr
                85                  90                  95

Gln Leu Asn Phe Asp Gln Thr Leu Arg Asn Val Asp Lys Ala Gly Ser
            100                 105                 110

Trp Ala Pro Arg Glu Leu Val Leu Val Val Gln Val His Asn Arg Pro
        115                 120                 125

Asp Tyr Leu Arg Leu Leu Leu Asp Ser Leu Arg Lys Ala Gln Gly Ile
    130                 135                 140

Asp Asn Val Leu Val Ile Phe Ser His Asp Phe Trp Ser Thr Glu Ile
145                 150                 155                 160

Asn Gln Leu Ile Ala Gly Val Asp Phe Cys Pro Val Leu Gln Val Phe
                165                 170                 175

Phe Pro Phe Ser Ile Gln Leu Tyr Pro Asn Glu Phe Pro Gly Ser Asp
            180                 185                 190

Pro Arg Asp Cys Pro Arg Asp Leu Glu Lys Asn Ala Ala Leu Lys Met
        195                 200                 205

Gly Cys Ile Asn Ala Glu Tyr Pro Asp Ser Phe Gly His Tyr Arg Glu
    210                 215                 220

Ala Lys Phe Ser Gln Thr Lys His His Trp Trp Lys Leu His Phe
225                 230                 235                 240

Val Trp Glu Arg Val Lys Val Leu Arg Asp Tyr Ala Gly Leu Ile Leu
                245                 250                 255

Phe Leu Glu Glu Asp His Tyr Leu Ala Pro Asp Phe Tyr His Val Phe
            260                 265                 270

Lys Lys Met Trp Lys Leu Lys Gln Glu Glu Cys Pro Glu Cys Asp Val
        275                 280                 285

Leu Ser Leu Gly Thr Tyr Thr Ala Ile Arg Ser Phe His Gly Ile Ala
    290                 295                 300

Asp Lys Val Asp Val Lys Thr Trp Lys Ser Thr Glu His Asn Met Gly
305                 310                 315                 320

Leu Ala Leu Thr Arg Asp Ala Tyr Gln Lys Leu Ile Glu Cys Thr Asp
                325                 330                 335

Thr Phe Cys Thr Tyr Asp Asp Tyr Asn Trp Asp Trp Thr Leu Gln Tyr
            340                 345                 350

Leu Thr Val Ser Cys Leu Pro Lys Phe Trp Lys Val Leu Val Pro Gln

```
                355                 360                 365
Val Pro Arg Ile Phe His Ala Gly Asp Cys Gly Met His His Lys Lys
    370                 375                 380

Thr Cys Lys Pro Ser Thr Gln Ser Ala Gln Ile Glu Ser Leu Leu Asn
385                 390                 395                 400

Ser Asn Lys Gln Tyr Leu Phe Pro Glu Thr Leu Ile Ile Ser Glu Lys
                405                 410                 415

Phe Val Ala Ala Ile Ser Pro Pro Arg Lys Asn Gly Gly Trp Gly Asp
            420                 425                 430

Ile Arg Asp His Glu Leu Cys Lys Ser Tyr Arg Arg Leu Gln
        435                 440                 445

<210> SEQ ID NO 25
<211> LENGTH: 446
<212> TYPE: PRT
<213> ORGANISM: Sus scrofa

<400> SEQUENCE: 25

Met Arg Phe Arg Ile Tyr Lys Arg Lys Val Leu Ile Leu Thr Phe Val
1               5                   10                  15

Val Ala Ala Cys Gly Phe Val Leu Trp Ser Ser Asn Gly Arg Gln Arg
            20                  25                  30

Lys Asn Glu Ala Leu Ala Pro Pro Leu Leu Asp Ala Glu Pro Val Arg
        35                  40                  45

Gly Ala Gly Ala Arg Ala Gly Asp His Pro Ala Ile Ser Val Gly Ile
    50                  55                  60

Arg Arg Gly Ser Asn Asp Ser Ala Ala Pro Leu Val Ala Ala Ala Pro
65                  70                  75                  80

Gln Pro Glu Val Asp Asn Leu Thr Leu Arg Tyr Arg Ser Leu Val Tyr
                85                  90                  95

Gln Leu Asn Phe Asp Gln Thr Leu Arg Asn Val Asp Lys Val Ser Ser
            100                 105                 110

Trp Val Pro Arg Glu Leu Val Leu Val Val Gln Val His Asn Arg Ala
        115                 120                 125

Glu Tyr Leu Lys Leu Leu Leu Asp Ser Leu Arg Lys Ala Gln Gly Ile
    130                 135                 140

Asp Asn Val Leu Val Ile Phe Ser His Asp Phe Trp Ser Thr Glu Ile
145                 150                 155                 160

Asn Gln Leu Ile Ala Gly Val Asp Phe Cys Pro Val Leu Gln Val Phe
                165                 170                 175

Phe Pro Phe Ser Ile Gln Leu Tyr Pro Asn Glu Phe Pro Gly Thr Asp
            180                 185                 190

Pro Arg Asp Cys Pro Arg Asp Leu Glu Lys Asn Ala Ala Leu Lys Met
        195                 200                 205

Gly Cys Ile Asn Ala Glu Tyr Pro Asp Ser Phe Gly His Tyr Arg Glu
    210                 215                 220

Ala Lys Phe Ser Gln Thr Lys His His Trp Trp Lys Leu His Phe
225                 230                 235                 240

Val Trp Glu Arg Val Lys Val Leu Arg Asp Tyr Ala Gly Leu Ile Leu
                245                 250                 255

Phe Leu Glu Glu Asp His Tyr Val Ala Pro Asp Phe Tyr His Val Phe
            260                 265                 270

Lys Lys Met Trp Asn Leu Lys Gln Gln Glu Cys Pro Glu Cys Asp Val
        275                 280                 285
```

-continued

```
Leu Ser Leu Gly Thr Tyr Thr Thr Val Arg Ser Phe Arg Asp Val Ala
        290                 295                 300

Asp Lys Val Asp Val Lys Thr Trp Lys Ser Thr Glu His Asn Met Gly
305                 310                 315                 320

Leu Ala Leu Thr Arg Asp Ala Tyr Gln Lys Leu Ile Glu Cys Thr Asp
                325                 330                 335

Thr Phe Cys Thr Tyr Asp Asp Tyr Asn Trp Asp Trp Thr Leu Gln Tyr
            340                 345                 350

Leu Thr Val Ser Cys Leu Pro Lys Phe Trp Lys Val Leu Val Pro Gln
        355                 360                 365

Val Pro Arg Ile Phe His Ala Gly Asp Cys Gly Met His His Lys Lys
370                 375                 380

Thr Cys Arg Pro Ser Thr Gln Ser Ala Gln Ile Glu Ser Leu Leu Asn
385                 390                 395                 400

Ser Asn Lys Gln Tyr Met Phe Pro Glu Thr Leu Thr Ile Ser Glu Lys
                405                 410                 415

Leu Thr Ala Ala Leu Ser Pro Arg Lys Asn Gly Gly Trp Gly Asp
            420                 425                 430

Ile Arg Asp His Glu Leu Cys Lys Ser Tyr Arg Arg Leu Gln
        435                 440                 445

<210> SEQ ID NO 26
<211> LENGTH: 446
<212> TYPE: PRT
<213> ORGANISM: Bos taurus

<400> SEQUENCE: 26

Met Arg Phe Arg Ile Tyr Lys Arg Lys Val Leu Ile Leu Met Leu Val
1               5                   10                  15

Val Ala Ala Cys Gly Phe Val Leu Trp Ser Ser Asn Gly Arg Gln Arg
                20                  25                  30

Lys Asn Glu Ala Leu Ala Pro Pro Leu Leu Asp Ala Asp Pro Val Arg
            35                  40                  45

Gly Ala Gly Ala Arg Ala Gly Asp His Pro Ala Val Ser Val Gly Ile
        50                  55                  60

Arg Arg Gly Ser Asn Glu Ser Ala Ala Pro Leu Val Ala Ala Ala Pro
65                  70                  75                  80

Gln Pro Glu Val Asp Asn Leu Thr Leu Arg Tyr Arg Ser Leu Val Tyr
                85                  90                  95

Gln Leu Asn Phe Asp Gln Thr Leu Arg Asn Val Asp Lys Ala Ala Ser
            100                 105                 110

Trp Thr Pro Arg Glu Leu Ala Leu Val Val Gln Val His Asn Arg Pro
        115                 120                 125

Glu Tyr Leu Lys Leu Leu Asp Ser Leu Arg Lys Ala Gln Gly Ile
    130                 135                 140

Asp Asp Val Leu Val Ile Phe Ser His Asp Phe Trp Ser Thr Glu Ile
145                 150                 155                 160

Asn Gln Leu Ile Ala Gly Val Asp Phe Cys Pro Val Leu Gln Val Phe
                165                 170                 175

Phe Pro Phe Ser Ile Gln Leu Tyr Pro Asn Glu Phe Pro Gly Thr Asp
            180                 185                 190

Pro Arg Asp Cys Pro Arg Asp Met Glu Lys Asn Ala Ala Leu Arg Met
        195                 200                 205

Gly Cys Ile Asn Ala Glu Tyr Pro Asp Ser Phe Gly His Tyr Arg Glu
    210                 215                 220
```

```
Ala Lys Phe Ser Gln Thr Lys His His Trp Trp Lys Leu His Phe
225                 230                 235                 240

Val Trp Glu Arg Val Lys Val Leu Arg Asp Tyr Ala Gly Leu Ile Leu
            245                 250                 255

Phe Leu Glu Glu Asp His Tyr Leu Ala Pro Asp Phe Tyr His Val Phe
        260                 265                 270

Lys Lys Met Trp Lys Leu Lys Gln Leu Glu Cys Pro Glu Cys Asp Val
            275                 280                 285

Leu Ser Leu Gly Thr Tyr Thr Ala Ile Arg Asn Phe Tyr Asp Val Ala
        290                 295                 300

Asp Lys Val Asp Val Lys Thr Trp Lys Ser Thr Glu His Asn Met Gly
305                 310                 315                 320

Leu Ala Leu Thr Arg Glu Ala Tyr Gln Lys Leu Ile Glu Cys Thr Asp
                325                 330                 335

Thr Phe Cys Thr Tyr Asp Asp Tyr Asn Trp Asp Trp Thr Leu Gln Tyr
            340                 345                 350

Leu Thr Val Ser Cys Leu Pro Lys Phe Trp Lys Val Leu Val Pro Gln
        355                 360                 365

Val Pro Arg Ile Phe His Ala Gly Asp Cys Gly Met His His Gln Lys
    370                 375                 380

Thr Cys Arg Pro Ala Thr Gln Ser Ala Gln Leu Glu Ser Leu Leu Asn
385                 390                 395                 400

Asn Asn Lys Gln Tyr Leu Phe Pro Glu Thr Leu Thr Ile Ser Glu Lys
                405                 410                 415

Phe Met Thr Ser Leu Ser Pro Pro Arg Lys Asn Gly Gly Trp Gly Asp
            420                 425                 430

Ile Arg Asp His Glu Leu Cys Lys Ser Tyr Arg Arg Leu Gln
        435                 440                 445

<210> SEQ ID NO 27
<211> LENGTH: 442
<212> TYPE: PRT
<213> ORGANISM: Rattus norvegicus

<400> SEQUENCE: 27

Met Arg Phe Arg Ile Tyr Lys Arg Lys Val Leu Ile Leu Thr Leu Val
1               5                   10                  15

Val Ala Ala Cys Gly Phe Val Leu Trp Ser Ser Asn Gly Arg Gln Arg
            20                  25                  30

Lys Asn Asp Ala Leu Ala Pro Pro Leu Leu Asp Ser Glu Pro Leu Arg
        35                  40                  45

Gly Ala Gly His Phe Ala Ala Ser Val Gly Ile Arg Arg Val Ser Asn
    50                  55                  60

Asp Ser Ala Ala Pro Leu Val Pro Ala Val Pro Arg Pro Glu Val Asp
65                  70                  75                  80

Asn Leu Thr Leu Arg Tyr Arg Ser Leu Val Tyr Gln Leu Asn Phe Asp
                85                  90                  95

Gln Met Leu Arg Asn Val Asp Lys Asp Gly Thr Trp Ser Pro Gly Glu
            100                 105                 110

Leu Val Leu Val Val Gln Val His Asn Arg Pro Glu Tyr Leu Arg Leu
        115                 120                 125

Leu Ile Asp Ser Leu Arg Lys Ala Gln Gly Ile Arg Glu Val Leu Val
    130                 135                 140

Ile Phe Ser His Asp Phe Trp Ser Ala Glu Ile Asn Ser Leu Ile Ser
```

```
            145                 150                 155                 160
        Ser Val Asp Phe Cys Pro Val Leu Gln Val Phe Phe Pro Phe Ser Ile
                        165                 170                 175

Gln Leu Tyr Pro Ser Glu Phe Pro Gly Ser Asp Pro Arg Asp Cys Pro
                        180                 185                 190

Arg Asp Leu Lys Lys Asn Ala Ala Leu Lys Leu Gly Cys Ile Asn Ala
                        195                 200                 205

Glu Tyr Pro Asp Ser Phe Gly His Tyr Arg Glu Ala Lys Phe Ser Gln
                        210                 215                 220

Thr Lys His His Trp Trp Lys Leu His Phe Val Trp Glu Arg Val
        225                 230                 235                 240

Lys Val Leu Gln Asp Tyr Thr Gly Leu Ile Leu Phe Leu Glu Glu Asp
                        245                 250                 255

His Tyr Leu Ala Pro Asp Phe Tyr His Val Phe Lys Lys Met Trp Lys
                        260                 265                 270

Leu Lys Gln Gln Glu Cys Pro Gly Cys Asp Val Leu Ser Leu Gly Thr
                        275                 280                 285

Tyr Thr Thr Ile Arg Ser Phe Tyr Gly Ile Ala Asp Lys Val Asp Val
                        290                 295                 300

Lys Thr Trp Lys Ser Thr Glu His Asn Met Gly Leu Ala Leu Thr Arg
        305                 310                 315                 320

Asp Ala Tyr Gln Lys Leu Ile Glu Cys Thr Asp Thr Phe Cys Thr Tyr
                        325                 330                 335

Asp Asp Tyr Asn Trp Asp Trp Thr Leu Gln Tyr Leu Thr Leu Ala Cys
                        340                 345                 350

Leu Pro Lys Val Trp Lys Val Leu Val Pro Gln Ala Pro Arg Ile Phe
                        355                 360                 365

His Ala Gly Asp Cys Gly Met His His Lys Lys Thr Cys Arg Pro Ser
                        370                 375                 380

Thr Gln Ser Ala Gln Ile Glu Ser Leu Leu Asn Asn Asn Lys Gln Tyr
        385                 390                 395                 400

Leu Phe Pro Glu Thr Leu Val Ile Gly Glu Lys Phe Pro Met Ala Ala
                        405                 410                 415

Ile Ser Pro Pro Arg Lys Asn Gly Gly Trp Gly Asp Ile Arg Asp His
                        420                 425                 430

Glu Leu Cys Lys Ser Tyr Arg Arg Leu Gln
                        435                 440

<210> SEQ ID NO 28
<211> LENGTH: 442
<212> TYPE: PRT
<213> ORGANISM: Mus musculus

<400> SEQUENCE: 28

Met Arg Phe Arg Ile Tyr Lys Arg Lys Val Leu Ile Leu Thr Leu Val
        1               5                   10                  15

Val Ala Ala Cys Gly Phe Val Leu Trp Ser Ser Asn Gly Arg Gln Arg
                        20                  25                  30

Lys Ser Asp Ala Leu Gly Pro Pro Leu Leu Asp Ala Glu Pro Val Arg
                        35                  40                  45

Gly Ala Gly His Leu Ala Val Ser Val Gly Ile Arg Arg Val Ser Asn
                        50                  55                  60

Glu Ser Ala Ala Pro Leu Val Pro Ala Val Pro Arg Pro Glu Val Asp
        65                  70                  75                  80
```

```
Asn Leu Thr Leu Arg Tyr Arg Ser Leu Val Tyr Gln Leu Asn Phe Asp
             85                  90                  95

Gln Met Leu Arg Asn Val Gly Asn Asp Gly Thr Trp Ser Pro Gly Glu
            100                 105                 110

Leu Val Leu Val Val Gln Val His Asn Arg Pro Glu Tyr Leu Arg Leu
            115                 120                 125

Leu Ile Asp Ser Leu Arg Lys Ala Gln Gly Ile Gln Glu Val Leu Val
            130                 135                 140

Ile Phe Ser His Asp Phe Trp Ser Ala Glu Ile Asn Ser Leu Ile Ser
145                 150                 155                 160

Arg Val Asp Phe Cys Pro Val Leu Gln Val Phe Phe Pro Phe Ser Ile
                165                 170                 175

Gln Leu Tyr Pro Asn Glu Phe Pro Gly Ser Asp Pro Arg Asp Cys Pro
            180                 185                 190

Arg Asp Leu Lys Lys Asn Ala Ala Leu Lys Leu Gly Cys Ile Asn Ala
            195                 200                 205

Glu Tyr Pro Asp Ser Phe Gly His Tyr Arg Glu Ala Lys Phe Ser Gln
210                 215                 220

Thr Lys His His Trp Trp Trp Lys Leu His Phe Val Trp Glu Arg Val
225                 230                 235                 240

Lys Val Leu Gln Asp Tyr Thr Gly Leu Ile Leu Phe Leu Glu Glu Asp
                245                 250                 255

His Tyr Leu Ala Pro Asp Phe Tyr His Val Phe Lys Lys Met Trp Lys
            260                 265                 270

Leu Lys Gln Gln Glu Cys Pro Gly Cys Asp Val Leu Ser Leu Gly Thr
            275                 280                 285

Tyr Thr Thr Ile Arg Ser Phe Tyr Gly Ile Ala Asp Lys Val Asp Val
290                 295                 300

Lys Thr Trp Lys Ser Thr Glu His Asn Met Gly Leu Ala Leu Thr Arg
305                 310                 315                 320

Asp Ala Tyr Gln Lys Leu Ile Glu Cys Thr Asp Thr Phe Cys Thr Tyr
                325                 330                 335

Asp Asp Tyr Asn Trp Asp Trp Thr Leu Gln Tyr Leu Thr Leu Ala Cys
            340                 345                 350

Leu Pro Lys Ile Trp Lys Val Leu Val Pro Gln Ala Pro Arg Ile Phe
            355                 360                 365

His Ala Gly Asp Cys Gly Met His His Lys Lys Thr Cys Arg Pro Ser
370                 375                 380

Thr Gln Ser Ala Gln Ile Glu Ser Leu Leu Asn Ser Asn Lys Gln Tyr
385                 390                 395                 400

Leu Phe Pro Glu Thr Leu Val Ile Gly Glu Lys Phe Pro Met Ala Ala
                405                 410                 415

Ile Ser Pro Pro Arg Lys Asn Gly Gly Trp Gly Asp Ile Arg Asp His
            420                 425                 430

Glu Leu Cys Lys Ser Tyr Arg Arg Leu Gln
            435                 440

<210> SEQ ID NO 29
<211> LENGTH: 444
<212> TYPE: PRT
<213> ORGANISM: Monodelphis domestica

<400> SEQUENCE: 29

Met Arg Phe Arg Ile Tyr Lys Arg Lys Val Leu Ile Leu Thr Leu Val
1               5                   10                  15
```

-continued

Val Ala Ala Cys Gly Phe Val Phe Trp Asn Ser Asn Gly Arg Gln Arg
             20                  25                  30

Lys Asn Glu Ala Phe Ala Gly Ser Val Pro Ala Pro Val Arg Ala Val
         35                  40                  45

Gly Pro Gly Asp Leu Arg Arg Phe Pro Asn Gly Ser Ala Ala Pro Pro
     50                  55                  60

Pro Glu Val Asp Asn Met Thr Leu Val Tyr Arg Ser Leu Val Tyr Gln
65                  70                  75                  80

Val Asn Phe Asp Gln Thr Leu Lys Asn Ala Leu Ala Ala Ala Ala Val
                 85                  90                  95

Gly Ala Gly Gly Ala Gly Gly Gly Gly Pro Ala Gln Leu Glu
             100                 105                 110

Leu Glu Leu Val Leu Val Val Gln Val His Asn Arg Pro Asp Tyr Leu
         115                 120                 125

Lys Leu Leu Leu Asp Ser Leu Arg Lys Val Gln Gly Ile Gly Asn Leu
     130                 135                 140

Leu Val Ile Phe Ser His Asp Phe Trp Ser Ala Glu Ile Asn Gln Leu
145                 150                 155                 160

Ile Ala Gly Val Asp Phe Cys Pro Val Leu Gln Val Phe Phe Pro Phe
                 165                 170                 175

Ser Ile Gln Leu Tyr Pro Asn Glu Phe Pro Gly Asn Asp Pro Lys Asp
             180                 185                 190

Cys Pro Arg Asp Leu Gln Lys Lys Ala Ala Leu Lys Met Gly Cys Ile
         195                 200                 205

Asn Ala Glu Tyr Pro Asp Ser Phe Gly His Tyr Arg Glu Ala Lys Phe
     210                 215                 220

Ser Gln Thr Lys His His Trp Trp Lys Leu His Phe Ala Trp Glu
225                 230                 235                 240

Arg Val Lys Ile Leu Arg Asn Tyr Ala Gly Leu Met Val Phe Leu Glu
                 245                 250                 255

Glu Asp His Tyr Leu Ala Pro Asp Phe Phe His Val Leu Lys Lys Met
             260                 265                 270

Trp Lys Leu Lys Leu Gln Glu Cys Pro Asp Cys Asp Val Leu Ser Leu
         275                 280                 285

Gly Ser Tyr Ala Val Ser Arg Ser Phe Phe Gly Lys Ala Asp Lys Val
     290                 295                 300

Glu Val Lys Thr Trp Lys Ser Thr Glu His Asn Met Gly Leu Ala Leu
305                 310                 315                 320

Thr Arg Asp Thr Tyr Gln Lys Leu Ile Glu Cys Thr Asp Thr Phe Cys
                 325                 330                 335

Thr Tyr Asp Asp Tyr Asn Trp Asp Trp Thr Leu Gln Tyr Leu Thr Thr
             340                 345                 350

Thr Cys Leu Lys Asn Phe Trp Lys Val Met Val Pro Glu Val Pro Arg
         355                 360                 365

Ile Tyr His Ala Gly Asp Cys Gly Met His His Lys Asp Pro Cys Arg
     370                 375                 380

Pro Ser Thr Gln Ser Ala Gln Ile Glu Leu Leu Leu Asn Lys Asn Lys
385                 390                 395                 400

Gln Tyr Leu Phe Pro Lys Thr Leu Ser Ile Ser Lys Lys Tyr Ser Met
                 405                 410                 415

Val Pro Leu Leu Pro His Gly Lys Asn Gly Gly Trp Gly Asp Ile Arg
             420                 425                 430

```
Asp His Glu Leu Cys Lys Ser Tyr Arg Arg Leu Gln
        435                 440

<210> SEQ ID NO 30
<211> LENGTH: 432
<212> TYPE: PRT
<213> ORGANISM: Xenopus laevis

<400> SEQUENCE: 30

Met Arg Cys Arg Ile Tyr Lys Arg Lys Val Ile Ile Leu Thr Leu Val
 1               5                  10                  15

Val Val Ala Cys Gly Leu Ala Leu Trp Ser Ser Gly Arg Gln Lys Lys
            20                  25                  30

Asn Gly Phe Val Pro Glu Val Glu Ser Asp Arg Phe Gln Asn Lys Gly
        35                  40                  45

His Ile Ser Pro Ala Ala Arg Lys Val Ser Asn Glu Ser Leu Ala Asn
    50                  55                  60

Lys Glu Gln Lys Thr Arg Val Asp Asn Met Thr Leu Val Tyr Arg Ser
65                  70                  75                  80

Val Val Phe Gln Trp Asn Phe Asp Gln Ala Ile Arg Asn Val Asp Lys
                85                  90                  95

Ile Asn Arg Pro Gln Asp Asp Val Val Val Val Gln Val His Asn
            100                 105                 110

Arg Pro Glu Phe Leu Arg Arg Leu Leu Asp Ser Leu Gly Lys Ala Lys
        115                 120                 125

Gly Ile Glu Asn Val Leu Leu Val Phe Ser His Asp Tyr Trp Ser Pro
    130                 135                 140

Glu Ile Asn Gln Ile Ile Ala Ser Val Asp Phe Cys Gln Val Leu Gln
145                 150                 155                 160

Ile Phe Phe Pro Phe Ser Ile Gln Leu Tyr Pro Asn Glu Phe Pro Gly
                165                 170                 175

His Asp Pro Lys Asp Cys Pro Arg Asp Ile Lys Lys Lys Asp Ala Val
            180                 185                 190

Glu Leu Gly Cys Ile Asn Ala Glu Tyr Pro Asp Ser Phe Gly His Tyr
        195                 200                 205

Arg Glu Ala Lys Phe Ser Gln Thr Lys His His Trp Trp Lys Leu
    210                 215                 220

Gln Phe Val Trp Asp Lys Leu Lys Val Leu Lys Glu His Asn Gly Leu
225                 230                 235                 240

Val Leu Phe Ile Glu Glu Asp His Tyr Leu Ser Pro Asp Phe Tyr Tyr
                245                 250                 255

Thr Leu Lys Lys Met Trp Ser Lys Lys Asn Glu Glu Cys Pro Asp Cys
            260                 265                 270

Asp Met Leu Cys Leu Gly Thr Tyr Ala His Thr Pro Phe Ala Asp Lys
        275                 280                 285

Ala Gly Lys Val Glu Val Lys Thr Trp Lys Ser Thr Glu His Asn Met
    290                 295                 300

Gly Met Ala Met Asn Arg Glu Thr Tyr Lys Lys Leu Val Ala Cys Ser
305                 310                 315                 320

Glu Thr Phe Cys Thr Tyr Asp Asp Tyr Asn Trp Asp Trp Thr Leu Gln
                325                 330                 335

Tyr Leu Thr Val Asn Cys Leu Pro Lys Phe Trp Lys Val Met Val Pro
            340                 345                 350

Glu Val Pro Arg Ile Tyr His Ile Gly Asp Cys Gly Met His His Asn
        355                 360                 365
```

```
Lys Pro Cys Arg Pro Thr Thr Glu Ser Ala Lys Leu Glu Ala Leu Phe
        370                 375                 380

Thr Ser Asn Gln Arg Asp Leu Phe Pro Glu Lys Ile Asp Ile Ser Arg
385                 390                 395                 400

Arg Tyr Thr Met Ala Ala Leu Ser Pro His Val Lys Asn Gly Gly Trp
                405                 410                 415

Gly Asp Ile Arg Asp His Glu Leu Cys Lys Ser Tyr His Arg Leu Gln
            420                 425                 430

<210> SEQ ID NO 31
<211> LENGTH: 450
<212> TYPE: PRT
<213> ORGANISM: Danio rerio

<400> SEQUENCE: 31

Met Arg Phe Arg Ile Tyr Lys Arg Lys Val Val Ile Leu Thr Leu Val
1               5                   10                  15

Val Ile Ile Cys Gly Phe Ala Val Trp Asn Ser Gly Lys Pro Lys Lys
            20                  25                  30

Ala Ser Thr Val Phe Pro Lys Glu Val Glu Thr Val Lys Arg Ser Ser
        35                  40                  45

Val Gly Ser Gln Ile Gln Ala Thr Ile Pro Val Thr Arg Lys Pro Ile
50                  55                  60

Asn Glu Ser Ile Pro Glu Lys Gln Gln Gln Gln Pro Val Ala Lys
65                  70                  75                  80

Ser Glu Ala Asp Asn Thr Thr Leu Val Tyr Arg Gly Ile Val Phe Gln
                85                  90                  95

Leu Asn Phe Asp Gln Asn Leu Lys Asn Glu Lys Phe Arg Ala Val
            100                 105                 110

Arg Gln Lys Asp Asp Leu Val Ile Val Val Gln Val His Asn Arg Pro
        115                 120                 125

Glu Tyr Leu Arg Leu Leu Val Asp Ser Leu Arg Lys Ser Lys Gly Ile
130                 135                 140

Glu Asn Ile Leu Leu Ile Phe Ser His Asp Phe Trp Ser Pro Glu Ile
145                 150                 155                 160

Asn Gln Ile Val Ala Ser Val Asp Phe Cys Leu Val Leu Gln Ile Phe
                165                 170                 175

Phe Pro Phe Ser Ile Gln Leu Tyr Pro Gln Glu Phe Pro Gly Asn Asp
            180                 185                 190

Pro Arg Asp Cys Pro Arg Asp Ile Pro Lys Lys Glu Ala Leu Thr Leu
        195                 200                 205

Gly Cys Ile Asn Ala Glu Tyr Pro Asp Ser Phe Gly His Tyr Arg Glu
210                 215                 220

Ala Lys Phe Ser Gln Thr Lys His His Trp Trp Lys Leu His Phe
225                 230                 235                 240

Val Trp Asp Arg Val Arg Val Leu Lys Asp His Lys Gly Leu Val Leu
                245                 250                 255

Leu Ile Glu Glu Asp His Tyr Leu Ala Pro Asp Phe Tyr His Leu Leu
            260                 265                 270

Lys Leu Met Ala Ser Leu Lys Lys Glu Gln Cys Pro Asp Cys Asp Ile
        275                 280                 285

Leu Ser Leu Gly Ser Tyr Gly His Ile Gly Tyr Ser Ser Lys Ala Asn
290                 295                 300

Lys Val Glu Val Lys Ala Trp Lys Ser Thr Glu His Asn Met Gly Met
```

```
305                 310                 315                 320
Ala Leu Asn Arg Asp Ala Tyr Gln Lys Leu Leu Arg Cys Thr Asp Ala
                325                 330                 335

Phe Cys Thr Tyr Asp Asp Tyr Asn Trp Asp Trp Ser Leu Gln His Leu
                340                 345                 350

Thr Val Thr Cys Leu Pro Ala Phe Leu Lys Val Met Val Ser Glu Ala
                355                 360                 365

Pro Arg Ile Phe His Ala Gly Asp Cys Gly Met His His Lys Lys Ser
    370                 375                 380

Ala Cys Met Pro Ser Gly Gln Lys Thr Lys Ile Glu Asn Val Leu Gln
385                 390                 395                 400

Asn Ser Gly Asn Gln Leu Phe Pro Lys Gln Leu Leu Ile Thr Lys Arg
                405                 410                 415

Leu Pro Ala Ser Gly Ala Lys Gly Val Ala Pro His Val Lys Asn Gly
                420                 425                 430

Gly Trp Gly Asp Ile Arg Asp His Glu Leu Cys Lys Ser Tyr Leu Arg
    435                 440                 445

Leu Gln
    450

<210> SEQ ID NO 32
<211> LENGTH: 465
<212> TYPE: PRT
<213> ORGANISM: Salmo salar

<400> SEQUENCE: 32

Met Arg Phe Arg Val Tyr Lys Arg Lys Val Val Ile Leu Thr Leu Val
1               5                   10                  15

Val Val Val Cys Gly Leu Ala Phe Trp Thr Ser Gly Lys Gln Lys Lys
                20                  25                  30

Ser Ser Gly Val Val Val Leu Lys Glu Ala Glu Gly Ala Arg Arg Ser
            35                  40                  45

Ser Ser Ser Gln Val Gln Pro Gln Pro Gln Ala Thr Pro Glu Val Ser
    50                  55                  60

Arg Ile Pro Asn Val Pro Pro Ile Ala Pro Val Asn Glu Thr His Pro
65                  70                  75                  80

Lys Asn Gln Pro Glu Lys His Leu Glu Lys Glu Val Val Lys Pro
                85                  90                  95

Glu Val Asp Asn Thr Thr Gln Val Tyr Arg Gly Ile Val Phe Gln Leu
                100                 105                 110

Asn Phe Asp Gln Thr Val Arg His Glu Glu Lys Phe Arg Ala Ala Arg
                115                 120                 125

Lys Lys Asp Asp Leu Val Val Val Gln Val His Asn Arg Pro Asp
    130                 135                 140

Tyr Leu Arg Leu Leu Val Glu Ser Leu Arg Lys Ala Arg Gly Val Glu
145                 150                 155                 160

Ser Ile Leu Leu Ile Phe Ser His Asp Phe Trp Ser Pro Glu Ile Asn
                165                 170                 175

Gln Val Val Ala Ser Val Asp Phe Cys Gln Val Leu Gln Ile Phe Phe
                180                 185                 190

Pro Phe Ser Ile Gln Leu Tyr Pro Gln Glu Phe Pro Gly His Asp Pro
                195                 200                 205

Arg Asp Cys Pro Arg Asp Ile Ser Lys Ile Asp Ala Leu Lys Leu Gly
    210                 215                 220
```

Cys Ile Asn Ala Glu Tyr Pro Asp Ser Phe Gly His Tyr Arg Glu Ala
225                 230                 235                 240

Lys Phe Ser Gln Thr Lys His His Trp Trp Lys Leu His Phe Val
        245                 250                 255

Trp Asp Arg Val Arg Ala Leu Lys Asp His Arg Gly Leu Val Leu Leu
            260                 265                 270

Ile Glu Glu Asp His Phe Leu Ser Pro Asp Phe Leu His Phe Leu Lys
            275                 280                 285

Leu Met Ser Ile Leu Lys Arg Glu Asn Cys Pro Asp Cys Asp Ile Leu
        290                 295                 300

Ser Leu Gly Ser Tyr Gly His Ile Ser Tyr Pro Ser Lys Ala Asn Lys
305                 310                 315                 320

Val Glu Val Lys Ala Trp Lys Ser Thr Glu His Asn Met Gly Met Ala
                325                 330                 335

Leu Ser Arg Glu Thr Tyr Gln Lys Leu Ile Gln Cys Thr Asp Ala Phe
            340                 345                 350

Cys Thr Tyr Asp Asp Tyr Asn Trp Asp Trp Ser Leu Gln His Leu Thr
            355                 360                 365

Val Thr Cys Leu Pro Ser Tyr Trp Lys Val Met Val Ser Glu Ala Pro
        370                 375                 380

Arg Val Phe His Ala Gly Asp Cys Gly Met His His Lys Lys Ser Val
385                 390                 395                 400

Cys Met Pro Ser Ser Gln Lys Ser Lys Ile Asp Thr Ile Leu Gln Ser
                405                 410                 415

Ser Ser Asn Gln Leu Phe Pro Lys Asn Leu Leu Ile Thr Lys Arg Leu
            420                 425                 430

Pro Ala Asn Gly Ala Gly Gly Val Ala Pro His Val Lys Asn Gly Gly
        435                 440                 445

Trp Gly Asp Ile Arg Asp His Glu Leu Cys Lys Ser Tyr Pro Arg Leu
    450                 455                 460

Gln
465

<210> SEQ ID NO 33
<211> LENGTH: 471
<212> TYPE: PRT
<213> ORGANISM: Drosophila melanogaster

<400> SEQUENCE: 33

Met Gly Arg Lys Arg Asn Asn Phe Tyr Met Arg Ser Leu Phe Leu Leu
1               5                   10                  15

Ala Leu Gly Ile Phe Gly Leu Leu Gln Tyr Asn Asn Phe Asn Tyr Leu
                20                  25                  30

Asp Ser Arg Asp Asn Val Leu Gly Asp Ala Val Thr Asn Asp Ser Asp
            35                  40                  45

Asp Ala Ile Leu Ala Met Val Pro Ala Thr Leu His Lys Tyr Leu Thr
        50                  55                  60

Pro His Ser Arg Asn His Ser Ala Ser Gly Ala Gly Ala Leu Asn Gly
65                  70                  75                  80

Ala Ala Leu Leu Leu Asn Ala Ser Ser Pro Gly Ala Thr Ala Ser
                85                  90                  95

Thr Ile Ser Phe Asp Val Tyr His Pro Pro Asn Ile Thr Glu Ile Lys
            100                 105                 110

Arg Gln Ile Val Arg Tyr Asn Asp Met Gln Met Val Leu Asn Glu Asp
        115                 120                 125

Val Phe Gly Pro Leu Gln Asn Asp Ser Val Ile Ile Val Gln Val
    130                 135                 140

His Thr Arg Ile Thr Tyr Leu Arg His Leu Ile Val Ser Leu Ala Gln
145                 150                 155                 160

Ala Arg Asp Ile Ser Lys Val Leu Leu Val Phe Ser His Asp Tyr Tyr
                165                 170                 175

Asp Asp Asp Ile Asn Asp Leu Val Gln Gln Ile Asp Phe Cys Lys Val
                180                 185                 190

Met Gln Ile Phe Tyr Pro Tyr Ser Ile Gln Thr His Pro Asn Glu Tyr
                195                 200                 205

Pro Gly Val Asp Pro Asn Asp Cys Pro Arg Asn Ile Lys Lys Glu Gln
    210                 215                 220

Ala Leu Ile Thr Asn Cys Asn Asn Ala Met Tyr Pro Asp Leu Tyr Gly
225                 230                 235                 240

His Tyr Arg Glu Ala Lys Phe Thr Gln Thr Lys His His Trp Ile Trp
                245                 250                 255

Lys Ala Asn Arg Val Phe Asn Glu Leu Glu Val Thr Arg Tyr His Thr
                260                 265                 270

Gly Leu Val Leu Phe Leu Glu Glu Asp His Tyr Val Ala Glu Asp Phe
            275                 280                 285

Leu Tyr Leu Leu Ala Met Met Gln Gln Arg Thr Lys Asp Leu Cys Pro
290                 295                 300

Gln Cys Asn Val Leu Ser Leu Gly Thr Tyr Leu Lys Thr Phe Asn Tyr
305                 310                 315                 320

Tyr Thr Tyr His Ser Lys Val Glu Val Met Pro Trp Val Ser Ser Lys
                325                 330                 335

His Asn Met Gly Phe Ala Phe Asn Arg Thr Thr Trp Ser Asn Ile Arg
                340                 345                 350

Lys Cys Ala Arg His Phe Cys Thr Tyr Asp Asp Tyr Asn Trp Asp Trp
                355                 360                 365

Ser Leu Gln His Val Ser Gln Gln Cys Leu Arg Arg Lys Leu His Ala
            370                 375                 380

Met Ile Val Lys Gly Pro Arg Val Phe His Ile Gly Glu Cys Gly Val
385                 390                 395                 400

His His Lys Asn Lys Asn Cys Glu Ser Asn Gln Val Ile Ser Lys Val
                405                 410                 415

Gln His Val Leu Arg Ile Ala Arg Asn Ser His Gln Leu Phe Pro Arg
                420                 425                 430

Ser Leu Thr Leu Thr Val Pro Ser Leu Met Lys Lys Ser Lys Leu Arg
            435                 440                 445

Lys Gly Asn Gly Gly Trp Gly Asp Met Arg Asp His Glu Leu Cys Leu
    450                 455                 460

Asn Met Thr Leu Ala Thr Arg
465                 470

<210> SEQ ID NO 34
<211> LENGTH: 54
<212> TYPE: PRT
<213> ORGANISM: Homo sapiens

<400> SEQUENCE: 34

Thr Arg Pro Ala Pro Gly Arg Pro Pro Ser Val Ser Ala Leu Asp Gly
1               5                   10                  15

Asp Pro Ala Ser Leu Thr Arg Glu Val Ile Arg Leu Ala Gln Asp Ala

```
                20                  25                  30
Glu Val Glu Leu Glu Arg Gln Arg Gly Leu Leu Gln Gln Ile Gly Asp
        35                  40                  45
Ala Leu Ser Ser Gln Arg
    50

<210> SEQ ID NO 35
<211> LENGTH: 15
<212> TYPE: PRT
<213> ORGANISM: Artificial Sequence
<220> FEATURE:
<223> OTHER INFORMATION: Synthesized Construct

<400> SEQUENCE: 35

Gly Gly Gly Gly Ser Gly Gly Gly Gly Ser Gly Gly Gly Gly Ser
1               5                  10                  15

<210> SEQ ID NO 36
<211> LENGTH: 10
<212> TYPE: PRT
<213> ORGANISM: Artificial Sequence
<220> FEATURE:
<223> OTHER INFORMATION: Synthesized Construct

<400> SEQUENCE: 36

Gly Gly Gly Gly Ser Gly Gly Gly Gly Ser
1               5                  10

<210> SEQ ID NO 37
<211> LENGTH: 21
<212> TYPE: PRT
<213> ORGANISM: Trichoderma reesei

<400> SEQUENCE: 37

Ser Ser Ala Ala Thr Ala Thr Ala Ser Ala Thr Val Pro Gly Gly Gly
1               5                  10                  15

Ser Gly Pro Thr Ser
            20

<210> SEQ ID NO 38
<211> LENGTH: 19
<212> TYPE: PRT
<213> ORGANISM: Trichoderma reesei

<400> SEQUENCE: 38

Ser Thr Gly Asn Pro Ser Gly Gly Asn Pro Pro Gly Gly Asn Pro Pro
1               5                  10                  15

Gly Ser Thr

<210> SEQ ID NO 39
<211> LENGTH: 10
<212> TYPE: PRT
<213> ORGANISM: Trichoderma reesei

<400> SEQUENCE: 39

Met Ala Ser Thr Asn Ala Arg Tyr Val Arg
1               5                  10

<210> SEQ ID NO 40
<211> LENGTH: 17
<212> TYPE: PRT
<213> ORGANISM: Trichoderma reesei

<400> SEQUENCE: 40
```

```
Tyr Leu Leu Ile Ala Phe Phe Thr Ile Leu Val Phe Tyr Phe Val Ser
 1               5                  10                  15
Asn

<210> SEQ ID NO 41
<211> LENGTH: 379
<212> TYPE: PRT
<213> ORGANISM: Trichoderma reesei

<400> SEQUENCE: 41

Ser Lys Tyr Glu Gly Val Asp Leu Asn Lys Gly Thr Phe Thr Ala Pro
 1               5                  10                  15

Asp Ser Thr Lys Thr Thr Pro Lys Pro Pro Ala Thr Gly Asp Ala Lys
            20                  25                  30

Asp Phe Pro Leu Ala Leu Thr Pro Asn Asp Pro Gly Phe Asn Asp Leu
        35                  40                  45

Val Gly Ile Ala Pro Gly Pro Arg Met Asn Ala Thr Phe Val Thr Leu
    50                  55                  60

Ala Arg Asn Ser Asp Val Trp Asp Ile Ala Arg Ser Ile Arg Gln Val
65                  70                  75                  80

Glu Asp Arg Phe Asn Arg Arg Tyr Asn Tyr Asp Trp Val Phe Leu Asn
                85                  90                  95

Asp Lys Pro Phe Asp Asn Thr Phe Lys Lys Val Thr Thr Ser Leu Val
            100                 105                 110

Ser Gly Lys Thr His Tyr Gly Glu Ile Ala Pro Glu His Trp Ser Phe
        115                 120                 125

Pro Asp Trp Ile Asp Gln Asp Lys Ala Lys Lys Val Arg Glu Asp Met
    130                 135                 140

Ala Glu Arg Lys Ile Ile Tyr Gly Asp Ser Val Ser Tyr Arg His Met
145                 150                 155                 160

Cys Arg Phe Glu Ser Gly Phe Phe Arg Gln Pro Leu Met Met Asn
                165                 170                 175

Tyr Glu Tyr Tyr Trp Arg Val Glu Pro Ser Ile Glu Leu Tyr Cys Asp
            180                 185                 190

Ile His Tyr Asp Pro Phe Arg Leu Met Val Glu Gln Gly Lys Lys Tyr
        195                 200                 205

Ser Phe Val Ile Ser Leu Tyr Glu Tyr Pro Ala Thr Ile Ala Thr Leu
    210                 215                 220

Trp Glu Ser Thr Lys Lys Phe Met Lys Asn His Pro Glu His Ile Ala
225                 230                 235                 240

Pro Asp Asn Ser Met Arg Phe Leu Ser Asp Asp Gly Gly Glu Thr Tyr
                245                 250                 255

Asn Asn Cys His Phe Trp Ser Asn Phe Glu Ile Gly Ser Leu Glu Trp
            260                 265                 270

Leu Arg Ser Lys Gln Tyr Ile Asp Phe Phe Glu Ser Leu Asp Lys Asp
        275                 280                 285

Gly Gly Phe Phe Tyr Glu Arg Trp Gly Asp Ala Pro Val His Ser Ile
    290                 295                 300

Ala Ala Gly Leu Met Leu Asn Arg Ser Glu Ile His Phe Phe Asn Asp
305                 310                 315                 320

Ile Ala Tyr Trp His Val Pro Phe Thr His Cys Pro Thr Gly Glu Lys
                325                 330                 335

Thr Arg Leu Asp Leu Lys Cys His Cys Asp Pro Lys Glu Asn Phe Asp
            340                 345                 350
```

```
Trp Lys Gly Tyr Ser Cys Thr Ser Arg Phe Phe Glu Met Asn Gly Met
        355                 360                 365

Asp Lys Pro Glu Gly Trp Glu Asn Gln Gln Asp
        370                 375

<210> SEQ ID NO 42
<211> LENGTH: 8
<212> TYPE: PRT
<213> ORGANISM: Trichoderma reesei

<400> SEQUENCE: 42

Met Ala Ile Ala Arg Pro Val Arg
  1               5

<210> SEQ ID NO 43
<211> LENGTH: 15
<212> TYPE: PRT
<213> ORGANISM: Trichoderma reesei

<400> SEQUENCE: 43

Ala Leu Gly Gly Leu Ala Ala Ile Leu Trp Cys Phe Phe Leu Tyr
  1               5                  10                  15

<210> SEQ ID NO 44
<211> LENGTH: 371
<212> TYPE: PRT
<213> ORGANISM: Trichoderma reesei

<400> SEQUENCE: 44

Gln Leu Leu Arg Pro Ser Ser Tyr Asn Ser Pro Gly Asp Arg Tyr
  1               5                  10                  15

Ile Asn Phe Glu Arg Asp Pro Asn Leu Asp Pro Thr Gly Glu Pro Glu
             20                  25                  30

Gly Ile Leu Val Arg Thr Ser Asp Arg Tyr Ala Pro Asp Ala Lys Asp
         35                  40                  45

Thr Asp Arg Ala Ser Ala Thr Leu Leu Ala Leu Val Arg Asn Glu Glu
     50                  55                  60

Val Asp Asp Met Val Ala Ser Met Val Asp Leu Glu Arg Thr Trp Asn
 65                  70                  75                  80

Ser Lys Phe Asn Tyr Pro Trp Thr Phe Phe Asn Asp Lys Pro Phe Ser
                 85                  90                  95

Glu Glu Phe Lys Lys Lys Thr Ser Ala Val Thr Asn Ala Thr Cys Asn
            100                 105                 110

Tyr Glu Leu Ile Pro Lys Glu His Trp Asp Ala Pro Ser Trp Ile Asp
        115                 120                 125

Pro Ala Ile Phe Glu Glu Ser Ala Ala Val Leu Lys Lys Asn Gly Val
    130                 135                 140

Gln Tyr Ala Asn Met Met Ser Tyr His Gln Met Cys Arg Trp Asn Ser
145                 150                 155                 160

Gly Met Phe Tyr Lys His Pro Ala Leu Lys Asp Val Arg Tyr Tyr Trp
                165                 170                 175

Arg Val Glu Pro Lys Val His Phe Phe Cys Asp Val Asp Tyr Asp Val
            180                 185                 190

Phe Arg Tyr Met Gln Asp Asn Asn Lys Thr Tyr Gly Phe Thr Ile Asn
        195                 200                 205

Leu Tyr Asp Asp Pro His Thr Leu Pro Thr Leu Trp Pro Gln Thr Ala
    210                 215                 220
```

-continued

```
Lys Phe Leu Ala Asp His Pro Asn Tyr Leu His Glu His Ser Ala Ile
225                 230                 235                 240

Lys Trp Val Ile Asp Asp Ala Arg Arg Pro Gln His Asn Arg Glu Ala
            245                 250                 255

Gln Gly Phe Ser Thr Cys His Phe Trp Ser Asn Phe Glu Val Ala Asp
        260                 265                 270

Met Glu Phe Trp Arg Ser Lys Val Tyr Glu Asp Tyr Phe Glu His Leu
    275                 280                 285

Asp Arg Ala Gly Gly Phe Phe Tyr Glu Arg Trp Gly Asp Ala Pro Val
290                 295                 300

His Ser Ile Ala Leu Gly Leu Phe Glu Asp Ser Ser Lys Ile His Trp
305                 310                 315                 320

Phe Arg Asp Ile Gly Tyr Gln His Ile Pro Phe Phe Asn Cys Pro Asn
            325                 330                 335

Ser Pro Lys Cys Lys Gly Cys Val Thr Gly Arg Leu Thr Asp Gly Glu
        340                 345                 350

Pro Phe Leu His Arg Glu Asp Cys Arg Pro Asn Trp Phe Lys Tyr Ala
    355                 360                 365

Gly Met Gly
    370

<210> SEQ ID NO 45
<211> LENGTH: 6
<212> TYPE: PRT
<213> ORGANISM: Trichoderma reesei

<400> SEQUENCE: 45

Met Leu Asn Pro Arg Arg
1               5

<210> SEQ ID NO 46
<211> LENGTH: 15
<212> TYPE: PRT
<213> ORGANISM: Trichoderma reesei

<400> SEQUENCE: 46

Ala Leu Ile Ala Ala Ala Phe Ile Leu Thr Val Phe Phe Leu Ile
1               5                   10                  15

<210> SEQ ID NO 47
<211> LENGTH: 352
<212> TYPE: PRT
<213> ORGANISM: Trichoderma reesei

<400> SEQUENCE: 47

Ser Arg Ser His Asn Ser Glu Ser Ala Ser Thr Ser Glu Pro Lys Asp
1               5                   10                  15

Ala Glu Ala Glu Ala Leu Ser Ala Ala Asn Ala Gln Gln Arg Ala Ala
            20                  25                  30

Pro Pro Pro Pro Pro Gln Lys Pro Met Ile Asp Met Ser Gly Met Ser
        35                  40                  45

Thr Tyr Asp Lys Leu Ala Tyr Ala Tyr Glu Tyr Asp Ile Glu Ser Lys
    50                  55                  60

Phe Pro Ala Tyr Ile Trp Gln Thr Trp Arg Lys Thr Pro Ser Glu Gly
65                  70                  75                  80

Asp Phe Glu Phe Arg Glu Gln Glu Ala Ser Trp Ser Ile Glu His Pro
                85                  90                  95

Gly Phe Ile His Glu Val Ile Thr Asp Ser Val Ala Asp Thr Leu Leu
```

```
                100                 105                 110
Gln Leu Leu Tyr Gly Ser Ile Pro Glu Val Leu Glu Ala Tyr His Ala
            115                 120                 125

Leu Pro Leu Pro Val Leu Lys Ala Asp Leu Phe Arg Tyr Leu Ile Leu
        130                 135                 140

Tyr Ala Arg Gly Gly Ile Tyr Ser Asp Ile Asp Thr Tyr Ala Ile Arg
145                 150                 155                 160

Ser Ala Leu Glu Trp Ile Pro Pro Gln Ile Pro Lys Glu Thr Val Gly
            165                 170                 175

Leu Val Ile Gly Ile Glu Ala Asp Pro Asp Arg Pro Asp Trp Ala Asp
        180                 185                 190

Trp Tyr Ser Arg Arg Ile Gln Phe Cys Gln Trp Thr Ile Gln Ser Lys
            195                 200                 205

Pro Gly His Pro Val Leu Arg Asp Ile Ile Ser Arg Ile Thr Asn Gln
        210                 215                 220

Thr Leu Glu Met Lys Lys Ser Gly Lys Leu Ser Ala Phe Gln Gly Asn
225                 230                 235                 240

Arg Val Val Asp Leu Thr Gly Pro Ala Val Trp Thr Asp Thr Ile Met
            245                 250                 255

Asp Tyr Phe Asn Asp Glu Arg Tyr Phe Asp Met Glu Asn Ser Lys Gly
        260                 265                 270

Arg Ile Asp Tyr Arg Asn Phe Thr Gly Met Glu Thr Ser Lys Arg Val
        275                 280                 285

Gly Asp Val Val Val Leu Pro Ile Thr Ser Phe Ser Pro Gly Val Gly
290                 295                 300

Gln Met Gly Ala Lys Asp Tyr Asp Asp Pro Met Ala Phe Val Lys His
305                 310                 315                 320

Asp Phe Glu Gly Thr Trp Lys Pro Glu Ser Glu Arg His Ile Gly Glu
            325                 330                 335

Ile Val Gln Glu Leu Gly Glu Gly Gln Gly Glu Ala Pro Lys Glu Gln
            340                 345                 350

<210> SEQ ID NO 48
<211> LENGTH: 22
<212> TYPE: PRT
<213> ORGANISM: Trichoderma reesei

<400> SEQUENCE: 48

Met Gly Met Gly Gln Cys Gln Trp Ser Pro Phe Arg Asn Lys Val Pro
1               5                   10                  15

Thr Gln Met Arg Arg Cys
            20

<210> SEQ ID NO 49
<211> LENGTH: 15
<212> TYPE: PRT
<213> ORGANISM: Trichoderma reesei

<400> SEQUENCE: 49

Leu Pro Leu Tyr Ile Thr Val Val Cys Val Phe Leu Val Ile Val
1               5                   10                  15

<210> SEQ ID NO 50
<211> LENGTH: 362
<212> TYPE: PRT
<213> ORGANISM: Trichoderma reesei

<400> SEQUENCE: 50
```

```
Asn Phe Asp Trp Ile Leu Ala Ile Pro Asn Pro Ala Ser Val Leu Arg
 1               5                  10                  15

Arg Glu Pro Lys Ala Pro Pro Leu Pro Gly Ser Thr Phe Pro Gln Lys
             20                  25                  30

Ile Trp Gln Thr Trp Lys Val Asp Pro Leu Asn Phe Asp Glu Arg Asp
         35                  40                  45

Leu Val Thr Ala Arg Thr Trp Thr Thr Ile Asn Pro Gly Met Arg Tyr
     50                  55                  60

Glu Val Val Thr Asp Ala Asn Glu Met Ala Tyr Ile Glu Asp Arg Tyr
 65                  70                  75                  80

Gly Pro Asn Gly Phe Asp Arg Pro Asp Ile Val Glu Phe Tyr Lys Met
                 85                  90                  95

Ile Asn Leu Pro Ile Ile Lys Ala Asp Leu Leu Arg Tyr Met Ile Met
             100                 105                 110

Tyr Ala Glu Gly Gly Ile Tyr Ala Asp Ile Asp Val Glu Thr Met Lys
         115                 120                 125

Pro Phe His Arg Phe Ile Pro Asp Arg Tyr Asp Glu Lys Asp Ile Asp
     130                 135                 140

Ile Ile Ile Gly Val Glu Ile Asp Gln Pro Asp Phe Lys Asp His Pro
145                 150                 155                 160

Ile Leu Gly Lys Lys Ser Met Ser Phe Cys Gln Trp Thr Phe Val Ala
             165                 170                 175

Arg Pro Gln Gln Pro Val Met Met Arg Leu Ile Glu Asn Ile Met Lys
         180                 185                 190

Trp Phe Lys Thr Val Ala Arg Asp Gln Gly Val Pro Leu Gly Glu Val
     195                 200                 205

Gln Leu Asp Phe Asp Gln Val Ile Ser Gly Thr Gly Pro Ser Ala Phe
 210                 215                 220

Thr Lys Ala Met Leu Glu Glu Met Asn Arg Lys Thr Lys Gly Pro Lys
225                 230                 235                 240

Val Thr Trp Asp Ala Phe His Asn Leu Asp Glu Ser Lys Leu Val Gly
             245                 250                 255

Gly Val Leu Val Leu Thr Val Glu Ala Phe Cys Ala Gly Gln Gly His
         260                 265                 270

Ser Asp Ser Gly Asn His Asn Ala Arg Asn Ala Leu Val Lys His His
     275                 280                 285

Phe His Ala Ser Asn Trp Pro Ser Arg His Pro Arg Tyr Lys His Pro
 290                 295                 300

Ala Tyr Gly Gln Val Glu Asp Cys Asn Trp Val Pro Glu Cys Val Arg
305                 310                 315                 320

Lys Trp Asp Glu Asp Thr Ser Asn Trp Asp Lys Tyr Ser Glu Asn Glu
             325                 330                 335

Gln Lys Lys Ile Leu Gln Asp Ile Glu Asn Ala Arg Leu Glu Arg Glu
         340                 345                 350

Arg Gln Gln Gln Ala Leu Ala Ala Leu Pro
     355                 360

<210> SEQ ID NO 51
<211> LENGTH: 17
<212> TYPE: PRT
<213> ORGANISM: Trichoderma reesei

<400> SEQUENCE: 51

Met Ala Arg Pro Met Gly Ser Val Arg Leu Lys Lys Ala Asn Pro Ser
```

-continued

```
                1               5                  10                 15
Thr

<210> SEQ ID NO 52
<211> LENGTH: 16
<212> TYPE: PRT
<213> ORGANISM: Trichoderma reesei

<400> SEQUENCE: 52

Leu Ile Leu Gly Ala Val Leu Cys Ile Phe Ile Ile Phe Leu Val
 1               5                  10                 15

<210> SEQ ID NO 53
<211> LENGTH: 339
<212> TYPE: PRT
<213> ORGANISM: Trichoderma reesei

<400> SEQUENCE: 53

Ser Pro Ser Ser Pro Ala Ser Ala Ser Arg Leu Ser Ile Val Ser Ala
 1               5                  10                 15

Gln His His Leu Ser Pro Pro Thr Ser Pro Tyr Gln Ser Pro Arg Ser
                20                  25                  30

Gly Ala Val Gln Gly Pro Pro Val Thr Arg Tyr Asn Leu Asn Lys
            35                  40                  45

Val Thr Val Thr Ser Asp Pro Val Arg Asn Gln Glu His Ile Leu Ile
 50                  55                  60

Leu Thr Pro Met Ala Arg Phe Tyr Gln Glu Tyr Trp Asp Asn Leu Leu
 65                  70                  75                  80

Arg Leu Asn Tyr Pro His Glu Leu Ile Thr Leu Gly Phe Ile Leu Pro
                85                  90                  95

Lys Thr Lys Glu Gly Asn Gln Ala Thr Ser Met Leu Gln Lys Gln Ile
            100                 105                 110

Gln Lys Thr Gln Asn Tyr Gly Pro Glu Lys Asp Arg Phe Lys Ser Ile
        115                 120                 125

Ile Ile Leu Arg Gln Asp Phe Asp Pro Ala Val Val Ser Gln Asp Glu
    130                 135                 140

Ser Glu Arg His Lys Leu Ala Asn Gln Lys Ala Arg Arg Glu Val Met
145                 150                 155                 160

Ala Lys Ala Arg Asn Ser Leu Leu Phe Thr Thr Leu Gly Pro Ser Thr
                165                 170                 175

Ser Trp Val Leu Trp Leu Asp Ala Asp Ile Thr Glu Thr Ala Pro Thr
            180                 185                 190

Leu Ile Gln Asp Leu Ala Ser His Asp Lys Pro Ile Ile Val Ala Asn
        195                 200                 205

Cys Phe Gln Lys Tyr Tyr Asp Pro Glu Ser Lys Lys Met Ala Glu Arg
    210                 215                 220

Pro Tyr Asp Phe Asn Ser Trp Gln Asp Ser Glu Thr Ala Leu Lys Met
225                 230                 235                 240

Ala Glu Gln Met Gly Pro Asp Ile Leu Leu Glu Gly Tyr Ala Glu
                245                 250                 255

Met Ala Thr Tyr Arg Thr Leu Leu Ala Tyr Met Ser Thr Pro Gly Gly
            260                 265                 270

Ser Lys Asp Leu Val Val Pro Leu Asp Gly Val Gly Thr Ala Leu
        275                 280                 285

Leu Val Lys Ala Asp Val His Arg Asp Gly Ala Met Phe Pro Pro Phe
    290                 295                 300
```

```
Ala Phe Tyr His Leu Ile Glu Ser Glu Gly Phe Ala Lys Met Ala Lys
305                 310                 315                 320

Arg Leu Gly Trp Gln Pro Tyr Gly Leu Pro Asn Tyr Lys Val Tyr His
                325                 330                 335

Tyr Asn Glu

<210> SEQ ID NO 54
<211> LENGTH: 31
<212> TYPE: PRT
<213> ORGANISM: Trichoderma reesei

<400> SEQUENCE: 54

Met Leu Leu Pro Lys Gly Gly Leu Asp Trp Arg Ser Ala Arg Ala Gln
1               5                   10                  15

Ile Pro Pro Thr Arg Ala Leu Trp Asn Ala Val Thr Arg Thr Arg
            20                  25                  30

<210> SEQ ID NO 55
<211> LENGTH: 15
<212> TYPE: PRT
<213> ORGANISM: Trichoderma reesei

<400> SEQUENCE: 55

Phe Ile Leu Leu Val Gly Ile Thr Gly Leu Ile Leu Leu Leu Trp
1               5                   10                  15

<210> SEQ ID NO 56
<211> LENGTH: 358
<212> TYPE: PRT
<213> ORGANISM: Trichoderma reesei

<400> SEQUENCE: 56

Arg Gly Val Ser Thr Ser Ala Ser Glu Met Gln Ser Phe Tyr Cys Trp
1               5                   10                  15

Gly Pro Ala Lys Pro Pro Met Glu Met Ser Pro Asn Glu His Asn Arg
                20                  25                  30

Trp Asn Gly His Leu Gln Thr Pro Val Ile Phe Asn His His Ala Pro
            35                  40                  45

Val Glu Val Asn Ser Ser Thr Ile Glu His Val Asp Leu Asn Pro Ile
50                  55                  60

Asn Ser Thr Lys Gln Ala Val Thr Lys Glu Glu Arg Ile Leu Ile Leu
65                  70                  75                  80

Thr Pro Leu Lys Asp Ala Ala Pro Tyr Leu Ser Lys Tyr Phe Glu Leu
                85                  90                  95

Leu Ala Glu Leu Thr Tyr Pro His Arg Leu Ile Asp Leu Ala Phe Leu
            100                 105                 110

Val Ser Asp Ser Thr Asp Thr Leu Ala Val Leu Ala Ser Glu Leu
        115                 120                 125

Asp Arg Ile Gln Lys Arg Pro Asp Gln Ile Pro Phe His Ser Ala Thr
130                 135                 140

Val Ile Glu Lys Asp Phe Gly Phe Lys Leu Ser Gln Asn Val Glu Glu
145                 150                 155                 160

Arg His Ser Phe Glu Ala Gln Gly Pro Arg Arg Lys Ala Met Gly Arg
                165                 170                 175

Ala Arg Asn Tyr Leu Leu Tyr Thr Ala Leu Lys Pro Glu His Ser Trp
            180                 185                 190

Val Tyr Trp Arg Asp Val Asp Ile Val Asp Ser Pro Thr Gly Ile Leu
```

```
            195                 200                 205
Glu Asp Phe Ile Ala His Asp Arg Asp Ile Leu Val Pro Asn Ile Trp
210                 215                 220

Phe His Arg Tyr Arg Asp Gly Val Asp Ile Glu Gly Arg Phe Asp Tyr
225                 230                 235                 240

Asn Ser Trp Val Glu Ser Asp Lys Gly Arg Lys Leu Ala Asn Ser Leu
                245                 250                 255

Asp Lys Asp Val Val Leu Ala Glu Gly Tyr Lys Gln Tyr Asp Thr Gly
            260                 265                 270

Arg Thr Tyr Met Ala Lys Met Gly Asp Trp Arg Glu Asn Lys Asp Val
        275                 280                 285

Glu Leu Glu Leu Asp Gly Ile Gly Gly Val Asn Ile Leu Val Lys Ala
290                 295                 300

Asp Val His Arg Ser Gly Ile Asn Phe Pro Cys Tyr Ala Phe Glu Asn
305                 310                 315                 320

Gln Ala Glu Thr Glu Gly Phe Ala Lys Met Ala Lys Arg Ala Gly Tyr
                325                 330                 335

Glu Val Tyr Gly Leu Pro Asn Tyr Val Val Trp His Ile Asp Thr Glu
            340                 345                 350

Glu Lys Gly Gly Asn Ala
        355
```

```
<210> SEQ ID NO 57
<211> LENGTH: 45
<212> TYPE: PRT
<213> ORGANISM: Trichoderma reesei

<400> SEQUENCE: 57
```

```
Met Met Pro Arg His His Ser Ser Gly Phe Ser Asn Gly Tyr Pro Arg
1               5                   10                  15

Ala Asp Thr Phe Glu Ile Ser Pro His Arg Phe Gln Pro Arg Ala Thr
            20                  25                  30

Leu Pro Pro His Arg Lys Arg Lys Arg Thr Ala Ile Arg
        35                  40                  45
```

```
<210> SEQ ID NO 58
<211> LENGTH: 16
<212> TYPE: PRT
<213> ORGANISM: Trichoderma reesei

<400> SEQUENCE: 58
```

```
Val Gly Ile Ala Val Val Ile Leu Val Leu Val Leu Trp Phe Gly
1               5                   10                  15
```

```
<210> SEQ ID NO 59
<211> LENGTH: 407
<212> TYPE: PRT
<213> ORGANISM: Trichoderma reesei

<400> SEQUENCE: 59
```

```
Gln Pro Arg Ser Val Ala Ser Leu Ile Ser Leu Gly Ile Leu Ser Gly
1               5                   10                  15

Tyr Asp Asp Leu Lys Leu Glu Thr Val Arg Tyr Tyr Asp Leu Ser Asn
            20                  25                  30

Val Gln Gly Thr Ala Arg Gly Trp Glu Arg Glu Glu Arg Ile Leu Leu
        35                  40                  45

Cys Val Pro Leu Arg Asp Ala Glu Gln His Leu Pro Met Phe Phe Ser
    50                  55                  60
```

His Leu Lys Asn Phe Thr Tyr Pro His Asn Leu Ile Asp Leu Ala Phe
 65                  70                  75                  80

Leu Val Ser Asp Ser Lys Asp His Thr Leu Glu Ser Leu Thr Glu His
                 85                  90                  95

Leu Glu Ala Ile Gln Ala Asp Pro Asp Pro Lys Gln Pro Tyr Gly Glu
            100                 105                 110

Ile Ser Ile Ile Glu Lys Asp Phe Gly Gln Lys Val Asn Gln Asp Val
        115                 120                 125

Glu Ser Arg His Gly Phe Ala Ala Gln Ala Ser Arg Arg Lys Leu Met
    130                 135                 140

Ala Gln Ala Arg Asn Trp Leu Leu Ser Ala Leu Arg Pro Tyr His
145                 150                 155                 160

Ser Trp Val Tyr Trp Arg Asp Val Asp Val Glu Thr Ala Pro Phe Thr
                165                 170                 175

Ile Leu Glu Asp Leu Met Arg His Asn Lys Asp Val Ile Val Pro Asn
            180                 185                 190

Val Trp Arg Pro Leu Pro Asp Trp Leu Gly Gly Glu Gln Pro Tyr Asp
        195                 200                 205

Leu Asn Ser Trp Gln Glu Ser Glu Thr Ala Leu Ala Leu Ala Asp Thr
    210                 215                 220

Leu Asp Glu Asp Ala Val Ile Val Gly Tyr Ala Glu Tyr Ala Thr
225                 230                 235                 240

Trp Arg Pro His Leu Ala Tyr Leu Arg Asp Pro Tyr Gly Asp Pro Asp
                245                 250                 255

Met Glu Met Glu Ile Asp Gly Val Gly Val Ser Ile Leu Ala Lys
            260                 265                 270

Ala Lys Val Phe Arg Ala Gly Val His Phe Pro Ala Phe Ser Phe Glu
        275                 280                 285

Lys His Ala Glu Thr Glu Gly Phe Gly Lys Met Ala Lys Arg Met His
    290                 295                 300

Phe Ser Val Val Gly Leu Pro His Tyr Thr Ile Trp His Leu Tyr Glu
305                 310                 315                 320

Pro Ser Val Asp Asp Ile Lys His Met Glu Glu Met Glu Arg Glu Arg
                325                 330                 335

Ile Ala Arg Glu Lys Glu Glu Glu Arg Lys Lys Lys Glu Ala Gln
            340                 345                 350

Ile Lys Glu Glu Phe Gly Asp Ala Asn Ser Gln Trp Glu Gln Asp Lys
        355                 360                 365

Gln Gln Met Gln Asp Leu Lys Leu Gln Asp Arg Gly Gly Asp Lys Glu
    370                 375                 380

Ala Ala Ala Ala Gly Val Asn Gln Gly Ala Ala Lys Ala Ala Gly
385                 390                 395                 400

Ala Met Glu Gly Gln Lys Asn
                405

<210> SEQ ID NO 60
<211> LENGTH: 119
<212> TYPE: PRT
<213> ORGANISM: Trichoderma reesei

<400> SEQUENCE: 60

Met Ser Leu Ser Arg Ser Pro Ser Pro Val Pro Gly Gly Gly Trp Ser
  1               5                  10                  15

Ser Pro Gly Leu Asn Ile Asn Ser Gly Arg Ser Ser Pro Ser Asn Ala

```
                   20                  25                  30
Ala Gly Ser Ser Val Ser Trp Glu Ser Ala Lys Met Arg Lys Gln Gly
            35                  40                  45

Ala Asn Gly Tyr Pro Ser Phe Ser Thr Gln Asn Gln Gly Phe Phe Thr
        50                  55                  60

Arg His Met Arg Arg Ile Ser Ser Ser Leu Pro Arg Phe Ala Ala Gly
65                  70                  75                  80

Pro Gly Asn Thr Tyr Ala Glu Arg Glu Lys Tyr Glu Arg Gly Gly His
                85                  90                  95

Ser Pro His Ala Gly Gly Gly Arg Leu Arg Ala Phe Leu Ala Arg Ile
            100                 105                 110

Gly Arg Arg Leu Lys Trp Arg
            115

<210> SEQ ID NO 61
<211> LENGTH: 15
<212> TYPE: PRT
<213> ORGANISM: Trichoderma reesei

<400> SEQUENCE: 61

Ile Leu Leu Pro Leu Ile Ile Ile Cys Thr Ile Val Ala Tyr Tyr
1               5                   10                  15

<210> SEQ ID NO 62
<211> LENGTH: 325
<212> TYPE: PRT
<213> ORGANISM: Trichoderma reesei

<400> SEQUENCE: 62

Gly Thr His Glu Ala Pro Gly Phe Val His Trp Arg Arg Ile Ser
1               5                   10                  15

Met Gly Gly Gly Gly Glu Lys Phe Val Ile Ile Leu Gly Ala Asn Val
                20                  25                  30

Gly Gly Gly Val Met Glu Trp Lys Gly Ala Arg Glu Trp Ala Ile Glu
            35                  40                  45

Arg Asp Ser Val Arg Asn Lys Arg Lys Tyr Ala Thr Arg Trp Gly Tyr
50                  55                  60

Asp Leu Glu Ile Val Asp Met Lys Thr Lys Lys Arg Tyr Ala His Glu
65                  70                  75                  80

Trp Arg Glu Ser Trp Glu Lys Val Asp Phe Ile Arg Ala Ala Met Arg
                85                  90                  95

Lys Tyr Pro Lys Ala Glu Trp Phe Trp Trp Leu Asp Leu Asn Thr Tyr
            100                 105                 110

Val Met Glu Pro Ser Tyr Ser Leu Gln Arg His Leu Phe Asn His Leu
        115                 120                 125

Asp Arg His Val Tyr Arg Asp Ile Asn Val Phe Asn Pro Leu Asn Ile
    130                 135                 140

Thr His Pro Pro Thr Glu Glu Tyr Leu Asp Ala Glu Ala Arg Ser Pro
145                 150                 155                 160

Val Gly Asp Gly Asn Ile Asn Ser Val Asn Leu Met Leu Thr Gln Asp
                165                 170                 175

Cys Ser Gly Phe Asn Leu Gly Ser Phe Phe Ile Arg Arg Ser Ala Trp
            180                 185                 190

Thr Glu Gln Leu Leu Asp Ile Trp Trp Asp Pro Val Leu Tyr Glu Gln
        195                 200                 205

Lys His Met Glu Trp Glu His Lys Glu Gln Asp Ala Leu Glu Gln Leu
```

-continued

```
                210                 215                 220
Tyr Arg Thr Gln Pro Trp Ile Arg Gln His Thr Gly Phe Leu Pro Gln
225                 230                 235                 240

Arg Leu Ile Asn Ser Phe Pro Pro Ala Ala Cys Ala Asp Glu Ser Gly
                245                 250                 255

Leu Asn Asn Thr Arg Ile His Tyr Asn Glu Lys Asp Arg Asp Phe Val
                260                 265                 270

Val Asn Met Ala Gly Cys Glu Trp Gly Arg Asp Cys Trp Gly Glu Met
                275                 280                 285

Tyr His Tyr Arg Glu Phe Ser Tyr Trp Leu Asn Arg Asn Pro Trp Glu
                290                 295                 300

Leu Phe Lys Glu Glu Ile Val Ala Val Ile Trp Tyr Lys Leu Thr Gly
305                 310                 315                 320

Gln Arg Val Lys Leu
                325

<210> SEQ ID NO 63
<211> LENGTH: 33
<212> TYPE: PRT
<213> ORGANISM: Trichoderma reesei

<400> SEQUENCE: 63

Met His Phe Ala Tyr Pro Ser Arg Lys Ser Ser Asn Pro Pro Pro Phe
1               5                   10                  15

Arg Pro Arg Ser Thr Arg Leu Pro Gly Leu Arg Arg Ser Arg Ile Lys
                20                  25                  30

Thr

<210> SEQ ID NO 64
<211> LENGTH: 15
<212> TYPE: PRT
<213> ORGANISM: Trichoderma reesei

<400> SEQUENCE: 64

Ile Gly Ile Val Leu Phe Leu Val Leu Ala Thr Leu Trp Phe Phe
1               5                   10                  15

<210> SEQ ID NO 65
<211> LENGTH: 262
<212> TYPE: PRT
<213> ORGANISM: Trichoderma reesei

<400> SEQUENCE: 65

Ser Asn Pro Arg Val Pro Arg Pro Asp Pro Glu Arg Val Pro Ser Gly
1               5                   10                  15

Arg Pro Pro Val Val Leu Val Thr Val Ile Asp Pro Thr Gln Tyr Pro
                20                  25                  30

Asn Ala Tyr Leu Lys Thr Ile Lys Glu Asn Arg Glu Gln Tyr Ala Ala
                35                  40                  45

Lys His Gly Tyr Glu Ala Phe Ile Val Lys Ala Tyr Asp Tyr Asp Thr
                50                  55                  60

Gln Gly Ala Pro Gln Ser Trp Ser Lys Leu Met Ala Met Arg His Ala
65                  70                  75                  80

Leu Thr Lys Phe Pro Glu Cys Arg Phe Val Trp Tyr Leu Asp Gln Asp
                85                  90                  95

Ala Tyr Ile Met Asp Met Ser Lys Ser Leu Glu Glu Gln Leu Leu Asn
                100                 105                 110
```

```
Arg Gln Lys Leu Glu Ser Leu Met Ile Lys Asn Tyr Pro Val Val Pro
            115                 120                 125

Pro Asp Ser Ile Ile Lys Thr Phe Ser His Leu Arg Pro Asp Glu Val
        130                 135                 140

Asp Leu Ile Val Ser Gln Asp Ser Ser Gly Leu Val Ala Gly Ser Val
145                 150                 155                 160

Val Val Arg Asn Ser Gln Trp Ser Lys Phe Leu Leu Glu Thr Trp Met
                165                 170                 175

Asp Pro Leu Tyr Arg Ser Tyr Asn Phe Gln Lys Ala Glu Arg His Ala
            180                 185                 190

Leu Glu His Ile Val Gln Trp His Pro Thr Ile Leu Ser Lys Leu Ala
        195                 200                 205

Leu Val Pro Gln Arg Thr Leu Gly Pro Tyr Thr Arg Thr Asp Gln Gly
        210                 215                 220

Asp Ala Tyr Gln Asp Gly Asp Phe Val Val Met Phe Thr Gly Cys Thr
225                 230                 235                 240

Lys Ser Gly Glu Gln Ser Cys Glu Thr Val Ser Ala Ser Tyr Tyr Gln
                245                 250                 255

Lys Trp Ser Ser Ser Leu
                260

<210> SEQ ID NO 66
<211> LENGTH: 90
<212> TYPE: PRT
<213> ORGANISM: Trichoderma reesei

<400> SEQUENCE: 66

Met Ile Arg Asp Pro Phe Gly Ile His Ser Lys Asn Ala Phe Lys Ala
1               5                   10                  15

Thr Ala Leu Arg Ala Ala Arg Asp Ile Lys Glu Ala Ala Thr Gln Ala
            20                  25                  30

Gly Ala Asn Ala Leu Glu Met Ser Phe Ser Leu Pro Lys His Val Pro
        35                  40                  45

Asp Phe Gly Asp Pro Ser Arg Ala Leu Glu Asp Arg Ala Trp Ala Ala
    50                  55                  60

Leu Leu Pro Met Tyr Lys Asp Lys Pro Tyr Ala Tyr Ala Pro Ser Met
65                  70                  75                  80

Arg Leu Arg Pro Trp Trp Arg Arg Lys
                85                  90

<210> SEQ ID NO 67
<211> LENGTH: 19
<212> TYPE: PRT
<213> ORGANISM: Trichoderma reesei

<400> SEQUENCE: 67

Val Leu Gly Met Ile Ala Ala Ala Val Met Phe Val Leu Tyr Val Thr
1               5                   10                  15

Gly Phe Phe

<210> SEQ ID NO 68
<211> LENGTH: 565
<212> TYPE: PRT
<213> ORGANISM: Trichoderma reesei

<400> SEQUENCE: 68

Ser Ser Gly Gln Thr Glu Glu Ala Lys Lys Lys Ala Ser Gly Ser Ala
1               5                   10                  15
```

```
Phe Ser Trp Leu Gly Leu Ser Gln Glu Arg Gly Gly Val Asp Trp Asp
            20                  25                  30

Glu Arg Arg Lys Ser Val Val Glu Ala Phe Glu Val Trp Asp Ala Tyr
        35                  40                  45

Glu Arg Tyr Ala Trp Gly Lys Asp Glu Phe His Pro Ile Ser Lys Asn
    50                  55                  60

Gly Arg Asn Met Ala Pro Lys Gly Leu Gly Trp Ile Ile Ile Asp Ser
65                  70                  75                  80

Leu Asp Thr Met Met Leu Met Asn Gln Thr Thr Arg Leu Gln His Ala
                85                  90                  95

Arg Glu Trp Ile Ser Thr Ser Leu Thr Trp Asp Gln Asp Gln Asp Val
            100                 105                 110

Asn Thr Phe Glu Thr Thr Ile Arg Met Leu Gly Gly Leu Leu Ser Ala
        115                 120                 125

His Tyr Leu Ser Thr Glu Phe Pro Glu Leu Ala Pro Leu Thr Glu Asp
    130                 135                 140

Asp Glu Gly Ala Pro Gly Glu Asp Leu Tyr Leu Glu Lys Ala Lys Asp
145                 150                 155                 160

Leu Ala Asp Arg Leu Leu Ser Ala Phe Glu Ser Glu Ser Gly Ile Pro
                165                 170                 175

Tyr Ala Ser Val Asn Ile Gly Glu Tyr Lys Gly Pro Ser His Ser Asp
            180                 185                 190

Asn Gly Ala Ser Ser Thr Ala Glu Ala Thr Thr Leu Gln Leu Glu Phe
        195                 200                 205

Lys Tyr Leu Ala Lys Leu Thr Gly Glu Lys Asn Phe Trp Asp Lys Val
    210                 215                 220

Glu Lys Val Met Glu Val Val Asp Asp Asn Gln Pro Glu Asp Gly Leu
225                 230                 235                 240

Val Pro Ile Tyr Ile Tyr Ala Thr Thr Gly Glu Phe Arg Gly Gln Asn
                245                 250                 255

Ile Arg Leu Gly Ser Arg Gly Asp Ser Tyr Tyr Glu Tyr Leu Ile Lys
            260                 265                 270

Gln Tyr Leu Gln Thr Asn Lys Gln Glu Pro Ile Tyr Glu Glu Met Trp
        275                 280                 285

Asp Glu Ala Leu Ala Gly Val Arg Lys His Leu Val Thr Tyr Thr Glu
    290                 295                 300

Pro Ser Glu Phe Thr Ile Ile Ala Glu Arg Pro Asp Gly Leu Glu His
305                 310                 315                 320

Pro Met Ser Pro Lys Met Asp His Leu Val Cys Phe Met Pro Gly Thr
                325                 330                 335

Ile Ala Leu Ala Ala Thr Gly Gly Leu Thr Glu Ala Gly Ala Arg Lys
            340                 345                 350

Leu Ser Thr Trp Asn Lys Lys Asp Asp Met Gln Leu Ala Arg
        355                 360                 365

Glu Leu Met His Thr Cys Trp Gly Met Tyr Lys Tyr Met Lys Thr Gly
    370                 375                 380

Leu Ala Pro Glu Ile Met Tyr Phe Asn Ile Pro Asn Pro Pro Glu
385                 390                 395                 400

Ser Ser Ala Pro His Gln Ala Pro Ala Phe Asp Glu Pro His
                405                 410                 415

Ala Glu Trp Arg Lys Asp Phe Val Val His Ser Asn Asp Val His Asn
            420                 425                 430
```

```
Leu Gln Arg Pro Glu Thr Val Glu Ser Leu Phe Tyr Met Trp Arg Ile
            435                 440                 445

Thr Gly Asp Val Lys Tyr Arg Glu Trp Gly Trp Asp Met Phe Lys Ser
        450                 455                 460

Phe Val Asn Tyr Thr Ala Val Glu Asp Gln Gly Gly Phe Thr Ser Leu
465                 470                 475                 480

Leu Asp Ala Asn Ser Ile Pro Pro Thr Pro Lys Asp Asn Met Glu Ser
                485                 490                 495

Phe Trp Leu Ala Glu Thr Leu Lys Tyr Met Tyr Leu Leu Phe Ser Pro
            500                 505                 510

Asn Asp Val Leu Pro Leu His Lys Ile Val Leu Asn Thr Glu Ala His
            515                 520                 525

Pro Phe Pro Arg Phe Asp Met Gly Pro Leu Phe Ser Thr Gly Trp Lys
        530                 535                 540

Arg Lys Pro Arg Asp Gly Ser Ala Lys Lys Lys Ala Thr Thr Ala Ala
545                 550                 555                 560

Thr Thr Asp Ala Glu
                565

<210> SEQ ID NO 69
<211> LENGTH: 7
<212> TYPE: PRT
<213> ORGANISM: Trichoderma reesei

<400> SEQUENCE: 69

Met Ala Arg Arg Arg Tyr Arg
1               5

<210> SEQ ID NO 70
<211> LENGTH: 15
<212> TYPE: PRT
<213> ORGANISM: Trichoderma reesei

<400> SEQUENCE: 70

Leu Phe Met Ile Cys Ala Ala Val Ile Leu Phe Leu Leu Tyr Arg
1               5                   10                  15

<210> SEQ ID NO 71
<211> LENGTH: 871
<212> TYPE: PRT
<213> ORGANISM: Trichoderma reesei

<400> SEQUENCE: 71

Val Ser Gln Asn Thr Trp Asp Asp Ser Ala His Tyr Ala Thr Leu Arg
1               5                   10                  15

His Pro Pro Ala Ser Asn Pro Ala Ala Gly Gly Glu Ser Pro Leu
            20                  25                  30

Lys Pro Ala Ala Lys Pro Glu His Glu His Glu Asn Gly Tyr
        35                  40                  45

Ala Pro Glu Ser Lys Pro Lys Pro Gln Ser Glu Pro Lys Pro Glu Ser
    50                  55                  60

Lys Pro Ala Pro Glu His Ala Ala Gly Gly Gln Lys Ser Gln Gly Lys
65                  70                  75                  80

Pro Ser Tyr Glu Asp Asp Glu Thr Gly Lys Asn Pro Pro Lys Ser
            85                  90                  95

Ala Val Ile Pro Ser Asp Thr Arg Leu Pro Pro Asp Asn Lys Val His
                100                 105                 110

Trp Arg Pro Val Lys Glu His Phe Pro Val Pro Ser Glu Ser Val Ile
```

-continued

```
            115                 120                 125
Ser Leu Pro Thr Gly Lys Pro Leu Lys Val Pro Arg Val Gln His Glu
    130                 135                 140

Phe Gly Val Glu Ser Pro Glu Ala Lys Ser Arg Arg Val Ala Arg Gln
145                 150                 155                 160

Glu Arg Val Gly Lys Glu Ile Glu Arg Ala Trp Ser Gly Tyr Lys Lys
                165                 170                 175

Phe Ala Trp Met His Asp Glu Leu Ser Pro Val Ser Ala Lys His Arg
                180                 185                 190

Asp Pro Phe Cys Gly Trp Ala Ala Thr Leu Val Asp Ser Leu Asp Thr
            195                 200                 205

Leu Trp Ile Ala Gly Leu Lys Glu Gln Phe Asp Glu Ala Ala Arg Ala
    210                 215                 220

Val Glu Gln Ile Asp Phe Thr Thr Thr Pro Arg Asn Asn Ile Pro Val
225                 230                 235                 240

Phe Glu Thr Thr Ile Arg Tyr Leu Gly Gly Leu Leu Gly Ala Phe Asp
                245                 250                 255

Val Ser Gly Gly His Asp Gly Gly Tyr Pro Met Leu Leu Thr Lys Ala
                260                 265                 270

Val Glu Leu Ala Glu Ile Leu Met Gly Ile Phe Asp Thr Pro Asn Arg
    275                 280                 285

Met Pro Ile Leu Tyr Tyr Gln Trp Gln Pro Glu Tyr Ala Ser Gln Pro
    290                 295                 300

His Arg Ala Gly Ser Val Gly Ile Ala Glu Leu Gly Thr Leu Ser Met
305                 310                 315                 320

Glu Phe Thr Arg Leu Ala Gln Leu Thr Ser Gln Tyr Lys Tyr Tyr Asp
                325                 330                 335

Ala Val Asp Arg Ile Thr Asp Ala Leu Ile Glu Leu Gln Lys Gln Gly
                340                 345                 350

Thr Ser Ile Pro Gly Leu Phe Pro Glu Asn Leu Asp Ala Ser Gly Cys
            355                 360                 365

Asn His Thr Ala Thr Ala Leu Arg Ser Ser Leu Ser Glu Ala Ala Gln
    370                 375                 380

Lys Gln Met Asp Glu Asp Leu Ser Asn Lys Pro Glu Asn Tyr Arg Pro
385                 390                 395                 400

Gly Lys Asn Ser Lys Ala Asp Pro Gln Thr Val Glu Lys Gln Pro Ala
                405                 410                 415

Lys Lys Gln Asn Glu Pro Val Glu Lys Ala Lys Gln Val Pro Thr Gln
                420                 425                 430

Gln Thr Ala Lys Arg Gly Lys Pro Pro Phe Gly Ala Asn Gly Phe Thr
            435                 440                 445

Ala Asn Trp Asp Cys Val Pro Gln Gly Leu Val Val Gly Gly Tyr Gly
    450                 455                 460

Phe Gln Gln Tyr His Met Gly Gly Gln Asp Ser Ala Tyr Glu Tyr
465                 470                 475                 480

Phe Pro Lys Glu Tyr Leu Leu Leu Gly Gly Leu Glu Ser Lys Tyr Gln
                485                 490                 495

Lys Leu Tyr Val Asp Ala Val Glu Ala Ile Asn Glu Trp Leu Leu Tyr
                500                 505                 510

Arg Pro Met Thr Asp Gly Asp Trp Asp Ile Leu Phe Pro Ala Lys Val
            515                 520                 525

Ser Thr Ala Gly Asn Pro Ser Gln Asp Leu Val Ala Thr Phe Glu Val
    530                 535                 540
```

-continued

```
Thr His Leu Thr Cys Phe Ile Gly Gly Met Tyr Gly Leu Gly Gly Lys
545                 550                 555                 560

Ile Phe Gly Arg Glu Lys Asp Leu Glu Thr Ala Lys Arg Leu Thr Asp
            565                 570                 575

Gly Cys Val Trp Ala Tyr Gln Ser Thr Val Ser Gly Ile Met Pro Glu
        580                 585                 590

Gly Ser Gln Val Leu Ala Cys Pro Thr Leu Glu Lys Cys Asp Phe Asn
    595                 600                 605

Glu Thr Leu Trp Trp Glu Lys Leu Asp Pro Ala Lys Asp Trp Arg Asp
610                 615                 620

Lys Gln Val Ala Asp Asp Lys Asp Lys Ala Thr Val Gly Glu Ala Leu
625                 630                 635                 640

Lys Glu Thr Ala Asn Ser His Asp Ala Ala Gly Gly Ser Lys Ala Val
            645                 650                 655

His Lys Arg Ala Ala Val Pro Leu Pro Lys Pro Gly Ala Asp Asp Asp
        660                 665                 670

Val Gly Ser Glu Leu Pro Gln Ser Leu Lys Asp Lys Ile Gly Phe Lys
    675                 680                 685

Asn Gly Glu Gln Lys Lys Pro Thr Gly Ser Ser Val Gly Ile Gln Arg
690                 695                 700

Asp Pro Asp Ala Pro Val Asp Ser Val Leu Glu Ala His Arg Leu Pro
705                 710                 715                 720

Pro Gln Glu Pro Glu Glu Gln Val Ile Leu Pro Asp Lys Pro Gln
            725                 730                 735

Thr His Glu Glu Phe Val Lys Gln Arg Ile Ala Glu Met Gly Phe Ala
        740                 745                 750

Pro Gly Val Val His Ile Gln Ser Arg Gln Tyr Ile Leu Arg Pro Glu
    755                 760                 765

Ala Ile Glu Ser Val Trp Tyr Met Tyr Arg Ile Thr Gly Asp Pro Ile
770                 775                 780

Trp Met Glu Lys Gly Trp Lys Met Phe Glu Ala Thr Ile Arg Ala Thr
785                 790                 795                 800

Arg Thr Glu Ile Ala Asn Ser Ala Ile Asp Asp Val Asn Ser Glu Glu
            805                 810                 815

Pro Gly Leu Lys Asp Glu Met Glu Ser Phe Trp Leu Ala Glu Thr Leu
        820                 825                 830

Lys Tyr Tyr Tyr Leu Leu Phe Ser Glu Pro Ser Val Ile Ser Leu Asp
    835                 840                 845

Glu Trp Val Leu Asn Thr Glu Ala His Pro Phe Lys Arg Pro Gly Gly
850                 855                 860

Ser Val Ile Gly His Ser Ile
865                 870
```

<210> SEQ ID NO 72
<211> LENGTH: 13
<212> TYPE: PRT
<213> ORGANISM: Trichoderma reesei

<400> SEQUENCE: 72

```
Met Leu Asn Gln Leu Gln Gly Arg Val Pro Arg Arg Tyr
1               5                   10
```

<210> SEQ ID NO 73
<211> LENGTH: 15
<212> TYPE: PRT

<213> ORGANISM: Trichoderma reesei

<400> SEQUENCE: 73

Ile Ala Leu Val Ala Phe Ala Phe Phe Val Ala Phe Leu Leu Trp
1               5                   10                  15

<210> SEQ ID NO 74
<211> LENGTH: 542
<212> TYPE: PRT
<213> ORGANISM: Trichoderma reesei

<400> SEQUENCE: 74

Ser Gly Tyr Asp Phe Val Pro Arg Thr Ala Thr Val Gly Arg Phe Lys
1               5                   10                  15

Tyr Val Pro Ser Ser Tyr Asp Trp Ser Lys Ala Lys Val Tyr Tyr Pro
                20                  25                  30

Val Lys Asp Met Lys Thr Leu Pro Gln Gly Thr Pro Val Thr Phe Pro
            35                  40                  45

Arg Leu Gln Leu Arg Asn Gln Ser Glu Ala Gln Asp Asp Thr Thr Lys
        50                  55                  60

Ala Arg Lys Gln Ala Val Lys Asp Ala Phe Val Lys Ser Trp Glu Ala
65                  70                  75                  80

Tyr Lys Thr Tyr Ala Trp Thr Lys Asp Gln Leu Gln Pro Leu Ser Leu
                85                  90                  95

Ser Gly Lys Glu Thr Phe Ser Gly Trp Ser Ala Gln Leu Val Asp Ala
            100                 105                 110

Leu Asp Thr Leu Trp Ile Met Asp Leu Lys Asp Phe Phe Leu Ala
        115                 120                 125

Val Lys Glu Val Ala Val Ile Asp Trp Ser Lys Thr Lys Asp Asn Lys
130                 135                 140

Val Ile Asn Leu Phe Glu Val Thr Ile Arg Tyr Leu Gly Gly Leu Ile
145                 150                 155                 160

Ala Ala Tyr Asp Leu Ser Gln Glu Pro Val Leu Arg Ala Lys Ala Ile
                165                 170                 175

Glu Leu Gly Asp Thr Leu Tyr Ala Thr Phe Asp Thr Pro Asn Arg Leu
            180                 185                 190

Pro Ser His Trp Leu Asp Tyr Ser Lys Ala Lys Lys Gly Thr Gln Arg
        195                 200                 205

Ala Asp Asp Ser Met Ser Gly Ala Ala Gly Gly Thr Leu Cys Met Glu
210                 215                 220

Phe Thr Arg Leu Ser Gln Ile Thr Gly Asp Pro Lys Tyr Tyr Asp Ala
225                 230                 235                 240

Thr Glu Arg Ile Lys Gln Phe Phe Tyr Arg Phe Gln Asn Glu Thr Thr
                245                 250                 255

Leu Pro Gly Met Trp Pro Val Met Met Asn Tyr Arg Glu Glu Thr Met
            260                 265                 270

Val Glu Ser Arg Tyr Ser Met Gly Gly Ser Ala Asp Ser Leu Tyr Glu
        275                 280                 285

Tyr Leu Val Lys Met Pro Ala Leu Leu Gly Gly Leu Asp Pro Gln Tyr
290                 295                 300

Pro Glu Met Ala Ile Arg Ala Leu Asp Thr Ala Arg Asp Asn Leu Leu
305                 310                 315                 320

Phe Arg Pro Met Thr Glu Lys Gly Asp Asn Ile Leu Ala Leu Gly Asn
                325                 330                 335

Ala Leu Val Asp His Gly Asn Val Gln Arg Ile Thr Glu Met Gln His

```
                    340                 345                 350
Leu Thr Cys Phe Ala Gly Gly Met Tyr Ala Met Ala Gly Lys Leu Phe
            355                 360                 365

Lys Arg Asp Asp Tyr Val Asp Leu Gly Ser Arg Ile Ser Ser Gly Cys
        370                 375                 380

Val Trp Ala Tyr Asp Ser Phe Pro Ser Gly Ile Met Pro Glu Ser Ala
385                 390                 395                 400

Asp Met Ala Ala Cys Ala Lys Leu Asp Gly Pro Cys Pro Tyr Asp Glu
                405                 410                 415

Val Lys Ala Pro Val Asp Pro Asp Gly Arg Arg Pro His Gly Phe Ile
            420                 425                 430

His Val Lys Ser Arg His Tyr Leu Leu Arg Pro Glu Ala Ile Glu Ser
        435                 440                 445

Val Phe Tyr Met Trp Arg Ile Thr Gly Asp Gln Val Trp Arg Asp Thr
    450                 455                 460

Ala Trp Arg Met Trp Glu Asn Ile Val Arg Glu Ala Glu Thr Glu His
465                 470                 475                 480

Ala Phe Ala Ile Val Glu Asp Val Thr Arg Thr Ala Ser Lys Leu Thr
                485                 490                 495

Asn Asn Tyr Leu Leu Gln Thr Phe Trp Leu Ala Glu Thr Leu Lys Tyr
            500                 505                 510

Phe Tyr Leu Ile Phe Asp Asp Glu Ser Ala Ile Asp Leu Asp Lys Trp
        515                 520                 525

Val Phe Asn Thr Glu Ala His Pro Phe Lys Arg Pro Ala Val
    530                 535                 540

<210> SEQ ID NO 75
<211> LENGTH: 13
<212> TYPE: PRT
<213> ORGANISM: Trichoderma reesei

<400> SEQUENCE: 75

Met Leu Val Val Gly Arg Pro Arg Leu Val Arg Asn Ser
1               5                   10

<210> SEQ ID NO 76
<211> LENGTH: 16
<212> TYPE: PRT
<213> ORGANISM: Trichoderma reesei

<400> SEQUENCE: 76

Ile Ile Leu Thr Leu Ala Ile Leu Ser Ile Trp His Leu Gly Leu Leu
1               5                   10                  15

<210> SEQ ID NO 77
<211> LENGTH: 576
<212> TYPE: PRT
<213> ORGANISM: Trichoderma reesei

<400> SEQUENCE: 77

Ser Arg Thr Pro Thr Ser Ala Ser Ala Leu Val Ser Ala Ser Val Ser
1               5                   10                  15

Ala Ser Ser Glu Trp Ser Arg Leu Glu Arg Leu Met Asn Arg Gly Ala
            20                  25                  30

Pro Leu Thr Pro Tyr Pro Asp Ser Asn Ser Ser Phe Asp Trp Ser Ala
        35                  40                  45

Ile Pro Phe Arg Tyr Pro Pro His Asn Thr Thr His Leu Pro Pro Arg
    50                  55                  60
```

```
His Lys Gln Pro Pro Leu Pro Arg Ile Gln His Arg Phe Gly Pro Glu
 65                  70                  75                  80

Ser Pro Ala Ala Ala Lys Glu Arg Ile Lys Arg Leu Lys Ala Val Lys
                 85                  90                  95

Gln Val Phe Leu Arg Ala Trp Gln Ala Tyr Lys Gly Tyr Ala Trp Lys
                100                 105                 110

Gln Asp Ala Leu Leu Pro Ile Ser Gly Gly Arg Glu Gln Phe Ser
                115                 120                 125

Gly Trp Ala Ala Thr Leu Val Asp Ala Leu Asp Thr Leu Trp Ile Met
130                 135                 140

Gly Leu Arg Glu Glu Phe Asp Glu Ala Val Ala Val Ala Glu Ile
145                 150                 155                 160

Asp Phe Gly Ser Ser Thr Ser Ser Arg Val Asn Ile Phe Glu Thr Asn
                165                 170                 175

Ile Arg Tyr Leu Gly Gly Leu Leu Ala Ala Tyr Asp Leu Ser Gly Arg
                180                 185                 190

Glu Val Leu Leu Lys Lys Ala Val Glu Leu Gly Asp Leu Ile Tyr Ala
                195                 200                 205

Gly Phe Asn Thr Glu Asn Gly Met Pro Val Asp Phe Leu Asn Phe Tyr
210                 215                 220

Ser Ala Lys Ser Gly Glu Gly Leu Val Val Glu Ser Ser Val Val Ser
225                 230                 235                 240

Ala Ser Pro Gly Thr Leu Ser Leu Glu Leu Ala His Leu Ser Gln Val
                245                 250                 255

Thr Gly Asp Asp Lys Tyr Tyr Ser Ala Val Ser Gln Val Met Asp Val
                260                 265                 270

Phe Tyr Gln Gly Gln Asn Lys Thr Arg Leu Pro Gly Val Trp Pro Ile
                275                 280                 285

Asp Val Asn Met Arg Ala Lys Asp Val Val Ser Gly Ser Arg Phe Thr
                290                 295                 300

Leu Gly Gly Cys Ala Asp Ser Leu Tyr Glu Tyr Leu Pro Lys Met His
305                 310                 315                 320

Gln Leu Leu Gly Gly Glu Pro Lys Tyr Glu Thr Met Ser Arg Thr
                325                 330                 335

Phe Leu Gln Ala Ala Asp Arg His Phe Val Phe Arg Pro Met Leu Pro
                340                 345                 350

Gly Ala Glu Glu Asp Val Leu Met Pro Gly Asn Val Asn Val Asp Glu
                355                 360                 365

Asp Ser Gly Glu Ala Val Leu Asp Pro Glu Thr Glu His Leu Ala Cys
                370                 375                 380

Phe Val Gly Gly Met Phe Gly Leu Ala Gly Arg Leu Phe Ser Arg Pro
385                 390                 395                 400

Asp Asp Val Glu Thr Gly Val Arg Leu Thr Asn Gly Cys Val Tyr Ala
                405                 410                 415

Tyr Arg Ala Phe Pro Thr Gly Met Met Pro Glu Arg Leu Asp Leu Ala
                420                 425                 430

Pro Cys Arg Asp Arg Ser Ser Arg Cys Pro Trp Asp Glu Glu His Trp
                435                 440                 445

Leu Glu Glu Arg Ala Lys Arg Pro Glu Trp Glu Pro His Leu Pro Arg
                450                 455                 460

Gly Phe Thr Ser Ala Lys Asp Pro Arg Tyr Leu Leu Arg Pro Glu Ala
465                 470                 475                 480
```

```
Ile Glu Ser Val Phe Tyr Ser Tyr Arg Ile Thr Gly Arg Gln Glu Phe
                485                 490                 495

Gln Thr Ala Ala Trp Asp Met Phe Thr Ala Val Glu Lys Gly Thr Arg
            500                 505                 510

Thr Gln Phe Ala Asn Ala Ala Val Leu Asp Val Thr Arg Ala Ala Asp
        515                 520                 525

Glu Leu Pro Gln Glu Asp Tyr Met Glu Ser Phe Trp Leu Ala Glu Thr
    530                 535                 540

Leu Lys Tyr Phe Tyr Leu Met Phe Thr Thr Pro Asp Ile Ile Ser Leu
545                 550                 555                 560

Asp Asp Tyr Val Leu Asn Thr Glu Ala His Pro Phe Lys Leu Val Gly
                565                 570                 575

<210> SEQ ID NO 78
<211> LENGTH: 17
<212> TYPE: PRT
<213> ORGANISM: Trichoderma reesei

<400> SEQUENCE: 78

Met Val Met Leu Val Ala Ile Ala Leu Ala Trp Leu Gly Cys Ser Leu
 1               5                  10                  15

Leu

<210> SEQ ID NO 79
<211> LENGTH: 1053
<212> TYPE: PRT
<213> ORGANISM: Trichoderma reesei

<400> SEQUENCE: 79

Arg Pro Val Asp Ala Met Arg Ala Asp Tyr Leu Ala Gln Leu Arg Gln
 1               5                  10                  15

Glu Thr Val Asp Met Phe Tyr His Gly Tyr Ser Asn Tyr Met Glu His
                20                  25                  30

Ala Phe Pro Glu Asp Glu Leu Arg Pro Ile Ser Cys Thr Pro Leu Thr
            35                  40                  45

Arg Asp Arg Asp Asn Pro Gly Arg Ile Ser Leu Asn Asp Ala Leu Gly
        50                  55                  60

Asn Tyr Ser Leu Thr Leu Ile Asp Ser Leu Ser Thr Leu Ala Ile Leu
65                  70                  75                  80

Ala Gly Gly Pro Gln Asn Gly Pro Tyr Thr Gly Pro Gln Ala Leu Ser
                85                  90                  95

Asp Phe Gln Asp Gly Val Ala Glu Phe Val Arg His Tyr Gly Asp Gly
            100                 105                 110

Arg Ser Gly Pro Ser Gly Ala Gly Ile Arg Ala Arg Gly Phe Asp Leu
        115                 120                 125

Asp Ser Lys Val Gln Val Phe Glu Thr Val Ile Arg Gly Val Gly Gly
    130                 135                 140

Leu Leu Ser Ala His Leu Phe Ala Ile Gly Glu Leu Pro Ile Thr Gly
145                 150                 155                 160

Tyr Val Pro Arg Pro Glu Gly Val Ala Gly Asp Asp Pro Leu Glu Leu
                165                 170                 175

Ala Pro Ile Pro Trp Pro Asn Gly Phe Arg Tyr Asp Gly Gln Leu Leu
            180                 185                 190

Arg Leu Ala Leu Asp Leu Ser Glu Arg Leu Pro Ala Phe Tyr Thr
        195                 200                 205

Pro Thr Gly Ile Pro Tyr Pro Arg Val Asn Leu Arg Ser Gly Ile Pro
```

```
            210                 215                 220
Phe Tyr Val Asn Ser Pro Leu His Gln Asn Leu Gly Glu Ala Val Glu
225                 230                 235                 240

Glu Gln Ser Gly Arg Pro Glu Ile Thr Glu Thr Cys Ser Ala Gly Ala
                245                 250                 255

Gly Ser Leu Val Leu Glu Phe Thr Val Leu Ser Arg Leu Thr Gly Asp
                260                 265                 270

Ala Arg Phe Glu Gln Ala Ala Lys Arg Ala Phe Trp Glu Val Trp His
            275                 280                 285

Arg Arg Ser Glu Ile Gly Leu Ile Gly Asn Gly Ile Asp Ala Glu Arg
        290                 295                 300

Gly Leu Trp Ile Gly Pro His Ala Gly Ile Gly Ala Gly Met Asp Ser
305                 310                 315                 320

Phe Phe Glu Tyr Ala Leu Lys Ser His Ile Leu Leu Ser Gly Leu Gly
                325                 330                 335

Met Pro Asn Ala Ser Thr Ser Arg Arg Gln Ser Thr Thr Ser Trp Leu
                340                 345                 350

Asp Pro Asn Ser Leu His Pro Pro Leu Pro Pro Glu Met His Thr Ser
                355                 360                 365

Asp Ala Phe Leu Gln Ala Trp His Gln Ala His Ala Ser Val Lys Arg
            370                 375                 380

Tyr Leu Tyr Thr Asp Arg Ser His Phe Pro Tyr Tyr Ser Asn Asn His
385                 390                 395                 400

Arg Ala Thr Gly Gln Pro Tyr Ala Met Trp Ile Asp Ser Leu Gly Ala
                405                 410                 415

Phe Tyr Pro Gly Leu Leu Ala Leu Ala Gly Glu Val Glu Glu Ala Ile
                420                 425                 430

Glu Ala Asn Leu Val Tyr Thr Ala Leu Trp Thr Arg Tyr Ser Ala Leu
            435                 440                 445

Pro Glu Arg Trp Ser Val Arg Glu Gly Asn Val Glu Ala Gly Ile Gly
        450                 455                 460

Trp Trp Pro Gly Arg Pro Glu Phe Ile Glu Ser Thr Tyr His Ile Tyr
465                 470                 475                 480

Arg Ala Thr Arg Asp Pro Trp Tyr Leu His Val Gly Glu Met Val Leu
                485                 490                 495

Arg Asp Ile Arg Arg Arg Cys Tyr Ala Glu Cys Gly Trp Ala Gly Leu
                500                 505                 510

Gln Asp Val Gln Thr Gly Glu Lys Gln Asp Arg Met Glu Ser Phe Phe
            515                 520                 525

Leu Gly Glu Thr Ala Lys Tyr Met Tyr Leu Leu Phe Asp Pro Asp His
        530                 535                 540

Pro Leu Asn Lys Leu Asp Ala Ala Tyr Val Phe Thr Thr Glu Gly His
545                 550                 555                 560

Pro Leu Ile Ile Pro Lys Ser Lys Arg Gly Ser Gly Ser His Asn Arg
                565                 570                 575

Gln Asp Arg Ala Arg Lys Ala Lys Lys Ser Arg Asp Val Ala Val Tyr
            580                 585                 590

Thr Tyr Tyr Asp Glu Ser Phe Thr Asn Ser Cys Pro Ala Pro Arg Pro
        595                 600                 605

Pro Ser Glu His His Leu Ile Gly Ser Ala Thr Ala Ala Arg Pro Asp
    610                 615                 620

Leu Phe Ser Val Ser Arg Phe Thr Asp Leu Tyr Arg Thr Pro Asn Val
625                 630                 635                 640
```

His Gly Pro Leu Glu Lys Val Glu Met Arg Asp Lys Lys Gly Arg
                645                 650                 655

Val Val Arg Tyr Arg Ala Thr Ser Asn His Thr Ile Phe Pro Trp Thr
            660                 665                 670

Leu Pro Pro Ala Met Leu Pro Glu Asn Gly Thr Cys Ala Ala Pro Pro
                675                 680                 685

Glu Arg Ile Ile Ser Leu Ile Glu Phe Pro Ala Asn Asp Ile Thr Ser
            690                 695                 700

Gly Ile Thr Ser Arg Phe Gly Asn His Leu Ser Trp Gln Thr His Leu
705                 710                 715                 720

Gly Pro Thr Val Asn Ile Leu Glu Gly Leu Arg Leu Gln Leu Glu Gln
                725                 730                 735

Val Ser Asp Pro Ala Thr Gly Glu Asp Lys Trp Arg Ile Thr His Ile
                740                 745                 750

Gly Asn Thr Gln Leu Gly Arg His Glu Thr Val Phe Phe His Ala Glu
            755                 760                 765

His Val Arg His Leu Lys Asp Glu Val Phe Ser Cys Arg Arg Arg Arg
    770                 775                 780

Asp Ala Val Glu Ile Glu Leu Leu Val Asp Lys Pro Ser Asp Thr Asn
785                 790                 795                 800

Asn Asn Asn Thr Leu Ala Ser Ser Asp Asp Val Val Val Asp Ala
                805                 810                 815

Lys Ala Glu Glu Gln Asp Gly Met Leu Ala Asp Asp Gly Asp Thr
                820                 825                 830

Leu Asn Ala Glu Thr Leu Ser Ser Asn Ser Leu Phe Gln Ser Leu Leu
                835                 840                 845

Arg Ala Val Ser Ser Val Phe Glu Pro Val Tyr Thr Ala Ile Pro Glu
    850                 855                 860

Ser Asp Pro Ser Ala Gly Thr Ala Lys Val Tyr Ser Phe Asp Ala Tyr
865                 870                 875                 880

Thr Ser Thr Gly Pro Gly Ala Tyr Pro Met Pro Ser Ile Ser Asp Thr
                885                 890                 895

Pro Ile Pro Gly Asn Pro Phe Tyr Asn Phe Arg Asn Pro Ala Ser Asn
            900                 905                 910

Phe Pro Trp Ser Thr Val Phe Leu Ala Gly Gln Ala Cys Glu Gly Pro
    915                 920                 925

Leu Pro Ala Ser Ala Pro Arg Glu His Gln Val Ile Val Met Leu Arg
    930                 935                 940

Gly Gly Cys Ser Phe Ser Arg Lys Leu Asp Asn Ile Pro Ser Phe Ser
945                 950                 955                 960

Pro His Asp Arg Ala Leu Gln Leu Val Val Leu Asp Glu Pro Pro
            965                 970                 975

Pro Pro Pro Pro Pro Pro Ala Asn Asp Arg Arg Asp Val Thr Arg
            980                 985                 990

Pro Leu Leu Asp Thr Glu Gln Thr Thr Pro Lys Gly Met Lys Arg Leu
            995                 1000                1005

His Gly Ile Pro Met Val Leu Val Arg Ala Ala Arg Gly Asp Tyr Glu
    1010                1015                1020

Leu Phe Gly His Ala Ile Gly Val Gly Met Arg Arg Lys Tyr Arg Val
1025                1030                1035                1040

Glu Ser Gln Gly Leu Val Val Glu Asn Ala Val Val Leu
                1045                1050

<210> SEQ ID NO 80
<211> LENGTH: 45
<212> TYPE: PRT
<213> ORGANISM: Trichoderma reesei

<400> SEQUENCE: 80

Met Met Pro Arg His His Ser Ser Gly Phe Ser Asn Gly Tyr Pro Arg
1               5                   10                  15

Ala Asp Thr Phe Glu Ile Ser Pro His Arg Phe Gln Pro Arg Ala Thr
            20                  25                  30

Leu Pro Pro His Arg Lys Arg Lys Arg Thr Ala Ile Arg
        35                  40                  45

<210> SEQ ID NO 81
<211> LENGTH: 16
<212> TYPE: PRT
<213> ORGANISM: Trichoderma reesei

<400> SEQUENCE: 81

Val Gly Ile Ala Val Val Ile Leu Val Leu Val Leu Trp Phe Gly
1               5                   10                  15

<210> SEQ ID NO 82
<211> LENGTH: 407
<212> TYPE: PRT
<213> ORGANISM: Trichoderma reesei

<400> SEQUENCE: 82

Gln Pro Arg Ser Val Ala Ser Leu Ile Ser Leu Gly Ile Leu Ser Gly
1               5                   10                  15

Tyr Asp Asp Leu Lys Leu Glu Thr Val Arg Tyr Tyr Asp Leu Ser Asn
            20                  25                  30

Val Gln Gly Thr Ala Arg Gly Trp Glu Arg Glu Arg Ile Leu Leu
        35                  40                  45

Cys Val Pro Leu Arg Asp Ala Glu Gln His Leu Pro Met Phe Phe Ser
    50                  55                  60

His Leu Lys Asn Phe Thr Tyr Pro His Asn Leu Ile Asp Leu Ala Phe
65                  70                  75                  80

Leu Val Ser Asp Ser Lys Asp His Thr Leu Glu Ser Leu Thr Glu His
                85                  90                  95

Leu Glu Ala Ile Gln Ala Asp Pro Asp Pro Lys Gln Pro Tyr Gly Glu
            100                 105                 110

Ile Ser Ile Ile Glu Lys Asp Phe Gly Gln Lys Val Asn Gln Asp Val
        115                 120                 125

Glu Ser Arg His Gly Phe Ala Ala Gln Ala Ser Arg Arg Lys Leu Met
    130                 135                 140

Ala Gln Ala Arg Asn Trp Leu Leu Ser Ala Ala Leu Arg Pro Tyr His
145                 150                 155                 160

Ser Trp Val Tyr Trp Arg Asp Val Asp Val Glu Thr Ala Pro Phe Thr
                165                 170                 175

Ile Leu Glu Asp Leu Met Arg His Asn Lys Asp Val Ile Val Pro Asn
            180                 185                 190

Val Trp Arg Pro Leu Pro Asp Trp Leu Gly Gly Glu Gln Pro Tyr Asp
        195                 200                 205

Leu Asn Ser Trp Gln Glu Ser Glu Thr Ala Leu Ala Leu Ala Asp Thr
    210                 215                 220

Leu Asp Glu Asp Ala Val Ile Val Glu Gly Tyr Ala Glu Tyr Ala Thr

```
              225                 230                 235                 240

Trp Arg Pro His Leu Ala Tyr Leu Arg Asp Pro Tyr Gly Asp Pro Asp
                245                 250                 255

Met Glu Met Glu Ile Asp Gly Val Gly Gly Val Ser Ile Leu Ala Lys
                260                 265                 270

Ala Lys Val Phe Arg Ala Gly Val His Phe Pro Ala Phe Ser Phe Glu
                275                 280                 285

Lys His Ala Glu Thr Glu Gly Phe Gly Lys Met Ala Lys Arg Met His
                290                 295                 300

Phe Ser Val Val Gly Leu Pro His Tyr Thr Ile Trp His Leu Tyr Glu
305                 310                 315                 320

Pro Ser Val Asp Asp Ile Lys His Met Glu Met Glu Arg Glu Arg
                325                 330                 335

Ile Ala Arg Glu Lys Glu Glu Glu Arg Lys Lys Lys Glu Ala Gln
                340                 345                 350

Ile Lys Glu Glu Phe Gly Asp Ala Asn Ser Gln Trp Glu Gln Asp Lys
                355                 360                 365

Gln Gln Met Gln Asp Leu Lys Leu Gln Asp Arg Gly Gly Asp Lys Glu
                370                 375                 380

Ala Ala Ala Ala Gly Val Asn Gln Gly Ala Ala Ala Lys Ala Ala Gly
385                 390                 395                 400

Ala Met Glu Gly Gln Lys Asn
                405

<210> SEQ ID NO 83
<211> LENGTH: 31
<212> TYPE: PRT
<213> ORGANISM: Trichoderma reesei

<400> SEQUENCE: 83

Met Leu Leu Pro Lys Gly Gly Leu Asp Trp Arg Ser Ala Arg Ala Gln
1               5                   10                  15

Ile Pro Pro Thr Arg Ala Leu Trp Asn Ala Val Thr Arg Thr Arg
                20                  25                  30

<210> SEQ ID NO 84
<211> LENGTH: 15
<212> TYPE: PRT
<213> ORGANISM: Trichoderma reesei

<400> SEQUENCE: 84

Phe Ile Leu Leu Val Gly Ile Thr Gly Leu Ile Leu Leu Leu Trp
1               5                   10                  15

<210> SEQ ID NO 85
<211> LENGTH: 358
<212> TYPE: PRT
<213> ORGANISM: Trichoderma reesei

<400> SEQUENCE: 85

Arg Gly Val Ser Thr Ser Ala Ser Glu Met Gln Ser Phe Tyr Cys Trp
1               5                   10                  15

Gly Pro Ala Lys Pro Pro Met Glu Met Ser Pro Asn Glu His Asn Arg
                20                  25                  30

Trp Asn Gly His Leu Gln Thr Pro Val Ile Phe Asn His His Ala Pro
                35                  40                  45

Val Glu Val Asn Ser Ser Thr Ile Glu His Val Asp Leu Asn Pro Ile
50                  55                  60
```

-continued

```
Asn Ser Thr Lys Gln Ala Val Thr Lys Glu Glu Arg Ile Leu Ile Leu
 65                  70                  75                  80

Thr Pro Leu Lys Asp Ala Ala Pro Tyr Leu Ser Lys Tyr Phe Glu Leu
             85                  90                  95

Leu Ala Glu Leu Thr Tyr Pro His Arg Leu Ile Asp Leu Ala Phe Leu
            100                 105                 110

Val Ser Asp Ser Thr Asp Thr Leu Ala Val Leu Ala Ser Glu Leu
        115                 120                 125

Asp Arg Ile Gln Lys Arg Pro Asp Gln Ile Pro Phe His Ser Ala Thr
        130                 135                 140

Val Ile Glu Lys Asp Phe Gly Phe Lys Leu Ser Gln Asn Val Glu Glu
145                 150                 155                 160

Arg His Ser Phe Glu Ala Gln Gly Pro Arg Arg Lys Ala Met Gly Arg
                165                 170                 175

Ala Arg Asn Tyr Leu Leu Tyr Thr Ala Leu Lys Pro Glu His Ser Trp
            180                 185                 190

Val Tyr Trp Arg Asp Val Asp Ile Val Asp Ser Pro Thr Gly Ile Leu
        195                 200                 205

Glu Asp Phe Ile Ala His Asp Arg Asp Ile Leu Val Pro Asn Ile Trp
210                 215                 220

Phe His Arg Tyr Arg Asp Gly Val Asp Ile Glu Gly Arg Phe Asp Tyr
225                 230                 235                 240

Asn Ser Trp Val Glu Ser Asp Lys Gly Arg Lys Leu Ala Asn Ser Leu
                245                 250                 255

Asp Lys Asp Val Val Leu Ala Glu Gly Tyr Lys Gln Tyr Asp Thr Gly
            260                 265                 270

Arg Thr Tyr Met Ala Lys Met Gly Asp Trp Arg Glu Asn Lys Asp Val
        275                 280                 285

Glu Leu Glu Leu Asp Gly Ile Gly Gly Val Asn Ile Leu Val Lys Ala
290                 295                 300

Asp Val His Arg Ser Gly Ile Asn Phe Pro Cys Tyr Ala Phe Glu Asn
305                 310                 315                 320

Gln Ala Glu Thr Glu Gly Phe Ala Lys Met Ala Lys Arg Ala Gly Tyr
                325                 330                 335

Glu Val Tyr Gly Leu Pro Asn Tyr Val Val Trp His Ile Asp Thr Glu
            340                 345                 350

Glu Lys Gly Gly Asn Ala
        355

<210> SEQ ID NO 86
<211> LENGTH: 17
<212> TYPE: PRT
<213> ORGANISM: Trichoderma reesei

<400> SEQUENCE: 86

Met Ala Arg Pro Met Gly Ser Val Arg Leu Lys Lys Ala Asn Pro Ser
 1               5                  10                  15

Thr

<210> SEQ ID NO 87
<211> LENGTH: 16
<212> TYPE: PRT
<213> ORGANISM: Trichoderma reesei

<400> SEQUENCE: 87
```

```
Leu Ile Leu Gly Ala Val Leu Cys Ile Phe Ile Ile Phe Leu Val
 1               5                  10                  15
```

<210> SEQ ID NO 88
<211> LENGTH: 339
<212> TYPE: PRT
<213> ORGANISM: Trichoderma reesei

<400> SEQUENCE: 88

```
Ser Pro Ser Ser Pro Ala Ser Ala Ser Arg Leu Ser Ile Val Ser Ala
 1               5                  10                  15

Gln His His Leu Ser Pro Pro Thr Ser Pro Tyr Gln Ser Pro Arg Ser
                20                  25                  30

Gly Ala Val Gln Gly Pro Pro Val Thr Arg Tyr Asn Leu Asn Lys
             35                  40                  45

Val Thr Val Thr Ser Asp Pro Val Arg Asn Gln Glu His Ile Leu Ile
 50                  55                  60

Leu Thr Pro Met Ala Arg Phe Tyr Gln Glu Tyr Trp Asp Asn Leu Leu
 65                  70                  75                  80

Arg Leu Asn Tyr Pro His Glu Leu Ile Thr Leu Gly Phe Ile Leu Pro
                85                  90                  95

Lys Thr Lys Glu Gly Asn Gln Ala Thr Ser Met Leu Gln Lys Gln Ile
                100                 105                 110

Gln Lys Thr Gln Asn Tyr Gly Pro Glu Lys Asp Arg Phe Lys Ser Ile
                115                 120                 125

Ile Ile Leu Arg Gln Asp Phe Asp Pro Ala Val Val Ser Gln Asp Glu
                130                 135                 140

Ser Glu Arg His Lys Leu Ala Asn Gln Lys Ala Arg Arg Glu Val Met
145                 150                 155                 160

Ala Lys Ala Arg Asn Ser Leu Leu Phe Thr Thr Leu Gly Pro Ser Thr
                165                 170                 175

Ser Trp Val Leu Trp Leu Asp Ala Asp Ile Thr Glu Thr Ala Pro Thr
                180                 185                 190

Leu Ile Gln Asp Leu Ala Ser His Asp Lys Pro Ile Ile Val Ala Asn
                195                 200                 205

Cys Phe Gln Lys Tyr Tyr Asp Pro Glu Ser Lys Lys Met Ala Glu Arg
                210                 215                 220

Pro Tyr Asp Phe Asn Ser Trp Gln Asp Ser Glu Thr Ala Leu Lys Met
225                 230                 235                 240

Ala Glu Gln Met Gly Pro Asp Asp Ile Leu Leu Glu Gly Tyr Ala Glu
                245                 250                 255

Met Ala Thr Tyr Arg Thr Leu Leu Ala Tyr Met Ser Thr Pro Gly Gly
                260                 265                 270

Ser Lys Asp Leu Val Val Pro Leu Asp Gly Val Gly Thr Ala Leu
                275                 280                 285

Leu Val Lys Ala Asp Val His Arg Asp Gly Ala Met Phe Pro Pro Phe
                290                 295                 300

Ala Phe Tyr His Leu Ile Glu Ser Glu Gly Phe Ala Lys Met Ala Lys
305                 310                 315                 320

Arg Leu Gly Trp Gln Pro Tyr Gly Leu Pro Asn Tyr Lys Val Tyr His
                325                 330                 335

Tyr Asn Glu
```

<210> SEQ ID NO 89
<211> LENGTH: 33

<212> TYPE: PRT
<213> ORGANISM: Trichoderma reesei

<400> SEQUENCE: 89

Met His Phe Ala Tyr Pro Ser Arg Lys Ser Asn Pro Pro Phe
1               5                   10                  15

Arg Pro Arg Ser Thr Arg Leu Pro Gly Leu Arg Arg Ser Arg Ile Lys
            20                  25                  30

Thr

<210> SEQ ID NO 90
<211> LENGTH: 15
<212> TYPE: PRT
<213> ORGANISM: Trichoderma reesei

<400> SEQUENCE: 90

Ile Gly Ile Val Leu Phe Leu Val Leu Ala Thr Leu Trp Phe Phe
1               5                   10                  15

<210> SEQ ID NO 91
<211> LENGTH: 262
<212> TYPE: PRT
<213> ORGANISM: Trichoderma reesei

<400> SEQUENCE: 91

Ser Asn Pro Arg Val Pro Arg Pro Asp Pro Glu Arg Val Pro Ser Gly
1               5                   10                  15

Arg Pro Pro Val Val Leu Val Thr Val Ile Asp Pro Thr Gln Tyr Pro
            20                  25                  30

Asn Ala Tyr Leu Lys Thr Ile Lys Glu Asn Arg Glu Gln Tyr Ala Ala
        35                  40                  45

Lys His Gly Tyr Glu Ala Phe Ile Val Lys Ala Tyr Asp Tyr Asp Thr
    50                  55                  60

Gln Gly Ala Pro Gln Ser Trp Ser Lys Leu Met Ala Met Arg His Ala
65                  70                  75                  80

Leu Thr Lys Phe Pro Glu Cys Arg Phe Val Trp Tyr Leu Asp Gln Asp
                85                  90                  95

Ala Tyr Ile Met Asp Met Ser Lys Ser Leu Glu Glu Gln Leu Leu Asn
            100                 105                 110

Arg Gln Lys Leu Glu Ser Leu Met Ile Lys Asn Tyr Pro Val Val Pro
        115                 120                 125

Pro Asp Ser Ile Ile Lys Thr Phe Ser His Leu Arg Pro Asp Glu Val
    130                 135                 140

Asp Leu Ile Val Ser Gln Asp Ser Ser Gly Leu Val Ala Gly Ser Val
145                 150                 155                 160

Val Val Arg Asn Ser Gln Trp Ser Lys Phe Leu Leu Glu Thr Trp Met
                165                 170                 175

Asp Pro Leu Tyr Arg Ser Tyr Asn Phe Gln Lys Ala Glu Arg His Ala
            180                 185                 190

Leu Glu His Ile Val Gln Trp His Pro Thr Ile Leu Ser Lys Leu Ala
        195                 200                 205

Leu Val Pro Gln Arg Thr Leu Gly Pro Tyr Thr Arg Thr Asp Gln Gly
    210                 215                 220

Asp Ala Tyr Gln Asp Gly Asp Phe Val Val Met Phe Thr Gly Cys Thr
225                 230                 235                 240

Lys Ser Gly Glu Gln Ser Cys Glu Thr Val Ser Ala Ser Tyr Tyr Gln
                245                 250                 255

Lys Trp Ser Ser Ser Leu
            260

<210> SEQ ID NO 92
<211> LENGTH: 119
<212> TYPE: PRT
<213> ORGANISM: Trichoderma reesei

<400> SEQUENCE: 92

Met Ser Leu Ser Arg Ser Pro Ser Pro Val Pro Gly Gly Gly Trp Ser
1               5                   10                  15

Ser Pro Gly Leu Asn Ile Asn Ser Gly Arg Ser Ser Pro Ser Asn Ala
            20                  25                  30

Ala Gly Ser Ser Val Ser Trp Glu Ser Ala Lys Met Arg Lys Gln Gly
        35                  40                  45

Ala Asn Gly Tyr Pro Ser Phe Ser Thr Gln Asn Gln Gly Phe Phe Thr
    50                  55                  60

Arg His Met Arg Arg Ile Ser Ser Ser Leu Pro Arg Phe Ala Ala Gly
65                  70                  75                  80

Pro Gly Asn Thr Tyr Ala Glu Arg Glu Lys Tyr Glu Arg Gly Gly His
                85                  90                  95

Ser Pro His Ala Gly Gly Arg Leu Arg Ala Phe Leu Ala Arg Ile
            100                 105                 110

Gly Arg Arg Leu Lys Trp Arg
            115

<210> SEQ ID NO 93
<211> LENGTH: 16
<212> TYPE: PRT
<213> ORGANISM: Trichoderma reesei

<400> SEQUENCE: 93

Ile Leu Leu Pro Leu Ile Ile Ile Cys Thr Ile Val Ala Tyr Tyr Gly
1               5                   10                  15

<210> SEQ ID NO 94
<211> LENGTH: 324
<212> TYPE: PRT
<213> ORGANISM: Trichoderma reesei

<400> SEQUENCE: 94

Thr His Glu Ala Pro Gly Phe Val His Trp Trp Arg Arg Ile Ser Met
1               5                   10                  15

Gly Gly Gly Gly Glu Lys Phe Val Ile Leu Gly Ala Asn Val Gly
            20                  25                  30

Gly Gly Val Met Glu Trp Lys Gly Ala Arg Glu Trp Ala Ile Glu Arg
        35                  40                  45

Asp Ser Val Arg Asn Lys Arg Lys Tyr Ala Thr Arg Trp Gly Tyr Asp
    50                  55                  60

Leu Glu Ile Val Asp Met Lys Thr Lys Arg Tyr Ala His Glu Trp
65                  70                  75                  80

Arg Glu Ser Trp Glu Lys Val Asp Phe Ile Arg Ala Ala Met Arg Lys
                85                  90                  95

Tyr Pro Lys Ala Glu Trp Phe Trp Leu Asp Leu Asn Thr Tyr Val
            100                 105                 110

Met Glu Pro Ser Tyr Ser Leu Gln Arg His Leu Phe Asn His Leu Asp
            115                 120                 125

Arg His Val Tyr Arg Asp Ile Asn Val Phe Asn Pro Leu Asn Ile Thr
130                 135                 140

His Pro Pro Thr Glu Glu Tyr Leu Asp Ala Glu Ala Arg Ser Pro Val
145                 150                 155                 160

Gly Asp Gly Asn Ile Asn Ser Val Asn Leu Met Leu Thr Gln Asp Cys
                165                 170                 175

Ser Gly Phe Asn Leu Gly Ser Phe Phe Ile Arg Arg Ser Ala Trp Thr
                180                 185                 190

Glu Gln Leu Leu Asp Ile Trp Trp Asp Pro Val Leu Tyr Glu Gln Lys
                195                 200                 205

His Met Glu Trp Glu His Lys Glu Gln Asp Ala Leu Glu Gln Leu Tyr
210                 215                 220

Arg Thr Gln Pro Trp Ile Arg Gln His Thr Gly Phe Leu Pro Gln Arg
225                 230                 235                 240

Leu Ile Asn Ser Phe Pro Pro Ala Ala Cys Ala Asp Glu Ser Gly Leu
                245                 250                 255

Asn Asn Thr Arg Ile His Tyr Asn Glu Lys Asp Arg Asp Phe Val Val
                260                 265                 270

Asn Met Ala Gly Cys Glu Trp Gly Arg Asp Cys Trp Gly Glu Met Tyr
                275                 280                 285

His Tyr Arg Glu Phe Ser Tyr Trp Leu Asn Arg Asn Pro Trp Glu Leu
290                 295                 300

Phe Lys Glu Glu Ile Val Ala Val Ile Trp Tyr Lys Leu Thr Gly Gln
305                 310                 315                 320

Arg Val Lys Leu

<210> SEQ ID NO 95
<211> LENGTH: 863
<212> TYPE: PRT
<213> ORGANISM: Homo sapiens

<400> SEQUENCE: 95

Met Arg Phe Arg Ile Tyr Lys Arg Lys Val Leu Ile Leu Thr Leu Val
1               5                   10                  15

Val Ala Ala Cys Gly Phe Val Leu Trp Ser Ser Asn Gly Arg Gln Arg
                20                  25                  30

Lys Asn Glu Ala Leu Ala Pro Pro Leu Leu Asp Ala Glu Pro Ala Arg
                35                  40                  45

Gly Ala Gly Gly Arg Gly Gly Asp His Pro Ser Val Ala Val Gly Ile
50                  55                  60

Arg Arg Val Ser Asn Val Ser Ala Ala Ser Leu Val Pro Ala Val Pro
65                  70                  75                  80

Gln Pro Glu Ala Asp Asn Leu Thr Leu Arg Tyr Arg Ser Leu Val Tyr
                85                  90                  95

Gln Leu Asn Phe Asp Gln Thr Leu Arg Asn Val Asp Lys Ala Gly Thr
                100                 105                 110

Trp Ala Pro Arg Glu Leu Val Leu Val Val Gln Val His Asn Arg Pro
                115                 120                 125

Glu Tyr Leu Arg Leu Leu Leu Asp Ser Leu Arg Lys Ala Gln Gly Ile
                130                 135                 140

Asp Asn Val Leu Val Ile Phe Ser His Asp Phe Trp Ser Thr Glu Ile
145                 150                 155                 160

Asn Gln Leu Ile Ala Gly Val Asn Phe Cys Pro Val Leu Gln Val Phe
                165                 170                 175

```
Phe Pro Phe Ser Ile Gln Leu Tyr Pro Asn Glu Phe Pro Gly Ser Asp
                180                 185                 190

Pro Arg Asp Cys Pro Arg Asp Leu Pro Lys Asn Ala Ala Leu Lys Leu
            195                 200                 205

Gly Cys Ile Asn Ala Glu Tyr Pro Asp Ser Phe Gly His Tyr Arg Glu
        210                 215                 220

Ala Lys Phe Ser Gln Thr Lys His His Trp Trp Lys Leu His Phe
225                 230                 235                 240

Val Trp Glu Arg Val Lys Ile Leu Arg Asp Tyr Ala Gly Leu Ile Leu
                245                 250                 255

Phe Leu Glu Glu Asp His Tyr Leu Ala Pro Asp Phe Tyr His Val Phe
                260                 265                 270

Lys Lys Met Trp Lys Leu Lys Gln Gln Glu Cys Pro Glu Cys Asp Val
            275                 280                 285

Leu Ser Leu Gly Thr Tyr Ser Ala Ser Arg Ser Phe Tyr Gly Met Ala
        290                 295                 300

Asp Lys Val Asp Val Lys Thr Trp Lys Ser Thr Glu His Asn Met Gly
305                 310                 315                 320

Leu Ala Leu Thr Arg Asn Ala Tyr Gln Lys Leu Ile Glu Cys Thr Asp
                325                 330                 335

Thr Phe Cys Thr Tyr Asp Asp Tyr Asn Trp Asp Trp Thr Leu Gln Tyr
                340                 345                 350

Leu Thr Val Ser Cys Leu Pro Lys Phe Trp Lys Val Leu Val Pro Gln
            355                 360                 365

Ile Pro Arg Ile Phe His Ala Gly Asp Cys Gly Met His His Lys Lys
        370                 375                 380

Thr Cys Arg Pro Ser Thr Gln Ser Ala Gln Ile Glu Ser Leu Leu Asn
385                 390                 395                 400

Asn Asn Lys Gln Tyr Met Phe Pro Glu Thr Leu Thr Ile Ser Glu Lys
                405                 410                 415

Phe Thr Val Val Ala Ile Ser Pro Pro Arg Lys Asn Gly Gly Trp Gly
            420                 425                 430

Asp Ile Arg Asp His Glu Leu Cys Lys Ser Tyr Arg Arg Leu Gln Thr
        435                 440                 445

Arg Pro Ala Pro Gly Arg Pro Pro Ser Val Ser Ala Leu Asp Gly Asp
450                 455                 460

Pro Ala Ser Leu Thr Arg Glu Val Ile Arg Leu Ala Gln Asp Ala Glu
465                 470                 475                 480

Val Glu Leu Glu Arg Gln Arg Gly Leu Leu Gln Gln Ile Gly Asp Ala
                485                 490                 495

Leu Ser Ser Gln Arg Gly Arg Val Pro Thr Ala Ala Pro Pro Ala Gln
            500                 505                 510

Pro Arg Val Pro Val Thr Pro Ala Pro Ala Val Ile Pro Ile Leu Val
        515                 520                 525

Ile Ala Cys Asp Arg Ser Thr Val Arg Arg Cys Leu Asp Lys Leu Leu
530                 535                 540

His Tyr Arg Pro Ser Ala Glu Leu Phe Pro Ile Ile Val Ser Gln Asp
545                 550                 555                 560

Cys Gly His Glu Glu Thr Ala Gln Ala Ile Ala Ser Tyr Gly Ser Ala
                565                 570                 575

Val Thr His Ile Arg Gln Pro Asp Leu Ser Ser Ile Ala Val Pro Pro
            580                 585                 590

Asp His Arg Lys Phe Gln Gly Tyr Tyr Lys Ile Ala Arg His Tyr Arg
```

```
                    595               600               605
    Trp Ala Leu Gly Gln Val Phe Arg Gln Phe Arg Phe Pro Ala Ala Val
                610                 615                 620
    Val Val Glu Asp Asp Leu Glu Val Ala Pro Asp Phe Phe Glu Tyr Phe
    625                 630                 635                 640
    Arg Ala Thr Tyr Pro Leu Leu Lys Ala Asp Pro Ser Leu Trp Cys Val
                    645                 650                 655
    Ser Ala Trp Asn Asp Asn Gly Lys Glu Gln Met Val Asp Ala Ser Arg
                660                 665                 670
    Pro Glu Leu Leu Tyr Arg Thr Asp Phe Phe Pro Gly Leu Gly Trp Leu
                    675                 680                 685
    Leu Leu Ala Glu Leu Trp Ala Glu Leu Glu Pro Lys Trp Pro Lys Ala
                690                 695                 700
    Phe Trp Asp Asp Trp Met Arg Arg Pro Glu Gln Arg Gln Gly Arg Ala
    705                 710                 715                 720
    Cys Ile Arg Pro Glu Ile Ser Arg Thr Met Thr Phe Gly Arg Lys Gly
                    725                 730                 735
    Val Ser His Gly Gln Phe Phe Asp Gln His Leu Lys Phe Ile Lys Leu
                740                 745                 750
    Asn Gln Gln Phe Val His Phe Thr Gln Leu Asp Leu Ser Tyr Leu Gln
                    755                 760                 765
    Arg Glu Ala Tyr Asp Arg Asp Phe Leu Ala Arg Val Tyr Gly Ala Pro
                770                 775                 780
    Gln Leu Gln Val Glu Lys Val Arg Thr Asn Asp Arg Lys Glu Leu Gly
    785                 790                 795                 800
    Glu Val Arg Val Gln Tyr Thr Gly Arg Asp Ser Phe Lys Ala Phe Ala
                    805                 810                 815
    Lys Ala Leu Gly Val Met Asp Asp Leu Lys Ser Gly Val Pro Arg Ala
                820                 825                 830
    Gly Tyr Arg Gly Ile Val Thr Phe Gln Phe Arg Gly Arg Arg Val His
                    835                 840                 845
    Leu Ala Pro Pro Pro Thr Trp Glu Gly Tyr Asp Pro Ser Trp Asn
    850                 855                 860

<210> SEQ ID NO 96
<211> LENGTH: 2592
<212> TYPE: DNA
<213> ORGANISM: Homo sapiens

<400> SEQUENCE: 96
atgcgcttcc gaatctacaa gcggaaggtc ctcattctga cccttgtcgt ggccgcttgc      60
ggctttgttc tctggtccag caacggtcgc cagcgtaaga acgaggccct ggcgcctccc     120
ctcttggacg ccgaaccggc cagaggcgca ggtggcaggg aggggatca ccctcggtc      180 gctgtcggca tccgccgcgt cagcaatgtg tccgccgcct ctctggtccc ggcggttccg     240
cagcctgagg cagacaacct cacgctgcgc taccgatcac tcgtgtatca acttaacttc     300
gaccagactc tgcggaacgt cgacaaggcc ggaacctggg ctccgcgtga gttggtcctc     360
gtcgttcagg tgcacaacag gcccgagtac ctccgcctcc tgctggattc gcttcgaaag     420
gcccagggca tcgacaacgt cctggtgatt ttcagccatg acttttggtc cacagagatc     480
aatcagctca ttgcgggtgt caacttttgc ccgtcttgc aagttttctt cccttttctct      540 atccaactct acccaaacga gttcccgggc agtgaccccc gcgactgtcc tcgggatctg     600
ccaaaaaacg ccgctctcaa gctgggctgc atcaacgccg aataccccga cagctttggc     660
```

```
cactatcgcg aggccaagtt ctcgcagacg aagcaccact ggtggtggaa gctccatttt      720
gtctgggagc gagtgaagat ccttcgtgat tacgcaggac tcattctgtt cttggaagag      780
gaccactacc tggccccgga cttctaccac gtctttaaga agatgtggaa gctcaagcag      840
caggaatgcc ccgagtgcga cgttctgtcc cttggcacct atagcgcgtc ccgctcgttc      900
tacggtatgg ctgacaaggt cgatgtgaaa acctggaagt caactgagca caatatgggc      960
ctcgccctga cgaggaacgc ctaccagaaa ctcatcgagt gtaccgacac cttctgcacg     1020
tacgacgact ataactggga ttggacactg cagtacttga ctgtcagctg cctccctaag     1080
ttttggaagg tccttgttcc ccagatcccg agaattttcc atgctggcga ctgcgggatg     1140
caccacaaga aaacctgtcg cccatccacg cagtctgccc aaatcgagtc gctcctgaac     1200
aacaacaagc agtacatgtt ccccgagaca ctgaccatta gcgagaagtt tacggtcgtg     1260
gcgatctccc cgcctcgaaa gaatggcggc tggggtgaca tccgcgatca cgagctgtgc     1320
aagtcttacc gccggctcca gacgcgccca gcacctggca ggccaccctc agtcagcgct     1380
ctcgatggcg accccgccag cctcacccgg gaagtgattc gcctggccca agacgccgag     1440
gtggagctgg agcggcagcg tgggctgctg cagcagatcg ggatgcccct gtcgagccag     1500
cgggggaggg tgcccaccgc cgcccctccc gcccagccgc gtgtgcctgt gaccccgcg      1560 ccggcggtga ttcccatcct ggtcatcgcc tgtgaccgca gcactgttcg gcgctgcctg     1620
gacaagctgc tgcattatcg gccctcggct gagctcttcc ccatcatcgt cagccaggac     1680
tgcgggcacg aggagacggc ccaggccatc gcctcctacg gcagcgcggt cacgcacatc     1740
cggcagcccg acctgagcag cattgcggtg ccgccggacc accgcaagtt ccagggctac     1800
tacaagatcg cgcgccacta ccgctgggcg ctgggccagg tcttccggca gtttcgcttc     1860
cccgccgccg tggtggtgga ggatgacctg gaggtggccc cggacttctt cgagtacttt     1920
cgggccacct atccgctgct gaaggccgac ccctccctgt ggtgcgtctc ggcctggaat     1980
gacaacggca aggagcagat ggtggacgcc agcaggcctg agctgctcta ccgcaccgac     2040
tttttccctg gcctgggctg gctgctgttg gccgagctct gggctgagct ggagcccaag     2100
tggccaaagg ccttctggga cgactggatg cggcggccgg agcagcggca ggggcgggcc     2160
tgcatccgcc ctgagatctc aagaacgatg acctttggcc gcaagggtgt gagccacggg     2220
cagttctttg accagcacct caagttcatc aagctgaacc agcagtttgt gcacttcacc     2280
cagctggacc tgtcttacct gcagcgggag gcctatgacc gagatttcct cgcccgcgtc     2340
tacggtgctc cccagctgca ggtggagaaa gtgaggacca atgaccggaa ggagctgggg     2400
gaggtgcggg tgcagtacac gggcagggac agcttcaagg ctttcgccaa ggctctgggt     2460
gtcatggatg acctcaagtc gggggttccg agagctggct accggggcat tgtcaccttc     2520
cagttccggg gccgccgtgt ccacctggcg cccccaccga cgtgggaggg ctatgatccc     2580
agctggaatt ag                                                         2592
```

<210> SEQ ID NO 97
<211> LENGTH: 1263
<212> TYPE: DNA
<213> ORGANISM: Trichoderma reesei

<400> SEQUENCE: 97

```
atggcgtcac tcatcaaaac tgccgtggac attgccaacg ccgccatgc gctgtccaga       60 tatgtcatct ttgggctctg gcttgcggat gcggtgctgt gcgggctgat tatctggaaa     120
```

-continued

```
gtgccttata cggaaatcga ctgggtcgcc tacatggagc aagtcaccca gttcgtccac    180
ggagagcgag actaccccaa gatggagggc ggcacagggc ccctggtgta tcccgcggcc    240
catgtgtaca tctacacagg gctctactac ctgacgaaca agggcaccga catcctgctg    300
gcgcagcagc tctttgccgt gctctacatg gctactctgg cggtcgtcat gacatgctac    360
tccaaggcca aggtcccgcc gtacatcttc ccgcttctca tcctctccaa aagacttcac    420
agcgtcttcg tcctgagatg cttcaacgac tgcttcgccg ccttcttcct ctggctctgc    480
atcttcttct tccagaggcg agagtggacc atcggagctc tcgcatacag catcggcctg    540
ggcgtcaaaa tgtcgctgct actggttctc cccgccgtgg tcatcgtcct ctacctcggc    600
cgcggcttca agggcgccct gcggctgctc tggctcatgg tgcaggtcca gctcctcctc    660 gccatacc ct tcatcacgac aaattggcgc ggctacctcg ccgtgcatt cgagctctcg    720 aggcagttca agtttgaatg gacagtcaat tggcgcatgc tgggcgagga tctgttcctc    780
agccggggct ctctctatca cgctactggca tttcacgcca tcttcctcct cgcctttatc    840
ctcggccggt ggctgaagat tagggaacgg accgtactcg ggatgatccc ctatgtcatc    900
cgattcagat cgccctttac cgagcaggaa gagcgcgcca tctccaaccg cgtcgtcacg    960
cccggctatg tcatgtccac catcttgtcg gccaacgtgg tgggactgct gtttgcccgg   1020
tctctgcact accagttcta tgcatatctg gcgtgggcga ccccctatct cctgtggacg   1080
gcctgcccca tcttttggt ggtggccccc ctctgggcgg cgcaagaatg ggcctggaac   1140
gtcttcccca gcacgcctct tagctcgagc gtcgtggtga gcgtgctggc cgtgacggtg   1200
gccatggcgt ttgcaggttc aaatccgcag ccacgtgaaa catcgaagcc gaagcagcac   1260
taa                                                                 1263
```

<210> SEQ ID NO 98
<211> LENGTH: 420
<212> TYPE: PRT
<213> ORGANISM: Trichoderma reesei

<400> SEQUENCE: 98

Met Ala Ser Leu Ile Lys Thr Ala Val Asp Ile Ala Asn Gly Arg His
 1               5                  10                  15

Ala Leu Ser Arg Tyr Val Ile Phe Gly Leu Trp Leu Ala Asp Ala Val
            20                  25                  30

Leu Cys Gly Leu Ile Ile Trp Lys Val Pro Tyr Thr Glu Ile Asp Trp
        35                  40                  45

Val Ala Tyr Met Glu Gln Val Thr Gln Phe Val His Gly Glu Arg Asp
    50                  55                  60

Tyr Pro Lys Met Glu Gly Gly Thr Gly Pro Leu Val Tyr Pro Ala Ala
65                  70                  75                  80

His Val Tyr Ile Tyr Thr Gly Leu Tyr Tyr Leu Thr Asn Lys Gly Thr
                85                  90                  95

Asp Ile Leu Leu Ala Gln Gln Leu Phe Ala Val Leu Tyr Met Ala Thr
            100                 105                 110

Leu Ala Val Val Met Thr Cys Tyr Ser Lys Ala Lys Val Pro Pro Tyr
        115                 120                 125

Ile Phe Pro Leu Leu Ile Leu Ser Lys Arg Leu His Ser Val Phe Val
    130                 135                 140

Leu Arg Cys Phe Asn Asp Cys Phe Ala Ala Phe Phe Leu Trp Leu Cys
145                 150                 155                 160

Ile Phe Phe Phe Gln Arg Arg Glu Trp Thr Ile Gly Ala Leu Ala Tyr

```
                165                 170                 175
Ser Ile Gly Leu Gly Val Lys Met Ser Leu Leu Val Leu Pro Ala
            180                 185                 190

Val Val Ile Val Leu Tyr Leu Gly Arg Gly Phe Lys Gly Ala Leu Arg
            195                 200                 205

Leu Leu Trp Leu Met Val Gln Val Gln Leu Leu Leu Ala Ile Pro Phe
            210                 215                 220

Ile Thr Thr Asn Trp Arg Gly Tyr Leu Gly Arg Ala Phe Glu Leu Ser
225                 230                 235                 240

Arg Gln Phe Lys Phe Glu Trp Thr Val Asn Trp Arg Met Leu Gly Glu
                245                 250                 255

Asp Leu Phe Leu Ser Arg Gly Phe Ser Ile Thr Leu Leu Ala Phe His
            260                 265                 270

Ala Ile Phe Leu Leu Ala Phe Ile Leu Gly Arg Trp Leu Lys Ile Arg
            275                 280                 285

Glu Arg Thr Val Leu Gly Met Ile Pro Tyr Val Ile Arg Phe Arg Ser
290                 295                 300

Pro Phe Thr Glu Gln Glu Glu Arg Ala Ile Ser Asn Arg Val Val Thr
305                 310                 315                 320

Pro Gly Tyr Val Met Ser Thr Ile Leu Ser Ala Asn Val Val Gly Leu
                325                 330                 335

Leu Phe Ala Arg Ser Leu His Tyr Gln Phe Tyr Ala Tyr Leu Ala Trp
            340                 345                 350

Ala Thr Pro Tyr Leu Leu Trp Thr Ala Cys Pro Asn Leu Leu Val Val
            355                 360                 365

Ala Pro Leu Trp Ala Ala Gln Glu Trp Ala Trp Asn Val Phe Pro Ser
            370                 375                 380

Thr Pro Leu Ser Ser Ser Val Val Val Ser Val Leu Ala Val Thr Val
385                 390                 395                 400

Ala Met Ala Phe Ala Gly Ser Asn Pro Gln Pro Arg Glu Thr Ser Lys
                405                 410                 415

Pro Lys Gln His
            420

<210> SEQ ID NO 99
<211> LENGTH: 21
<212> TYPE: DNA
<213> ORGANISM: Artificial Sequence
<220> FEATURE:
<223> OTHER INFORMATION: Synthesized Construct

<400> SEQUENCE: 99
gcaaatggca ttctgacatc c                                             21

<210> SEQ ID NO 100
<211> LENGTH: 21
<212> TYPE: DNA
<213> ORGANISM: Artificial Sequence
<220> FEATURE:
<223> OTHER INFORMATION: Synthesized Construct

<400> SEQUENCE: 100
gactggttcc aattgacaag c                                             21

<210> SEQ ID NO 101
<211> LENGTH: 42
<212> TYPE: DNA
<213> ORGANISM: Artificial Sequence
```

<220> FEATURE:
<223> OTHER INFORMATION: Synthesized Construct

<400> SEQUENCE: 101
cagtggtacc ctaattccag ctaggatcat agccctccca cg                42

<210> SEQ ID NO 102
<211> LENGTH: 18
<212> TYPE: DNA
<213> ORGANISM: Artificial Sequence
<220> FEATURE:
<223> OTHER INFORMATION: Synthesized Construct

<400> SEQUENCE: 102
cggaccaccg caagttcc                                           18

<210> SEQ ID NO 103
<211> LENGTH: 54
<212> TYPE: DNA
<213> ORGANISM: Artificial Sequence
<220> FEATURE:
<223> OTHER INFORMATION: Synthesized Construct

<400> SEQUENCE: 103
atgcggaatt ctgcatcatc atcatcatca tcgccagcgt aagaacgagg ccct   54

<210> SEQ ID NO 104
<211> LENGTH: 22
<212> TYPE: DNA
<213> ORGANISM: Artificial Sequence
<220> FEATURE:
<223> OTHER INFORMATION: Synthesized Construct

<400> SEQUENCE: 104
cctttctcta tccaactcta cc                                      22

<210> SEQ ID NO 105
<211> LENGTH: 18
<212> TYPE: DNA
<213> ORGANISM: Artificial Sequence
<220> FEATURE:
<223> OTHER INFORMATION: Synthesized Construct

<400> SEQUENCE: 105
ggaacttgcg gtggtccg                                           18

<210> SEQ ID NO 106
<211> LENGTH: 66
<212> TYPE: DNA
<213> ORGANISM: Artificial Sequence
<220> FEATURE:
<223> OTHER INFORMATION: Synthesized Construct

<400> SEQUENCE: 106
ccgccggctc cagggaggtg ggggcagtgg aggtggcggc agtgggaggg tgcccaccgc   60
cgcccc                                                            66

<210> SEQ ID NO 107
<211> LENGTH: 66
<212> TYPE: DNA
<213> ORGANISM: Artificial Sequence
<220> FEATURE:
<223> OTHER INFORMATION: Synthesized Construct

<400> SEQUENCE: 107

```
gcggtgggca ccctcccact gccgccacct ccactgcccc cacctccctg gagccggcgg    60
taagac                                                               66

<210> SEQ ID NO 108
<211> LENGTH: 65
<212> TYPE: DNA
<213> ORGANISM: Artificial Sequence
<220> FEATURE:
<223> OTHER INFORMATION: Synthesized Construct

<400> SEQUENCE: 108
aggtgggggc agtggaggtg gcggcagtgg cggcggtgga agtgggaggg tgcccaccgc    60
cgccc                                                                65

<210> SEQ ID NO 109
<211> LENGTH: 64
<212> TYPE: DNA
<213> ORGANISM: Artificial Sequence
<220> FEATURE:
<223> OTHER INFORMATION: Synthesized Construct

<400> SEQUENCE: 109
cggtgggcac cctcccactt ccaccgccgc cactgccgcc acctccactg cccccacctc    60
cctg                                                                 64

<210> SEQ ID NO 110
<211> LENGTH: 65
<212> TYPE: DNA
<213> ORGANISM: Artificial Sequence
<220> FEATURE:
<223> OTHER INFORMATION: Synthesized Construct

<400> SEQUENCE: 110
gtttccgccg ggagggttgc cgccgctagg gttgccggtg ctctggagcc ggcggtaaga    60
cttgc                                                                65

<210> SEQ ID NO 111
<211> LENGTH: 66
<212> TYPE: DNA
<213> ORGANISM: Artificial Sequence
<220> FEATURE:
<223> OTHER INFORMATION: Synthesized Construct

<400> SEQUENCE: 111
gcaaccctcc cggcggaaac ccgcctggca gcaccgggag ggtgcccacc gccgcccctc    60
ccgccc                                                               66

<210> SEQ ID NO 112
<211> LENGTH: 70
<212> TYPE: DNA
<213> ORGANISM: Artificial Sequence
<220> FEATURE:
<223> OTHER INFORMATION: Synthesized Construct

<400> SEQUENCE: 112
ccgcctccag gaacagtggc gctggcggtg gccgtcgcgg cggagctctg gagccggcgg    60
taagacttgc                                                           70

<210> SEQ ID NO 113
<211> LENGTH: 71
<212> TYPE: DNA
<213> ORGANISM: Artificial Sequence
```

-continued

```
<220> FEATURE:
<223> OTHER INFORMATION: Synthesized Construct

<400> SEQUENCE: 113
cgccactgtt cctggaggcg gtagcggccc caccagcggg agggtgccca ccgccgcccc    60
tcccgcccag c                                                         71

<210> SEQ ID NO 114
<211> LENGTH: 20
<212> TYPE: DNA
<213> ORGANISM: Artificial Sequence
<220> FEATURE:
<223> OTHER INFORMATION: Synthesized Construct

<400> SEQUENCE: 114
cattagcgag aagtttacgg                                                20

<210> SEQ ID NO 115
<211> LENGTH: 106
<212> TYPE: PRT
<213> ORGANISM: Trichoderma reesei

<400> SEQUENCE: 115
```

Met Ala Ser Thr Asn Ala Arg Tyr Val Arg Tyr Leu Leu Ile Ala Phe
1               5                   10                  15

Phe Thr Ile Leu Val Phe Tyr Phe Val Ser Asn Ser Lys Tyr Glu Gly
            20                  25                  30

Val Asp Leu Asn Lys Gly Thr Phe Thr Ala Pro Asp Ser Thr Lys Thr
        35                  40                  45

Thr Pro Lys Pro Pro Ala Thr Gly Asp Ala Lys Asp Phe Pro Leu Ala
    50                  55                  60

Leu Thr Pro Asn Asp Pro Gly Phe Asn Asp Leu Val Gly Ile Ala Pro
65                  70                  75                  80

Gly Pro Arg Met Asn Ala Thr Phe Val Thr Leu Ala Arg Asn Ser Asp
                85                  90                  95

Val Trp Asp Ile Ala Arg Ser Ile Arg Gln
            100                 105

```
<210> SEQ ID NO 116
<211> LENGTH: 83
<212> TYPE: PRT
<213> ORGANISM: Trichoderma reesei

<400> SEQUENCE: 116
```

Met Ala Ser Thr Asn Ala Arg Tyr Val Arg Tyr Leu Leu Ile Ala Phe
1               5                   10                  15

Phe Thr Ile Leu Val Phe Tyr Phe Val Ser Asn Ser Lys Tyr Glu Gly
            20                  25                  30

Val Asp Leu Asn Lys Gly Thr Phe Thr Ala Pro Asp Ser Thr Lys Thr
        35                  40                  45

Thr Pro Lys Pro Pro Ala Thr Gly Asp Ala Lys Asp Phe Pro Leu Ala
    50                  55                  60

Leu Thr Pro Asn Asp Pro Gly Phe Asn Asp Leu Val Gly Ile Ala Pro
65                  70                  75                  80

Gly Pro Arg

```
<210> SEQ ID NO 117
<211> LENGTH: 8
<212> TYPE: PRT
```

<213> ORGANISM: Artificial Sequence
<220> FEATURE:
<223> OTHER INFORMATION: Synthesized Construct

<400> SEQUENCE: 117

Asp Tyr Lys Asp Asp Asp Asp Lys
1               5

<210> SEQ ID NO 118
<211> LENGTH: 15
<212> TYPE: PRT
<213> ORGANISM: Artificial Sequence
<220> FEATURE:
<223> OTHER INFORMATION: Synthesized Construct

<400> SEQUENCE: 118

Gly Gly Gly Gly Ser Gly Gly Gly Gly Ser Gly Gly Gly Gly Ser
1               5                   10                  15

<210> SEQ ID NO 119
<211> LENGTH: 824
<212> TYPE: PRT
<213> ORGANISM: Artificial Sequence
<220> FEATURE:
<223> OTHER INFORMATION: Synthesized Construct

<400> SEQUENCE: 119

Met Arg Phe Arg Ile Tyr Lys Arg Lys Val Leu Ile Leu Thr Leu Val
1               5                   10                  15

Val Ala Ala Cys Gly Phe Val Leu Trp Ser Ser Asn Gly Arg Gln Arg
            20                  25                  30

Lys Asn Glu Ala Leu Ala Pro Pro Leu Leu Asp Ala Glu Pro Ala Arg
        35                  40                  45

Gly Ala Gly Gly Arg Gly Asp His Pro Ser Val Ala Val Gly Ile
    50                  55                  60

Arg Arg Val Ser Asn Val Ser Ala Ala Ser Leu Val Pro Ala Val Pro
65                  70                  75                  80

Gln Pro Glu Ala Asp Asn Leu Thr Leu Arg Tyr Arg Ser Leu Val Tyr
                85                  90                  95

Gln Leu Asn Phe Asp Gln Thr Leu Arg Asn Val Asp Lys Ala Gly Thr
            100                 105                 110

Trp Ala Pro Arg Glu Leu Val Leu Val Gln Val His Asn Arg Pro
        115                 120                 125

Glu Tyr Leu Arg Leu Leu Leu Asp Ser Leu Arg Lys Ala Gln Gly Ile
    130                 135                 140

Asp Asn Val Leu Val Ile Phe Ser His Asp Phe Trp Ser Thr Glu Ile
145                 150                 155                 160

Asn Gln Leu Ile Ala Gly Val Asn Phe Cys Pro Val Leu Gln Val Phe
                165                 170                 175

Phe Pro Phe Ser Ile Gln Leu Tyr Pro Asn Glu Phe Pro Gly Ser Asp
            180                 185                 190

Pro Arg Asp Cys Pro Arg Asp Leu Pro Lys Asn Ala Ala Leu Lys Leu
        195                 200                 205

Gly Cys Ile Asn Ala Glu Tyr Pro Asp Ser Phe Gly His Tyr Arg Glu
    210                 215                 220

Ala Lys Phe Ser Gln Thr Lys His His Trp Trp Trp Lys Leu His Phe
225                 230                 235                 240

Val Trp Glu Arg Val Lys Ile Leu Arg Asp Tyr Ala Gly Leu Ile Leu
                245                 250                 255

```
Phe Leu Glu Glu Asp His Tyr Leu Ala Pro Asp Phe Tyr His Val Phe
            260                 265                 270

Lys Lys Met Trp Lys Leu Lys Gln Gln Glu Cys Pro Glu Cys Asp Val
            275                 280                 285

Leu Ser Leu Gly Thr Tyr Ser Ala Ser Arg Ser Phe Tyr Gly Met Ala
290                 295                 300

Asp Lys Val Asp Val Lys Thr Trp Lys Ser Thr Glu His Asn Met Gly
305                 310                 315                 320

Leu Ala Leu Thr Arg Asn Ala Tyr Gln Lys Leu Ile Glu Cys Thr Asp
                325                 330                 335

Thr Phe Cys Thr Tyr Asp Asp Tyr Asn Trp Asp Trp Thr Leu Gln Tyr
            340                 345                 350

Leu Thr Val Ser Cys Leu Pro Lys Phe Trp Lys Val Leu Val Pro Gln
            355                 360                 365

Ile Pro Arg Ile Phe His Ala Gly Asp Cys Gly Met His His Lys Lys
370                 375                 380

Thr Cys Arg Pro Ser Thr Gln Ser Ala Gln Ile Glu Ser Leu Leu Asn
385                 390                 395                 400

Asn Asn Lys Gln Tyr Met Phe Pro Glu Thr Leu Thr Ile Ser Glu Lys
                405                 410                 415

Phe Thr Val Val Ala Ile Ser Pro Pro Arg Lys Asn Gly Gly Trp Gly
            420                 425                 430

Asp Ile Arg Asp His Glu Leu Cys Lys Ser Tyr Arg Leu Gln Gly
            435                 440                 445

Gly Gly Gly Ser Gly Gly Gly Ser Gly Gly Gly Ser Gly Arg
450                 455                 460

Val Pro Thr Ala Ala Pro Pro Ala Gln Pro Arg Val Pro Val Thr Pro
465                 470                 475                 480

Ala Pro Ala Val Ile Pro Ile Leu Val Ile Ala Cys Asp Arg Ser Thr
                485                 490                 495

Val Arg Arg Cys Leu Asp Lys Leu Leu His Tyr Arg Pro Ser Ala Glu
            500                 505                 510

Leu Phe Pro Ile Ile Val Ser Gln Asp Cys Gly His Glu Glu Thr Ala
            515                 520                 525

Gln Ala Ile Ala Ser Tyr Gly Ser Ala Val Thr His Ile Arg Gln Pro
530                 535                 540

Asp Leu Ser Ser Ile Ala Val Pro Pro Asp His Arg Lys Phe Gln Gly
545                 550                 555                 560

Tyr Tyr Lys Ile Ala Arg His Tyr Arg Trp Ala Leu Gly Gln Val Phe
                565                 570                 575

Arg Gln Phe Arg Phe Pro Ala Val Val Val Glu Asp Asp Leu Glu
            580                 585                 590

Val Ala Pro Asp Phe Phe Glu Tyr Phe Arg Ala Thr Tyr Pro Leu Leu
            595                 600                 605

Lys Ala Asp Pro Ser Leu Trp Cys Val Ser Ala Trp Asn Asp Asn Gly
610                 615                 620

Lys Glu Gln Met Val Asp Ala Ser Arg Pro Glu Leu Leu Tyr Arg Thr
625                 630                 635                 640

Asp Phe Phe Pro Gly Leu Gly Trp Leu Leu Leu Ala Glu Leu Trp Ala
                645                 650                 655

Glu Leu Glu Pro Lys Trp Pro Lys Ala Phe Trp Asp Asp Trp Met Arg
            660                 665                 670
```

```
Arg Pro Glu Gln Arg Gln Gly Arg Ala Cys Ile Arg Pro Glu Ile Ser
            675                 680                 685

Arg Thr Met Thr Phe Gly Arg Lys Gly Val Ser His Gly Gln Phe Phe
    690                 695                 700

Asp Gln His Leu Lys Phe Ile Lys Leu Asn Gln Gln Phe Val His Phe
705                 710                 715                 720

Thr Gln Leu Asp Leu Ser Tyr Leu Gln Arg Glu Ala Tyr Asp Arg Asp
                725                 730                 735

Phe Leu Ala Arg Val Tyr Gly Ala Pro Gln Leu Gln Val Glu Lys Val
                740                 745                 750

Arg Thr Asn Asp Arg Lys Glu Leu Gly Glu Val Arg Val Gln Tyr Thr
            755                 760                 765

Gly Arg Asp Ser Phe Lys Ala Phe Ala Lys Ala Leu Gly Val Met Asp
    770                 775                 780

Asp Leu Lys Ser Gly Val Pro Arg Ala Gly Tyr Arg Gly Ile Val Thr
785                 790                 795                 800

Phe Gln Phe Arg Gly Arg Val His Leu Ala Pro Pro Thr Trp
                805                 810                 815

Glu Gly Tyr Asp Pro Ser Trp Asn
            820

<210> SEQ ID NO 120
<211> LENGTH: 10
<212> TYPE: PRT
<213> ORGANISM: Artificial Sequence
<220> FEATURE:
<223> OTHER INFORMATION: Synthesized Construct

<400> SEQUENCE: 120

Gly Gly Gly Gly Ser Gly Gly Gly Gly Ser
1               5                   10

<210> SEQ ID NO 121
<211> LENGTH: 819
<212> TYPE: PRT
<213> ORGANISM: Artificial Sequence
<220> FEATURE:
<223> OTHER INFORMATION: Synthesized Construct

<400> SEQUENCE: 121

Met Arg Phe Arg Ile Tyr Lys Arg Lys Val Leu Ile Leu Thr Leu Val
1               5                   10                  15

Val Ala Ala Cys Gly Phe Val Leu Trp Ser Ser Asn Gly Arg Gln Arg
            20                  25                  30

Lys Asn Glu Ala Leu Ala Pro Pro Leu Leu Asp Ala Glu Pro Ala Arg
        35                  40                  45

Gly Ala Gly Gly Arg Gly Gly Asp His Pro Ser Val Ala Val Gly Ile
    50                  55                  60

Arg Arg Val Ser Asn Val Ser Ala Ala Ser Leu Val Pro Ala Val Pro
65                  70                  75                  80

Gln Pro Glu Ala Asp Asn Leu Thr Leu Arg Tyr Arg Ser Leu Val Tyr
                85                  90                  95

Gln Leu Asn Phe Asp Gln Thr Leu Arg Asn Val Asp Lys Ala Gly Thr
                100                 105                 110

Trp Ala Pro Arg Glu Leu Val Leu Val Val Gln Val His Asn Arg Pro
            115                 120                 125

Glu Tyr Leu Arg Leu Leu Leu Asp Ser Leu Arg Lys Ala Gln Gly Ile
        130                 135                 140
```

```
Asp Asn Val Leu Val Ile Phe Ser His Asp Phe Trp Ser Thr Glu Ile
145                 150                 155                 160

Asn Gln Leu Ile Ala Gly Val Asn Phe Cys Pro Val Leu Gln Val Phe
            165                 170                 175

Phe Pro Phe Ser Ile Gln Leu Tyr Pro Asn Glu Phe Pro Gly Ser Asp
        180                 185                 190

Pro Arg Asp Cys Pro Arg Asp Leu Pro Lys Asn Ala Ala Leu Lys Leu
    195                 200                 205

Gly Cys Ile Asn Ala Glu Tyr Pro Asp Ser Phe Gly His Tyr Arg Glu
    210                 215                 220

Ala Lys Phe Ser Gln Thr Lys His His Trp Trp Lys Leu His Phe
225                 230                 235                 240

Val Trp Glu Arg Val Lys Ile Leu Arg Asp Tyr Ala Gly Leu Ile Leu
            245                 250                 255

Phe Leu Glu Glu Asp His Tyr Leu Ala Pro Asp Phe Tyr His Val Phe
        260                 265                 270

Lys Lys Met Trp Lys Leu Lys Gln Gln Glu Cys Pro Glu Cys Asp Val
    275                 280                 285

Leu Ser Leu Gly Thr Tyr Ser Ala Ser Arg Ser Phe Tyr Gly Met Ala
290                 295                 300

Asp Lys Val Asp Val Lys Thr Trp Lys Ser Thr Glu His Asn Met Gly
305                 310                 315                 320

Leu Ala Leu Thr Arg Asn Ala Tyr Gln Lys Leu Ile Glu Cys Thr Asp
            325                 330                 335

Thr Phe Cys Thr Tyr Asp Asp Tyr Asn Trp Asp Trp Thr Leu Gln Tyr
        340                 345                 350

Leu Thr Val Ser Cys Leu Pro Lys Phe Trp Lys Val Leu Val Pro Gln
    355                 360                 365

Ile Pro Arg Ile Phe His Ala Gly Asp Cys Gly Met His His Lys Lys
    370                 375                 380

Thr Cys Arg Pro Ser Thr Gln Ser Ala Gln Ile Glu Ser Leu Leu Asn
385                 390                 395                 400

Asn Asn Lys Gln Tyr Met Phe Pro Glu Thr Leu Thr Ile Ser Glu Lys
            405                 410                 415

Phe Thr Val Val Ala Ile Ser Pro Pro Arg Lys Asn Gly Gly Trp Gly
        420                 425                 430

Asp Ile Arg Asp His Glu Leu Cys Lys Ser Tyr Arg Arg Leu Gln Gly
    435                 440                 445

Gly Gly Gly Ser Gly Gly Gly Ser Gly Arg Val Pro Thr Ala Ala
    450                 455                 460

Pro Pro Ala Gln Pro Arg Val Pro Val Thr Pro Ala Pro Ala Val Ile
465                 470                 475                 480

Pro Ile Leu Val Ile Ala Cys Asp Arg Ser Thr Val Arg Arg Cys Leu
            485                 490                 495

Asp Lys Leu Leu His Tyr Arg Pro Ser Ala Glu Leu Phe Pro Ile Ile
        500                 505                 510

Val Ser Gln Asp Cys Gly His Glu Glu Thr Ala Gln Ala Ile Ala Ser
    515                 520                 525

Tyr Gly Ser Ala Val Thr His Ile Arg Gln Pro Asp Leu Ser Ser Ile
    530                 535                 540

Ala Val Pro Pro Asp His Arg Lys Phe Gln Gly Tyr Tyr Lys Ile Ala
545                 550                 555                 560
```

Arg His Tyr Arg Trp Ala Leu Gly Gln Val Phe Arg Gln Phe Arg Phe
            565                 570                 575

Pro Ala Val Val Glu Asp Leu Glu Val Ala Pro Asp Phe
        580                 585                 590

Phe Glu Tyr Phe Arg Ala Thr Tyr Pro Leu Leu Lys Ala Asp Pro Ser
            595                 600                 605

Leu Trp Cys Val Ser Ala Trp Asn Asp Asn Gly Lys Glu Gln Met Val
610                 615                 620

Asp Ala Ser Arg Pro Glu Leu Leu Tyr Arg Thr Asp Phe Phe Pro Gly
625                 630                 635                 640

Leu Gly Trp Leu Leu Leu Ala Glu Leu Trp Ala Glu Leu Glu Pro Lys
            645                 650                 655

Trp Pro Lys Ala Phe Trp Asp Asp Trp Met Arg Arg Pro Glu Gln Arg
            660                 665                 670

Gln Gly Arg Ala Cys Ile Arg Pro Glu Ile Ser Arg Thr Met Thr Phe
            675                 680                 685

Gly Arg Lys Gly Val Ser His Gly Gln Phe Phe Asp Gln His Leu Lys
            690                 695                 700

Phe Ile Lys Leu Asn Gln Gln Phe Val His Phe Thr Gln Leu Asp Leu
705                 710                 715                 720

Ser Tyr Leu Gln Arg Glu Ala Tyr Asp Arg Asp Phe Leu Ala Arg Val
                725                 730                 735

Tyr Gly Ala Pro Gln Leu Gln Val Glu Lys Val Arg Thr Asn Asp Arg
            740                 745                 750

Lys Glu Leu Gly Glu Val Arg Val Gln Tyr Thr Gly Arg Asp Ser Phe
            755                 760                 765

Lys Ala Phe Ala Lys Ala Leu Gly Val Met Asp Asp Leu Lys Ser Gly
            770                 775                 780

Val Pro Arg Ala Gly Tyr Arg Gly Ile Val Thr Phe Gln Phe Arg Gly
785                 790                 795                 800

Arg Arg Val His Leu Ala Pro Pro Thr Trp Glu Gly Tyr Asp Pro
                805                 810                 815

Ser Trp Asn

<210> SEQ ID NO 122
<211> LENGTH: 19
<212> TYPE: PRT
<213> ORGANISM: Trichoderma reesei

<400> SEQUENCE: 122

Ser Thr Gly Asn Pro Ser Gly Gly Asn Pro Pro Gly Gly Asn Pro Pro
1               5                   10                  15

Gly Ser Thr

<210> SEQ ID NO 123
<211> LENGTH: 828
<212> TYPE: PRT
<213> ORGANISM: Trichoderma reesei

<400> SEQUENCE: 123

Met Arg Phe Arg Ile Tyr Lys Arg Lys Val Leu Ile Leu Thr Leu Val
1               5                   10                  15

Val Ala Ala Cys Gly Phe Val Leu Trp Ser Ser Asn Gly Arg Gln Arg
            20                  25                  30

Lys Asn Glu Ala Leu Ala Pro Pro Leu Leu Asp Ala Glu Pro Ala Arg
        35                  40                  45

```
Gly Ala Gly Gly Arg Gly Asp His Pro Ser Val Ala Gly Ile
    50                  55                  60

Arg Arg Val Ser Asn Val Ser Ala Ala Ser Leu Val Pro Ala Val Pro
 65                  70                  75                  80

Gln Pro Glu Ala Asp Asn Leu Thr Leu Arg Tyr Arg Ser Leu Val Tyr
                 85                  90                  95

Gln Leu Asn Phe Asp Gln Thr Leu Arg Asn Val Asp Lys Ala Gly Thr
            100                 105                 110

Trp Ala Pro Arg Glu Leu Val Leu Val Val Gln Val His Asn Arg Pro
        115                 120                 125

Glu Tyr Leu Arg Leu Leu Leu Asp Ser Leu Arg Lys Ala Gln Gly Ile
    130                 135                 140

Asp Asn Val Leu Val Ile Phe Ser His Asp Phe Trp Ser Thr Glu Ile
145                 150                 155                 160

Asn Gln Leu Ile Ala Gly Val Asn Phe Cys Pro Val Leu Gln Val Phe
                165                 170                 175

Phe Pro Phe Ser Ile Gln Leu Tyr Pro Asn Glu Phe Pro Gly Ser Asp
            180                 185                 190

Pro Arg Asp Cys Pro Arg Asp Leu Pro Lys Asn Ala Ala Leu Lys Leu
        195                 200                 205

Gly Cys Ile Asn Ala Glu Tyr Pro Asp Ser Phe Gly His Tyr Arg Glu
    210                 215                 220

Ala Lys Phe Ser Gln Thr Lys His His Trp Trp Lys Leu His Phe
225                 230                 235                 240

Val Trp Glu Arg Val Lys Ile Leu Arg Asp Tyr Ala Gly Leu Ile Leu
                    245                 250                 255

Phe Leu Glu Glu Asp His Tyr Leu Ala Pro Asp Phe Tyr His Val Phe
            260                 265                 270

Lys Lys Met Trp Lys Leu Lys Gln Gln Glu Cys Pro Glu Cys Asp Val
        275                 280                 285

Leu Ser Leu Gly Thr Tyr Ser Ala Ser Arg Ser Phe Tyr Gly Met Ala
    290                 295                 300

Asp Lys Val Asp Val Lys Thr Trp Lys Ser Thr Glu His Asn Met Gly
305                 310                 315                 320

Leu Ala Leu Thr Arg Asn Ala Tyr Gln Lys Leu Ile Glu Cys Thr Asp
                325                 330                 335

Thr Phe Cys Thr Tyr Asp Asp Tyr Asn Trp Asp Trp Thr Leu Gln Tyr
            340                 345                 350

Leu Thr Val Ser Cys Leu Pro Lys Phe Trp Lys Val Leu Val Pro Gln
        355                 360                 365

Ile Pro Arg Ile Phe His Ala Gly Asp Cys Gly Met His His Lys Lys
    370                 375                 380

Thr Cys Arg Pro Ser Thr Gln Ser Ala Gln Ile Glu Ser Leu Leu Asn
385                 390                 395                 400

Asn Asn Lys Gln Tyr Met Phe Pro Glu Thr Leu Thr Ile Ser Glu Lys
                405                 410                 415

Phe Thr Val Val Ala Ile Ser Pro Pro Arg Lys Asn Gly Gly Trp Gly
            420                 425                 430

Asp Ile Arg Asp His Glu Leu Cys Lys Ser Tyr Arg Arg Leu Gln Ser
        435                 440                 445

Thr Gly Asn Pro Ser Gly Gly Asn Pro Pro Gly Gly Asn Pro Pro Gly
    450                 455                 460
```

Ser Thr Gly Arg Val Pro Thr Ala Ala Pro Ala Gln Pro Arg Val
465                 470                 475                 480

Pro Val Thr Pro Ala Pro Ala Val Ile Pro Ile Leu Val Ile Ala Cys
            485                 490                 495

Asp Arg Ser Thr Val Arg Arg Cys Leu Asp Lys Leu Leu His Tyr Arg
            500                 505                 510

Pro Ser Ala Glu Leu Phe Pro Ile Ile Val Ser Gln Asp Cys Gly His
            515                 520                 525

Glu Glu Thr Ala Gln Ala Ile Ala Ser Tyr Gly Ser Ala Val Thr His
            530                 535                 540

Ile Arg Gln Pro Asp Leu Ser Ser Ile Ala Val Pro Pro Asp His Arg
545                 550                 555                 560

Lys Phe Gln Gly Tyr Tyr Lys Ile Ala Arg His Tyr Arg Trp Ala Leu
            565                 570                 575

Gly Gln Val Phe Arg Gln Phe Arg Phe Pro Ala Ala Val Val Val Glu
            580                 585                 590

Asp Asp Leu Glu Val Ala Pro Asp Phe Glu Tyr Phe Arg Ala Thr
            595                 600                 605

Tyr Pro Leu Leu Lys Ala Asp Pro Ser Leu Trp Cys Val Ser Ala Trp
610                 615                 620

Asn Asp Asn Gly Lys Glu Gln Met Val Asp Ala Ser Arg Pro Glu Leu
625                 630                 635                 640

Leu Tyr Arg Thr Asp Phe Phe Pro Gly Leu Gly Trp Leu Leu Ala
            645                 650                 655

Glu Leu Trp Ala Glu Leu Glu Pro Lys Trp Pro Lys Ala Phe Trp Asp
            660                 665                 670

Asp Trp Met Arg Arg Pro Glu Gln Arg Gln Gly Arg Ala Cys Ile Arg
            675                 680                 685

Pro Glu Ile Ser Arg Thr Met Thr Phe Gly Arg Lys Gly Val Ser His
690                 695                 700

Gly Gln Phe Phe Asp Gln His Leu Lys Phe Ile Lys Leu Asn Gln Gln
705                 710                 715                 720

Phe Val His Phe Thr Gln Leu Asp Leu Ser Tyr Leu Gln Arg Glu Ala
            725                 730                 735

Tyr Asp Arg Asp Phe Leu Ala Arg Val Tyr Gly Ala Pro Gln Leu Gln
            740                 745                 750

Val Glu Lys Val Arg Thr Asn Asp Arg Lys Glu Leu Gly Glu Val Arg
            755                 760                 765

Val Gln Tyr Thr Gly Arg Asp Ser Phe Lys Ala Phe Ala Lys Ala Leu
            770                 775                 780

Gly Val Met Asp Asp Leu Lys Ser Gly Val Pro Arg Ala Gly Tyr Arg
785                 790                 795                 800

Gly Ile Val Thr Phe Gln Phe Arg Gly Arg Arg Val His Leu Ala Pro
            805                 810                 815

Pro Pro Thr Trp Glu Gly Tyr Asp Pro Ser Trp Asn
            820                 825

<210> SEQ ID NO 124
<211> LENGTH: 21
<212> TYPE: PRT
<213> ORGANISM: Trichoderma reesei

<400> SEQUENCE: 124

Ser Ser Ala Ala Thr Ala Thr Ala Ser Ala Thr Val Pro Gly Gly Gly
1               5                   10                  15

Ser Gly Pro Thr Ser
            20

<210> SEQ ID NO 125
<211> LENGTH: 830
<212> TYPE: PRT
<213> ORGANISM: Trichoderma reesei

<400> SEQUENCE: 125

Met Arg Phe Arg Ile Tyr Lys Arg Lys Val Leu Ile Leu Thr Leu Val
 1               5                  10                  15

Val Ala Ala Cys Gly Phe Val Leu Trp Ser Ser Asn Gly Arg Gln Arg
            20                  25                  30

Lys Asn Glu Ala Leu Ala Pro Pro Leu Leu Asp Ala Glu Pro Ala Arg
        35                  40                  45

Gly Ala Gly Gly Arg Gly Gly Asp His Pro Ser Val Ala Val Gly Ile
    50                  55                  60

Arg Arg Val Ser Asn Val Ser Ala Ala Ser Leu Val Pro Ala Val Pro
65                  70                  75                  80

Gln Pro Glu Ala Asp Asn Leu Thr Leu Arg Tyr Arg Ser Leu Val Tyr
                85                  90                  95

Gln Leu Asn Phe Asp Gln Thr Leu Arg Asn Val Asp Lys Ala Gly Thr
            100                 105                 110

Trp Ala Pro Arg Glu Leu Val Leu Val Val Gln Val His Asn Arg Pro
        115                 120                 125

Glu Tyr Leu Arg Leu Leu Leu Asp Ser Leu Arg Lys Ala Gln Gly Ile
    130                 135                 140

Asp Asn Val Leu Val Ile Phe Ser His Asp Phe Trp Ser Thr Glu Ile
145                 150                 155                 160

Asn Gln Leu Ile Ala Gly Val Asn Phe Cys Pro Val Leu Gln Val Phe
                165                 170                 175

Phe Pro Phe Ser Ile Gln Leu Tyr Pro Asn Glu Phe Pro Gly Ser Asp
            180                 185                 190

Pro Arg Asp Cys Pro Arg Asp Leu Pro Lys Asn Ala Ala Leu Lys Leu
        195                 200                 205

Gly Cys Ile Asn Ala Glu Tyr Pro Asp Ser Phe Gly His Tyr Arg Glu
    210                 215                 220

Ala Lys Phe Ser Gln Thr Lys His His Trp Trp Lys Leu His Phe
225                 230                 235                 240

Val Trp Glu Arg Val Lys Ile Leu Arg Asp Tyr Ala Gly Leu Ile Leu
                245                 250                 255

Phe Leu Glu Glu Asp His Tyr Leu Ala Pro Asp Phe Tyr His Val Phe
            260                 265                 270

Lys Lys Met Trp Lys Leu Lys Gln Gln Glu Cys Pro Glu Cys Asp Val
        275                 280                 285

Leu Ser Leu Gly Thr Tyr Ser Ala Ser Arg Ser Phe Tyr Gly Met Ala
    290                 295                 300

Asp Lys Val Asp Val Lys Thr Trp Lys Ser Thr Glu His Asn Met Gly
305                 310                 315                 320

Leu Ala Leu Thr Arg Asn Ala Tyr Gln Lys Leu Ile Glu Cys Thr Asp
                325                 330                 335

Thr Phe Cys Thr Tyr Asp Asp Tyr Asn Trp Asp Trp Thr Leu Gln Tyr
            340                 345                 350

Leu Thr Val Ser Cys Leu Pro Lys Phe Trp Lys Val Leu Val Pro Gln

```
            355                 360                 365
Ile Pro Arg Ile Phe His Ala Gly Asp Cys Gly Met His His Lys Lys
370                 375                 380

Thr Cys Arg Pro Ser Thr Gln Ser Ala Gln Ile Glu Ser Leu Leu Asn
385                 390                 395                 400

Asn Asn Lys Gln Tyr Met Phe Pro Glu Thr Leu Thr Ile Ser Glu Lys
                405                 410                 415

Phe Thr Val Val Ala Ile Ser Pro Pro Arg Lys Asn Gly Gly Trp Gly
                420                 425                 430

Asp Ile Arg Asp His Glu Leu Cys Lys Ser Tyr Arg Arg Leu Gln Ser
                435                 440                 445

Ser Ala Thr Ala Thr Ala Ser Ala Thr Val Pro Gly Gly Gly Ser
450                 455                 460

Gly Pro Thr Ser Gly Arg Val Pro Thr Ala Ala Pro Ala Gln Pro
465                 470                 475                 480

Arg Val Pro Val Thr Pro Ala Pro Ala Val Ile Pro Ile Leu Val Ile
                485                 490                 495

Ala Cys Asp Arg Ser Thr Val Arg Arg Cys Leu Asp Lys Leu Leu His
                500                 505                 510

Tyr Arg Pro Ser Ala Glu Leu Phe Pro Ile Ile Val Ser Gln Asp Cys
                515                 520                 525

Gly His Glu Glu Thr Ala Gln Ala Ile Ala Ser Tyr Gly Ser Ala Val
                530                 535                 540

Thr His Ile Arg Gln Pro Asp Leu Ser Ser Ile Ala Val Pro Pro Asp
545                 550                 555                 560

His Arg Lys Phe Gln Gly Tyr Tyr Lys Ile Ala Arg His Tyr Arg Trp
                565                 570                 575

Ala Leu Gly Gln Val Phe Arg Gln Phe Arg Phe Pro Ala Ala Val Val
                580                 585                 590

Val Glu Asp Asp Leu Glu Val Ala Pro Asp Phe Phe Glu Tyr Phe Arg
                595                 600                 605

Ala Thr Tyr Pro Leu Leu Lys Ala Asp Pro Ser Leu Trp Cys Val Ser
                610                 615                 620

Ala Trp Asn Asp Asn Gly Lys Glu Gln Met Val Asp Ala Ser Arg Pro
625                 630                 635                 640

Glu Leu Leu Tyr Arg Thr Asp Phe Phe Pro Gly Leu Gly Trp Leu Leu
                645                 650                 655

Leu Ala Glu Leu Trp Ala Glu Leu Glu Pro Lys Trp Pro Lys Ala Phe
                660                 665                 670

Trp Asp Asp Trp Met Arg Arg Pro Glu Gln Arg Gln Gly Arg Ala Cys
                675                 680                 685

Ile Arg Pro Glu Ile Ser Arg Thr Met Thr Phe Gly Arg Lys Gly Val
                690                 695                 700

Ser His Gly Gln Phe Phe Asp Gln His Leu Lys Phe Ile Lys Leu Asn
705                 710                 715                 720

Gln Gln Phe Val His Phe Thr Gln Leu Asp Leu Ser Tyr Leu Gln Arg
                725                 730                 735

Glu Ala Tyr Asp Arg Asp Phe Leu Ala Arg Val Tyr Gly Ala Pro Gln
                740                 745                 750

Leu Gln Val Glu Lys Val Arg Thr Asn Asp Arg Lys Glu Leu Gly Glu
                755                 760                 765

Val Arg Val Gln Tyr Thr Gly Arg Asp Ser Phe Lys Ala Phe Ala Lys
                770                 775                 780
```

```
Ala Leu Gly Val Met Asp Asp Leu Lys Ser Gly Val Pro Arg Ala Gly
785                 790                 795                 800

Tyr Arg Gly Ile Val Thr Phe Gln Phe Arg Gly Arg Val His Leu
            805                 810                 815

Ala Pro Pro Thr Trp Glu Gly Tyr Asp Pro Ser Trp Asn
            820                 825                 830

<210> SEQ ID NO 126
<211> LENGTH: 420
<212> TYPE: PRT
<213> ORGANISM: Trichoderma reesei

<400> SEQUENCE: 126

Met Ala Ser Leu Ile Lys Thr Ala Val Asp Ile Ala Asn Gly Arg His
1               5                   10                  15

Ala Leu Ser Arg Tyr Val Ile Phe Gly Leu Trp Leu Ala Asp Ala Val
            20                  25                  30

Leu Cys Gly Leu Ile Ile Trp Lys Val Pro Tyr Thr Glu Ile Asp Trp
        35                  40                  45

Val Ala Tyr Met Glu Gln Val Thr Gln Phe Val His Gly Glu Arg Asp
50                  55                  60

Tyr Pro Lys Met Glu Gly Gly Thr Gly Pro Leu Val Tyr Pro Ala Ala
65                  70                  75                  80

His Val Tyr Ile Tyr Thr Gly Leu Tyr Tyr Leu Thr Asn Lys Gly Thr
                85                  90                  95

Asp Ile Leu Leu Ala Gln Gln Leu Phe Ala Val Leu Tyr Met Ala Thr
            100                 105                 110

Leu Ala Val Val Met Thr Cys Tyr Ser Lys Ala Lys Val Pro Pro Tyr
        115                 120                 125

Ile Phe Pro Leu Leu Ile Leu Ser Lys Arg Leu His Ser Val Phe Val
130                 135                 140

Leu Arg Cys Phe Asn Asp Cys Phe Ala Ala Phe Phe Trp Leu Cys
145                 150                 155                 160

Ile Phe Phe Phe Gln Arg Arg Glu Trp Thr Ile Gly Ala Leu Ala Tyr
                165                 170                 175

Ser Ile Gly Leu Gly Val Lys Met Ser Leu Leu Val Leu Pro Ala
            180                 185                 190

Val Val Ile Val Leu Tyr Leu Gly Arg Gly Phe Lys Gly Ala Leu Arg
        195                 200                 205

Leu Leu Trp Leu Met Val Gln Val Gln Leu Leu Ala Ile Pro Phe
210                 215                 220

Ile Thr Thr Asn Trp Arg Gly Tyr Leu Gly Arg Ala Phe Glu Leu Ser
225                 230                 235                 240

Arg Gln Phe Lys Phe Glu Trp Thr Val Asn Trp Arg Met Leu Gly Glu
                245                 250                 255

Asp Leu Phe Leu Ser Arg Gly Phe Ser Ile Thr Leu Leu Ala Phe His
            260                 265                 270

Ala Ile Phe Leu Leu Ala Phe Ile Leu Gly Arg Trp Leu Lys Ile Arg
        275                 280                 285

Glu Arg Thr Val Leu Gly Met Ile Pro Tyr Val Ile Arg Phe Arg Ser
290                 295                 300

Pro Phe Thr Glu Gln Glu Glu Arg Ala Ile Ser Asn Arg Val Val Thr
305                 310                 315                 320

Pro Gly Tyr Val Met Ser Thr Ile Leu Ser Ala Asn Val Val Gly Leu
```

```
            325                 330                 335
Leu Phe Ala Arg Ser Leu His Tyr Gln Phe Tyr Ala Tyr Leu Ala Trp
            340                 345                 350

Ala Thr Pro Tyr Leu Leu Trp Thr Ala Cys Pro Asn Leu Leu Val Val
            355                 360                 365

Ala Pro Leu Trp Ala Ala Gln Glu Trp Ala Trp Asn Val Phe Pro Ser
            370                 375                 380

Thr Pro Leu Ser Ser Val Val Ser Val Leu Ala Val Thr Val
385                 390                 395                 400

Ala Met Ala Phe Ala Gly Ser Asn Pro Gln Pro Arg Glu Thr Ser Lys
            405                 410                 415

Pro Lys Gln His
            420

<210> SEQ ID NO 127
<211> LENGTH: 525
<212> TYPE: PRT
<213> ORGANISM: Trichoderma atroviride

<400> SEQUENCE: 127

Met Ala Ser Leu Ile Lys Phe Ala Ser Asp Val Ala Thr Gly Arg His
1               5                   10                  15

Ala Leu Ser Lys Leu Ile Pro Val Gly Leu Phe Leu Ala Asp Ala Ile
            20                  25                  30

Leu Cys Gly Leu Val Ile Trp Lys Val Pro Tyr Thr Glu Ile Asp Trp
            35                  40                  45

Thr Ala Tyr Met Glu Gln Val Thr Gln Phe Val Asn Gly Glu Arg Asp
        50                  55                  60

Tyr Pro Lys Met Glu Gly Gly Thr Gly Pro Leu Val Tyr Pro Ala Ala
65              70                  75                  80

His Val Tyr Ile Tyr Thr Gly Leu Tyr Tyr Leu Thr Asn Arg Gly Thr
            85                  90                  95

Asp Ile Leu Leu Ala Gln Gln Leu Phe Ala Val Leu Tyr Met Ala Thr
            100                 105                 110

Leu Gly Val Val Met Leu Ser Tyr Trp Lys Ala Arg Val Pro Pro Tyr
            115                 120                 125

Ile Phe Pro Leu Leu Ile Leu Ser Lys Arg Leu His Ser Val Phe Val
            130                 135                 140

Leu Arg Cys Phe Asn Asp Cys Phe Ala Ala Phe Phe Leu Trp Leu Cys
145                 150                 155                 160

Ile Tyr Ser Phe Gln Asn Arg Ala Trp Thr Phe Gly Ala Leu Ala Tyr
            165                 170                 175

Thr Leu Gly Leu Gly Val Lys Met Ser Leu Leu Leu Val Leu Pro Ala
            180                 185                 190

Val Val Ile Ile Leu Phe Leu Gly Arg Gly Phe Lys Gly Ala Leu Arg
            195                 200                 205

Leu Val Trp Leu Met Ala Gln Val Gln Leu Val Leu Ala Ile Pro Phe
            210                 215                 220

Ile Thr Thr Asn Trp Ala Gly Tyr Leu Gly Arg Ala Phe Glu Leu Ser
225                 230                 235                 240

Arg Gln Phe Lys Phe Glu Trp Thr Val Asn Trp Arg Met Met Gly Glu
            245                 250                 255

Glu Thr Phe Leu Ser Arg Gly Phe Ser Ile Thr Leu Leu Thr Phe His
            260                 265                 270
```

```
Val Val Thr Leu Leu Val Phe Ile Ala Ala Arg Trp Leu Lys Leu Gln
            275                 280                 285

Glu Arg Ser Leu Leu Gly Ile Ile Thr Tyr Ala Val Arg Phe Gln Ser
        290                 295                 300

Pro Phe Thr Glu Gln Glu Ala Lys Val Ser Lys Lys Val Val Thr
305                 310                 315                 320

Pro Arg Tyr Val Leu Ala Thr Ile Leu Ser Ala Asn Val Ile Gly Leu
                325                 330                 335

Leu Phe Ala Arg Ser Leu His Tyr Gln Phe Tyr Ala Tyr Leu Ala Trp
            340                 345                 350

Ala Thr Pro Phe Leu Leu Trp Thr Ala Tyr Pro Asn Leu Leu Val Val
        355                 360                 365

Val Pro Leu Trp Leu Ala Gln Glu Trp Ala Trp Asn Val Phe Pro Ser
    370                 375                 380

Thr Pro Leu Ser Ser Ser Val Val Ile Ser Leu Val Pro Val Cys Leu
385                 390                 395                 400

Leu Ser Pro Gln Leu Leu Val Ser His Asp Ile Tyr Asn Phe Ala Asn
                405                 410                 415

Cys Ser Ala Ile Leu Arg Pro Arg Gly Ile Ala Phe Gly Gln Asp Ile
            420                 425                 430

Ser Ala Thr Leu Asn Pro Asp Gly Val Ala Lys Pro Leu Gly Glu Leu
        435                 440                 445

Glu Asn Asp Gly Leu Arg Val Trp His Leu Ala Ser Val Gln Val Val
    450                 455                 460

Ser Phe Gly Leu His His Ala His Asn Glu Leu Gly Gly Leu Gln Phe
465                 470                 475                 480

Gly Trp Trp Arg Glu Arg Phe Leu Arg Gly Gly Glu Asp Val Ala Leu
                485                 490                 495

Trp Phe Ala His Gly Gly Phe Glu Phe Arg Phe Ser Glu Leu Leu
            500                 505                 510

Val Arg Leu Ala Asp Thr Ser Asp Ile Lys Lys Ser Phe
        515                 520                 525

<210> SEQ ID NO 128
<211> LENGTH: 419
<212> TYPE: PRT
<213> ORGANISM: Trichoderma virens

<400> SEQUENCE: 128

Met Ala Ser Leu Ile Lys Phe Ala Ser Asp Val Ala Asn Gly Arg His
1               5                   10                  15

Ala Leu Ser Lys Phe Ile Pro Met Gly Leu Trp Leu Ala Asp Ala Val
            20                  25                  30

Leu Cys Gly Leu Ile Ile Trp Lys Val Pro Tyr Thr Glu Ile Asp Trp
        35                  40                  45

Val Ala Tyr Met Glu Gln Ile Thr Gln Phe Val His Gly Glu Arg Asp
    50                  55                  60

Tyr Pro Lys Met Glu Gly Gly Thr Gly Pro Leu Val Tyr Pro Ala Ala
65                  70                  75                  80

His Val Tyr Ile Tyr Thr Gly Leu Tyr Leu Thr Asn Lys Gly Thr
                85                  90                  95

Asp Ile Leu Leu Ala Gln Gln Leu Phe Ala Val Leu Tyr Met Ala Thr
            100                 105                 110

Leu Gly Val Val Met Leu Cys Tyr Trp Lys Ala Lys Val Pro Pro Tyr
        115                 120                 125
```

-continued

```
Ile Phe Pro Leu Leu Ile Leu Ser Lys Arg Leu His Ser Val Phe Val
        130                 135                 140
Leu Arg Cys Phe Asn Asp Cys Phe Ala Ala Phe Leu Trp Leu Ser
145                 150                 155                 160
Ile Phe Phe Phe Gln Arg Arg Val Trp Thr Leu Gly Ala Ile Ala Tyr
                165                 170                 175
Thr Ile Gly Leu Gly Val Lys Met Ser Leu Leu Val Leu Pro Ala
        180                 185                 190
Val Val Ile Val Leu Phe Leu Gly Arg Gly Phe Lys Gly Ala Leu Arg
                195                 200                 205
Leu Leu Trp Leu Met Val Gln Val Gln Leu Leu Ala Ile Pro Phe
210                 215                 220
Ile Thr Thr Asn Trp Lys Gly Tyr Leu Gly Arg Ala Phe Glu Leu Ser
225                 230                 235                 240
Arg Gln Phe Lys Phe Glu Trp Thr Val Asn Trp Arg Met Leu Gly Glu
                245                 250                 255
Glu Leu Phe Leu Ser Arg Gly Phe Ser Ile Thr Leu Leu Ala Phe His
                260                 265                 270
Ala Leu Phe Leu Leu Ile Phe Ile Leu Gly Arg Trp Leu Arg Ile Lys
        275                 280                 285
Glu Arg Ser Phe Leu Gly Met Ile Pro Tyr Val Leu Arg Phe Thr Ser
290                 295                 300
Pro Phe Thr Glu His Glu Glu Ala Ser Ile Ser His Arg Val Val Thr
305                 310                 315                 320
Pro Glu Tyr Ile Met Ser Ala Met Leu Ser Ala Asn Val Val Gly Leu
                325                 330                 335
Leu Phe Ala Arg Ser Leu His Tyr Gln Phe Tyr Ala Tyr Leu Ala Trp
                340                 345                 350
Ala Thr Pro Phe Leu Leu Trp Thr Ala Ser Pro Asn Leu Leu Val Val
                355                 360                 365
Val Pro Leu Trp Ala Ala Gln Glu Trp Ala Trp Asn Val Phe Pro Ser
370                 375                 380
Thr Pro Leu Ser Ser Asn Val Val Val Ser Val Leu Ala Val Thr Val
385                 390                 395                 400
Ala Met Ala Phe Val Gly Ser Asn Pro Gln Arg Gly Ala Pro Lys Pro
                405                 410                 415
Lys Gln Leu
```

<210> SEQ ID NO 129
<211> LENGTH: 434
<212> TYPE: PRT
<213> ORGANISM: Fusarium oxysporum

<400> SEQUENCE: 129

```
Met Pro Glu Ser Ala Ser Gly Thr Leu Ser Gln Gly Val Arg Phe Leu
1               5                   10                  15
Arg Asn Val Leu Asn Gly Arg His Ala Leu Ser Lys Leu Ile Pro Ile
            20                  25                  30
Ala Leu Trp Leu Val Asp Ala Leu Gly Cys Gly Leu Ile Ile Trp Lys
        35                  40                  45
Ile Pro Tyr Thr Glu Ile Asp Trp Val Ala Tyr Met Gln Gln Ile Ser
    50                  55                  60
Gln Phe Val Ser Gly Glu Arg Asp Tyr Thr Lys Met Glu Gly Asp Thr
65                  70                  75                  80
```

Gly Pro Leu Val Tyr Pro Ala Ala His Val Tyr Thr Tyr Thr Gly Leu
                85                  90                  95

Tyr Tyr Ile Thr Asp Lys Gly Thr Asn Ile Leu Leu Ala Gln Gln Ile
            100                 105                 110

Phe Ala Val Leu Tyr Met Ala Thr Leu Ala Val Val Met Leu Cys Tyr
        115                 120                 125

Trp Lys Ala Lys Val Pro Pro Tyr Met Phe Ile Phe Leu Ile Ala Ser
130                 135                 140

Lys Arg Leu His Ser Leu Phe Val Leu Arg Cys Phe Asn Asp Cys Phe
145                 150                 155                 160

Ala Val Phe Phe Leu Trp Leu Thr Ile Phe Leu Phe Gln Arg Arg Gln
                165                 170                 175

Trp Thr Val Gly Ser Leu Val Tyr Ser Trp Gly Leu Gly Ile Lys Met
            180                 185                 190

Ser Leu Leu Leu Val Leu Pro Ala Ile Gly Val Ile Leu Phe Leu Gly
        195                 200                 205

Arg Gly Leu Trp Pro Ser Leu Arg Leu Ala Trp Leu Met Ala Gln Ile
210                 215                 220

Gln Phe Ala Ile Gly Leu Pro Phe Ile Thr Lys Asn Pro Arg Gly Tyr
225                 230                 235                 240

Ala Ala Arg Ala Phe Glu Leu Ser Arg Gln Phe Gln Phe Lys Trp Thr
                245                 250                 255

Val Asn Trp Arg Met Leu Gly Glu Val Phe Leu Ser Lys Tyr Phe
            260                 265                 270

Ala Leu Ser Leu Leu Ala Cys His Ile Leu Val Leu Leu Ile Phe Ile
        275                 280                 285

Ser Lys Arg Trp Ile Gln Pro Thr Gly Arg Ser Leu Tyr Asp Leu Ile
290                 295                 300

Pro Ser Phe Leu Arg Leu Lys Ser Pro Phe Thr Met Gln Glu Gln Leu
305                 310                 315                 320

Arg Ile Ser His Tyr Val Thr Pro Glu Tyr Ala Met Thr Thr Met Leu
                325                 330                 335

Thr Ala Asn Leu Ile Gly Leu Leu Phe Ala Arg Ser Leu His Tyr Gln
            340                 345                 350

Phe Tyr Ala Tyr Leu Ala Trp Ala Thr Pro Tyr Leu Leu Trp Arg Ala
        355                 360                 365

Thr Glu Asp Pro Val Ile Val Ala Ile Ile Trp Ala Ala Gln Glu Trp
370                 375                 380

Ala Trp Asn Val Tyr Pro Ser Thr Asp Leu Ser Ser Thr Ile Ala Val
385                 390                 395                 400

Asn Thr Met Leu Ala Thr Val Val Leu Val Tyr Leu Gly Thr Ala Arg
                405                 410                 415

Arg Ala Val Pro Ala Pro Ala Ala Gln Val Gly Asn Val Asp Asp Lys
            420                 425                 430

Asn Lys

<210> SEQ ID NO 130
<211> LENGTH: 432
<212> TYPE: PRT
<213> ORGANISM: Gibberella zeae

<400> SEQUENCE: 130

Met Ala Asp Pro Ala Pro Gly Ala Leu Ala Arg Gly Thr Arg Phe Val
1               5                   10                  15

```
Arg Asn Val Leu Thr Gly Gln His Ala Leu Ser Lys Leu Ile Pro Val
            20                  25                  30

Ala Leu Trp Leu Ala Asp Ala Val Gly Thr Ser Leu Ile Ile Trp Lys
        35                  40                  45

Val Pro Tyr Thr Glu Ile Asp Trp Glu Ala Tyr Met Gln Gln Val Ser
50                  55                  60

Gln Phe Ile Ser Gly Glu Arg Asp Tyr Thr Lys Ile Glu Gly Gly Thr
65                  70                  75                  80

Gly Pro Leu Val Tyr Pro Ala Ala His Val Tyr Thr Phe Thr Gly Leu
                85                  90                  95

Tyr His Ile Thr Asn Glu Gly Glu Asn Ile Phe Leu Ala Gln Gln Ile
                100                 105                 110

Phe Gly Val Leu Tyr Met Ala Thr Leu Ala Val Val Met Leu Cys Tyr
            115                 120                 125

Trp Lys Ala Lys Val Pro Pro Tyr Met Phe Val Phe Leu Ile Ala Ser
130                 135                 140

Lys Arg Leu His Ser Leu Phe Val Leu Arg Cys Phe Asn Asp Cys Phe
145                 150                 155                 160

Ala Val Phe Phe Leu Trp Leu Ser Ile Tyr Phe Phe Gln Arg Arg Asn
                165                 170                 175

Trp Thr Phe Gly Ser Leu Ala Tyr Thr Trp Gly Leu Gly Ile Lys Met
            180                 185                 190

Ser Leu Leu Leu Val Leu Pro Ala Ile Gly Val Ile Leu Leu Leu Gly
            195                 200                 205

Arg Gly Phe Trp Pro Gly Leu Arg Leu Ala Trp Leu Met Ala Gln Val
210                 215                 220

Gln Phe Ala Ile Gly Ile Pro Phe Ile Met Lys Asn Ser Arg Gly Tyr
225                 230                 235                 240

Ala Ala Arg Ala Phe Glu Leu Ser Arg Glu Phe Lys Phe Glu Trp Thr
                245                 250                 255

Val Asn Trp Arg Met Leu Gly Glu Glu Val Phe Leu Ser Lys Ser Phe
            260                 265                 270

Ala Ile Phe Leu Leu Ala Cys His Val Thr Ala Leu Leu Val Phe Ile
            275                 280                 285

Ser Gln Arg Trp Leu Gln Pro Thr Gly Arg Pro Leu Ser Ala Met Ile
290                 295                 300

Pro Ser Phe Leu Gln Leu Lys Ser Pro Phe Thr Leu Gln Glu Gln Leu
305                 310                 315                 320

Arg Ile Ser His Tyr Val Thr Pro Glu Tyr Val Met Thr Thr Met Leu
                325                 330                 335

Ser Ala Asn Val Ile Gly Leu Leu Phe Ala Arg Ser Leu His Tyr Gln
            340                 345                 350

Phe Tyr Ala Tyr Leu Ala Trp Ala Ser Pro Tyr Leu Ile Trp Arg Ala
            355                 360                 365

Thr Glu Asp Pro Phe Ile Val Leu Leu Ile Trp Ala Ala Gln Glu Trp
            370                 375                 380

Ala Trp Asn Val Phe Pro Ser Thr Asp Leu Ser Ser Arg Val Thr Val
385                 390                 395                 400

Gly Ala Met Leu Ala Thr Val Val Leu Ala Tyr Arg Gly Thr Ala Arg
                405                 410                 415

Leu Ala Val Pro Pro Ser Gln Ala Arg Lys Ile Glu Ala Lys Asn Lys
            420                 425                 430
```

<210> SEQ ID NO 131
<211> LENGTH: 446
<212> TYPE: PRT
<213> ORGANISM: Myceliophthora thermophila

<400> SEQUENCE: 131

```
Met Thr Arg Met Arg Ser Ser Pro Lys Thr Pro Ala Thr Met Ala
 1               5                  10                  15

Asp Gln Asn Arg Pro Ile His Ile Arg Ala Thr Arg Leu Val Phe Asp
                20                  25                  30

Ile Leu Asn Gly Arg His Val Leu Ser Lys Leu Ile Pro Pro Leu Val
                35                  40                  45

Phe Leu Ala Asp Ala Leu Leu Cys Ala Leu Ile Ile Trp Lys Val Pro
 50                  55                  60

Tyr Thr Glu Ile Asp Trp Asn Ala Tyr Met Glu Gln Val Ala Gln Ile
 65                  70                  75                  80

Leu Ser Gly Glu Arg Asp Tyr Thr Lys Ile Arg Gly Asn Thr Gly Pro
                85                  90                  95

Leu Val Tyr Pro Ala Ala His Val Tyr Ile Tyr Thr Gly Leu Tyr His
                100                 105                 110

Leu Thr Asp Glu Gly Arg Asn Ile Leu Thr Ala Gln Lys Leu Phe Gly
                115                 120                 125

Phe Leu Tyr Met Val Thr Leu Ala Val Val Met Ala Cys Tyr Trp Gln
130                 135                 140

Ala Lys Val Pro Pro Tyr Val Phe Pro Leu Leu Ile Leu Ser Lys Arg
145                 150                 155                 160

Leu His Ser Ile Phe Val Leu Arg Cys Phe Asn Asp Cys Phe Ala Thr
                165                 170                 175

Leu Phe Leu Trp Leu Ala Ile Phe Ala Leu Gln Arg Arg Ala Trp Arg
                180                 185                 190

Thr Gly Ala Leu Met Tyr Thr Leu Gly Leu Gly Val Lys Met Ser Leu
                195                 200                 205

Leu Leu Val Leu Pro Ala Val Gly Val Val Leu Leu Gly Ala Gly
                210                 215                 220

Phe Ala Thr Ser Leu Arg Leu Ala Ala Val Ile Gly Leu Val Gln Val
225                 230                 235                 240

Leu Ile Ala Val Pro Phe Leu Ser Asn Asn Pro Trp Gly Tyr Leu Gly
                245                 250                 255

Arg Ala Phe Glu Leu Ser Arg Gln Phe Phe Lys Trp Thr Val Asn
                260                 265                 270

Trp Arg Phe Val Gly Glu Glu Val Phe Leu Ser Lys Glu Phe Ser Leu
                275                 280                 285

Ala Leu Leu Gly Leu His Val Ala Leu Ala Ile Phe Val Thr Thr
                290                 295                 300

Arg Trp Leu Lys Pro Ala Arg Lys Pro Val Ser Gln Leu Ile Val Pro
305                 310                 315                 320

Ile Leu Leu Gly Lys Ser Pro Phe Thr Glu Glu Gln Arg Ala Val
                325                 330                 335

Ser Arg Asp Val Thr Pro Arg Phe Ile Leu Thr Ser Ile Leu Ser Ala
                340                 345                 350

Asn Val Val Gly Leu Leu Phe Ala Arg Ser Leu His Tyr Gln Phe Tyr
                355                 360                 365

Ser Tyr Leu Ala Trp Met Thr Pro Tyr Leu Leu Trp Arg Ser Gly Val
370                 375                 380
```

```
His Pro Ile Leu Gln Tyr Ala Ile Trp Thr Ala Gln Glu Trp Ala Trp
385                 390                 395                 400

Asn Val Tyr Pro Ser Thr Pro Ile Ser Ser Gly Val Val Gly Val
            405                 410                 415

Leu Ala Leu Thr Ala Ala Leu Val Trp Leu Gly Ala Arg Glu Asp Trp
            420                 425                 430

Glu Pro Arg Arg Val Leu Leu Lys Gly Glu Ala Ala Lys Arg
            435                 440                 445

<210> SEQ ID NO 132
<211> LENGTH: 442
<212> TYPE: PRT
<213> ORGANISM: Neurospora crassa

<400> SEQUENCE: 132

Met Ala Ala Pro Ser Ser Arg Pro Glu Ser Asn Pro Pro Leu Tyr Lys
1               5                   10                  15

Gln Ala Leu Asp Phe Ala Leu Asp Val Ala Asn Gly Arg His Ala Leu
            20                  25                  30

Ser Lys Leu Ile Pro Pro Ala Leu Phe Leu Val Asp Ala Leu Leu Cys
        35                  40                  45

Gly Leu Ile Ile Trp Lys Val Pro Tyr Thr Glu Ile Asp Trp Ala Ala
50                  55                  60

Tyr Met Glu Gln Val Ser Gln Ile Leu Ser Gly Glu Arg Asp Tyr Thr
65                  70                  75                  80

Lys Val Arg Gly Gly Thr Gly Pro Leu Val Tyr Pro Ala Ala His Val
                85                  90                  95

Tyr Ile Tyr Thr Gly Leu Tyr His Leu Thr Asp Glu Gly Arg Asn Ile
            100                 105                 110

Leu Leu Ala Gln Gln Leu Phe Ala Gly Leu Tyr Met Val Thr Leu Ala
        115                 120                 125

Val Val Met Gly Cys Tyr Trp Gln Ala Lys Ala Pro Pro Tyr Leu Phe
130                 135                 140

Pro Leu Leu Thr Leu Ser Lys Arg Leu His Ser Ile Phe Val Leu Arg
145                 150                 155                 160

Cys Phe Asn Asp Cys Phe Ala Val Leu Phe Leu Trp Leu Ala Ile Phe
                165                 170                 175

Phe Phe Gln Arg Arg Asn Trp Gln Ala Gly Ala Leu Leu Tyr Thr Leu
            180                 185                 190

Gly Leu Gly Val Lys Met Thr Leu Leu Ser Leu Pro Ala Val Gly
        195                 200                 205

Ile Val Leu Phe Leu Gly Ser Gly Ser Phe Val Thr Thr Leu Gln Leu
210                 215                 220

Val Ala Thr Met Gly Leu Val Gln Ile Leu Ile Gly Val Pro Phe Leu
225                 230                 235                 240

Ala His Tyr Pro Thr Glu Tyr Leu Ser Arg Ala Phe Glu Leu Ser Arg
                245                 250                 255

Gln Phe Phe Lys Trp Thr Val Asn Trp Arg Phe Val Gly Glu Glu
            260                 265                 270

Ile Phe Leu Ser Lys Gly Phe Ala Leu Thr Leu Leu Ala Leu His Val
            275                 280                 285

Leu Val Leu Gly Ile Phe Ile Thr Thr Arg Trp Ile Lys Pro Ala Arg
        290                 295                 300

Lys Ser Leu Val Gln Leu Ile Ser Pro Val Leu Leu Ala Gly Lys Pro
```

```
                305                 310                 315                 320
Pro Leu Thr Val Pro Glu His Arg Ala Ala Arg Asp Val Thr Pro
                325                 330                 335
Arg Tyr Ile Met Thr Thr Ile Leu Ser Ala Asn Ala Val Gly Leu Leu
                340                 345                 350
Phe Ala Arg Ser Leu His Tyr Gln Phe Tyr Ala Tyr Val Ala Trp Ser
                355                 360                 365
Thr Pro Phe Leu Leu Trp Arg Ala Gly Leu His Pro Val Leu Val Tyr
370                 375                 380
Leu Leu Trp Ala Val His Glu Trp Ala Trp Asn Val Phe Pro Ser Thr
385                 390                 395                 400
Pro Ala Ser Ser Ala Val Val Gly Val Leu Gly Val Thr Val Ala
                405                 410                 415
Gly Val Trp Phe Gly Ala Arg Glu Glu Trp Pro Gly Met Lys Ser
                420                 425                 430
Ser Ser Lys Lys Glu Glu Ala Ala Met Arg
                435                 440
```

<210> SEQ ID NO 133
<211> LENGTH: 413
<212> TYPE: PRT
<213> ORGANISM: Aspergillus oryzae

<400> SEQUENCE: 133

```
Met Glu Leu Lys His Phe Ile His Glu Leu Cys Leu Asn Pro Arg His
1               5                   10                  15
Thr Lys Trp Ile Ala Pro Leu Leu Val Ile Gly Asp Ala Phe Leu Cys
                20                  25                  30
Ala Leu Ile Ile Trp Lys Ile Pro Tyr Thr Glu Ile Asp Trp Thr Thr
            35                  40                  45
Tyr Met Gln Gln Ile Ala Leu Tyr Ile Ser Gly Glu Arg Asp Tyr Thr
        50                  55                  60
Leu Ile Lys Gly Ser Thr Gly Pro Leu Val Tyr Pro Ala Ala His Val
65                  70                  75                  80
Tyr Ser Tyr Met Ala Leu Tyr His Leu Thr Asp Glu Gly Arg Asp Ile
                85                  90                  95
Leu Phe Gly Gln Ile Leu Phe Ala Val Leu Tyr Leu Val Thr Leu Ala
                100                 105                 110
Val Val Met Val Cys Tyr Arg Gln Ser Gly Ala Pro Pro Tyr Leu Phe
                115                 120                 125
Pro Leu Leu Val Leu Ser Lys Arg Leu His Ser Val Phe Val Leu Arg
                130                 135                 140
Leu Phe Asn Asp Gly Leu Ala Val Cys Ala Met Trp Ile Ala Ile Leu
145                 150                 155                 160
Leu Phe Gln Asn Lys Lys Trp Thr Ala Gly Val Thr Ala Trp Thr Val
                165                 170                 175
Gly Val Gly Ile Lys Met Thr Leu Leu Leu Ala Pro Ala Ile Ala
                180                 185                 190
Val Val Thr Val Leu Ser Leu Ser Leu Val Pro Ser Ile Arg Leu Gly
                195                 200                 205
Ile Leu Ala Leu Leu Ile Gln Val Leu Leu Ala Ile Pro Phe Leu Gln
            210                 215                 220
Gly Asn Pro Ile Gly Tyr Val Ala Arg Ala Phe Glu Leu Thr Arg Gln
225                 230                 235                 240
```

-continued

```
Phe Met Phe Lys Trp Thr Val Asn Trp Arg Phe Val Gly Glu Asp Leu
            245                 250                 255

Phe Leu Ser Lys Gln Phe Ser Leu Ala Leu Leu Gly Leu His Ile Phe
        260                 265                 270

Leu Leu Gly Leu Phe Val Thr Thr Gly Trp Leu Arg Pro Ser Gly Ser
    275                 280                 285

Asn Val Pro Asp Phe Leu Arg Ser Leu Leu Gln Gly Arg Gln Arg Thr
290                 295                 300

Val Val Leu Ser Lys Ser Phe Ile Met Thr Val Met Leu Thr Ser Leu
305                 310                 315                 320

Ala Ile Gly Leu Leu Cys Ala Arg Ser Leu His Tyr Gln Phe Phe Ala
                325                 330                 335

Tyr Leu Ser Trp Ala Thr Pro Cys Leu Leu Trp Arg Ala Arg Leu His
            340                 345                 350

Pro Ile Leu Ile Tyr Ala Ile Trp Ala Leu Gln Glu Trp Ala Trp Asn
        355                 360                 365

Val Tyr Pro Ser Thr Asn Ala Ser Ser Val Val Phe Ser Leu
    370                 375                 380

Ala Val Gln Val Phe Gly Val Leu Leu Asn Ser Arg Asn Ala Leu Ser
385                 390                 395                 400

Asp Ala Pro Pro Arg Arg Lys Gly Lys Glu His Ile Gln
                405                 410
```

```
<210> SEQ ID NO 134
<211> LENGTH: 411
<212> TYPE: PRT
<213> ORGANISM: Neosartorya fischeri

<400> SEQUENCE: 134
```

```
Met Asp Leu Lys His Thr Leu Arg Asp Leu Cys Met Asn Pro Arg His
  1               5                  10                  15

Thr Arg Trp Val Ala Pro Leu Leu Ile Leu Gly Asp Ala Val Leu Cys
             20                  25                  30

Ala Leu Ile Ile Trp Lys Val Pro Tyr Thr Glu Ile Asp Trp Thr Thr
         35                  40                  45

Tyr Met Gln Gln Ile Ser Leu Tyr Ile Ser Gly Glu Arg Asp Tyr Thr
     50                  55                  60

Leu Ile Lys Gly Ser Thr Gly Pro Leu Val Tyr Pro Ala Ala His Val
 65                  70                  75                  80

Tyr Ile Phe Asn Ile Leu Tyr His Leu Thr Asp Glu Gly Arg Asp Ile
                 85                  90                  95

Phe Leu Gly Gln Ile Leu Phe Ala Ile Leu Tyr Leu Ala Thr Leu Thr
            100                 105                 110

Val Ala Met Thr Cys Tyr Arg Gln Ala Gly Ala Pro Pro Tyr Leu Leu
        115                 120                 125

Val Pro Leu Val Leu Ser Lys Arg Leu His Ser Val Phe Met Leu Arg
    130                 135                 140

Leu Phe Asn Asp Gly Phe Ala Ala Tyr Ala Met Trp Val Ser Ile Leu
145                 150                 155                 160

Leu Phe Met Asn Lys Lys Trp Thr Ala Gly Ala Ile Val Trp Ser Thr
                165                 170                 175

Gly Val Gly Ile Lys Met Thr Leu Leu Leu Ala Pro Ala Ile Ala
            180                 185                 190

Val Val Leu Val Leu Ser Leu Ser Leu Gly Pro Ser Met Gln Leu Gly
        195                 200                 205
```

```
Phe Leu Ala Val Leu Ile Gln Val Leu Phe Gly Ile Pro Phe Leu Gln
    210                 215                 220

Asn Asn Pro Ala Gly Tyr Val Ser Arg Ala Phe Glu Leu Thr Arg Gln
225                 230                 235                 240

Phe Met Phe Lys Trp Thr Val Asn Trp Arg Phe Val Gly Glu Leu
            245                 250                 255

Phe Leu Ser Arg Lys Phe Ser Leu Ala Leu Leu Ala Leu His Ile Leu
            260                 265                 270

Leu Leu Gly Leu Phe Val Ala Thr Val Trp Leu Lys Pro Ser Gly Ser
        275                 280                 285

Asp Leu Pro Ser Phe Leu Gln Arg Leu Ile Gln Arg Arg Tyr Arg Thr
    290                 295                 300

Ala Ser Leu Ser Lys Ser Phe Ile Met Thr Ala Met Leu Ser Ser Leu
305                 310                 315                 320

Ala Ile Gly Leu Leu Cys Ala Arg Ser Leu His Tyr Gln Phe Phe Ala
            325                 330                 335

Tyr Leu Ala Cys Ala Thr Pro Phe Leu Leu Trp Gln Ala Gly Phe His
            340                 345                 350

Pro Ile Leu Val Tyr Val Val Trp Val Ala Gln Glu Trp Ala Trp Asn
        355                 360                 365

Thr Tyr Pro Ser Thr Asn Ala Ser Ser Leu Val Ile Leu Ser Leu
    370                 375                 380

Ala Ala Gln Val Phe Gly Val Leu Gly Asn Ser Phe Ser Arg Lys His
385                 390                 395                 400

Leu Asp Gln Ser Ser Gln Lys Glu His Leu Gln
            405                 410

<210> SEQ ID NO 135
<211> LENGTH: 413
<212> TYPE: PRT
<213> ORGANISM: Aspergillus niger

<400> SEQUENCE: 135

Met Asp Trp Met Arg Leu Ile Arg Asp Leu Cys Phe Asn Pro Arg His
 1               5                  10                  15

Thr Lys Trp Met Ala Pro Leu Leu Val Leu Gly Asp Ala Phe Leu Cys
            20                  25                  30

Ala Leu Ile Ile Trp Lys Val Pro Tyr Thr Glu Ile Asp Trp Ala Thr
        35                  40                  45

Tyr Met Gln Gln Ile Ser Leu Tyr Leu Ser Gly Glu Arg Asp Tyr Thr
    50                  55                  60

Leu Ile Arg Gly Ser Thr Gly Pro Leu Val Tyr Pro Ala Ala His Val
65                  70                  75                  80

Tyr Ser Tyr Thr Ala Leu Tyr His Leu Thr Asp Glu Gly Arg Asp Ile
                85                  90                  95

Phe Phe Gly Gln Ile Leu Phe Ala Val Leu Tyr Leu Ile Thr Leu Val
            100                 105                 110

Val Val Leu Cys Cys Tyr Arg Gln Ser Gly Ala Pro Pro Tyr Leu Leu
        115                 120                 125

Pro Leu Leu Val Leu Ser Lys Arg Leu His Ser Val Tyr Val Leu Arg
    130                 135                 140

Leu Phe Asn Asp Gly Leu Ala Ala Leu Ala Met Trp Val Ala Ile Leu
145                 150                 155                 160

Leu Phe Met Asn Arg Lys Trp Thr Ala Ala Val Ala Val Trp Ser Thr
```

```
                165                 170                 175

Gly Val Ala Ile Lys Met Thr Leu Leu Leu Leu Ala Pro Ala Ile Ala
            180                 185                 190

Val Val Thr Val Leu Ser Leu Ser Leu Gly Pro Ser Val Gly Leu Gly
        195                 200                 205

Val Leu Ala Val Leu Val Gln Val Leu Leu Ala Ile Pro Phe Leu Gln
    210                 215                 220

Asn Asn Pro Ala Gly Tyr Leu Ser Arg Ala Phe Glu Leu Thr Arg Gln
225                 230                 235                 240

Phe Met Phe Lys Trp Thr Val Asn Trp Arg Phe Val Gly Glu Glu Val
                245                 250                 255

Phe Leu Ser Lys Ser Phe Ser Leu Ala Leu Leu Ala Val His Ile Val
            260                 265                 270

Leu Leu Gly Ala Phe Ala Val Thr Gly Trp Leu Arg Tyr Ser Arg Ser
        275                 280                 285

Ser Leu Pro Ala Phe Ile Arg Asn Leu Leu Ala Gly Arg His Arg Thr
    290                 295                 300

Val Ser Leu Pro Lys Pro Tyr Ile Met Ser Val Met Leu Ser Ser Leu
305                 310                 315                 320

Thr Val Gly Leu Leu Cys Ala Arg Ser Leu His Tyr Gln Phe Phe Ala
                325                 330                 335

Tyr Leu Ser Trp Ala Thr Pro Phe Leu Leu Trp Arg Ala Gly Phe His
            340                 345                 350

Pro Ile Leu Leu Tyr Leu Ile Trp Ala Met Gln Glu Trp Ala Trp Asn
        355                 360                 365

Thr Phe Pro Ser Thr Asn Leu Ser Ser Ile Ile Val Val Leu Ser Leu
    370                 375                 380

Ala Thr Gln Ser Phe Gly Val Leu Ala Asn Ser Ala Ser Ala Phe Tyr
385                 390                 395                 400

Thr Met Arg Ser Asn Pro Ser Gly Lys Glu His Asn Gln
                405                 410

<210> SEQ ID NO 136
<211> LENGTH: 357
<212> TYPE: PRT
<213> ORGANISM: Magnaporthe oryzae

<400> SEQUENCE: 136

Met Ala Ala Glu Arg Pro Ser Thr Leu Gly Lys Pro Val Gln Phe Val
 1               5                  10                  15

Phe Asp Val Ala Asn Gly Arg His Pro Leu Ser Arg Ala Ile Pro Pro
            20                  25                  30

Met Leu Leu Ala Phe Asp Gly Leu Leu Cys Gly Leu Ile Ile Lys Lys
        35                  40                  45

Val Pro Ser Cys Tyr Arg Lys Ala Lys Val Pro Pro Tyr Val Leu Pro
    50                  55                  60

Leu Leu Val Leu Ser Lys Arg Leu His Ser Ile Phe Val Leu Arg Cys
65                  70                  75                  80

Phe Asn Asp Cys Phe Ala Val Leu Phe Phe Trp Leu Ala Ile Tyr Cys
                85                  90                  95

Phe Gln Arg Arg Ala Trp Ser Leu Gly Gly Val Phe Tyr Ser Phe Gly
            100                 105                 110

Leu Gly Ile Lys Met Thr Val Leu Leu Ser Leu Pro Ala Val Gly Val
        115                 120                 125
```

```
Ile Leu Leu Gly Arg Gly Phe Gly Ala Leu Asn Val Ala Ser
    130                 135                 140

Ile Met Gly Gln Leu Gln Val Ala Ile Gly Leu Pro Phe Leu Ser Lys
145                 150                 155                 160

Asn Ala Trp Gly Tyr Leu Ser Arg Ala Phe Glu Leu Ser Arg Gln Phe
                165                 170                 175

Met Phe Lys Trp Thr Val Asn Trp Arg Phe Val Gly Glu Glu Thr Phe
            180                 185                 190

Leu Ser Lys Pro Phe Ala Ile Thr Leu Ala Leu His Ala Ser Val
        195                 200                 205

Leu Leu Ala Phe Val Thr Lys Arg Trp Leu Lys Pro Ala Ser Lys Ser
    210                 215                 220

Ile Gly Gly Leu Ile Ala Pro Leu Leu Ser Gly Arg Pro Ile Phe Thr
225                 230                 235                 240

Ala Glu Glu Ala Gln Thr Ala Ala Arg Ala Val Thr Pro Glu Tyr Val
                245                 250                 255

Met Thr Thr Met Leu Thr Ala Asn Ile Val Gly Met Leu Phe Ala Arg
            260                 265                 270

Ser Leu His Tyr Gln Phe Tyr Ala Tyr Leu Ala Trp Ser Thr Pro Tyr
        275                 280                 285

Leu Leu Trp Arg Ser Gly Ile His Pro Leu Leu Gln Trp Gly Leu Trp
    290                 295                 300

Ala Leu Gln Glu Trp Ala Trp Asn Val Tyr Pro Ser Thr Pro Val Ser
305                 310                 315                 320

Ser Gly Val Val Val Gly Val Met Ala Ile Thr Val Gly Ala Val Met
                325                 330                 335

Val Gly Ala Lys Ala Glu Phe Arg Pro Gln Val Pro Val Ala Lys Lys
            340                 345                 350

Val Glu Ala Lys Arg
        355

<210> SEQ ID NO 137
<211> LENGTH: 406
<212> TYPE: PRT
<213> ORGANISM: Schizosaccharomyces pombe

<400> SEQUENCE: 137

Met Ser Ser Val Glu Thr Arg Asn Ser Phe Asn Pro Phe Arg Val Leu
1               5                   10                  15

Phe Asp Leu Gly Ser Tyr Gly Trp Leu His Pro Ser Arg Leu Leu Leu
            20                  25                  30

Leu Glu Ile Pro Phe Val Phe Ala Ile Ile Ser Lys Val Pro Tyr Thr
        35                  40                  45

Glu Ile Asp Trp Ile Ala Tyr Met Glu Gln Val Asn Ser Phe Leu Leu
    50                  55                  60

Gly Glu Arg Asp Tyr Lys Ser Leu Val Gly Cys Thr Gly Pro Leu Val
65                  70                  75                  80

Tyr Pro Gly Gly His Val Phe Leu Tyr Thr Leu Leu Tyr Tyr Leu Thr
                85                  90                  95

Asp Gly Gly Thr Asn Ile Val Arg Ala Gln Tyr Ile Phe Ala Phe Val
            100                 105                 110

Tyr Trp Ile Thr Thr Ala Ile Val Gly Tyr Leu Phe Lys Ile Val Arg
        115                 120                 125

Ala Pro Phe Tyr Ile Tyr Val Leu Leu Ile Leu Ser Lys Arg Leu His
    130                 135                 140
```

| | | | | | | | | | | | | | | |
|---|---|---|---|---|---|---|---|---|---|---|---|---|---|---|
| Ser | Ile | Phe | Ile | Leu | Arg | Leu | Phe | Asn | Asp | Gly | Phe | Asn | Ser | Leu | Phe |
| 145 | | | | | 150 | | | | | 155 | | | | | 160 |

Ser Ile Phe Ile Leu Arg Leu Phe Asn Asp Gly Phe Asn Ser Leu Phe
145                 150                 155                 160

Ser Ser Leu Phe Ile Leu Ser Ser Cys Lys Lys Trp Val Arg Ala
            165                 170                 175

Ser Ile Leu Leu Ser Val Ala Cys Ser Val Lys Met Ser Ser Leu Leu
        180                 185                 190

Tyr Val Pro Ala Tyr Leu Val Leu Leu Gln Ile Leu Gly Pro Lys
            195                 200                 205

Lys Thr Trp Met His Ile Phe Val Ile Ile Val Gln Ile Leu Phe
210                 215                 220

Ser Ile Pro Phe Leu Ala Tyr Phe Trp Ser Tyr Trp Thr Gln Ala Phe
225                 230                 235                 240

Asp Phe Gly Arg Ala Phe Asp Tyr Lys Trp Thr Val Asn Trp Arg Phe
            245                 250                 255

Ile Pro Arg Ser Ile Phe Glu Ser Thr Ser Phe Ser Thr Ser Ile Leu
            260                 265                 270

Phe Leu His Val Ala Leu Leu Val Ala Phe Thr Cys Lys His Trp Asn
        275                 280                 285

Lys Leu Ser Arg Ala Thr Pro Phe Ala Met Val Asn Ser Met Leu Thr
290                 295                 300

Leu Lys Pro Leu Pro Lys Leu Gln Leu Ala Thr Pro Asn Phe Ile Phe
305                 310                 315                 320

Thr Ala Leu Ala Thr Ser Asn Leu Ile Gly Ile Leu Cys Ala Arg Ser
            325                 330                 335

Leu His Tyr Gln Phe Tyr Ala Trp Phe Ala Trp Tyr Ser Pro Tyr Leu
            340                 345                 350

Cys Tyr Gln Ala Ser Phe Pro Ala Pro Ile Val Ile Gly Leu Trp Met
        355                 360                 365

Leu Gln Glu Tyr Ala Trp Asn Val Phe Pro Ser Thr Lys Leu Ser Ser
370                 375                 380

Leu Ile Ala Val Cys Val Pro Leu Ile Thr Ile Leu Lys Leu Tyr Thr
385                 390                 395                 400

Ser Asp Tyr Arg Lys Pro
                405

<210> SEQ ID NO 138
<211> LENGTH: 30
<212> TYPE: DNA
<213> ORGANISM: Artificial Sequence
<220> FEATURE:
<223> OTHER INFORMATION: Synthesized Construct

<400> SEQUENCE: 138
ggaggtgggg gcagtggagg tggcggcagt                                      30

<210> SEQ ID NO 139
<211> LENGTH: 2460
<212> TYPE: DNA
<213> ORGANISM: Artificial Sequence
<220> FEATURE:
<223> OTHER INFORMATION: Synthesized Construct

<400> SEQUENCE: 139
atgcgcttcc gaatctacaa gcggaaggtc tcattctga cccttgtcgt ggccgcttgc      60
ggctttgttc tctggtccag caacggtcgc cagcgtaaga acgaggccct ggcgcctccc    120
ctcttggacg ccgaaccggc cagaggcgca ggtggcaggg gagggatca cccctcggtc     180

```
gctgtcggca tccgccgcgt cagcaatgtg tccgccgcct ctctggtccc ggcggttccg      240
cagcctgagg cagacaacct cacgctgcgc taccgatcac tcgtgtatca acttaacttc      300
gaccagactc tgcggaacgt cgacaaggcc ggaacctggg ctccgcgtga gttggtcctc      360
gtcgttcagg tgcacaacag gcccgagtac ctccgcctcc tgctggattc gcttcgaaag      420
gcccagggca tcgacaacgt cctggtgatt ttcagccatg acttttggtc cacagagatc      480
aatcagctca ttgcgggtgt caacttttgc cccgtcttgc aagttttctt cccttttctct      540 atccaactct accccaacga gttcccgggc agtgaccccc gcgactgtcc tcgggatctg      600
ccaaaaaacg ccgctctcaa gctgggctgc atcaacgccg aataccccga cagctttggc      660
cactatcgcg aggccaagtt ctcgcagacg aagcaccact ggtggtggaa gctccatttt      720
gtctgggagc gagtgaagat ccttcgtgat tacgcaggac tcattctgtt cttggaagag      780
gaccactacc tggccccgga cttctaccac gtctttaaga gatgtggaa gctcaagcag      840 caggaatgcc ccgagtgcga cgttctgtcc cttggcacct atagcgcgtc ccgctcgttc      900
tacggtatgg ctgacaaggt cgatgtgaaa acctggaagt caactgagca caatatgggc      960
ctcgccctga cgaggaacgc ctaccagaaa ctcatcgagt gtaccgacac cttctgcacg     1020
tacgacgact ataactggga ttggacactg cagtacttga ctgtcagctg cctccctaag     1080
ttttggaagg tccttgttcc ccagatcccg agaattttcc atgctggcga ctgcgggatg     1140
caccacaaga aaacctgtcg cccatccacg cagtctgccc aaatcgagtc gctcctgaac     1200
aacaacaagc agtacatgtt ccccgagaca ctgaccatta gcgagaagtt tacggtcgtg     1260
gcgatctccc cgcctcgaaa gaatggcggc tggggtgaca tccgcgatca cgagctgtgc     1320
aagtcttacc gccggctcca gggaggtggg ggcagtggag gtggcggcag tgggagggtg     1380
cccaccgccg cccctcccgc ccagccgcgt gtgcctgtga ccccgcgcc ggcggtgatt     1440 cccatcctgg tcatcgcctg tgaccgcagc actgttcggc gctgcctgga caagctgctg     1500
cattatcggc cctcggctga gctcttcccc atcatcgtca gccaggactg cgggcacgag     1560
gagacggccc aggccatcgc ctcctacggc agcgcggtca cgcacatccg gcagcccgac     1620
ctgagcagca ttgcggtgcc gccggaccac cgcaagttcc agggctacta caagatcgcg     1680
cgccactacc gctgggcgct gggccaggtc ttccggcagt ttcgcttccc cgccgccgtg     1740
gtggtggagg atgacctgga ggtggccccg gacttcttcg agtactttcg ggccacctat     1800
ccgctgctga aggccgaccc ctccctgtgg tgcgtctcgg cctggaatga caacggcaag     1860
gagcagatgg tggacgccag caggcctgag ctgctctacc gcaccgactt tttccctggc     1920
ctgggctggc tgctgttggc cgagctctgg gctgagctgg agcccaagtg gccaaaggcc     1980 ttctggacg actggatgcg gcggccgag cagcggcagg ggcgggcctg catccgccct     2040
gagatctcaa gaacgatgac ctttggccgc aagggtgtga ccacgggca gttctttgac     2100 cagcacctca gttcatcaa gctgaaccag cagtttgtgc acttcaccca gctggacctg     2160
tcttacctgc agcgggaggc ctatgaccga gatttcctcg cccgcgtcta cggtgctccc     2220
cagctgcagg tggagaaagt gaggaccaat gaccggaagg agctggggga ggtgcgggtg     2280
cagtacacgg gcagggacag cttcaaggct ttcgccaagg ctctgggtgt catggatgac     2340
ctcaagtcgg gggttccgag agctggctac cggggcattg tcaccttcca gttccggggc     2400
cgccgtgtcc acctggcgcc cccaccgacg tgggagggct atgatcccag ctggaattag    2460
```

<210> SEQ ID NO 140

```
<211> LENGTH: 45
<212> TYPE: DNA
<213> ORGANISM: Artificial Sequence
<220> FEATURE:
<223> OTHER INFORMATION: Synthesized Construct

<400> SEQUENCE: 140
ggaggtgggg gcagtggagg tggcggcagt ggcggcggtg gaagt            45

<210> SEQ ID NO 141
<211> LENGTH: 2475
<212> TYPE: DNA
<213> ORGANISM: Artificial Sequence
<220> FEATURE:
<223> OTHER INFORMATION: Synthesized Construct

<400> SEQUENCE: 141
atgcgcttcc gaatctacaa gcggaaggtc ctcattctga cccttgtcgt ggccgcttgc      60
ggctttgttc tctggtccag caacggtcgc cagcgtaaga acgaggccct ggcgcctccc     120
ctcttggacg ccgaaccggc cagaggcgca ggtggcaggg gaggggatca cccctcggtc     180
gctgtcggca tccgccgcgt cagcaatgtg tccgccgcct ctctggtccc ggcggttccg     240
cagcctgagg cagacaacct cacgctgcgc taccgatcac tcgtgtatca acttaacttc     300
gaccagactc tgcggaacgt cgacaaggcc ggaacctggg ctccgcgtga gttggtcctc     360
gtcgttcagg tgcacaacag gcccgagtac ctccgcctcc tgctggattc gcttcgaaag     420
gcccagggca tcgacaacgt cctggtgatt ttcagccatg acttttggtc cacagagatc     480
aatcagctca ttgcgggtgt caacttttgc cccgtcttgc aagttttctt cccttttctct    540 atccaactct accccaacga gttcccgggc agtgaccccc gcgactgtcc tcgggatctg     600
ccaaaaaacg ccgctctcaa gctgggctgc atcaacgccg aatacccga cagctttggc      660 cactatcgcg aggccaagtt ctcgcagacg aagcaccact ggtggtggaa gctccatttt     720
gtctgggagc gagtgaagat ccttcgtgat tacgcaggac tcattctgtt cttggaagag     780
gaccactacc tggccccgga cttctaccac gtctttaaga agatgtggaa gctcaagcag     840
caggaatgcc ccgagtgcga cgttctgtcc cttggcacct atagcgcgtc ccgctcgttc     900
tacggtatgg ctgacaaggt cgatgtgaaa acctggaagt caactgagca aatatgggc      960 ctcgccctga cgaggaacgc ctaccagaaa ctcatcgagt gtaccgacac cttctgcacg    1020
tacgacgact ataactggga ttggacactg cagtacttga ctgtcagctg cctccctaag    1080
ttttggaagg tccttgttcc ccagatcccg agaattttcc atgctggcga ctgcgggatg    1140
caccacaaga aaacctgtcg cccatccacg cagtctgccc aaatcgagtc gctcctgaac    1200
aacaacaagc agtacatgtt ccccgagaca ctgaccatta gcgagaagtt tacggtcgtg    1260
gcgatctccc cgcctcgaaa gaatggcggc tggggtgaca tccgcgatca cgagctgtgc    1320
aagtcttacc gccggctcca gggaggtggg gcagtggag gtggcggcag tggaggtggc    1380
ggcagtggga gggtgcccac cgccgcccct cccgcccagc cgcgtgtgcc tgtgaccccc    1440
gcgccggcgg tgattcccat cctggtcatc gcctgtgacc gcagcactgt tcggcgctgc    1500
ctggacaagc tgctgcatta tcggcccctcg gctgagctct tccccatcat cgtcagccag    1560
gactgcgggc acgaggagac ggcccaggcc atcgcctcct acggcagcgc ggtcacgcac    1620
atccggcagc ccgacctgag cagcattgcg gtgccgccgg accaccgcaa gttccagggc    1680
tactacaaga tcgcgcgcca ctaccgctgg gcgctgggcc aggtcttccg gcagtttcgc    1740
ttccccgccg ccgtggtggt ggaggatgac ctggaggtgg ccccggactt cttcgagtac    1800
```

```
tttcgggcca cctatccgct gctgaaggcc gacccctccc tgtggtgcgt ctcggcctgg    1860
aatgacaacg gcaaggagca gatggtggac gccagcaggc ctgagctgct ctaccgcacc    1920 gacttttcc  ctggcctggg ctggctgctg ttggccgagc tctgggctga gctggagccc    1980
aagtggccaa aggccttctg ggacgactgg atgcggcggc cggagcagcg gcaggggcgg    2040
gcctgcatcc gccctgagat ctcaagaacg atgacctttg ccgcaaggg  tgtgagccac    2100 gggcagttct tgaccagca  cctcaagttc atcaagctga accagcagtt tgtgcacttc    2160
acccagctgg acctgtctta cctgcagcgg gaggcctatg accgagattt cctcgcccgc    2220
gtctacggtg ctccccagct gcaggtggag aaagtgagga ccaatgaccg gaaggagctg    2280
ggggaggtgc gggtgcagta cacgggcagg gacagcttca aggctttcgc caaggctctg    2340
ggtgtcatgg atgacctcaa gtcggggggtt ccgagagctg gctaccgggg cattgtcacc    2400
ttccagttcc ggggccgccg tgtccacctg gcgcccccac cgacgtggga gggctatgat    2460
cccagctgga attag                                                    2475

<210> SEQ ID NO 142
<211> LENGTH: 57
<212> TYPE: DNA
<213> ORGANISM: Trichoderma reesei

<400> SEQUENCE: 142
agcaccggca accctagcgg cggcaaccct cccggcggaa acccgcctgg cagcacc        57

<210> SEQ ID NO 143
<211> LENGTH: 2487
<212> TYPE: DNA
<213> ORGANISM: Artificial Sequence
<220> FEATURE:
<223> OTHER INFORMATION: Synthesized Construct

<400> SEQUENCE: 143
atgcgcttcc gaatctacaa gcggaaggtc ctcattctga cccttgtcgt ggccgcttgc      60
ggctttgttc tctggtccag caacggtcgc cagcgtaaga acgaggccct ggcgcctccc     120
ctcttggacg ccgaaccggc cagaggcgca ggtggcaggg gaggggatca cccctcggtc     180
gctgtcggca tccgccgcgt cagcaatgtg tccgccgcct ctctggtccc ggcggttccg     240
cagcctgagg cagacaacct cacgctgcgc taccgatcac tcgtgtatca acttaacttc     300
gaccagactc tgcggaacgt cgacaaggcc ggaacctggg ctccgcgtga gttggtcctc     360
gtcgttcagg tgcacaacag gcccgagtac ctccgcctcc tgctggattc gcttcgaaag     420
gcccagggca tcgacaacgt cctggtgatt ttcagccatg acttttggtc cacagagatc     480
aatcagctca ttgcgggtgt caacttttgc cccgtcttgc aagttttctt cccttctctct    540 atccaactct accccaacga gttcccgggc agtgaccccc gcgactgtcc tcgggatctg     600
ccaaaaaacg ccgctctcaa gctgggctgc atcaacgccg aatacccga  cagctttggc     660 cactatcgcg aggccaagtt ctcgcagacg aagcaccact ggtggtggaa gctccatttt     720
gtctgggagc gagtgaagat ccttcgtgat tacgcaggac tcattctgtt cttggaagag     780
gaccactacc tggccccgga cttctaccac gtctttaaga gatgtggaa  gctcaagcag     840 caggaatgcc ccgagtgcga cgttctgtcc cttggcacct atagcgcgtc ccgctcgttc     900
tacggtatgg ctgacaaggt cgatgtgaaa acctggaagt caactgagca aatatgggc      960 ctcgccctga cgaggaacgc ctaccagaaa ctcatcgagt gtaccgacac cttctgcacg    1020
```

```
tacgacgact ataactggga ttggacactg cagtacttga ctgtcagctg cctccctaag    1080
ttttggaagg tccttgttcc ccagatcccg agaattttcc atgctggcga ctgcgggatg    1140
caccacaaga aacctgtcg cccatccacg cagtctgccc aaatcgagtc gctcctgaac    1200
aacaacaagc agtacatgtt ccccgagaca ctgaccatta gcgagaagtt tacggtcgtg    1260
gcgatctccc cgcctcgaaa gaatggcggc tggggtgaca tccgcgatca cgagctgtgc    1320
aagtcttacc gccggctcca gagcaccggc aaccctagcg cggcaaccc tcccggcgga    1380 aacccgcctg gcagcaccgg gagggtgccc accgccgccc ctcccgccca gccgcgtgtg    1440
cctgtgaccc ccgcgccggc ggtgattccc atcctggtca tcgcctgtga ccgcagcact    1500
gttcggcgct gcctggacaa gctgctgcat tatcggcccct cggctgagct cttccccatc    1560
atcgtcagcc aggactgcgg gcacgaggag acggcccagg ccatcgcctc ctacggcagc    1620
gcggtcacgc acatccggca gcccgacctg agcagcattg cggtgccgcc ggaccaccgc    1680
aagttccagg gctactacaa gatcgcgcgc cactaccgct gggcgctggg ccaggtcttc    1740
cggcagtttc gcttccccgc cgccgtgtg gtggaggatg acctggaggt ggccccggac    1800
ttcttcgagt actttcgggc cacctatccg ctgctgaagg ccgacccctc cctgtggtgc    1860
gtctcggcct ggaatgacaa cggcaaggag cagatggtgg acgccagcag gcctgagctg    1920
ctctaccgca ccgactttt ccctggcctg gctggctgc tgttggccga gctctgggct    1980
gagctggagc ccaagtggcc aaaggccttc tgggacgact ggatgcggcg gccggagcag    2040
cggcaggggc gggcctgcat ccgccctgag atctcaagaa cgatgacctt tggccgcaag    2100
ggtgtgagcc acgggcagtt cttttgaccag cacctcaagt tcatcaagct gaaccagcag    2160
tttgtgcact tcacccagct ggacctgtct tacctgcagc gggaggccta tgaccgagat    2220
ttcctcgccc gcgtctacgg tgctccccag ctgcaggtgg agaaagtgag gaccaatgac    2280
cggaaggagc tggggaggt gcgggtgcag tacacgggca gggacagctt caaggctttc    2340
gccaaggctc tgggtgtcat ggatgacctc aagtcggggg ttccgagagc tggctaccgg    2400
ggcattgtca ccttccagtt ccggggccgc cgtgtccacc tggcgccccc accgacgtgg    2460
gagggctatg atcccagctg gaattag                                        2487

<210> SEQ ID NO 144
<211> LENGTH: 65
<212> TYPE: DNA
<213> ORGANISM: Trichoderma reesei

<400> SEQUENCE: 144
agctccgccg cgacggccac cgccagcgcc actgttcctg gaggcggtag cggccccacc    60
agcgg                                                                65

<210> SEQ ID NO 145
<211> LENGTH: 2493
<212> TYPE: DNA
<213> ORGANISM: Artificial Sequence
<220> FEATURE:
<223> OTHER INFORMATION: Synthesized Construct

<400> SEQUENCE: 145
atgcgcttcc gaatctacaa gcggaaggtc ctcattctga cccttgtcgt ggccgcttgc    60
ggctttgttc tctggtccag caacggtcgc cagcgtaaga cgaggccct ggcgcctccc    120 ctcttggacg ccgaaccggc cagaggcgca ggtggcaggg gaggggatca cccctcggtc    180
gctgtcggca tccgccgcgt cagcaatgtg tccgccgcct ctctggtccc ggcggttccg    240
```

```
cagcctgagg cagacaacct cacgctgcgc taccgatcac tcgtgtatca acttaacttc    300
gaccagactc tgcggaacgt cgacaaggcc ggaacctggg ctccgcgtga gttggtcctc    360
gtcgttcagg tgcacaacag gcccgagtac ctccgcctcc tgctggattc gcttcgaaag    420
gcccagggca tcgacaacgt cctggtgatt ttcagccatg acttttggtc cacagagatc    480
aatcagctca ttgcgggtgt caacttttgc cccgtcttgc aagttttctt ccctttctct    540
atccaactct accccaacga gttcccgggc agtgaccccc gcgactgtcc tcgggatctg    600
ccaaaaaacg ccgctctcaa gctgggctgc atcaacgccg aatacccccga cagctttggc    660 cactatcgcg aggccaagtt ctcgcagacg aagcaccact ggtggtggaa gctccatttt    720
gtctgggagc gagtgaagat ccttcgtgat tacgcaggac tcattctgtt cttggaagag    780
gaccactacc tggccccgga cttctaccac gtctttaaga gatgtggaa gctcaagcag    840 caggaatgcc ccgagtgcga cgttctgtcc cttggcacct atagcgcgtc ccgctcgttc    900
tacggtatgg ctgacaagt cgatgtgaaa acctggaagt caactgagca caatatgggc    960
ctcgccctga cgaggaacgc ctaccagaaa ctcatcgagt gtaccgacac cttctgcacg   1020
tacgacgact ataactggga ttggacactg cagtacttga ctgtcagctg cctccctaag   1080
ttttggaagg tccttgttcc ccagatcccg agaattttcc atgctggcga ctgcgggatg   1140
caccacaaga aaacctgtcg cccatccacg cagtctgccc aaatcgagtc gctcctgaac   1200
aacaacaagc agtacatgtt ccccgagaca ctgaccatta gcgagaagtt tacggtcgtg   1260
gcgatctccc cgcctcgaaa gaatggcggc tggggtgaca tccgcgatca cgagctgtgc   1320
aagtcttacc gccggctcca gagctccgcc gcgacggcca ccgccagcgc cactgttcct   1380
ggaggcggta gcggcccgac cagcggggagg gtgcccaccg ccgcccctcc cgcccagccg   1440
cgtgtgcctg tgacccccgc gccggcggtg attcccatcc tggtcatcgc ctgtgaccgc   1500
agcactgttc ggcgctgcct ggacaagctg ctgcattatc ggcctcggc tgagctcttc   1560 cccatcatcg tcagccagga ctgcgggcac gaggagacgg cccaggccat cgcctcctac   1620
ggcagcgcgg tcacgcacat ccggcagccc gacctgagca gcattgcggt gccgccggac   1680
caccgcaagt tccagggcta ctacaagatc gcgcgccact accgctgggc gctgggccag   1740
gtcttccggc agtttcgctt ccccgccgcc gtggtggtgg aggatgacct ggaggtggcc   1800
ccggacttct tcgagtactt tcgggccacc tatccgctgc tgaaggccga ccctccctg   1860 tggtgcgtct cggcctggaa tgacaacggc aaggagcaga tggtggacgc cagcaggcct   1920
gagctgctct accgcaccga cttttttccct ggcctgggct ggctgctgtt ggccgagctc   1980
tgggctgagc tggagcccaa gtggccaaag gccttctggg acgactggat gcggcggccg   2040
gagcagcgga aggggcggc ctgcatccgc cctgagatct caagaacgat gaccttggc    2100 cgcaagggtg tgagccacgg gcagttcttt gaccagcacc tcaagttcat caagctgaac   2160
cagcagtttg tgcacttcac ccagctggac ctgtcttacc tgcagcggga ggcctatgac   2220
cgagatttcc tcgcccgcgt ctacggtgct ccccagctgc aggtggagaa agtgaggacc   2280
aatgaccgga aggagctggg ggaggtgcgg gtgcagtaca cgggcaggga cagcttcaag   2340
gctttcgcca aggctctggg tgtcatggat gacctcaagt cggggttcc gagagctggc   2400 taccggggca ttgtcaccct ccagttccgg ggccgccgtg tccacctggc gccccaccg   2460 acgtgggagg gctatgatcc cagctggaat tag                                2493

<210> SEQ ID NO 146
```

```
<211> LENGTH: 45
<212> TYPE: DNA
<213> ORGANISM: Artificial Sequence
<220> FEATURE:
<223> OTHER INFORMATION: Synthesized Construct

<400> SEQUENCE: 146
ggtaccgggc ccactgcgca tcatgcgctt ccgaatctac aagcg            45

<210> SEQ ID NO 147
<211> LENGTH: 38
<212> TYPE: DNA
<213> ORGANISM: Artificial Sequence
<220> FEATURE:
<223> OTHER INFORMATION: Synthesized Construct

<400> SEQUENCE: 147
ggcgcgccac tagtctaatt ccagctggga tcatagcc                    38
```